US012729195B2

(12) United States Patent
Li et al.

(10) Patent No.: US 12,729,195 B2
(45) Date of Patent: Sep. 8, 2026

(54) IMMUNOMODULATOR

(71) Applicant: HitGen Inc., Chengdu (CN)

(72) Inventors: Jin Li, Chengdu (CN); Dengyou Zhang, Chengdu (CN); Xiaoguang Bai, Chengdu (CN); Yi Gong, Chengdu (CN); Xiansi Zhou, Chengdu (CN); Lichuan Liu, Chengdu (CN); Qingran Li, Chengdu (CN); Xin Chen, Chengdu (CN); Yan Lan, Chengdu (CN)

(73) Assignee: HitGen Inc., Chengdu (CN)

( * ) Notice: Subject to any disclaimer, the term of this patent is extended or adjusted under 35 U.S.C. 154(b) by 657 days.

(21) Appl. No.: 18/148,958

(22) Filed: Dec. 30, 2022

(65) Prior Publication Data

US 2023/0227437 A1 Jul. 20, 2023

Related U.S. Application Data

(63) Continuation of application No. PCT/CN2021/087553, filed on Apr. 15, 2021.

(30) Foreign Application Priority Data

| | | |
|---|---|---|
| Jul. 4, 2020 | (CN) | 202010610045.6 |
| Jul. 14, 2020 | (CN) | 202010661625.8 |
| Feb. 9, 2021 | (CN) | 202110172530.4 |

(51) Int. Cl.

| | |
|---|---|
| ***C07D 405/14*** | (2006.01) |
| ***A61P 17/06*** | (2006.01) |
| ***A61P 25/00*** | (2006.01) |
| ***A61P 29/00*** | (2006.01) |
| ***C07D 231/14*** | (2006.01) |
| ***C07D 401/12*** | (2006.01) |
| ***C07D 401/14*** | (2006.01) |
| ***C07D 413/12*** | (2006.01) |
| ***C07D 413/14*** | (2006.01) |
| ***C07F 9/6503*** | (2006.01) |
| ***C07F 9/6558*** | (2006.01) |

(52) U.S. Cl.

CPC ............ *C07D 405/14* (2013.01); *A61P 17/06* (2018.01); *A61P 25/00* (2018.01); *A61P 29/00* (2018.01); *C07D 231/14* (2013.01); *C07D 401/12* (2013.01); *C07D 401/14* (2013.01); *C07D 413/12* (2013.01); *C07D 413/14* (2013.01); *C07F 9/65031* (2013.01); *C07F 9/65583* (2013.01); *C07F 9/65586* (2013.01)

(58) Field of Classification Search

CPC .................................................... C07D 405/14

See application file for complete search history.

(56) References Cited

FOREIGN PATENT DOCUMENTS

| | | | |
|---|---|---|---|
| WO | 2019138017 | A1 | 7/2019 |
| WO | 2019223718 | A1 | 11/2019 |

OTHER PUBLICATIONS

American Chemical Society. Chemical Abstract Service. RN 2609683-08-9. Entered into STN: Mar. 12, 2021. (Year: 2021).*

Jill F. Wright et al."The Human IL-17F/IL-17A Heterodimeric Cytokine Signals through the IL-17RA/IL-17RC Receptor Complex", The Journal of immunology, 2008, 181, pp. 2799-2805.

Al-Ramli et al."TH17-associated cytokines (IL-17A and IL-17F) in severe asthma", J Allergy Clin Immunol, 2009, vol. 123, No. 5, pp. 1185-1187.

Sarah L Gaffen et al."Biology of recently discovered cytokines: Interleukin-17—a unique inflammatory cytokine with roles in bone biology and arthritis" Arthritis Research & Therapy, 2004, vol. 6, No. 6, pp. 240-247.

Yutaka Komiyama et al.,"IL-17 Plays an Important Role in the Development of Experimental Autoimmune Encephalomyelitis", The Journal of immunology, 2006, 177, pp. 566-573.

* cited by examiner

*Primary Examiner* — John S Kenyon

(57) ABSTRACT

Disclosed is a compound capable of inhibiting interleukin 17A (IL-17A), which is represented by formula (I). An application of the compound or a stereoisomer thereof in the preparation of drugs for inhibiting IL-17A is also provided.

(I)

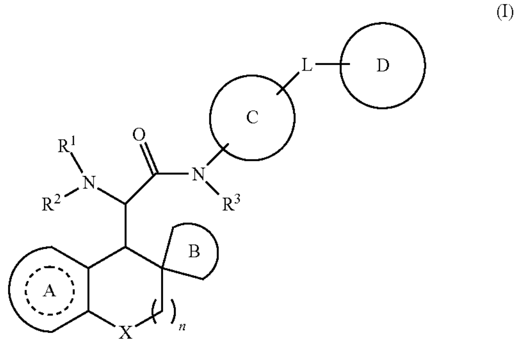

24 Claims, 6 Drawing Sheets

Positive compound
inhibition on IL17A/IL17RA(Coating)
after jump dilution

Compound 26 inhibition on
IL17A/IL17RA(Coating)
after jump dilution

Compound 43 inhibition on
IL17A/IL17RA(Coating)
after jump dilution

Compound 47 inhibition on
IL17A/IL17RA(Coating)
after jump dilution

IMMUNOMODULATOR

CROSS-REFERENCE TO RELATED APPLICATIONS

This application is a continuation of International Patent Application No. PCT/CN2021/087553, filed on Apr. 15, 2021, which claims the benefit of priority from Chinese Patent Application Nos. 202010610045.6, 202010661625.8 and 202110172530.4, filed on Jul. 4, 2020, Jul. 14, 2020 and Feb. 9, 2021, respectively. The content of the aforementioned application, including any intervening amendments thereto, is incorporated herein by reference in its entirety.

TECHNICAL FIELD

This application relates to an immunomodulator and an application thereof on a drug.

BACKGROUND

Interleukin 17 (IL-17) is a proinflammatory cytokine that plays a role in the induction of other inflammatory cytokines, chemokine, and adhesion factor. An IL-17 family consists of cytokines that are involved in acute and chronic inflammatory responses, including interleukin 17A (IL-17A or CTLA-8), interleukin 17B (IL-17B), interleukin 17C (IL-17C), interleukin 17D (IL-17D), interleukin 17E (IL-17E or IL-25) and interleukin 17F (IL-17F). The IL-17A is expressed by T helper cell 17 (TH17), and is involved in the pathogenesis of inflammatory and autoimmune diseases. The IL-17A of human is a glycoprotein with a molecular weight of approximately 17000 daltons. The IL-17A transmits signals into the cell through an IL-17 receptor, such as interleukin 17RA (IL-17RA) and interleukin 17RC (IL-17RC) (Wright, et al. *Journal of immunology,* 2008, 181: 2799-2805). A primary function of IL-17A is to coordinate local tissue inflammation through upregulation of proinflammatory and neutrophil migratory cytokines and chemokines (including IL-6, G-CSF, TNF-α, IL-1, CXCL1, CCL2, CXCL2), and to allow activated T cells to penetrate the extracellular matrix though matrix metalloproteinases. The IL-17A has been shown to play an important role in severe asthma and chronic obstructive pulmonary disease (COPD), and those patients having severe asthma or COPD typically do not respond or respond poorly to currently available medications (Al-Ramli et al. *J Allergy Clin Immunol,* 2009, 123: 1185-1187). An upregulation of IL-17A is related to many diseases, such as rheumatoid arthritis (RA), bone erosion, intraperitoneal abscess, inflammatory bowel disease, allograft rejection, psoriasis, atherosclerosis, asthma, and multiple sclerosis (Gaffen, S L et al. *Arthritis Research & Therapy,* 2004, 6: 240-247). The binding of targeting IL-17A to IL-17RA is an effective strategy to treat autoimmune inflammatory diseases mediated by IL-17 A. A morbidity and severity of autoimmune encephalomyelitis can be reduced in animals through IL-17A and monoclonal antibody therapy (Komiyama Y et al. *J. Immunol.,* 2006, 177: 566-573). The existing IL-17A antibodies have shown promising results on IL-7A-mediated inflammatory diseases, including asthma, psoriasis, rheumatoid arthritis, ankylosing spondylitis, and multiple sclerosis. The IL-17A (Cosentyx/secukinumab of Novartis) approved by the *Food and Drug Administration* (FDA) for the treatment of psoriasis in January 2015.

Whereas, despite there are multiple IL-17A antibodies, few of them have been conducted on small molecule-specific inhibitors of IL-17 with oral bioavailability. In view of the cost of antibody generation and administration route, it is promising to develop IL-17A small molecule inhibitor drugs.

SUMMARY

In a first aspect, the present disclosure provides a compound of formula (I), or a deuterated compound, a stereoisomer or a pharmacologically acceptable salt thereof:

(I)

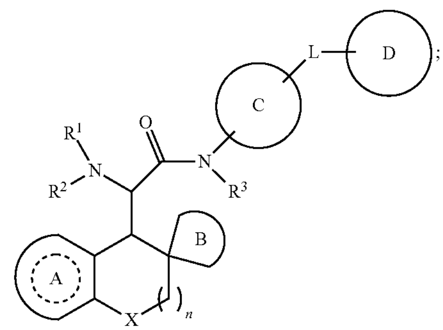

wherein:

$R^1$ is selected from the group consisting of —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring), —$C_{0-2}$ alkylidene-(5 to 10-membered heteroaromatic ring), —$C_{0-2}$ alkylidene-C(O)$R^{11}$, —$C_{0-2}$ alkylidene-C(O)$NR^{11}R^{12}$, —$C_{0-2}$ alkylidene-C(O)$OR^{11}$, —$C_{0-2}$ alkylidene-S(O)$R^{11}$, —$C_{0-2}$ alkylidene-S(O)$NR^{11}R^{12}$, —$C_{0-2}$ alkylidene-S(O)$OR^{11}$, —$C_{0-2}$ alkylidene-$S(O)_2R^{11}$, —$C_{0-2}$ alkylidene-$S(O)_2NR^{11}R^{12}$, —$C_{0-2}$ alkylidene-$S(O)_2OR^{11}$, —$C_{0-2}$ alkylidene-P(O)$R^{11}R^{12}$, —$C_{0-2}$ alkylidene-P(O)($OR^{11}$)$R^{12}$ and —$C_{0-2}$ alkylidene-P(O)($OR^{11}$)($OR^{12}$), wherein alkylidene, cycloalkyl, heterocycloalkyl, aromatic ring and heteroaromatic ring are independently unsubstituted or substituted with one, two or three $R^{1a}$;

$R^{11}$ and $R^{12}$ are independently selected from the group consisting of hydrogen, —$C_{1-6}$ alkyl, halogen-substituted —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted by one, two or three $R^{1a}$;

each $R^{1a}$ is independently selected from the group consisting of hydrogen, halogen, cyano group, ═O, ═S, nitro, —$C_{1-6}$ alkyl, halogen-substituted —$C_{1-6}$ alkyl, —$C_{0-2}$ alkylidene-$OR^{1b}$, —$C_{0-2}$ alkylidene-C(O)$R^{1b}$, —$C_{0-2}$ alkylidene-C(O)$NR^{1b}R^{1c}$, —$C_{0-2}$ alkylidene-$NR^{1b}R^{1c}$, —$C_{0-2}$ alkylidene-$NR^{1b}C(O)R^{1c}$, —$C_{0-4}$ alkylidene-$S(O)_2R^{1b}R^{1c}$, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1b}$;

$R^{1b}$ and $R^{1c}$ are independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl); and $R^2$ and $R^3$ are independently selected from the group consisting of hydrogen, —$C_{1-6}$ alkyl and —$C_{0-2}$ alkylidene-(3 to 10-membered cycloalkyl);

A ring is selected from the group consisting of 5 to 10-membered aromatic ring and 5 to 10-membered heteroaromatic ring, wherein aromatic ring and heteroaromatic ring are independently unsubstituted or substituted with one, two or three $R^{A1}$; and each $R^{A1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

X is O, S, $NR^{x1}$ or $CR^{x2}R^{x3}$;

$R^{x1}$ is selected from the group consisting of hydrogen, —$C_{1-6}$ alkyl and —$C_{0-2}$ alkylidene-(3 to 10-membered cycloalkyl); and $R^{x2}$ and $R^{x3}$ are independently selected from the group consisting of hydrogen, —$C_{1-6}$ alkyl, halogen-substituted —$C_{1-6}$ alkyl, halogen, cyano group, nitro, —OH, —O($C_{1-6}$ alkyl), —$NH_2$, —NH($C_{1-6}$ alkyl) and —N($C_{1-6}$ alkyl)($C_{1-6}$ alkyl);

n is 0, 1, 2 or 3;

B ring is selected from the group consisting of 5 to 10-membered cycloalkane and 3 to 6-membered heterocyclic alkylidene, wherein cycloalkane and heterocyclic alkylidene are independently unsubstituted or substituted with one, two or three $R^{B1}$; and each $R^{B1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

C ring is selected from the group consisting of 3 to 10-membered cycloalkyl, 3 to 10-membered heterocycloalkyl, 5 to 10-membered aromatic ring, 5 to 10-membered heteroaromatic ring, 5 to 12-membered spiro ring, 5 to 12-membered spiro heterocycle, 5 to 12-membered bridged ring and 5 to 12-membered bridged heterocycle, wherein cycloalkyl, heterocycloalkyl, aromatic ring, heteroaromatic ring, spiro ring, spiro heterocycle, bridged ring and bridged heterocycle are independently unsubstituted or substituted with one, two or three $R^{C1}$;

each $R^{C1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{C2}$, —$C_{0-2}$ alkylidene-C(O)$R^{C2}$, —$C_{0-2}$ alkylidene-C(O)$NR^{C2}R^{C3}$, —$C_{0-2}$ alkylidene-$NR^{C2}R^{C3}$, —$C_{0-2}$ alkylidene-$NR^{C2}$C(O)$R^{C3}{}_2$, 3 to 10-membered cycloalkyl and 3 to 10-membered heterocycloalkyl, wherein alkyl and alkylidene are independently unsubstituted or substituted with one, two or three $R^{C4}$;

$R^{C2}$ and $R^{C3}$ are independently selected from the group consisting of hydrogen, —$C_{1-6}$ alkyl, —$C_{0-2}$ alkylidene-(3 to 10-membered cycloalkyl) and —$C_{0-2}$ alkylidene-(3 to 10-membered heterocycloalkyl), wherein alkyl and alkylidene are independently unsubstituted or substituted with one, two or three $R^{C4}$; and each $R^{C4}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl); or if two $R^{C1}$ are linked to the same atom, the two $R^{C1}$ are linked to form 3 to 10-membered cycloalkyl or 3 to 10-membered heterocycloalkyl;

L is O, S, $CR^{D1}R^{D1}$, $NR^L$, $NR^L$C(O), $NR^L$S(O), $NR^L$S(O)$_2$, C(O)$NR^L$, C(O), S(O)$NR^L$ or S(O)$_2NR^L$, or absent;

$R^L$ is hydrogen, —$C_{1-6}$ alkyl or —$C_{0-2}$ alkylidene-(3 to 10-membered cycloalkyl);

D ring is 3 to 10-membered cycloalkyl, 3 to 10-membered heterocycloalkyl, 5 to 10-membered aromatic ring, 5 to 10-membered heteroaromatic ring, 5 to 12-membered spiro ring, 5 to 12-membered spiro heterocycle, 5 to 12-membered bridged ring, or 5 to 12-membered bridged heterocycle, or absent, wherein cycloalkyl, heterocycloalkyl, aromatic ring, heteroaromatic ring, spiro ring, spiro heterocycle, bridged ring and bridged heterocycle are independently unsubstituted or substituted by one, two or three $R^{D1}$;

when L is absent and the D ring is not absent, the C ring is directly linked to the D ring;

each $R^{D1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-C(O)$R^{D2}$, —$C_{0-2}$ alkylidene-OC(O)$R^{D2}$, —$C_{0-2}$ alkylidene-C(O)$NR^{D2}R^{D3}$, —$C_{0-2}$ alkylidene-$NR^{D2}R^{D3}$, —$C_{0-2}$ alkylidene-$NR^{D2}$C(O)$R^{D3}$, —$C_{0-4}$ alkylidene-OP(O)(OH)$_2$, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{D4}$;

$R^{D2}$ and $R^{D3}$ are independently selected from the group consisting of hydrogen, —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{D4}$; and each $R^{D4}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl), —N($C_{1-6}$ alkyl)($C_{1-6}$ alkyl), —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring).

In some embodiments, $R^1$ is —C(O)$R^{11}$; $R^{11}$ is 3 to 6-membered cycloalkyl or 5 to 6-membered heteroaromatic ring, wherein heteroaromatic ring is unsubstituted or substituted by one, two or three $R^{1a}$; each $R^{1a}$ is independently selected from the group consisting of hydrogen, halogen, cyano group, =O, =S, —$C_{1-6}$ alkyl, halogen-substituted —$C_{1-6}$ alkyl, —$C_{0-2}$ alkylidene-$OR^{1b}$, 3 to 6-membered cycloalkyl and 3 to 6-membered heterocycloalkyl; and $R^{1b}$ is hydrogen, —$C_{1-6}$ alkyl or halogen-substituted —$C_{1-6}$ alkyl.

In some embodiments, $R^1$ is —$C(O)R^{11}$; $R^{11}$ is selected from the group consisting of

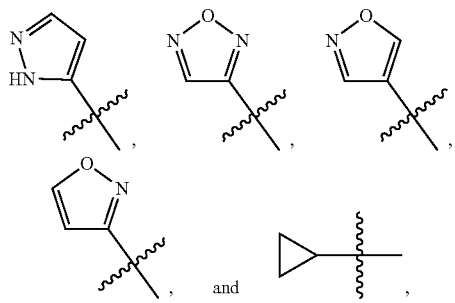

wherein a ring selected for $R^{11}$ is unsubstituted or substituted by one, two or three $R^{1a}$; each $R^{1a}$ is independently selected from the group consisting of hydrogen, halogen, cyano group, —$C_{1-6}$ alkyl, halogen-substituted —$C_{1-6}$ alkyl, 3 to 6-membered cycloalkyl and —$C_{0-2}$ alkylidene-$OR^{1b}$; and $R^{1b}$ is hydrogen, —$C_{1-6}$ alkyl or halogen-substituted —$C_{1-6}$ alkyl.

In some embodiments, $R^1$ is —$C(O)R^{11}$; and $R^{11}$ is selected from the group consisting of

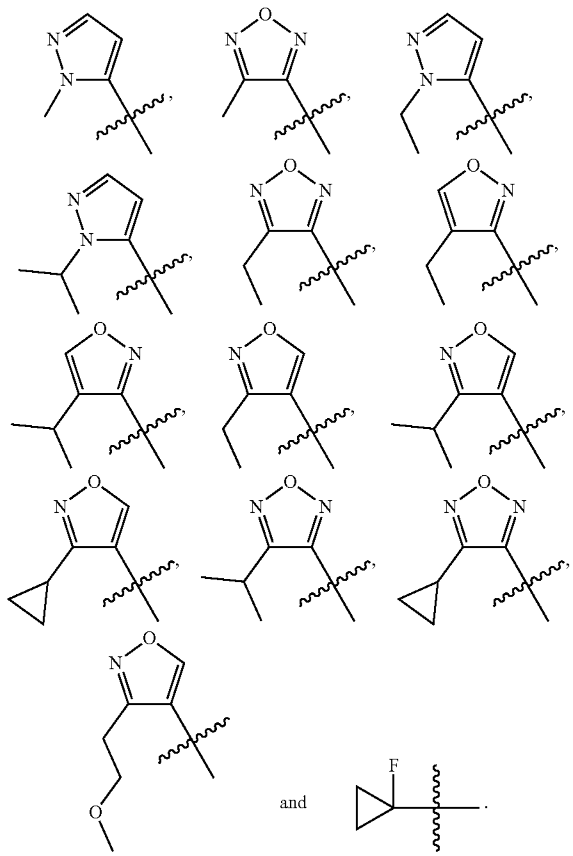

In some embodiments, $R^1$ is —$C(O)OR^{11}$; and $R^{11}$ is —$C_{1-6}$ alkyl or 3 to 6-membered cycloalkyl.

In some embodiments, $R^1$ is selected from the group consisting of

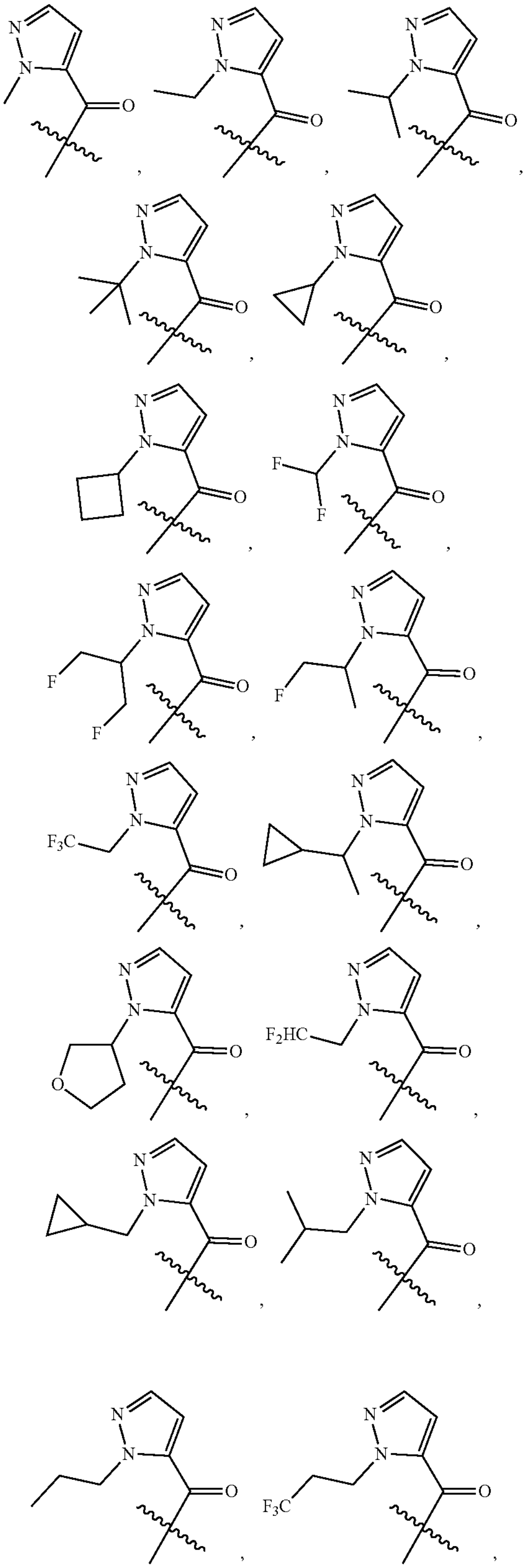

-continued
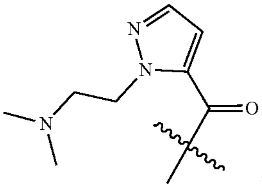,
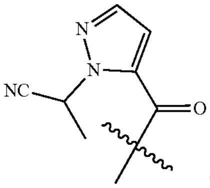,
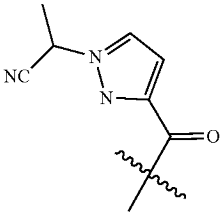,
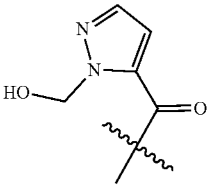,
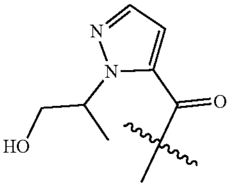,
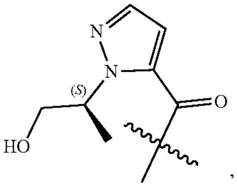,
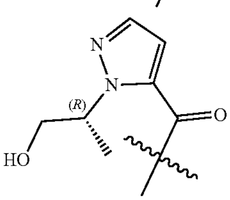,
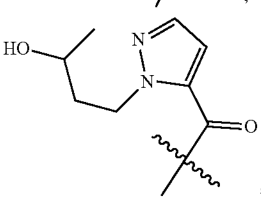,
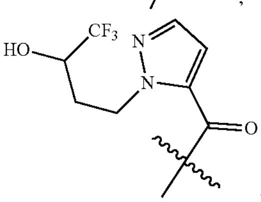,
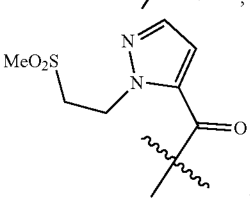,
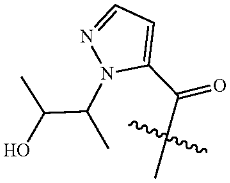,
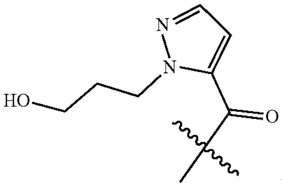,
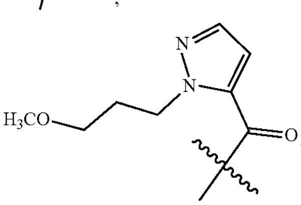
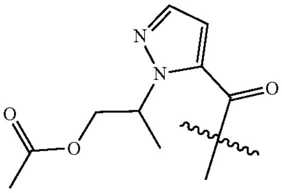,
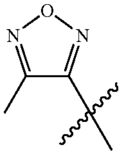,
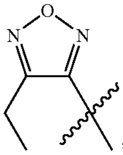,
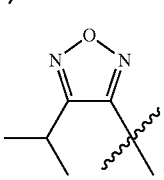,
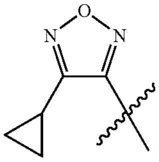,
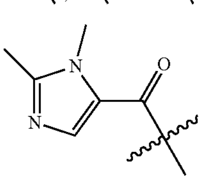,
-continued
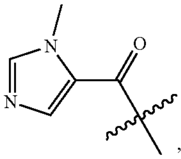,
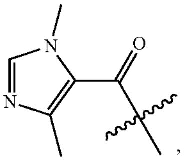,
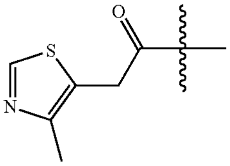,
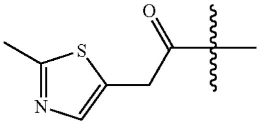,
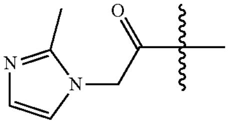,
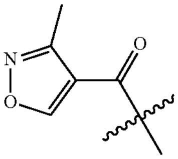,
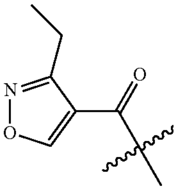,
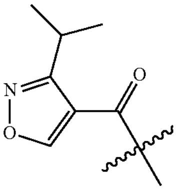,
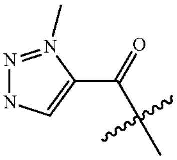,
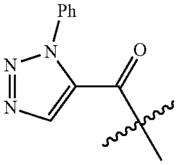,
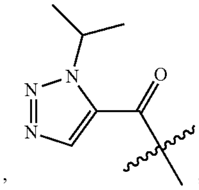,
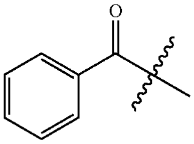,
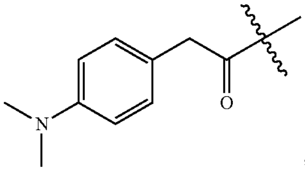,
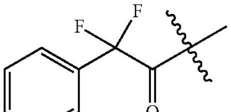,
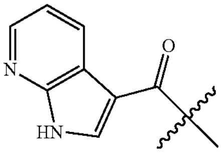,
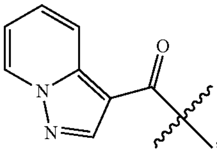,
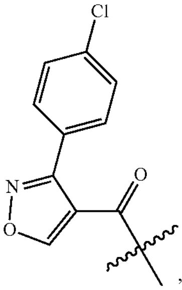,
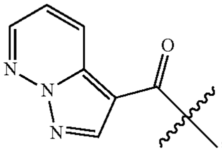,
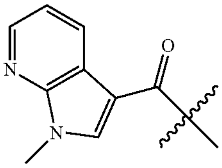, -continued

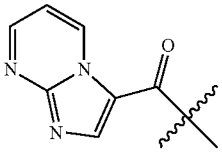, 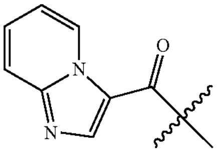,

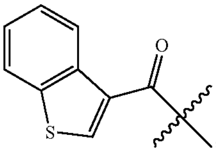, 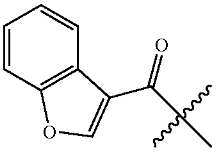,

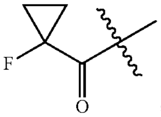, 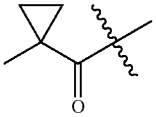, 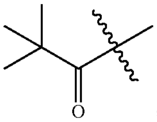,

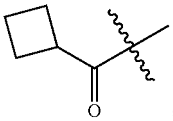, 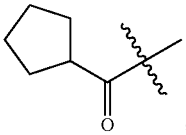, 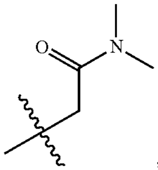,

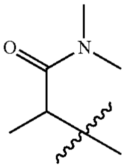, 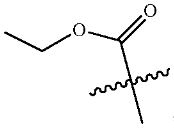, 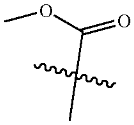,

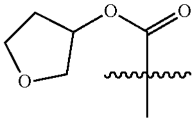, 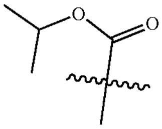, 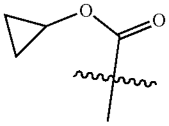,

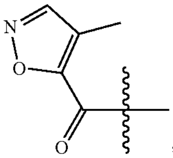, 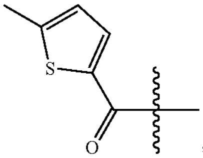, 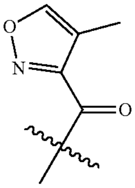,

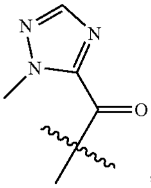, 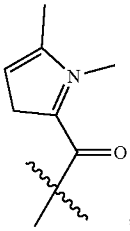, 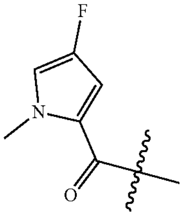,

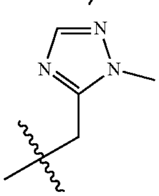, 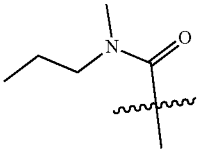, 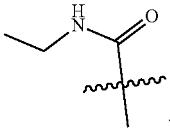,

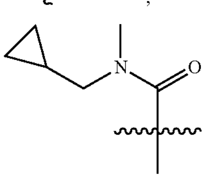, 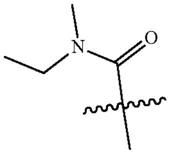, 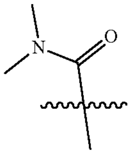,

-continued

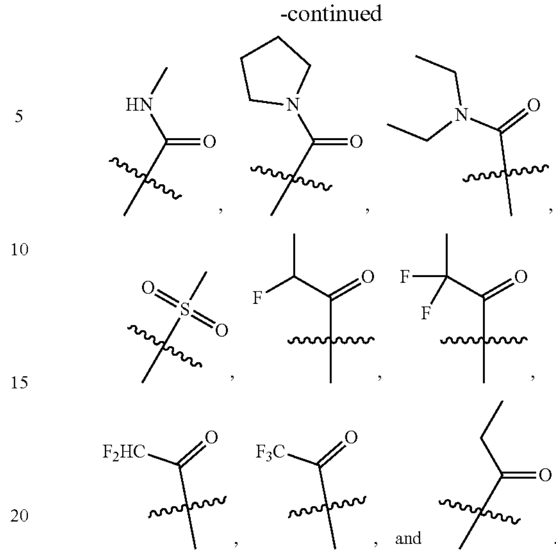

In some embodiments, A ring is benzene ring or 6-membered heteroaromatic ring, wherein the benzene ring and the heteroaromatic ring are independently unsubstituted or substituted with one, two or three $R^{A1}$; and each $R^{A1}$ is independently selected from the group consisting of hydrogen, $—C_{1-6}$ alkyl, halogen-substituted $—C_{1-6}$ alkyl, halogen and cyano group.

In some embodiments, A ring is selected from the group consisting of

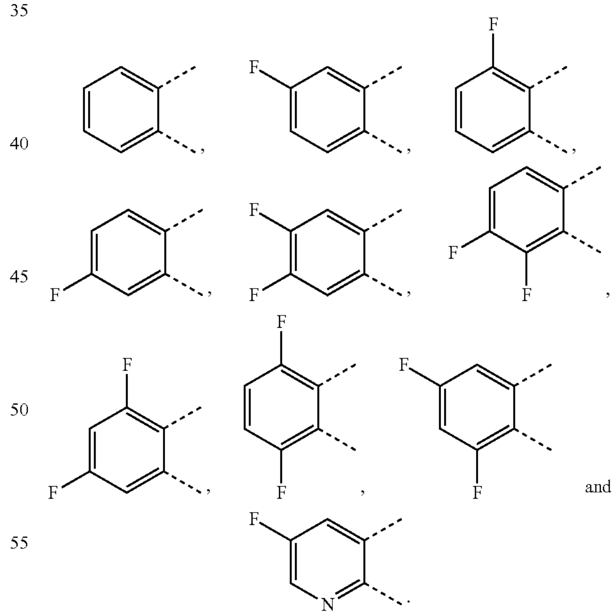

In some embodiments, A ring is benzene ring, wherein the benzene ring is unsubstituted or substituted with one, two or three halogen.

In some embodiments, X is O or $CH_2$. Preferably, if X is O, n is 1; and if X is $CH_2$, n is 0.

In some embodiments, B ring is 3-4-membered cycloalkane, preferably cyclopropane.

In some embodiments,

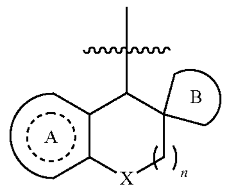

in formula (I) is selected from the group consisting of

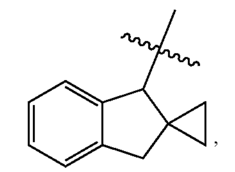

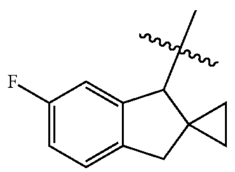

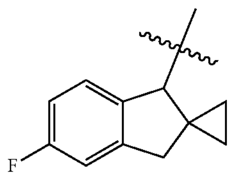

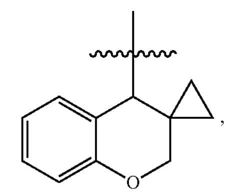

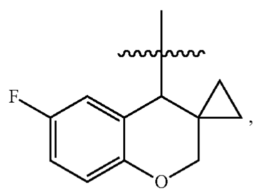

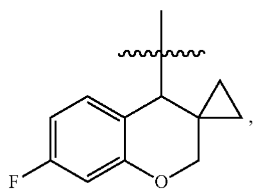

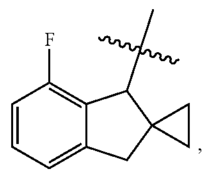

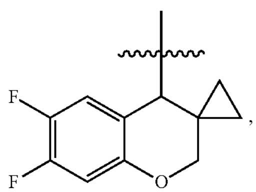

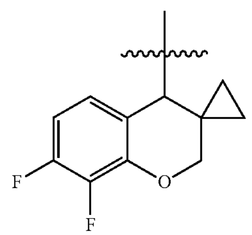

-continued

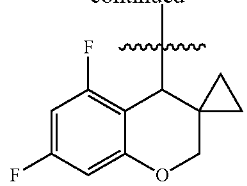

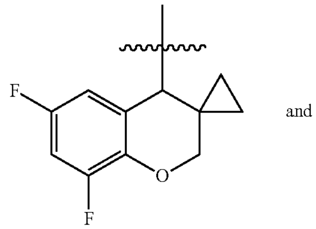

and

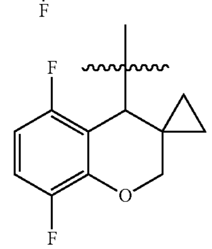

In some embodiments, C ring is selected from the group consisting of 6-membered heterocycloalkyl, benzene ring and 5-membered heteroaromatic ring, wherein heterocycloalkyl, benzene ring and heteroaromatic ring are independently unsubstituted or substituted with one, two or three $R^{C1}$; and each $R^{C1}$ is independently selected from the group consisting of hydrogen, halogen, ═O, ═S, cyano group, —$C_{1-6}$ alkyl and halogen-substituted —$C_{1-6}$ alkyl.

In some embodiments, C ring is selected from the group consisting of

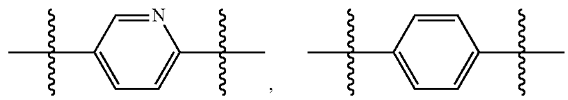

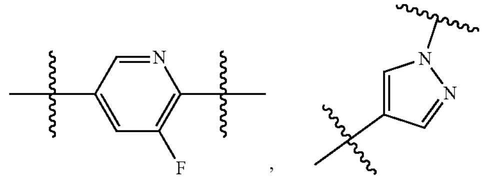

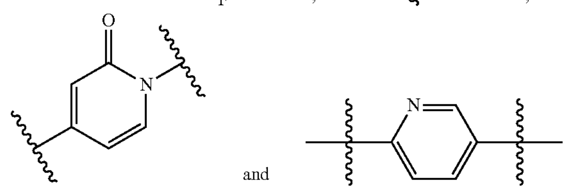

In some embodiments, C ring is selected from the group consisting of benzene ring and 5 to 6-membered heteroaromatic ring, wherein benzene ring and heteroaromatic ring are independently unsubstituted or substituted with one, two or three $R^{C1}$; and each $R^{C1}$ is independently selected from the group consisting of hydrogen, halogen, cyano group, ═O, ═S, nitro, —$C_{1-6}$ alkyl, halogen-substituted —$C_{1-6}$ alkyl, —$OR^{C2}$, —$C(O)R^{C2}$, —$C(O)NR^{C2}R^{C3}$, —$NR^{C2}R^{C3}$, —$NR^{C2}C(O)R^{C3}{}_2$, 3 to 6-membered cycloalkyl and 3 to 6-membered heterocycloalkyl.

In some embodiments, C ring is selected from the group consisting of

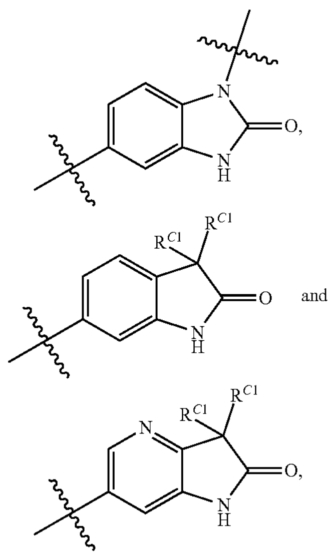

and wherein two $R^{C1}$ are capable of connecting to form 3 to 10-membered cycloalkyl or 3 to 10-membered heterocycloalkyl.

In some embodiments, D ring is selected from the group consisting of 5 to 6-membered cycloalkyl, 5 to 6-membered heterocycloalkyl, 5 to 6-membered aromatic ring and 5 to 6-membered heteroaromatic ring, wherein cycloalkyl, heterocycloalkyl, the aromatic ring and the heteroaromatic ring are independently unsubstituted or substituted with one, two or three $R^{D1}$; each $R^{D1}$ is independently selected from the group consisting of hydrogen, halogen, cyano group, —$C_{1-6}$ alkyl, halogen-substituted —$C_{1-6}$ alkyl, —$C_{0-2}$ alkylidene-$OR^{D2}$, —$C_{0-2}$ alkylidene-$NR^{D2}R^{D33}$ and —$C_{0-2}$ alkylidene-$OP(O)(OH)_2$; and $R^{D2}$ and $R^{D3}$ are independently selected from the group consisting of hydrogen and —$C_{1-6}$ alkyl.

In some embodiments, D ring is selected from the group consisting of

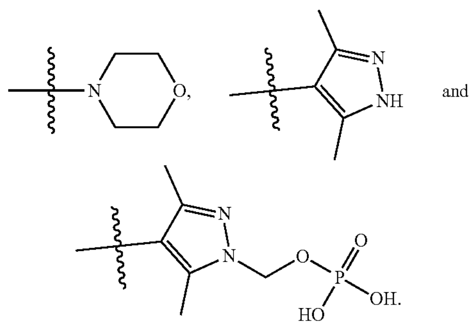

and

In some embodiments, D ring is 5 to 6-membered cycloalkyl, 5 to 6-membered heterocycloalkyl, benzene ring or 5 to 6-membered heteroaromatic ring, or absent, wherein cycloalkyl, heterocycloalkyl, benzene ring and heteroaromatic ring are independently unsubstituted or substituted with one, two or three $R^{D1}$.

In some embodiments, the compound is represented by formula (II):

(II)

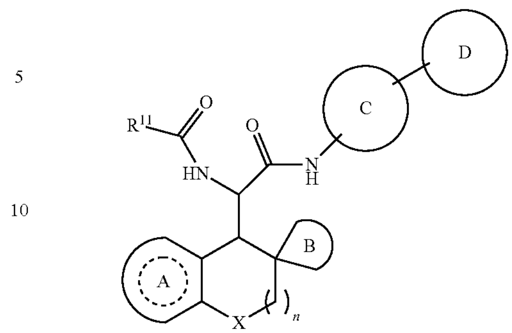

wherein $R^{11}$ is selected from the group consisting of hydrogen, —$C_{1-6}$ alkyl, halogen-substituted —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1a}$;

each $R^{1a}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{1b}$, —$C_{0-2}$ alkylidene-$C(O)R^{1b}$, —$C_{0-2}$ alkylidene-$C(O)NR^{1b}R^{1c}$, —$C_{0-2}$ alkylidene-$NR^{1b}R^{1c}$, —$C_{0-2}$ alkylidene-$NR^{1b}C(O)R^{1c}$, —$C_{0-4}$ alkylidene-$S(O)_2R^{1b}R^{1c}$, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1b}$;

$R^{1b}$ and $R^{1c}$ are independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

the A ring is selected from the group consisting of 5 to 10-membered aromatic ring and 5 to 10-membered heteroaromatic ring, wherein aromatic ring and heteroaromatic ring are independently unsubstituted or substituted with one, two or three $R^{A1}$; and each $R^{A1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

X is O, S or —$CH_2$—;

n is 0 or 1;

the B ring is selected from the group consisting of 3-membered cycloalkane, 4-membered cycloalkane, 5-membered cycloalkane and 6-membered cycloalkane, wherein cycloalkane is unsubstituted or substituted with one, two or three $R^{B1}$;

each $R^{B1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

the C ring is selected from the group consisting of 5 to 10-membered heterocycloalkyl, 5 to 10-membered aromatic ring and 5 to 10-membered heteroaromatic ring, wherein heterocycloalkyl, aromatic ring and heteroaromatic ring are independently unsubstituted or substituted with one, two or three $R^{C1}$; and each $R^{C1}$ is independently selected from the group consisting of hydrogen, halogen, cyano group, =O, =S, nitro, —$C_{1-6}$ alkyl and halogen-substituted —$C_{1-6}$ alkyl;

the D ring is selected from the group consisting of 3 to 10-membered cycloalkyl, 3 to 10-membered heterocycloalkyl, 5 to 10-membered aromatic ring and 5 to 10-membered heteroaromatic ring, wherein cycloalkyl, heterocycloalkyl, aromatic ring and heteroaromatic ring are independently unsubstituted or substituted with one, two or three $R^{D1}$;

each $R^{D1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{D2}$, —$C_{0-2}$ alkylidene-C(O)$R^{D2}$, —$C_{0-2}$ alkylidene-C(O)$NR^{D2}R^{D3}$, —$C_{0-2}$ alkylidene-$NR^{D2}R^{D3}$, —$C_{0-2}$ alkylidene-$NR^{D2}C(O)R^{D3}$ and —$C_{0-4}$ alkylidene-OP(O)$(OH)_2$; and $R^{D2}$ and $R^{D3}$ are independently selected from the group consisting of hydrogen, —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring).

In some embodiments, $R^{11}$ is selected from the group consisting of 3 to 6-membered cycloalkyl, 3 to 6-membered heterocycloalkyl, 5 to 6-membered aromatic ring and 5 to 6-membered heteroaromatic ring, wherein cycloalkyl, heterocycloalkyl, aromatic ring and heteroaromatic ring are independently unsubstituted or substituted with one, two or three $R^{1a}$.

In some embodiments, $R^{11}$ is selected from the group consisting of

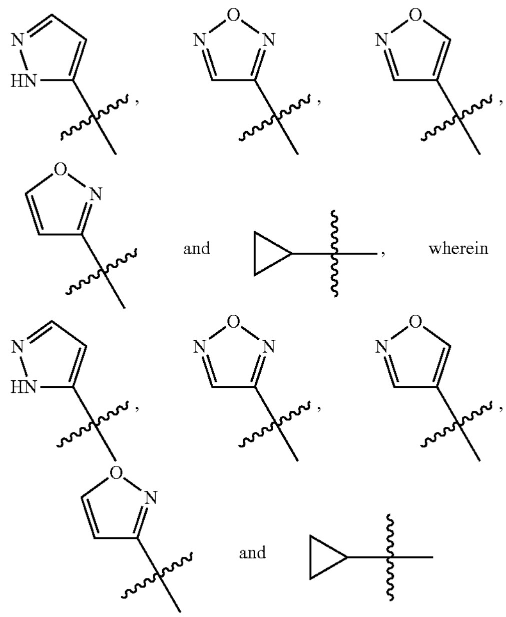

and , wherein and are independently unsubstituted or substituted with one, two or three $R^{1a}$;

each $R^{1a}$ is independently selected from the group consisting of hydrogen, halogen, cyano group, —$C_{1-6}$ alkyl, halogen-substituted —$C_{1-6}$ alkyl, 3 to 6-membered cycloalkyl and —$C_{0-2}$ alkylidene-$OR^{1b}$; and $R^{1b}$ is selected from the group consisting of hydrogen, —$C_{1-6}$ alkyl and halogen-substituted —$C_{1-6}$ alkyl.

In some embodiments, $R^{11}$ is selected from the group consisting of

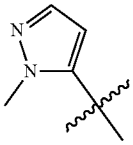, 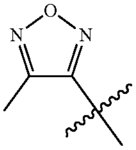,

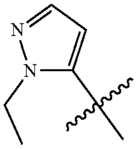, 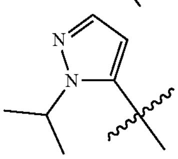,

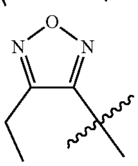, 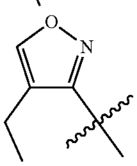,

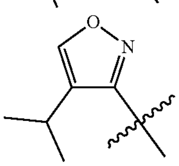, 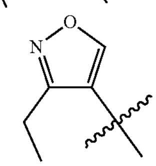,

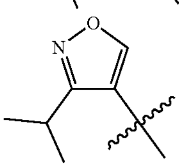, 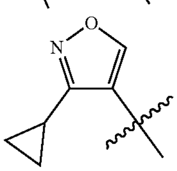,

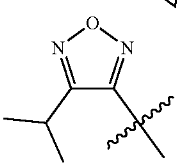,

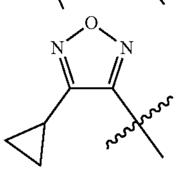,

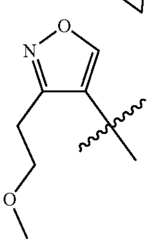 and 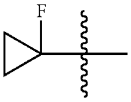.

In some embodiments, the A ring is selected from the group consisting of benzene ring and 6-membered heteroaromatic ring, wherein the benzene and the 6-membered heteroaromatic ring are independently unsubstituted or substituted with one, two or three $R^{A1}$; and each $R^{A1}$ is independently selected from the group consisting of hydrogen, $—C_{1-6}$ alkyl, halogen-substituted $—C_{1-6}$ alkyl, halogen and cyano group.

In some embodiments, the A ring is selected from the group consisting of

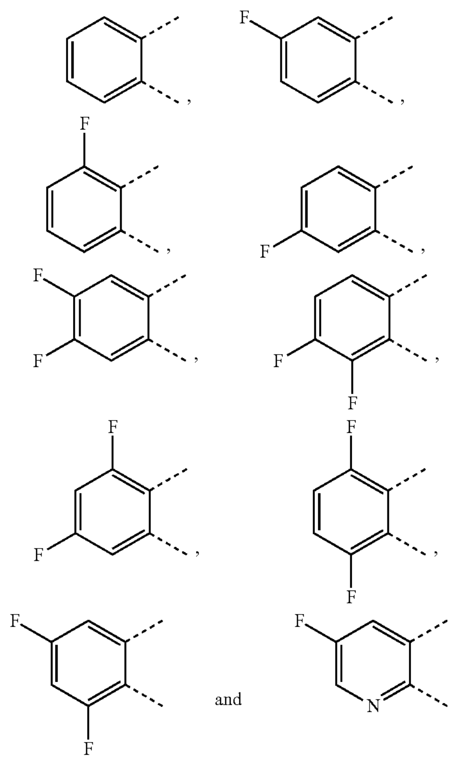

and

In some embodiments, the B ring is cyclopropane.

In some embodiments,

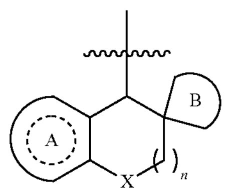

in the formula (II) is selected from the group consisting of

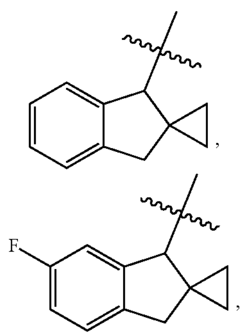

-continued

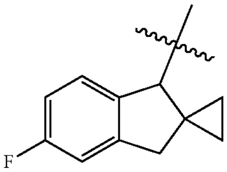

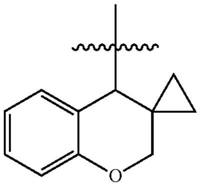

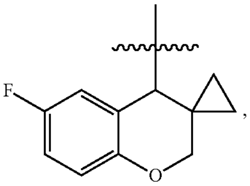

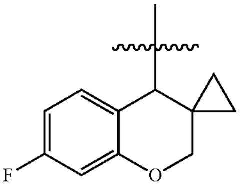

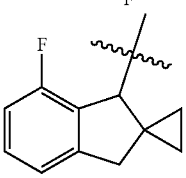

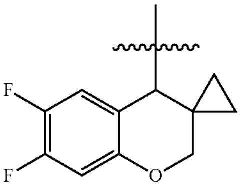

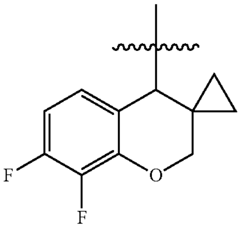

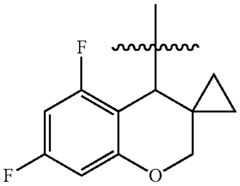

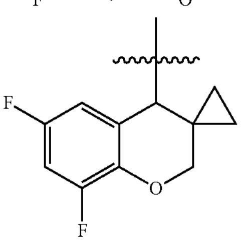

and

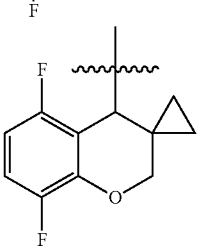

In some embodiments, the C ring is selected from the group consisting of 6-membered heterocycloalkyl, benzene ring, 5-membered heteroaromatic ring and 6-membered heteroaromatic ring, wherein heterocycloalkyl, benzene ring and heteroaromatic ring are independently unsubstituted or substituted with one, two or three $R^{C1}$; and each $R^{C1}$ is independently selected from the group consisting of hydrogen, halogen, =O, =S, cyano group, —$C_{1-6}$ alkyl and halogen-substituted —$C_{1-6}$ alkyl.

In some embodiments, the C ring is selected from the group consisting of

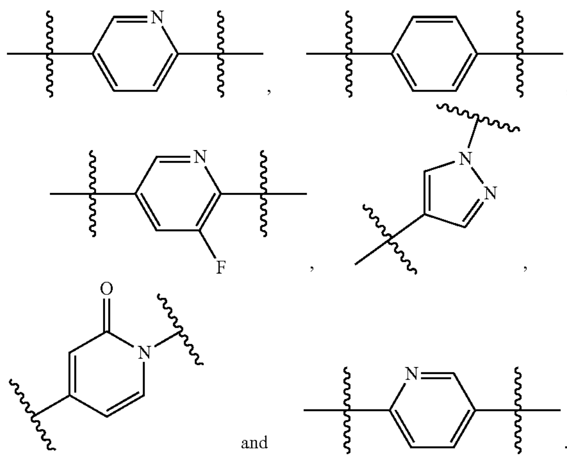

, , , , and .

In some embodiments, the D ring is selected from the group consisting of 5 to 6-membered cycloalkyl, 5 to 6-membered heterocycloalkyl, 5 to 6-membered aromatic ring and 5 to 6-membered heteroaromatic ring, wherein cycloalkyl, heterocycloalkyl, aromatic ring and heteroaromatic ring are independently unsubstituted or substituted with one, two or three $R^{D1}$;

each $R^{D1}$ is independently selected from the group consisting of hydrogen, halogen, cyano group, —$C_{1-6}$ alkyl, halogen-substituted —$C_{1-6}$ alkyl, —$C_{0-2}$ alkylidene-$OR^{D2}$, —$C_{0-2}$ alkylidene-$NR^{D2}R^{D33}$ and —$C_{0-4}$ alkylidene-$OP(O)(OH)_2$; and $R^{D2}$ and $R^{D3}$ are independently selected from the group consisting of hydrogen and —$C_{1-6}$ alkyl.

In some embodiments, the D ring is selected from the group consisting of

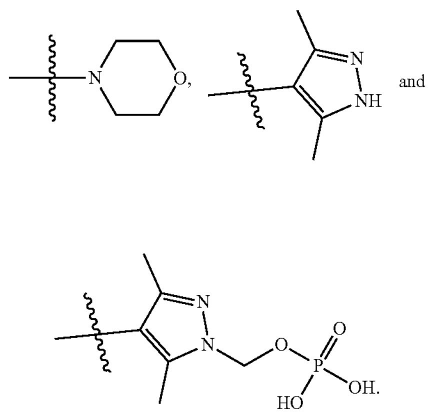

, and .

In some embodiments, the compound is represented by formula (III):

(III)

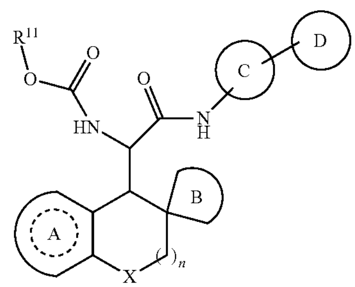

;

wherein $R^{11}$ is selected from the group consisting of —$C_{1-6}$ alkyl, halogen-substituted —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1a}$;

each $R^{1a}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{1b}$, —$C_{0-2}$ alkylidene-$C(O)R^{1b}$, —$C_{0-2}$ alkylidene-$C(O)NR^{1b}R^{1c}$, —$C_{0-2}$ alkylidene-$NR^{1b}R^{1c}$, —$C_{0-2}$ alkylidene-$NR^{1b}C(O)R^{1c}$, —$C_{0-4}$ alkylidene-$S(O)_2R^{1b}R^{1c}$, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1b}$;

$R^{1b}$ and $R^{1c}$ are independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

the A ring is selected from the group consisting of 5 to 10-membered aromatic ring and 5 to 10-membered heteroaromatic ring, wherein aromatic ring and heteroaromatic ring are independently unsubstituted or substituted with one, two or three $R^{A1}$;

each $R^{A1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

X is O, S or —$CH_2$—;

n is 0 or 1;

the B ring is selected from the group consisting of 3-membered cycloalkane, 4-membered cycloalkane, 5-membered cycloalkane and 6-membered cycloalkane, wherein cycloalkane is unsubstituted or substituted with one, two or three $R^{B1}$; and each $R^{B1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

the C ring is selected from the group consisting of 5 to 10-membered heterocycloalkyl, 5 to 10-membered aromatic ring and 5 to 10-membered heteroaromatic ring, wherein aromatic ring and heteroaromatic ring are independently unsubstituted or substituted with one, two or three $R^{C1}$;

each $R^{C1}$ is independently selected from the group consisting of hydrogen, halogen, cyano group, =O, =S, nitro, —$C_{1-6}$ alkyl and halogen-substituted —$C_{1-6}$ alkyl;

the D ring is selected from the group consisting of 3 to 10-membered cycloalkyl, 3 to 10-membered heterocycloalkyl, 5 to 10-membered aromatic ring and 5 to 10-membered heteroaromatic ring, wherein cycloalkyl, heterocycloalkyl, aromatic ring and heteroaromatic ring are independently unsubstituted or substituted with one, two or three $R^{D1}$;

each $R^{D1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{D2}$, —$C_{0-2}$ alkylidene-$C(O)R^{D2}$, —$C_{0-2}$ alkylidene-$C(O)NR^{D2}R^{D3}$, —$C_{0-2}$ alkylidene-$NR^{D2}R^{D3}$, —$C_{0-2}$ alkylidene-$NR^{D2}C(O)R^{D3}$ and —$C_{0-4}$ alkylidene-$OP(O)(OH)_2$; and $R^{D2}$ and $R^{D3}$ are independently selected from the group consisting of hydrogen, —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring).

In some embodiments, $R^{11}$ is selected from the group consisting of —$C_{1-6}$ alkyl and 3 to 6-membered cycloalkyl;

the A ring is selected from the group consisting of

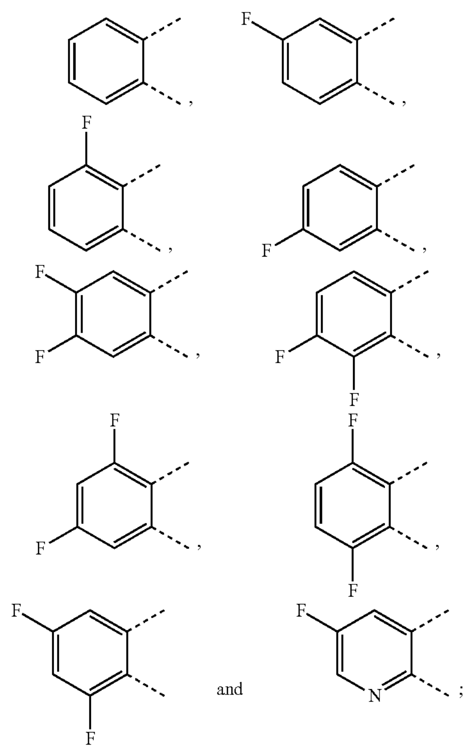

the B ring is cyclopropane;

the C ring is selected from the group consisting of

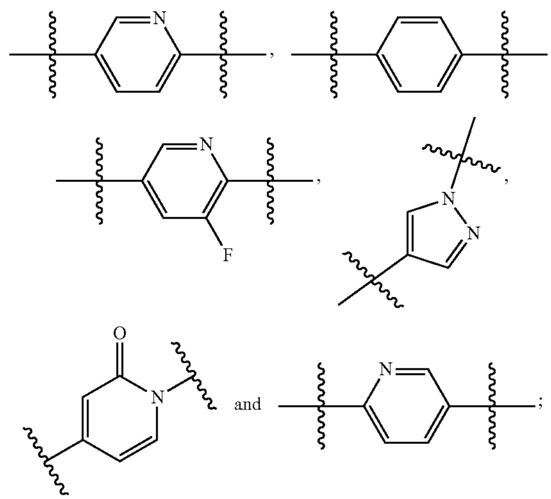

and the D ring is selected from the group consisting of

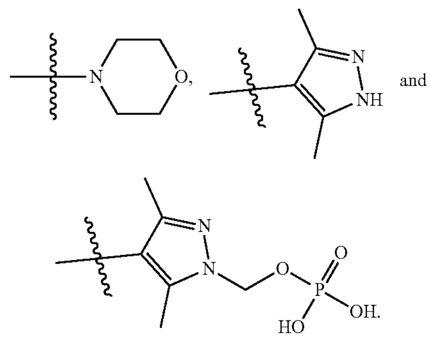

In some embodiments,

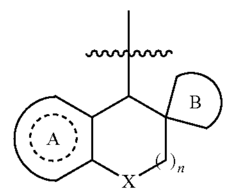

in formula (III) is selected from the group consisting of

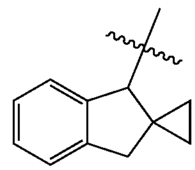

-continued
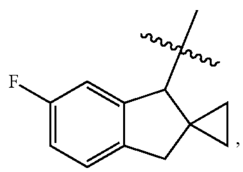,
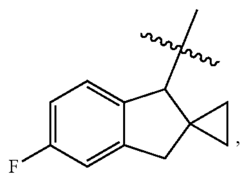,
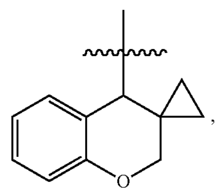,
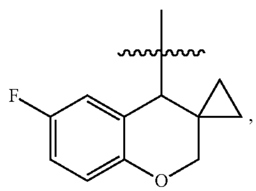, 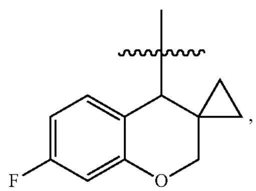,
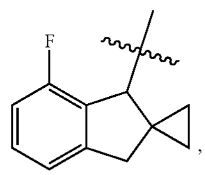,
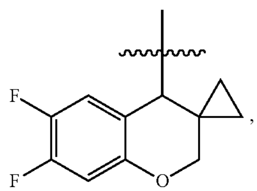, 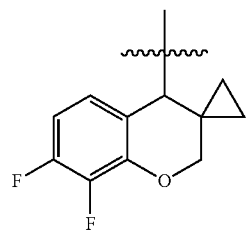,
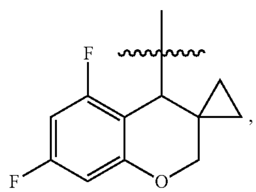,
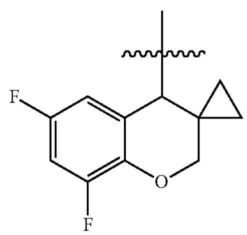 and
-continued
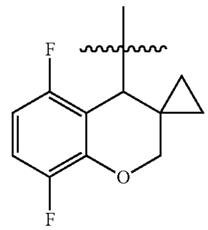.
In some embodiments, the compound of formula (I) is selected from the group consisting of
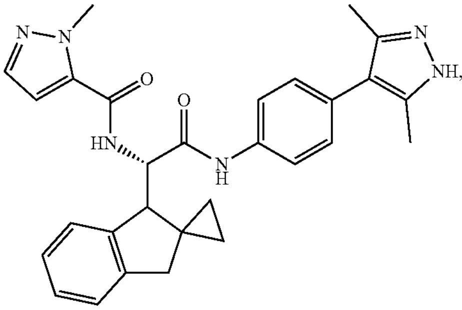,
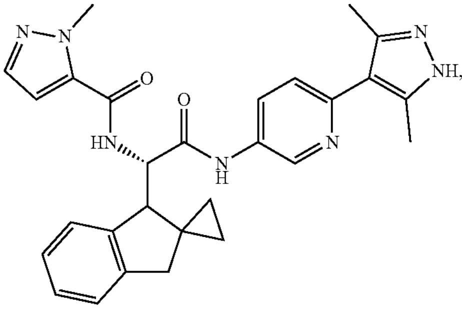,
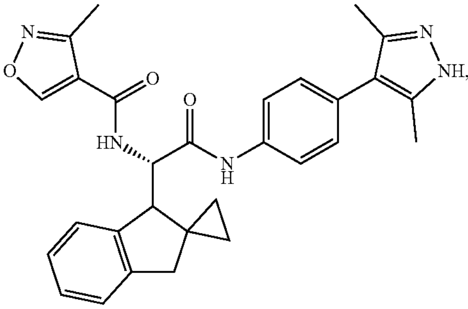,
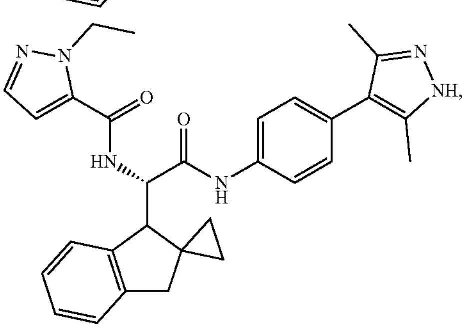, -continued
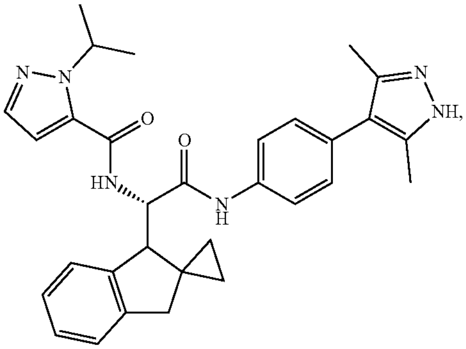
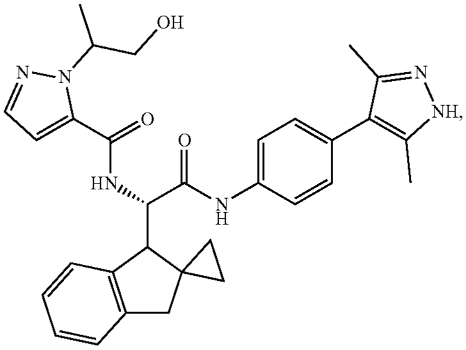
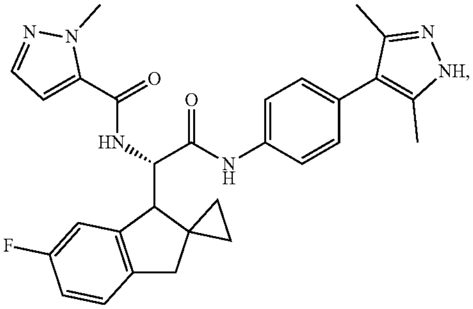
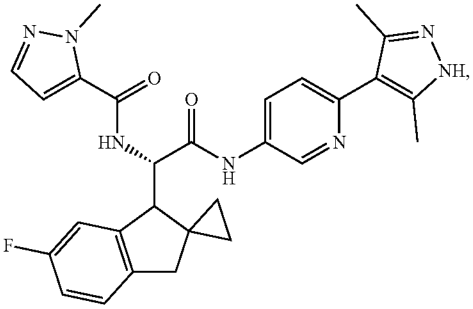
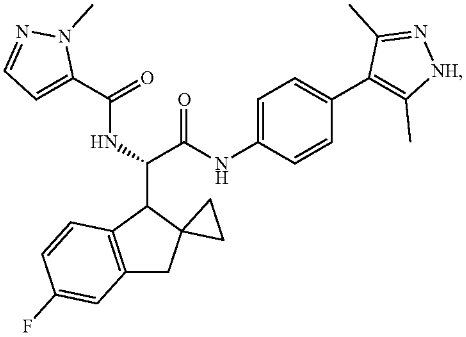
-continued
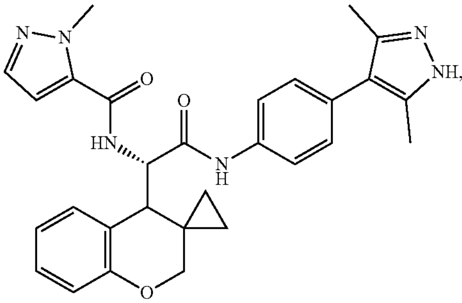
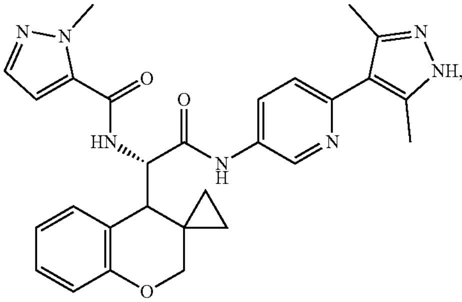
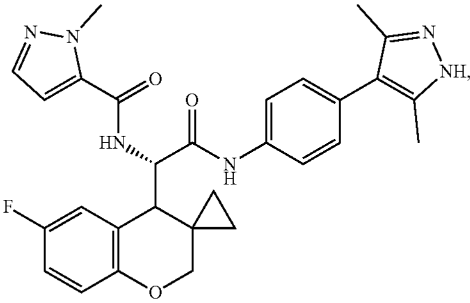
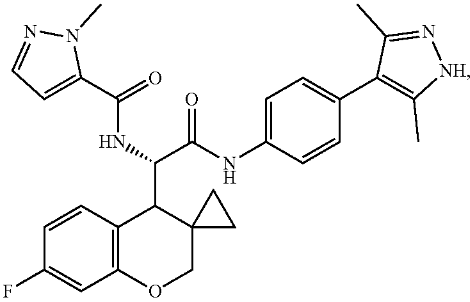
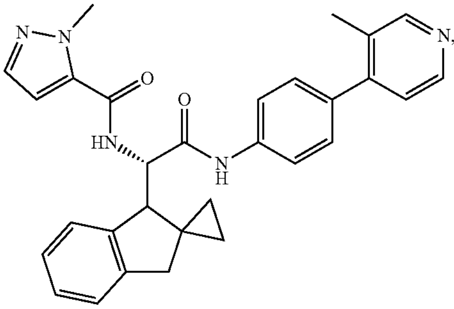

-continued
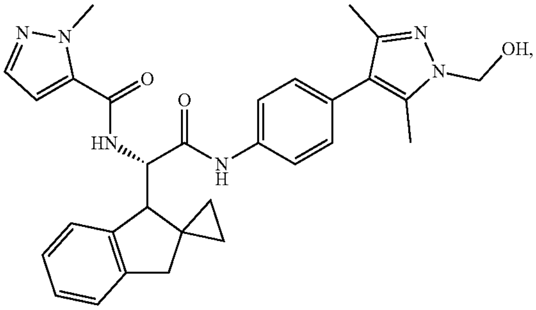
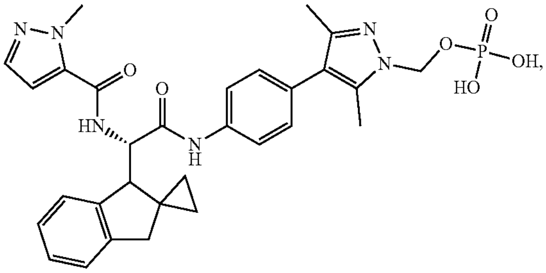
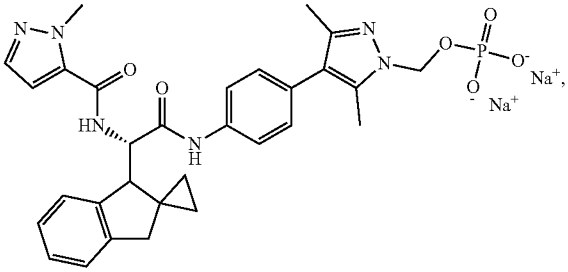
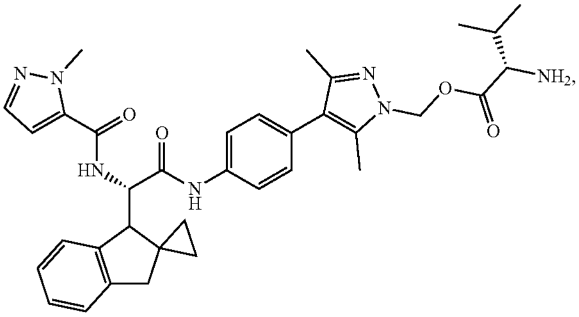
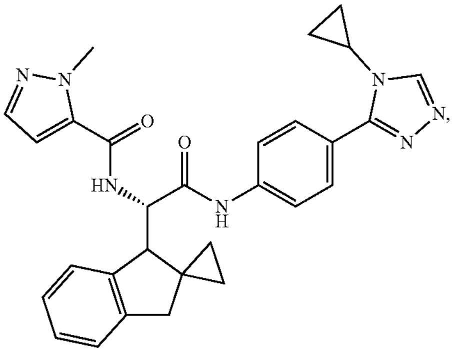
-continued
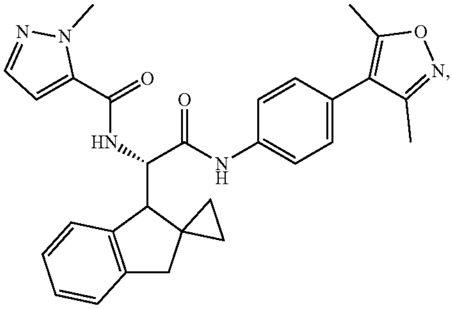
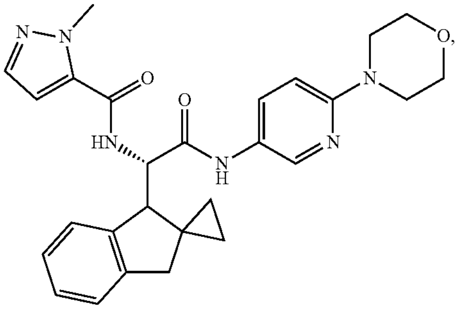
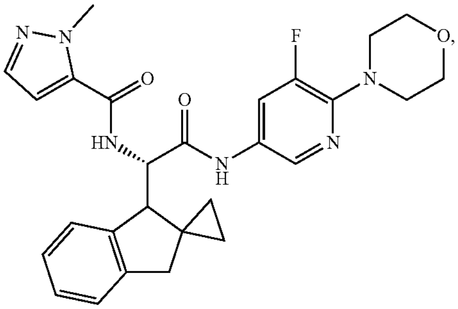
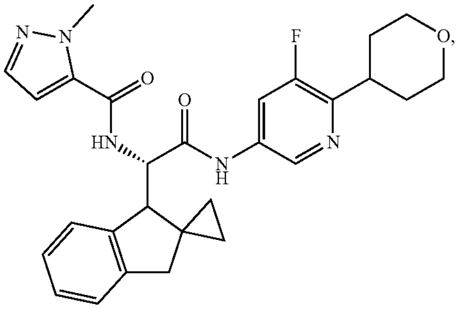
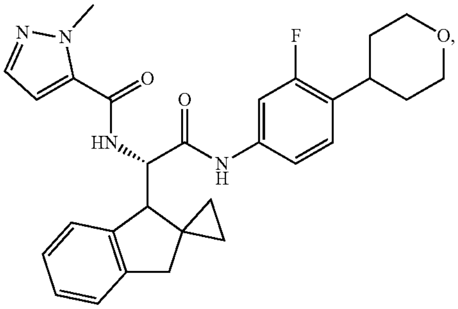

-continued
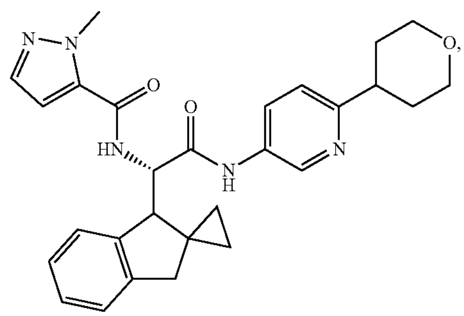
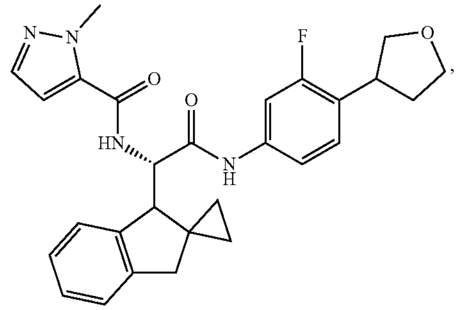
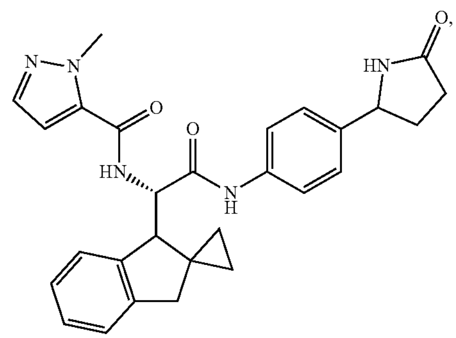
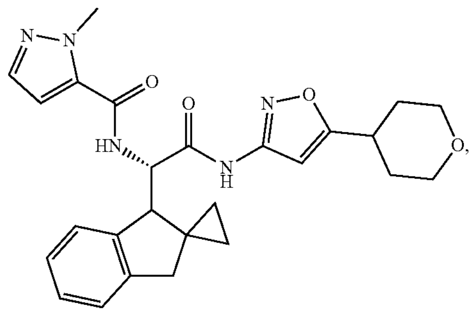
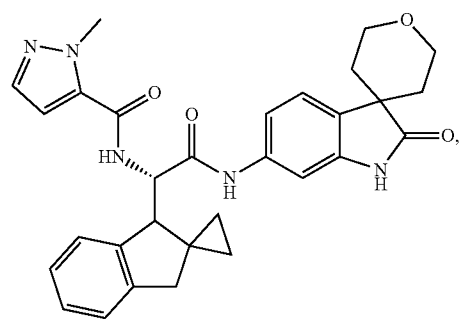
-continued
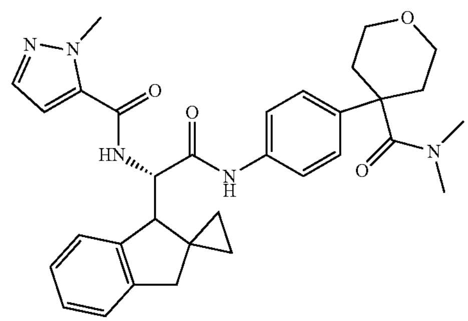
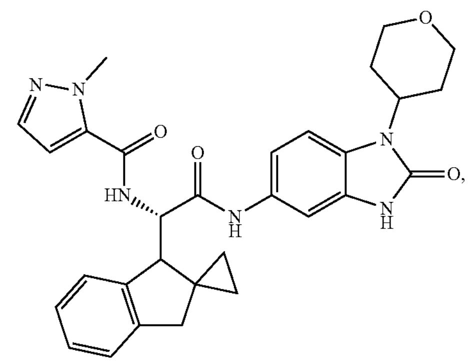
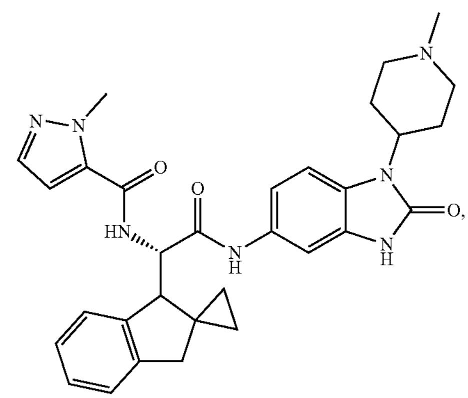
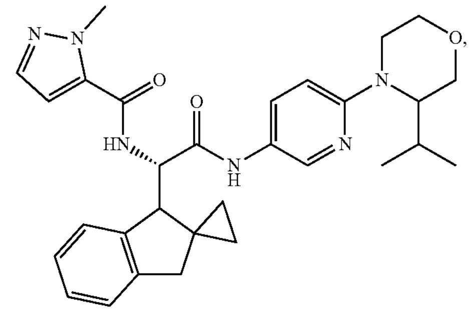
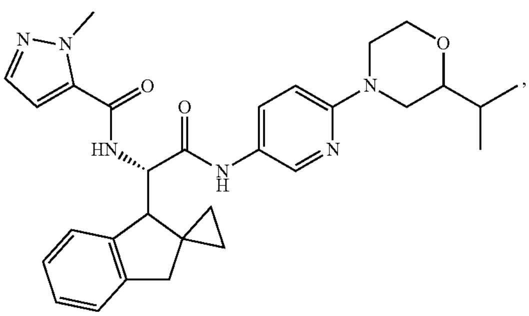

-continued
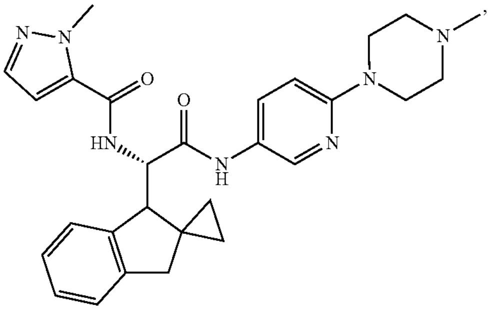
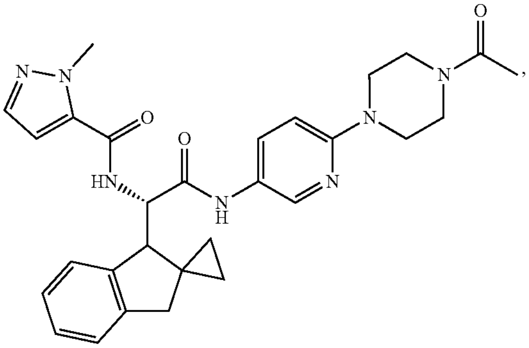
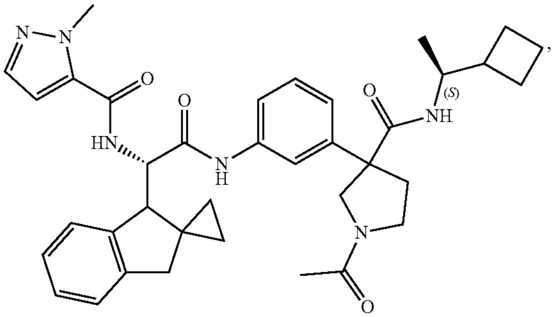
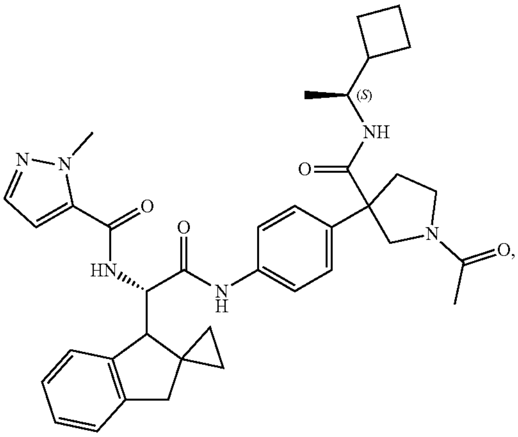
-continued
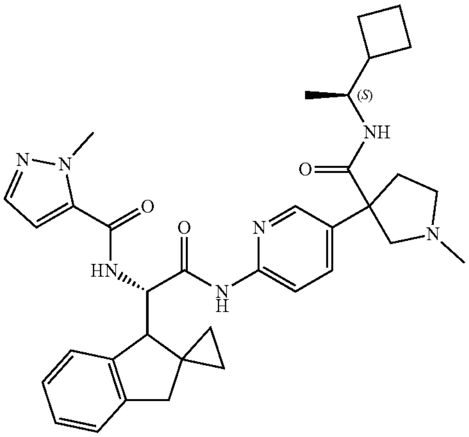
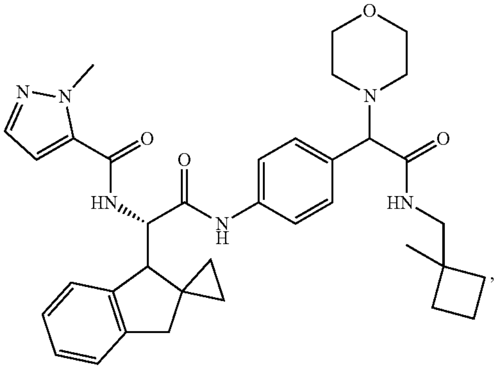
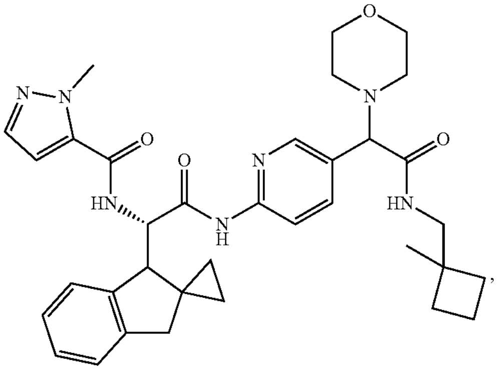
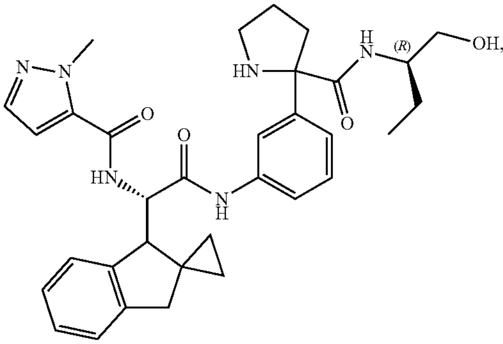

-continued
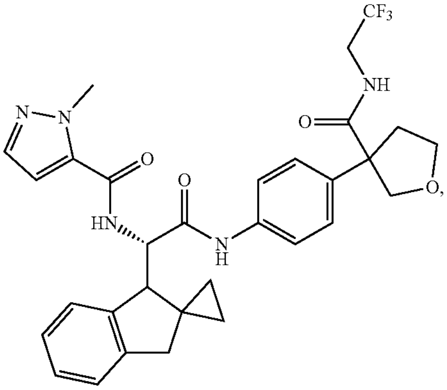,
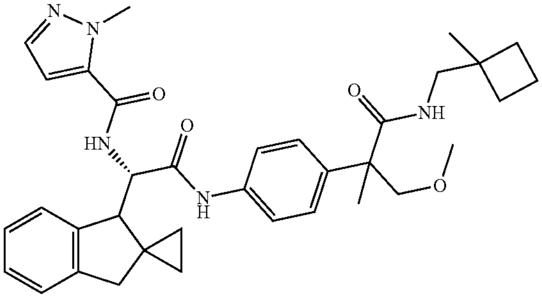,
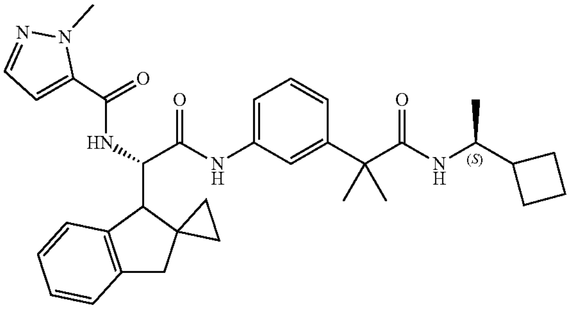,
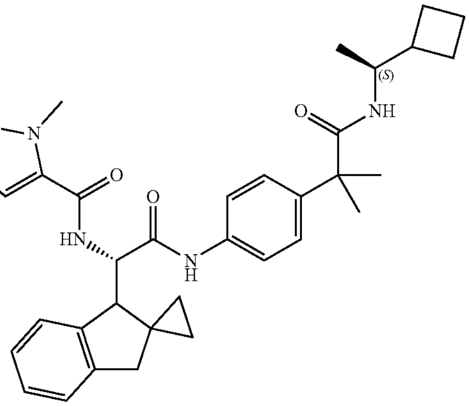,
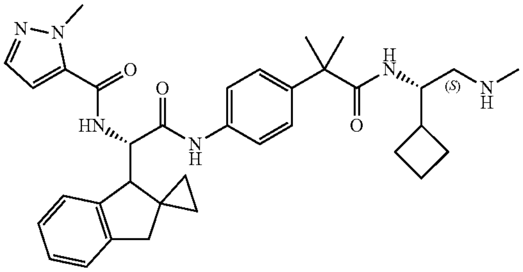,
-continued
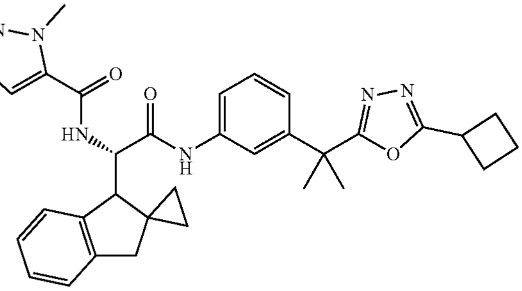,
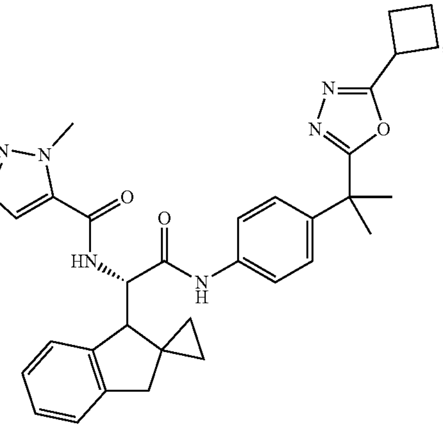,
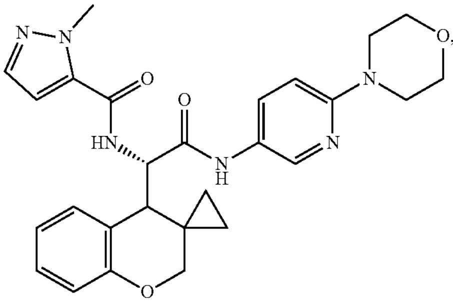,
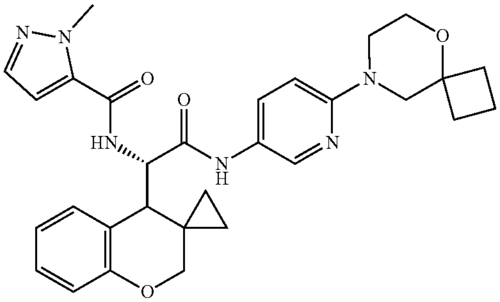,
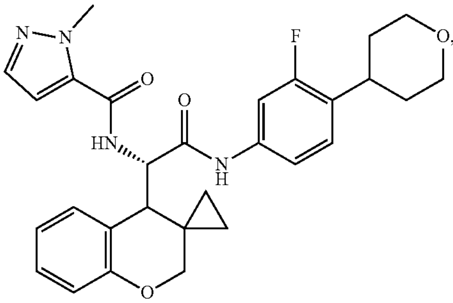, -continued
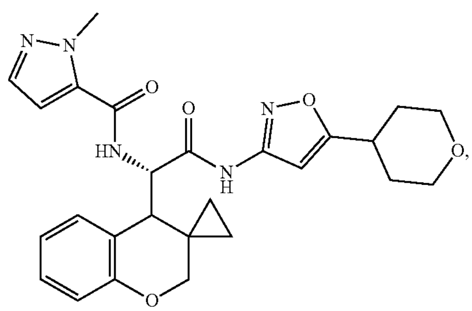
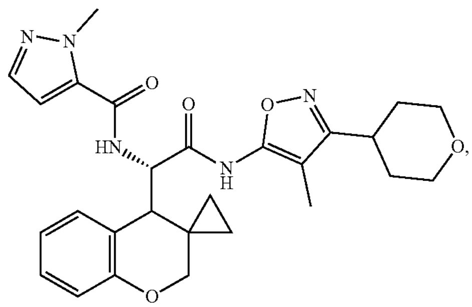
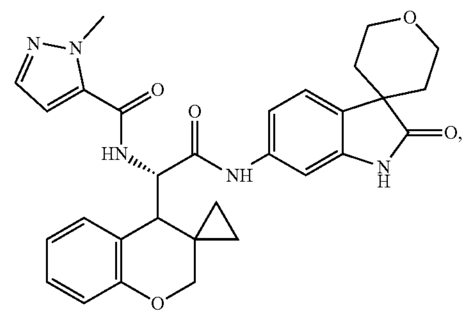
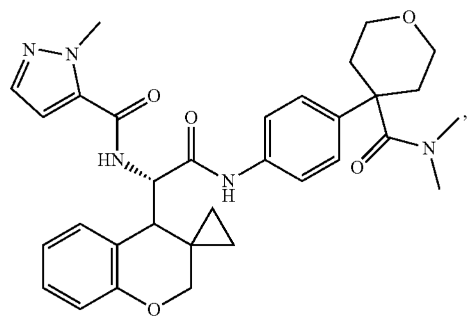
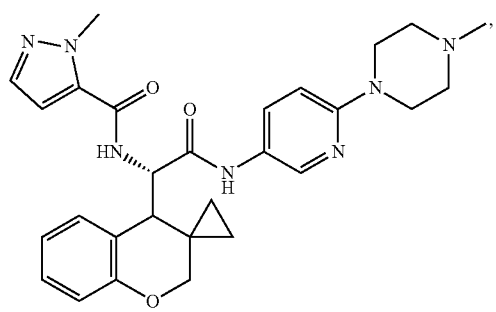
-continued
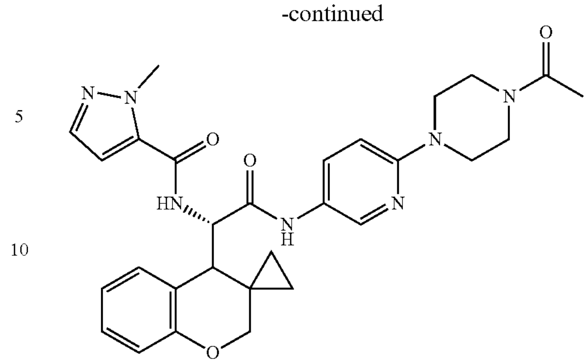
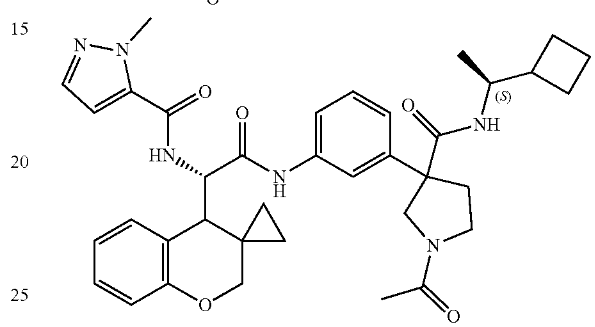
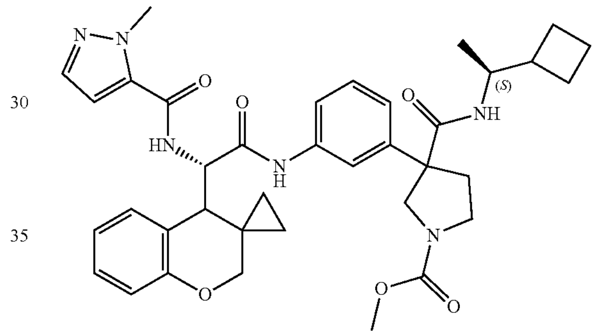
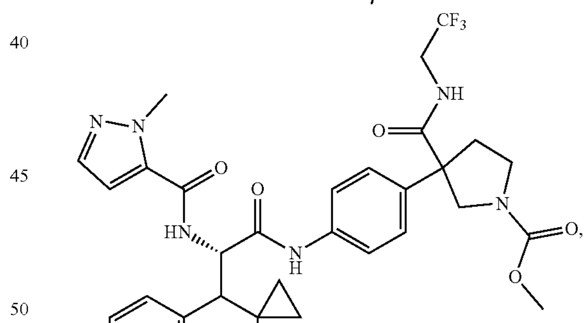
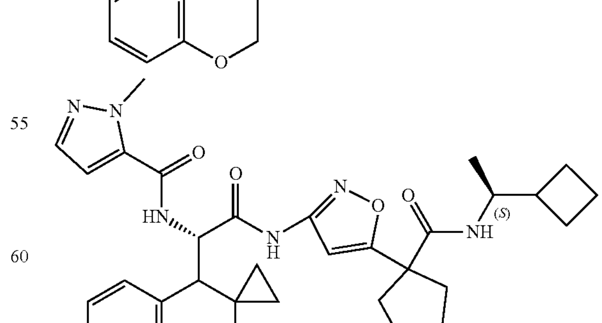
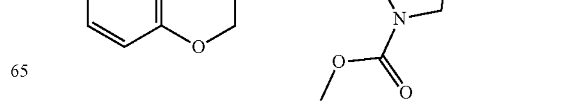

-continued
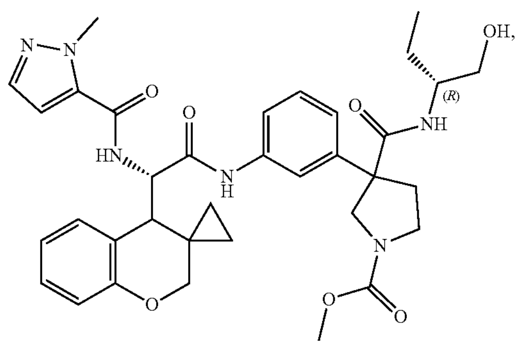
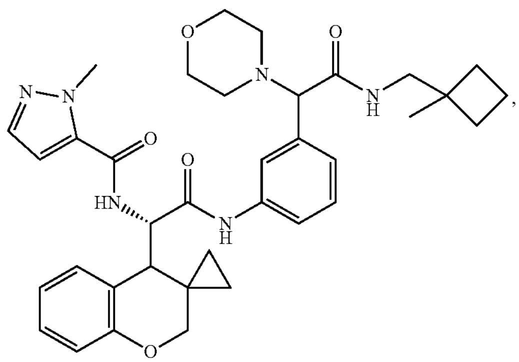
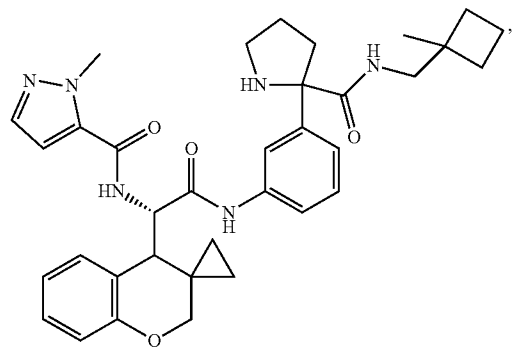
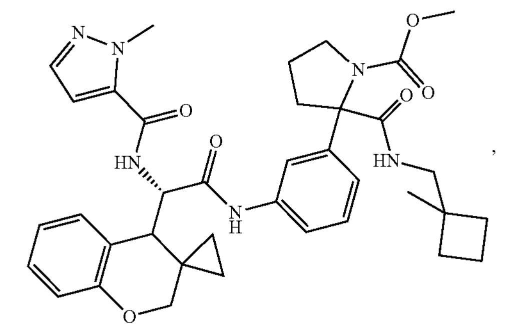
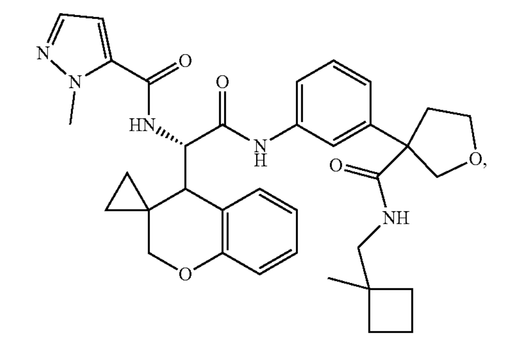
-continued
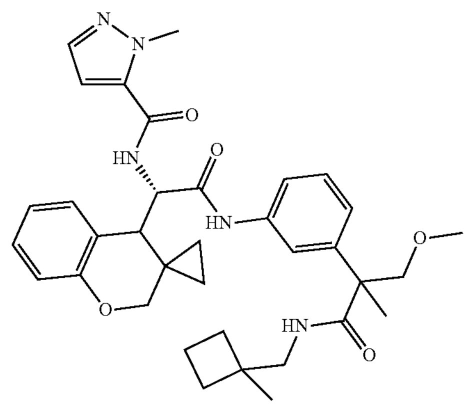
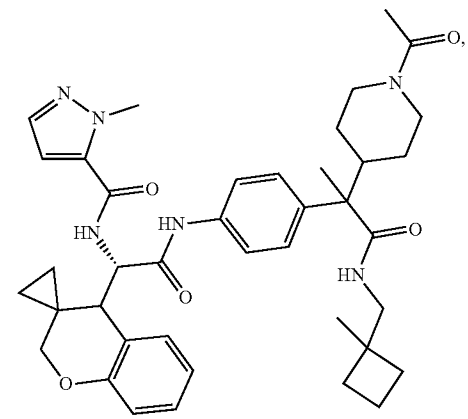
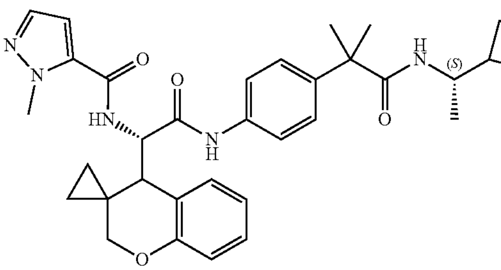
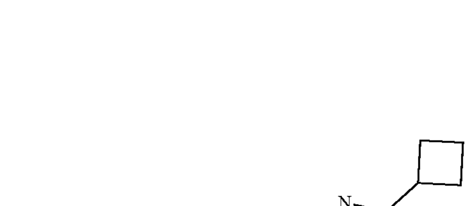
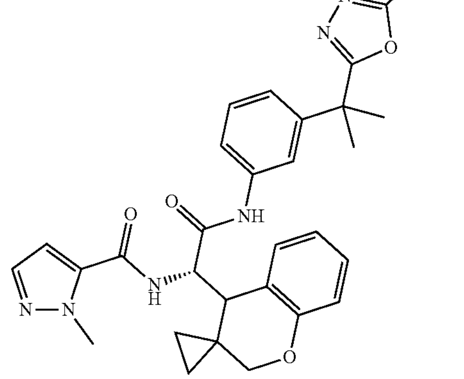

-continued
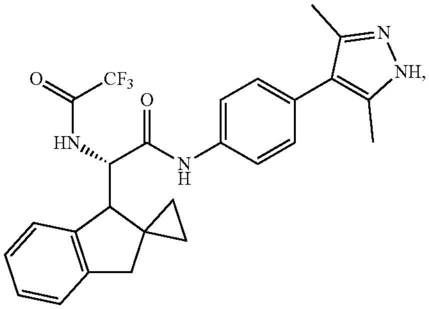
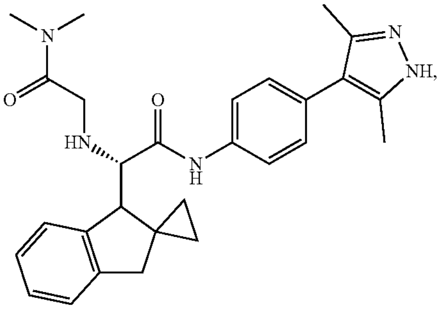
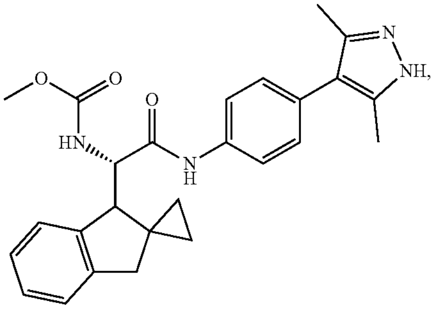
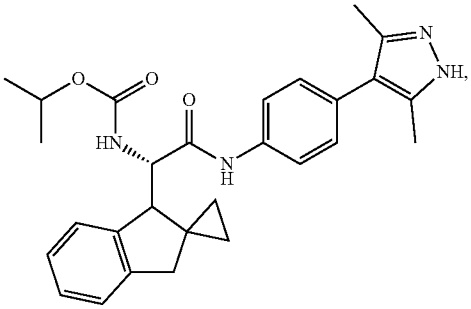
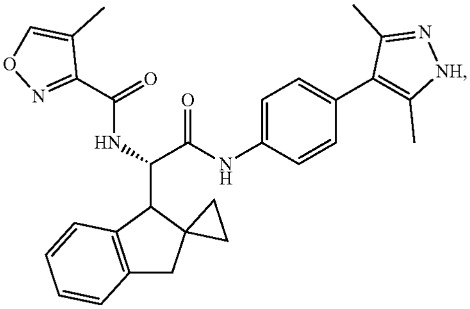
-continued
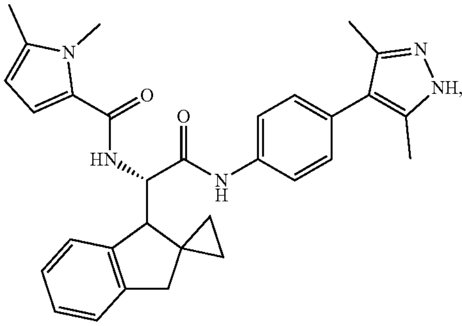
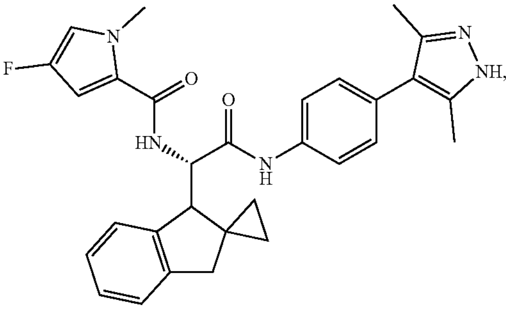
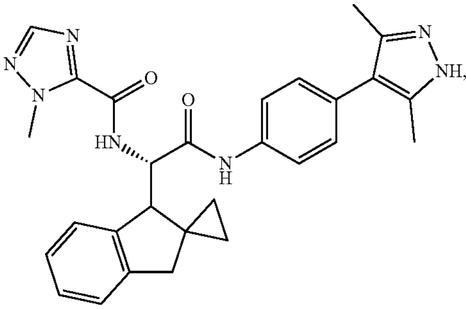
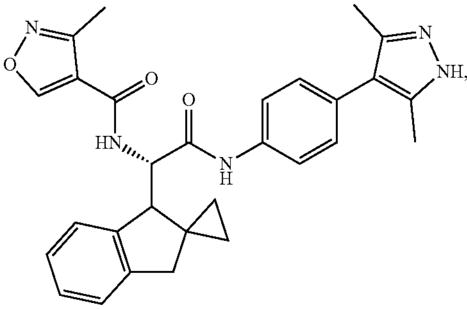
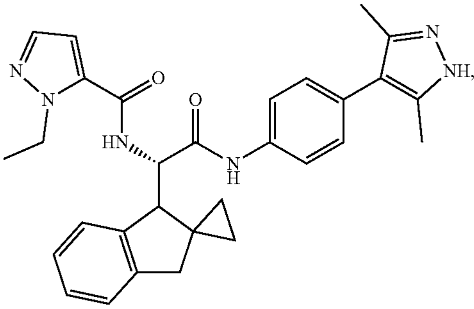

-continued
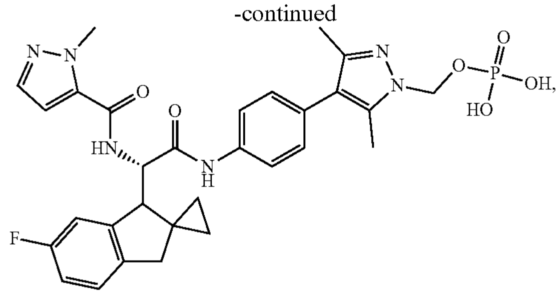
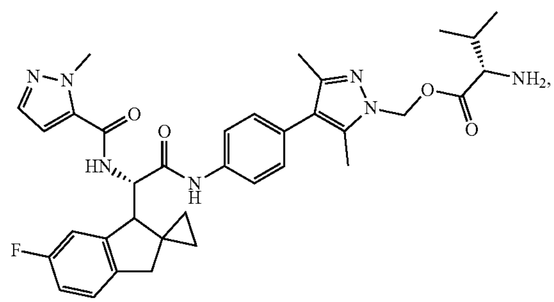
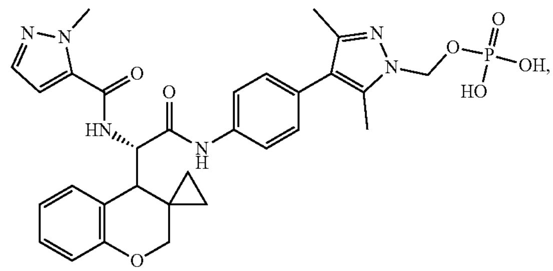
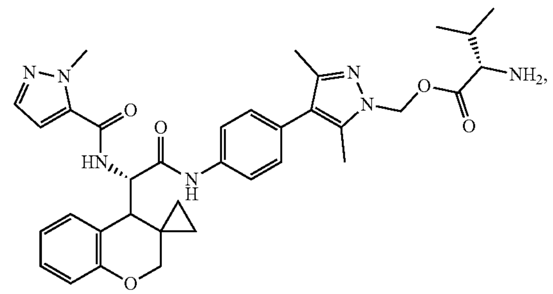
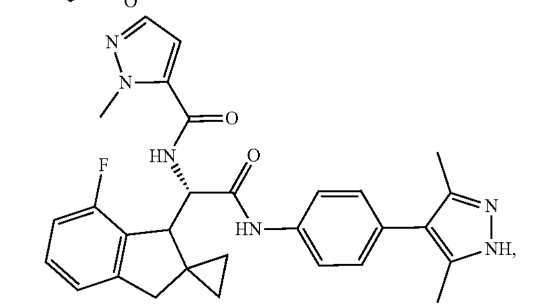
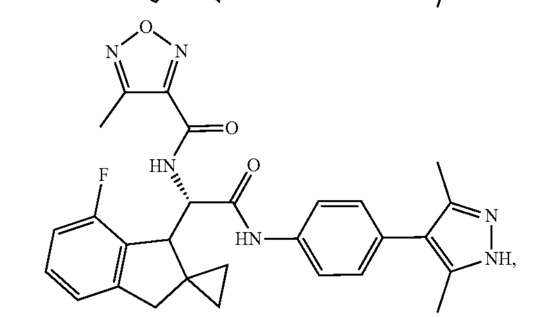
-continued
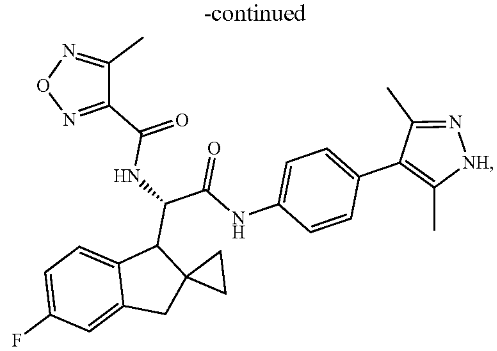
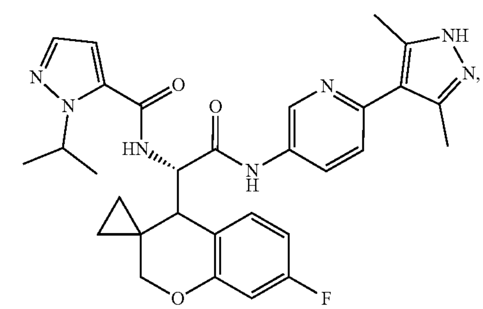
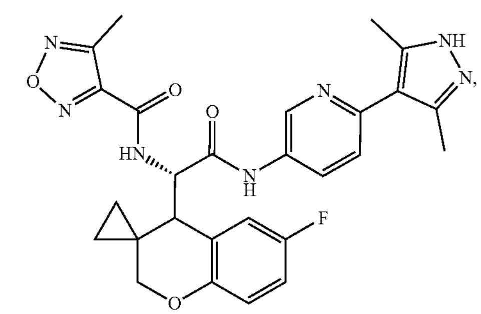
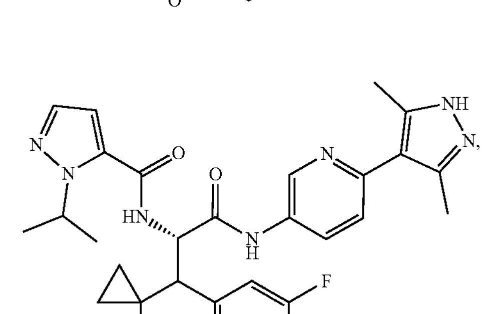
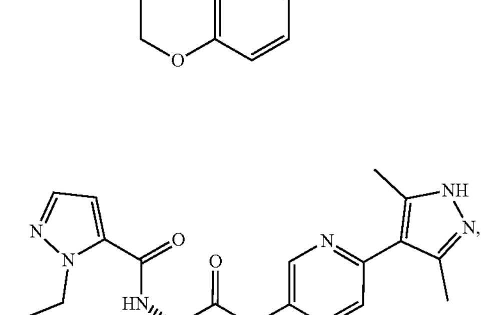
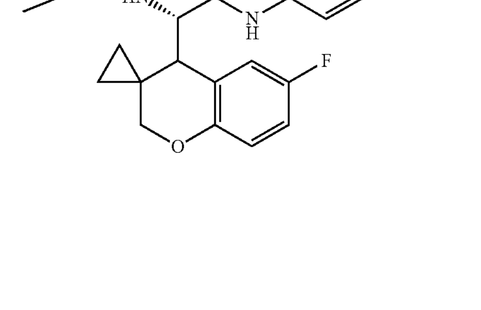

-continued
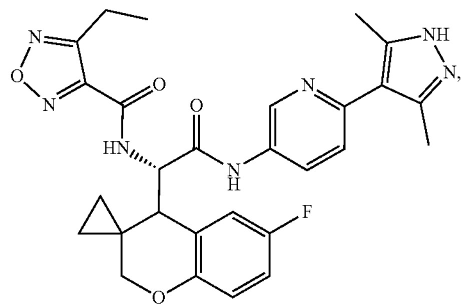
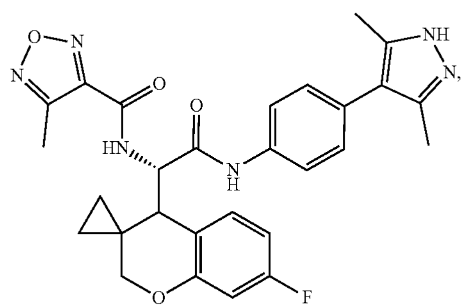
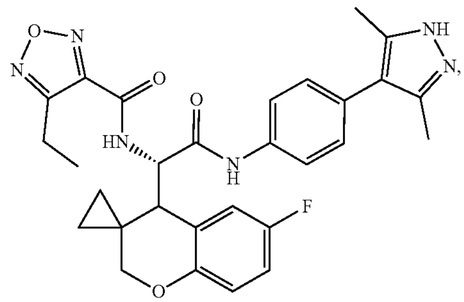
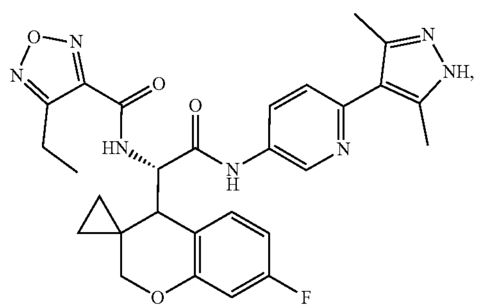
-continued
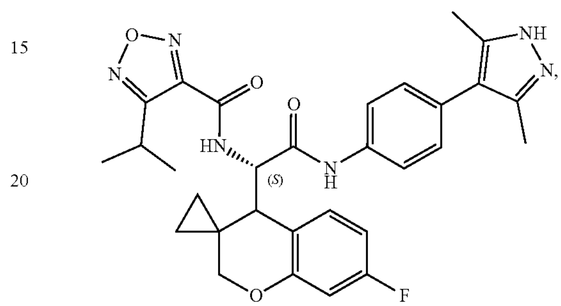
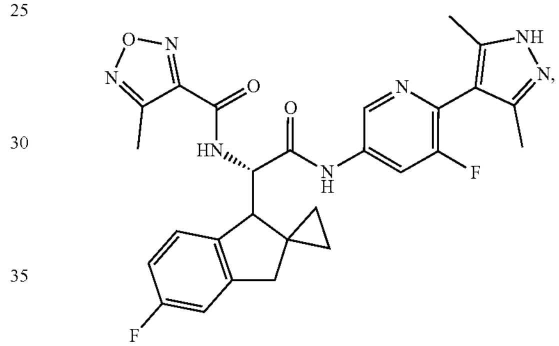
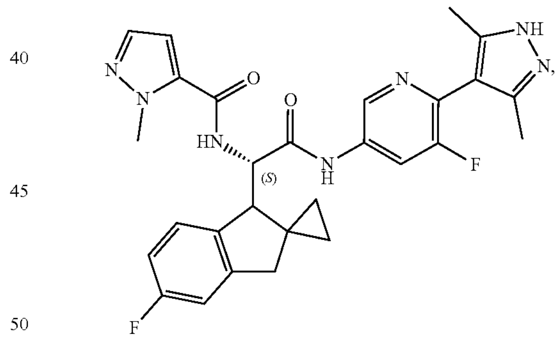
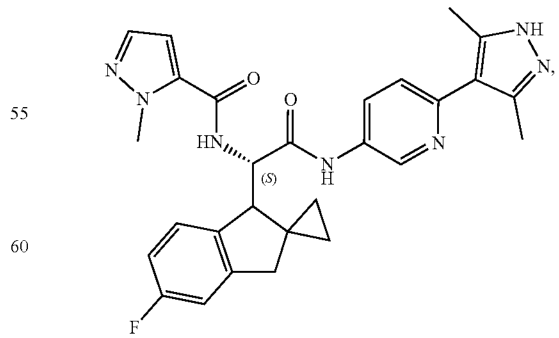

-continued
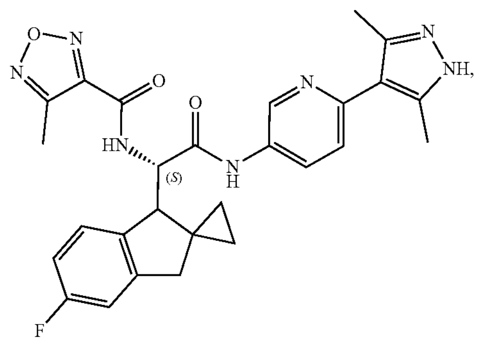
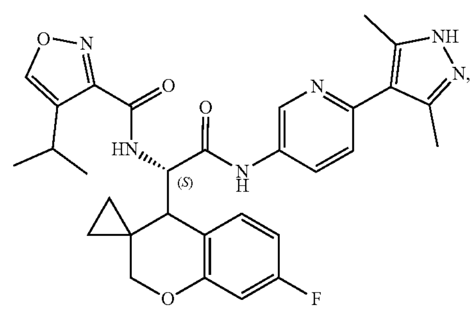
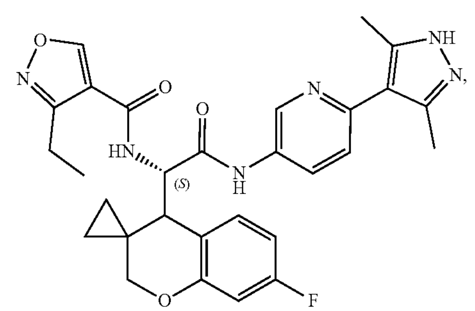
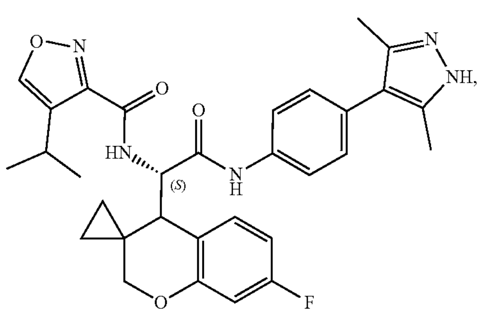
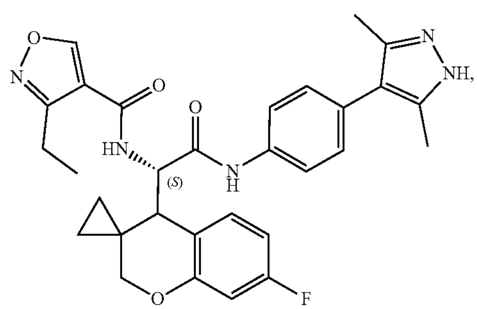
-continued
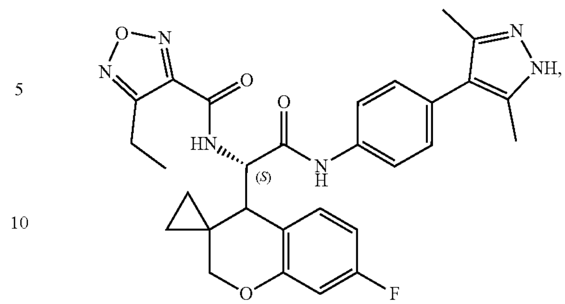
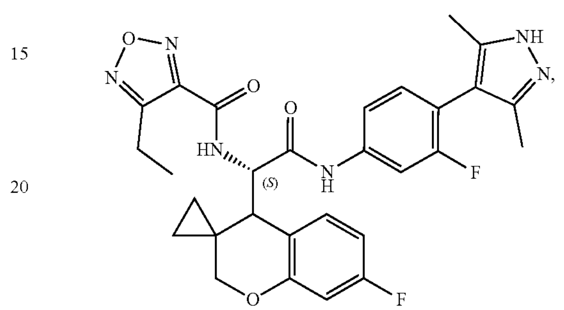
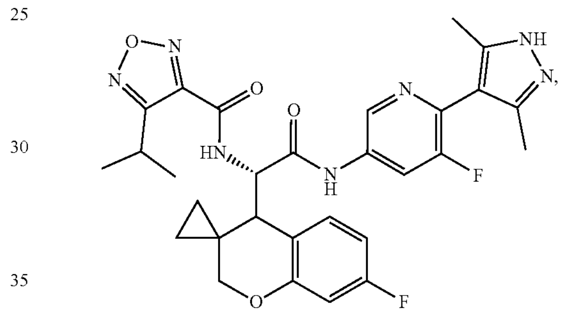
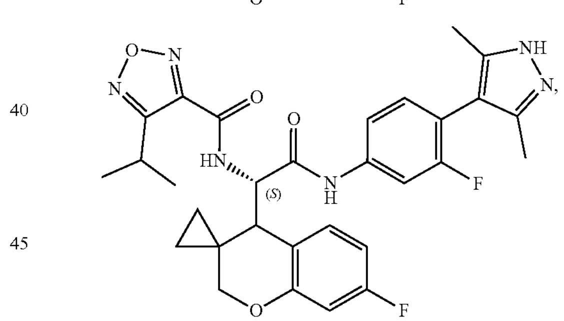
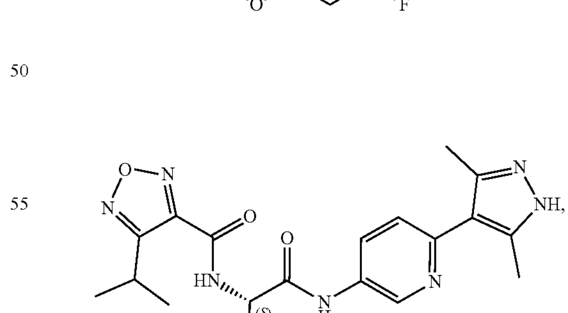
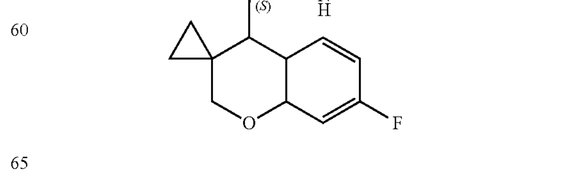

-continued
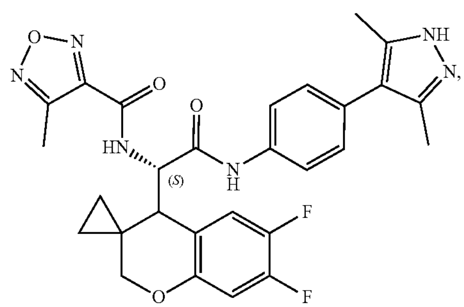
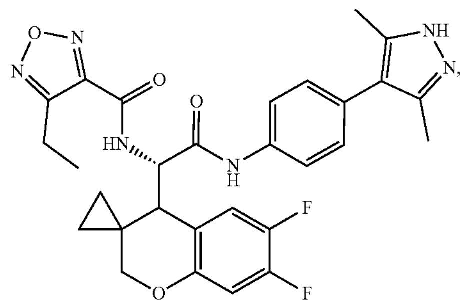
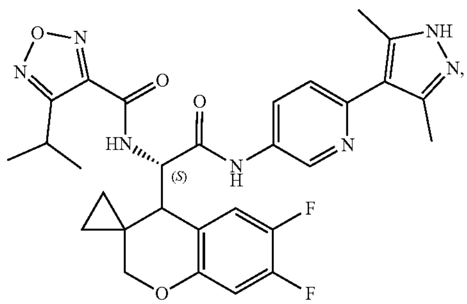
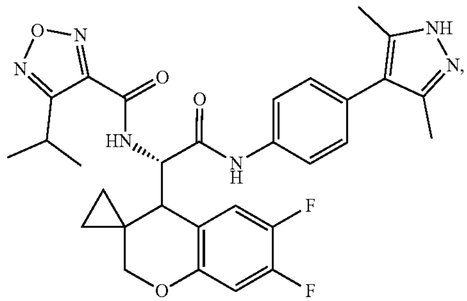
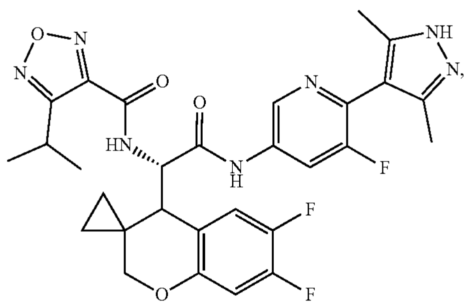
-continued
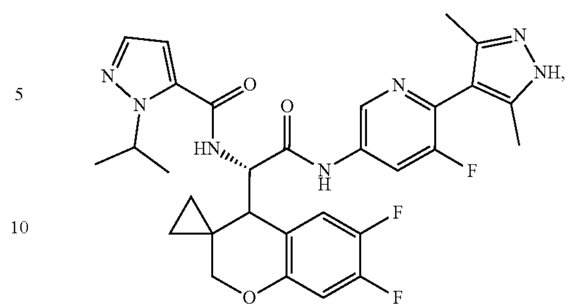
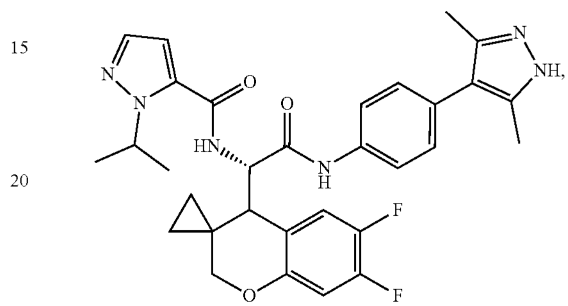
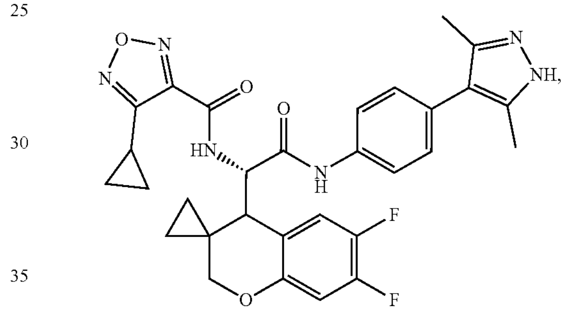
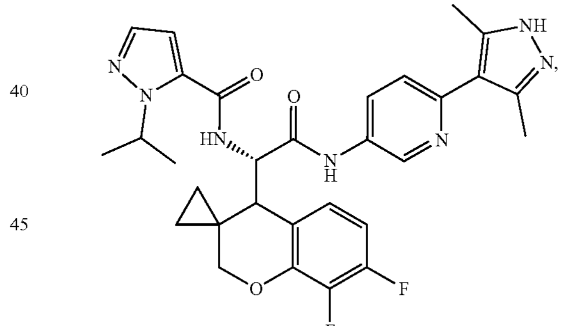
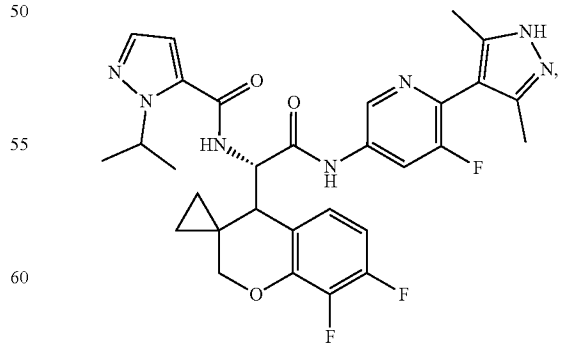

-continued
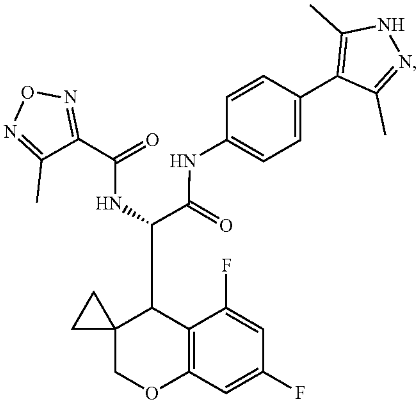
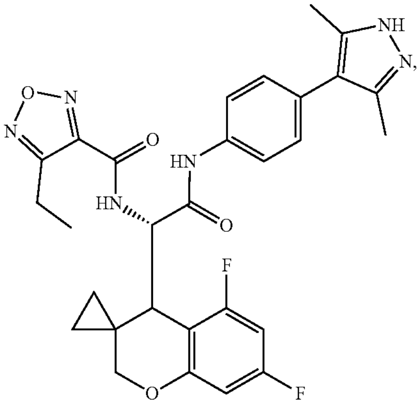
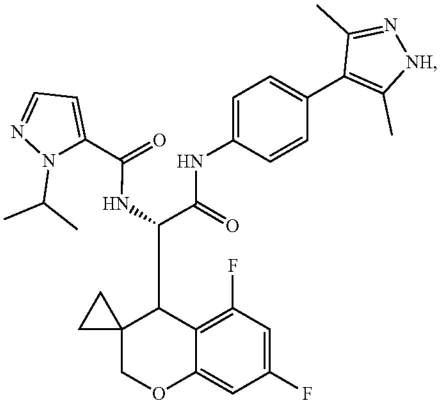
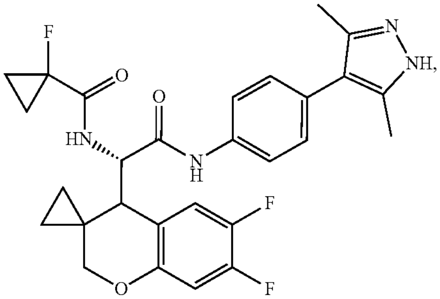
-continued
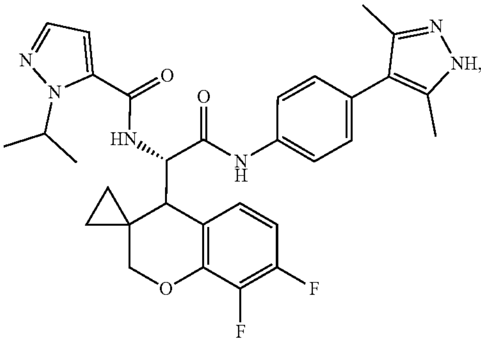
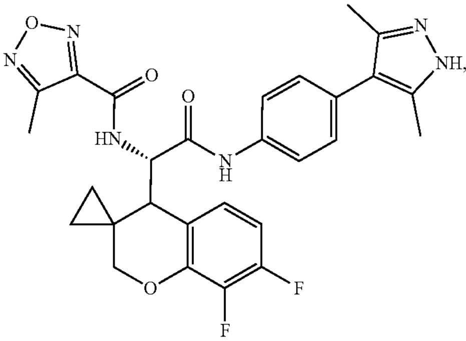
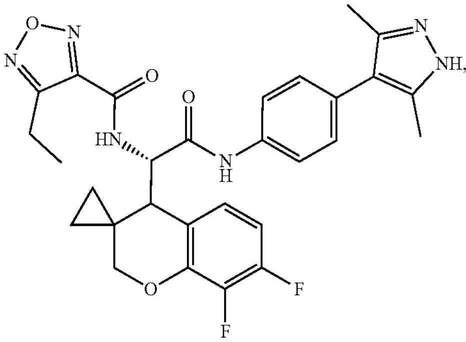
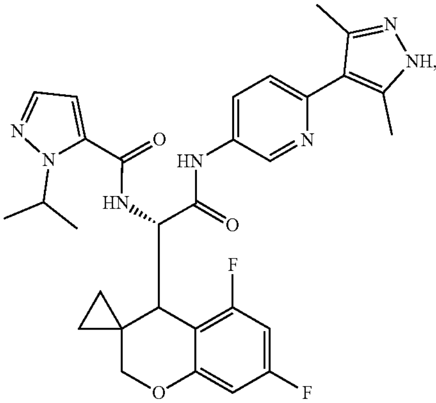

-continued
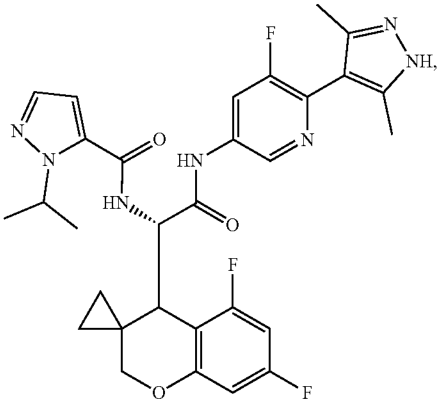
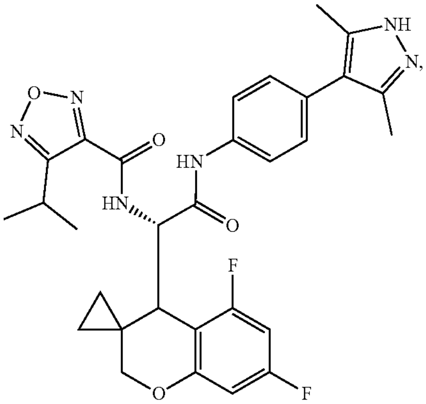
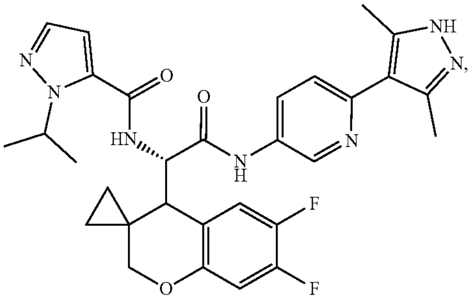
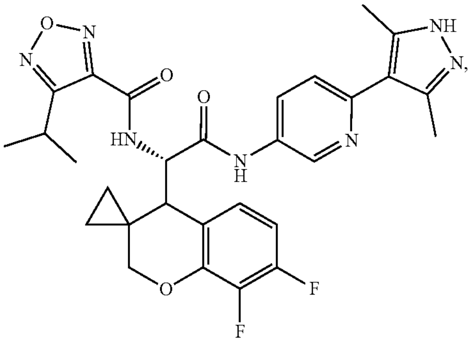
-continued
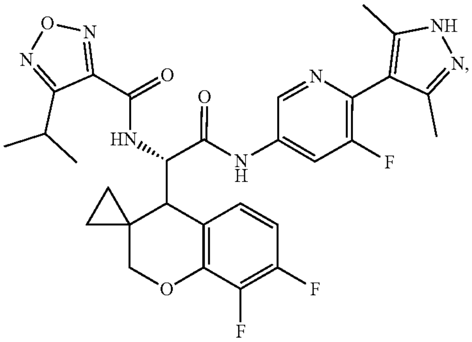
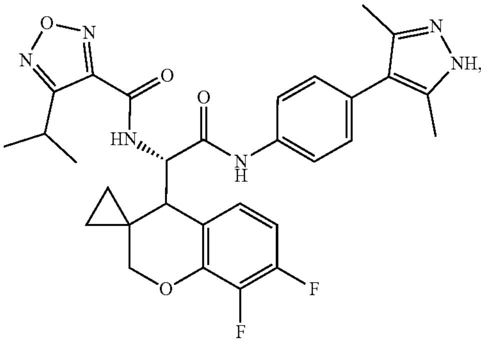
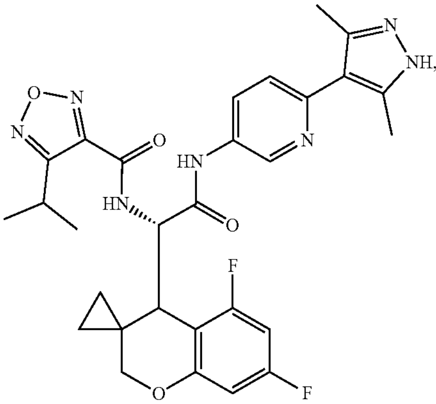
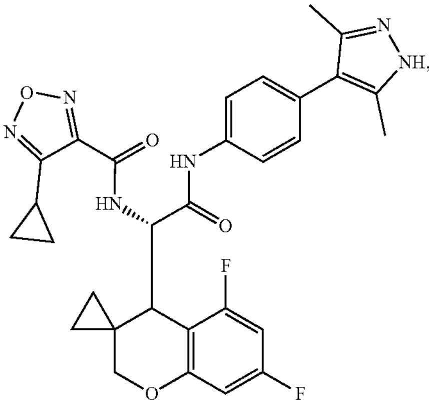

-continued
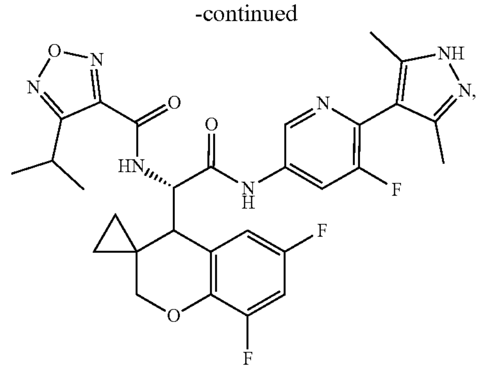
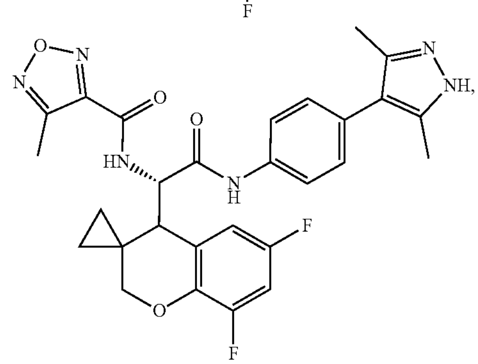
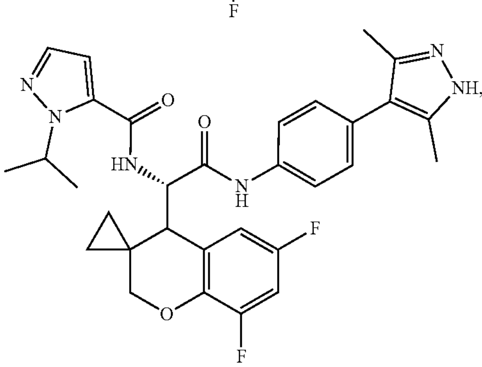
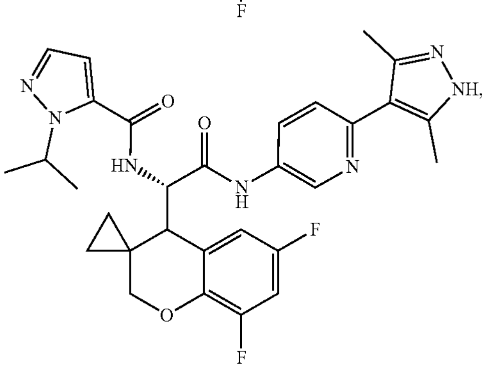
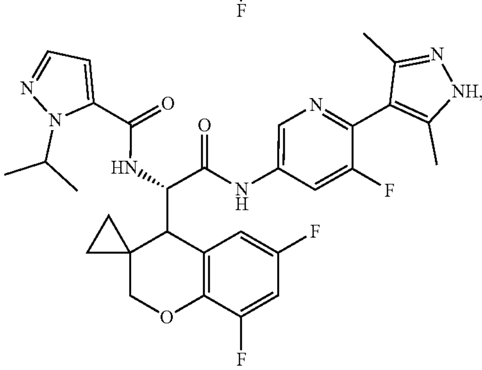
-continued
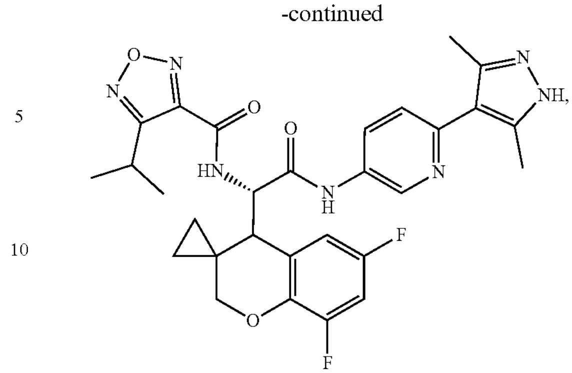
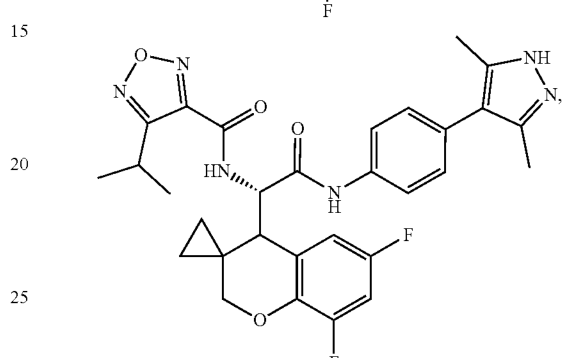
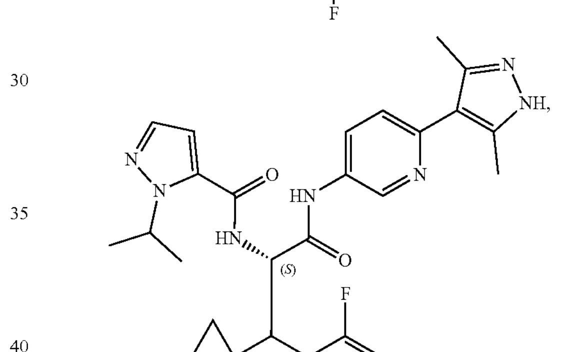
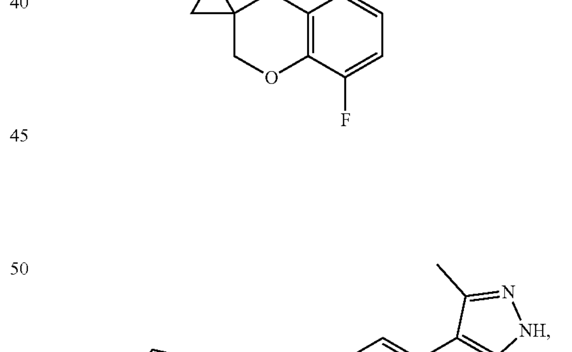
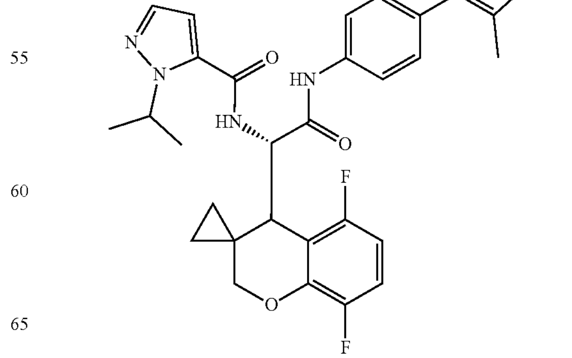

-continued
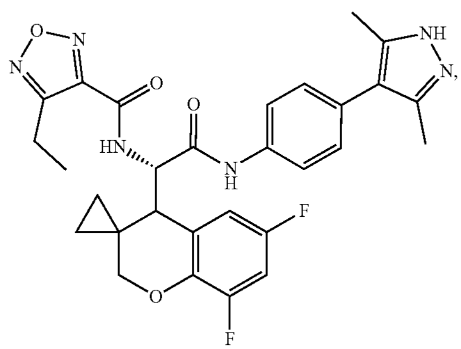
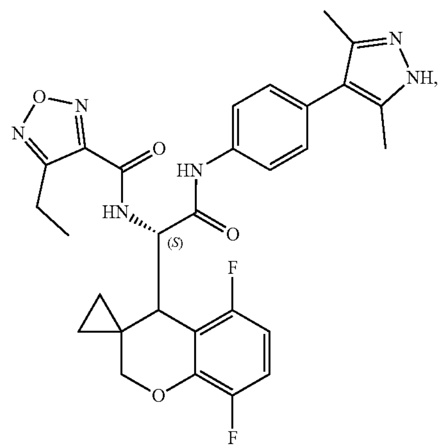
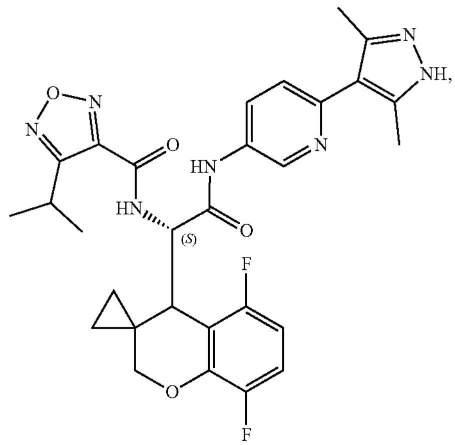
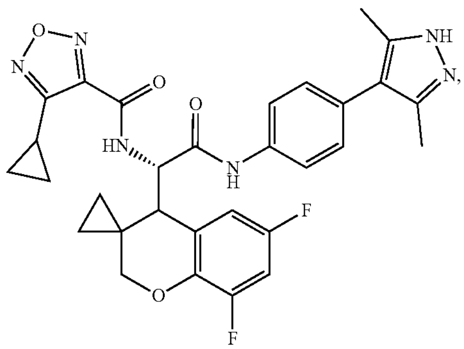
-continued
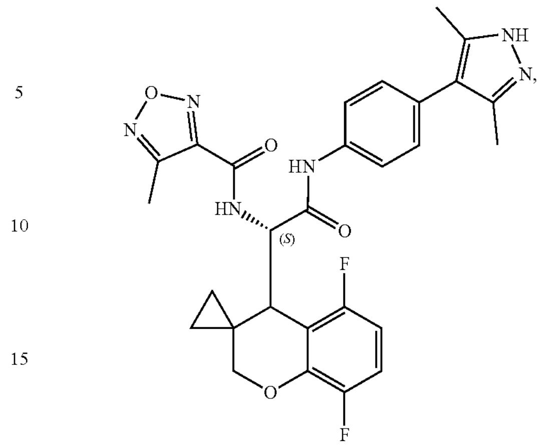
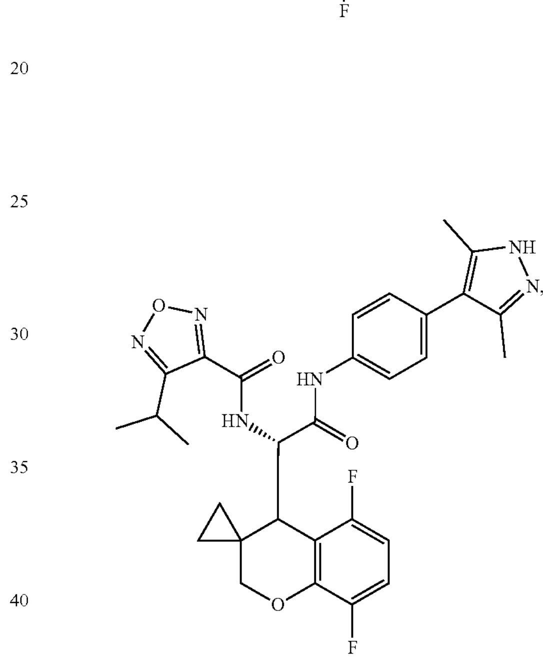
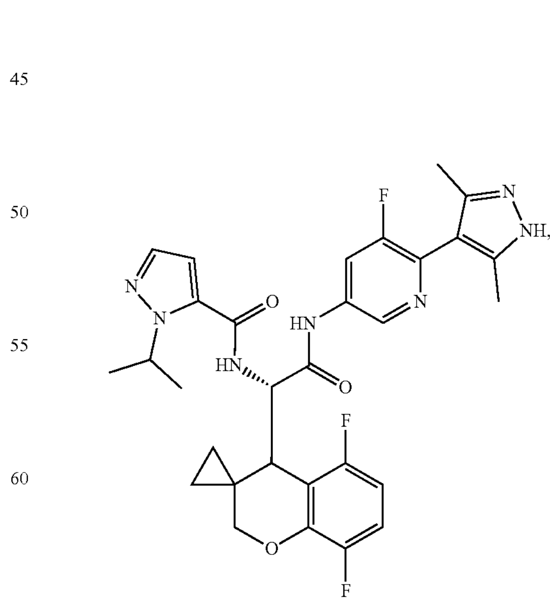

-continued
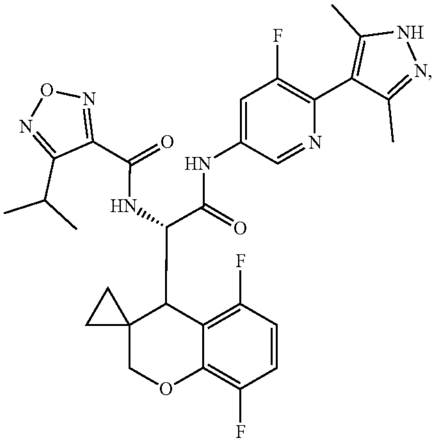
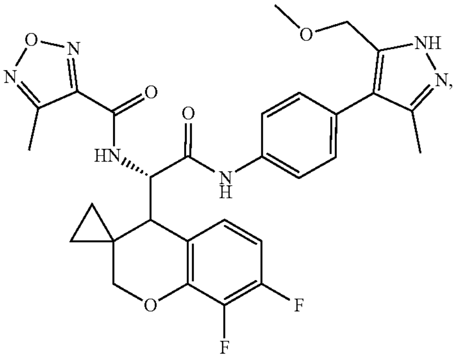
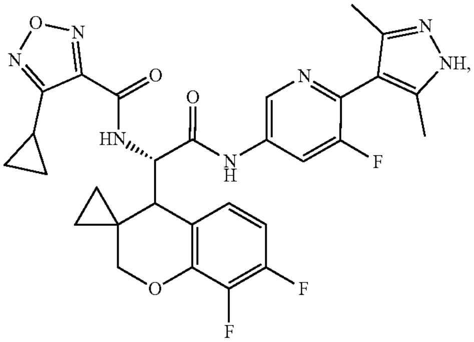
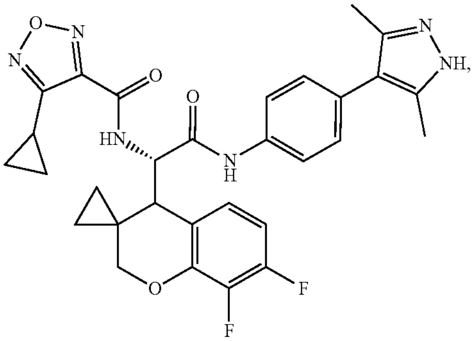
-continued
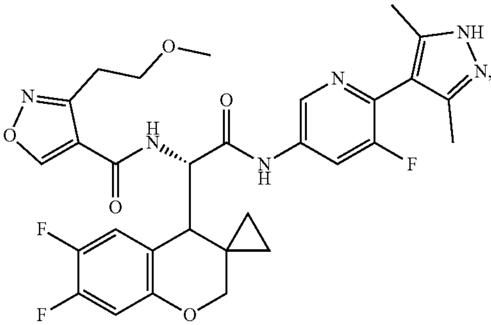
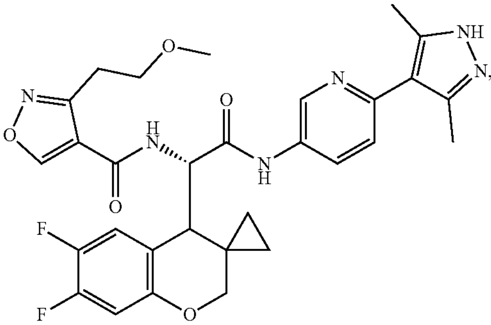
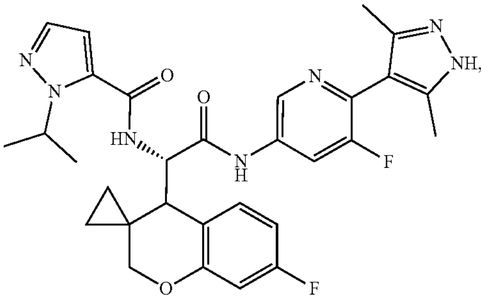
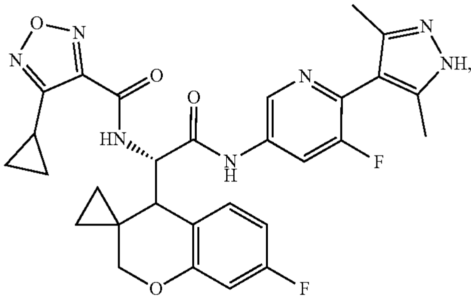
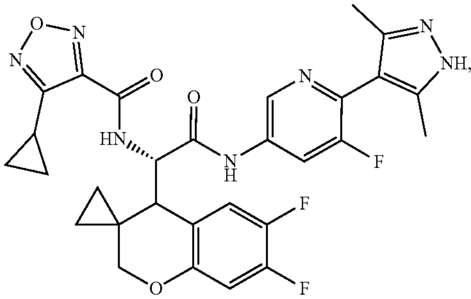

-continued
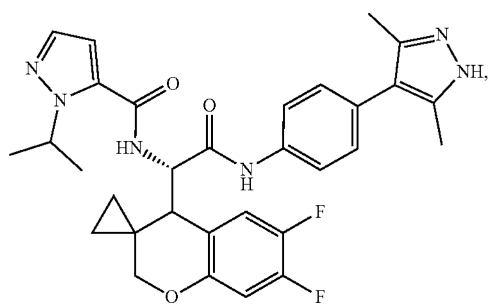
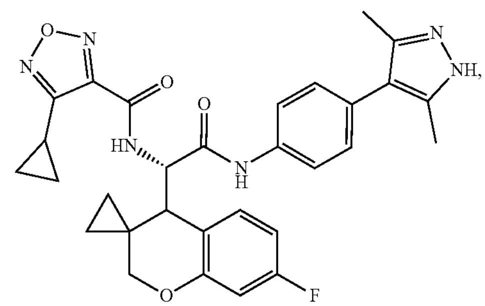
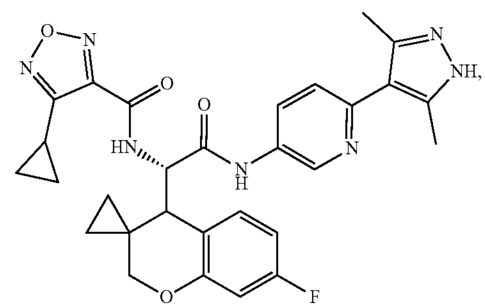
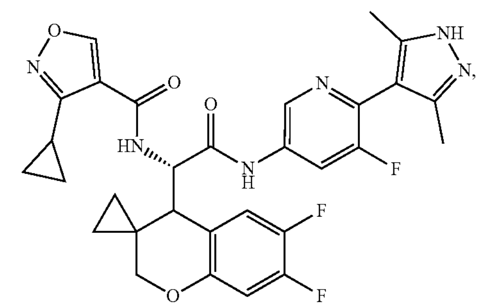
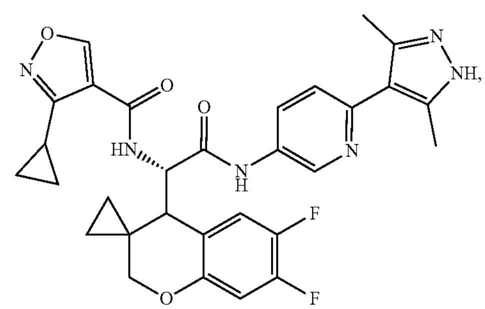
-continued
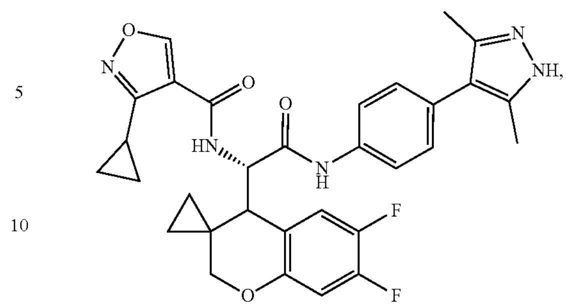
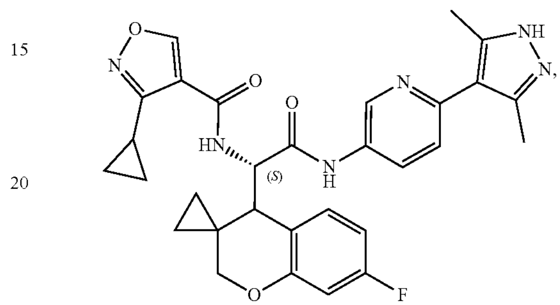
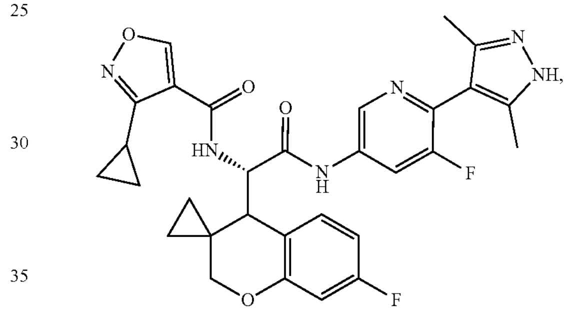
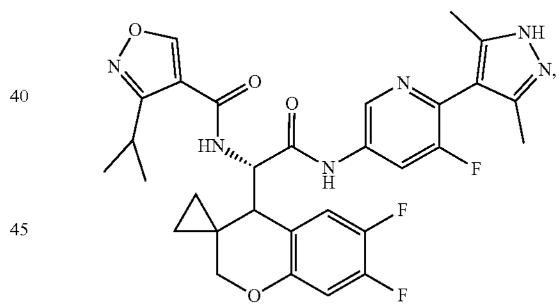
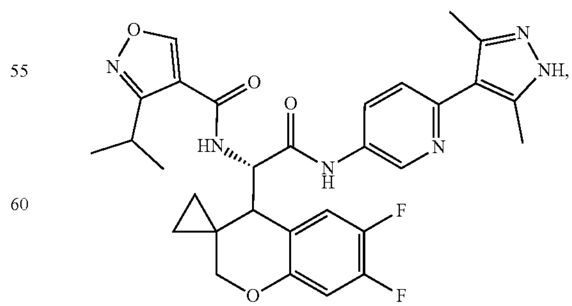

-continued
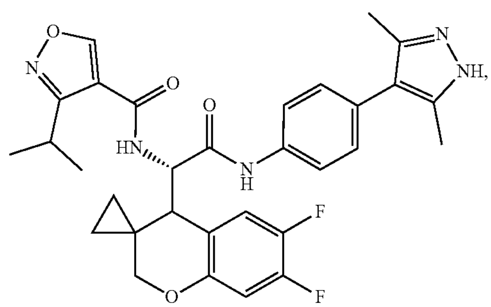
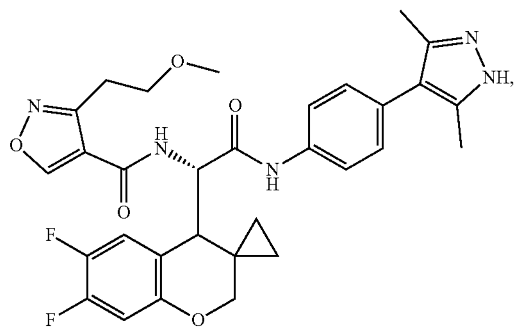
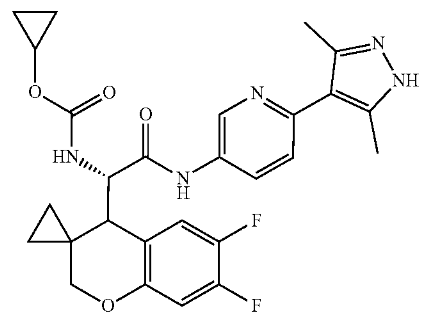
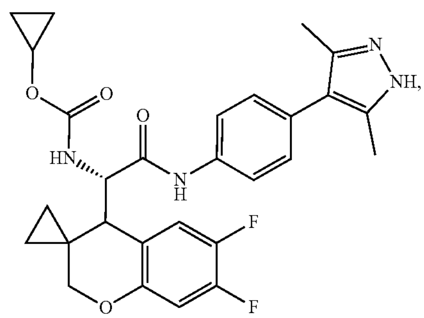
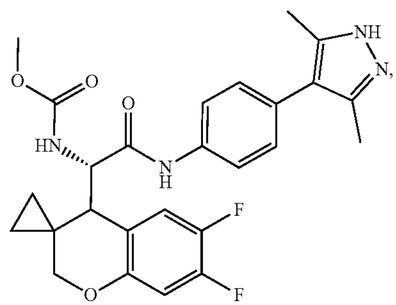
-continued
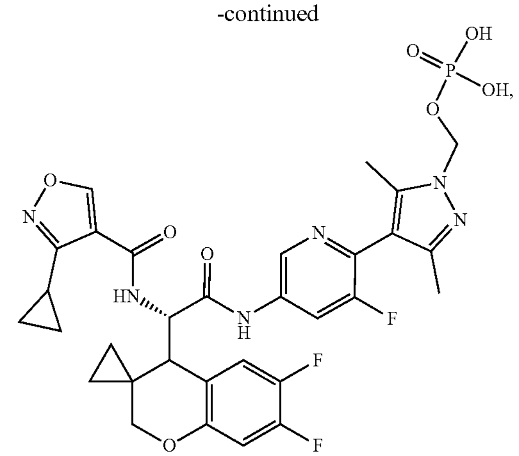
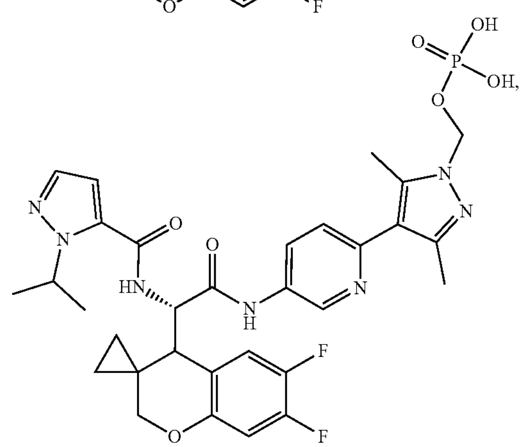
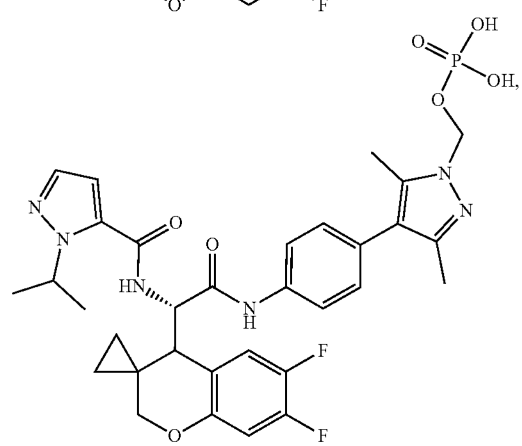
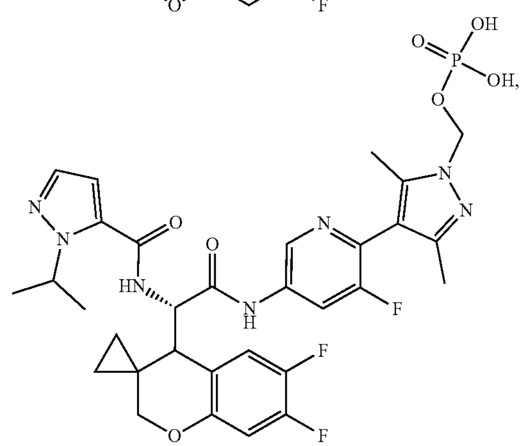

-continued

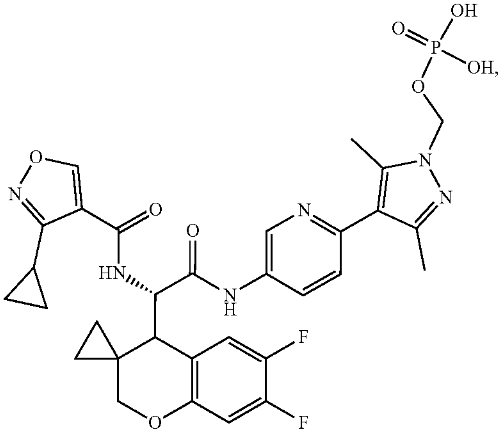

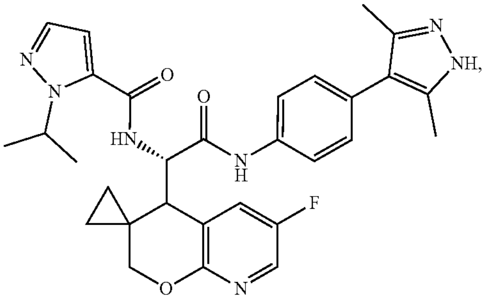

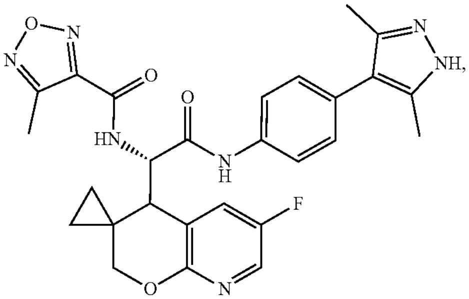

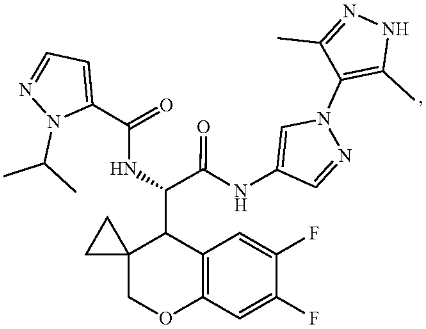

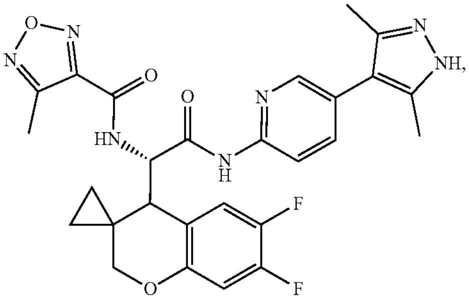

-continued

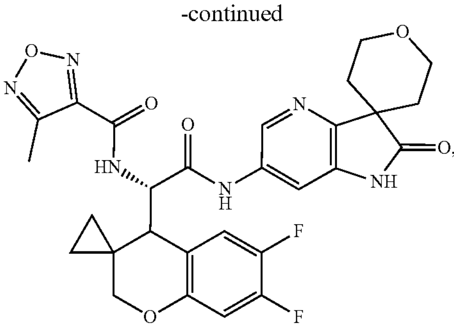

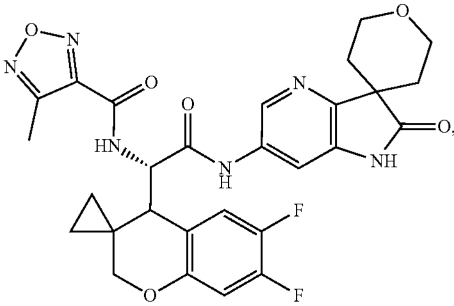

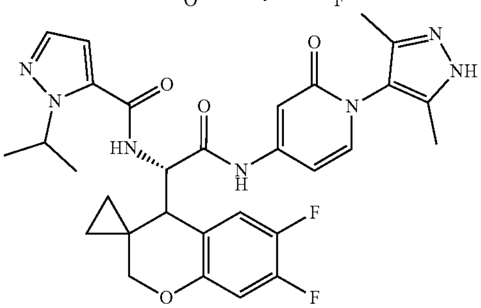

and

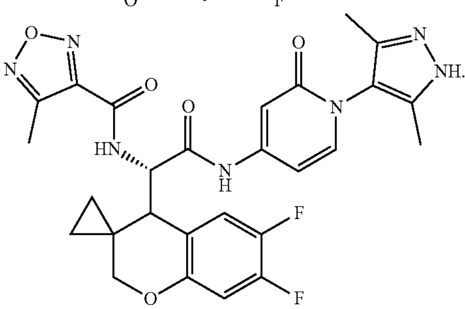

In a second aspect, the present disclosure provides a method for treating an interleukin-17A (IL-17A)-mediated disease in a subject in need thereof, comprising:

administering to the subject a therapeutically effective amount of the above-mentioned compound, or a deuterated compound, a stereoisomer or a pharmacologically acceptable salt thereof.

In some embodiments, the IL-17A-mediated disease is selected from the group consisting of inflammation, autoimmune disease, infectious disease, cancer, precancerous syndrome and a combination thereof.

In a third aspect, the present disclosure provides a pharmaceutical composition, comprising:

the above-mentioned compound, or a deuterated compound, a stereoisomer or a pharmacologically acceptable salt thereof, and a pharmaceutically acceptable excipient.

This present disclosure further provides an application of the above-mentioned compound of formula (I), the deuterated compound thereof, the stereoisomer thereof, the pharmacologically acceptable salt thereof, solvate thereof, a prodrug thereof or a metabolite thereof in preparing a drug for the treating the IL-17A-mediated disease.

The IL-17A-mediated disease is a disease in which IL-17A plays an important role in a pathogenesis of the disease. A primary function of IL-17A is to coordinate local tissue inflammation, thereby playing a role in various diseases. the IL-17A-mediated disease is selected from the group consisting of inflammation, autoimmune disease, infectious disease, cancer and precancerous syndrome.

The cancer or malignancy refers to any of a variety of diseases characterized by uncontrolled abnormal proliferation of cells. The affected cells of body or many characteristic structural and/or molecular features spread to other parts of the body locally or through the bloodstream and lymphatic system (i.e., metastasis). Cancer cells are cells that have undergone multiple steps of tumor progression in early, intermediate or late stages. Cancers include sarcoma, breast cancer, lung cancer, brain cancer, bone cancer, liver cancer, kidney cancer, colon cancer, and prostate cancer. In some embodiments, the compound of formula (I) is used to treat a cancer selected from the group consisting of colon cancer, brain cancer, breast cancer, fibrosarcoma, and squamous cell carcinoma. In some embodiments, the cancer is melanoma, breast cancer, colon cancer, lung cancer, and ovarian cancer. In some embodiments, the cancer being treated is a metastatic cancer.

The autoimmune diseases are caused by an immune response of body to substances and tissues normally present in the body. The autoimmune disease includes myocarditis, lupus nephritis, primary biliary cirrhosis, psoriasis, Type 1 diabetes mellitus, Grave's disease, celiac disease, Crohn's disease, autoimmune neutropenia, juvenile arthritis, rheumatoid arthritis, fibromyalgia, Guillain-Barre syndrome, multiple sclerosis, and autoimmune retinopathy. In this application, the autoimmune disease includes psoriasis and multiple sclerosis.

The inflammation includes a variety of conditions characterized by pathological inflammation of tissues, such as acne vulgaris, asthma, coeliac disease, chronic prostatitis, glomerulonephritis, inflammatory bowel disease, pelvic inflammatory disease, reperfusion injury, rheumatoid arthritis, sarcoidosis, vasculitis, airway inflammation due to house dust mites, and interstitial cystitis. There is a significant overlap between the inflammation and the autoimmune diseases. In this application, the inflammation includes asthma. The immune system is often involved in inflammatory diseases, which are manifested in allergic reactions and some myopathies. Many immune system diseases cause abnormal inflammation. The IL-17A-mediated disease also includes autoimmune inflammatory diseases.

The compounds and derivatives provided herein are named according to the nomenclature system of the International Union of Pure and Applied Chemistry (IUPAC) or Chemical Abstracts Service (CAS), Columbus, Ohio.

Unless otherwise specified, the definition of terms in this disclosure apply to the terms throughout the specification. Terms that are not specifically defined herein can be understood by the skilled in the art based on the disclosure The term "substitute" indicates the replacement of a hydrogen atom in a molecule by a different atom or group; or the replacement of a lone pair of electrons of an atom in a molecule by another atom or group. For example, a lone pair of electrons on an S atom can be replaced with an O atom to form

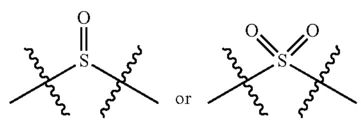

or .

The limitation "capable of being substituted" indicates that a "substitution" may occur, but not necessary. The description includes instances where it does or does not occur.

A minimum and a maximum of a content of carbon atoms in a hydrocarbon group are indicated by the prefix. For example, a prefix $C_{a-b}$ alkyl indicates any alkyl group containing a-b carbon atoms, i.e., $C_{1-6}$ alkyl indicates the alkyl group contains 1-6 carbon atoms.

The alkyl refers to a saturated hydrocarbon chain having the specified number of member atoms. The alkyl group can be straight-chain or branched. Representative branched alkyl groups have one, two or three branched chains. The alkyl group may optionally be substituted with one or more substituents as defined herein. The alkyl includes methyl, ethyl, propyl (n-propyl and isopropyl), butyl (n-butyl, isobutyl and tert-butyl), pentyl (n-pentyl, isopentyl and neopentyl) and hexyl. The alkyl can also be a part of other groups, and the other groups includes —O($C_{1-6}$ alkyl).

The alkylidene means a divalent saturated aliphatic hydrocarbon group having a specified number of membered atoms. The $C_{a-b}$ alkylidene refers to alkylidene groups with a-b carbon atoms. The alkylidene includes branched and straight chain alkyl. For example, propylidene is

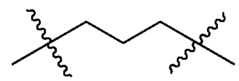

, and dimethylbutylidene is

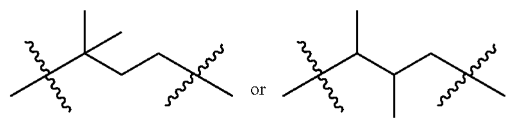

or .

The $C_{0-2}$ alkylidene is alkylidene with $C_0$, alkylidene with $C_1$ (such as —$CH_2$—), or alkylidene with $C_2$ (such as —$CH_2CH_2$—). $C_0$ alkylidene refers to the absence of the group here, and a connection here is chemical bonding. For example, A-$C_0$ alkylidene-B refers to A-B, that is, A is directly connected to B through a chemical bond.

The cycloalkyl and cycloalkyl indicate a saturated or partially saturated cyclic group having a carbon atom and no heterocyclic atom, and having a single ring or a plurality of rings (including thickening and bridging). The terms "cycloalkyl" and "cycloalkyl" include cycloalkenyl groups, such as cyclohexenyl. The cycloalkyl includes adamantyl, cyclopropyl, cyclobutyl, cyclohexyl, cyclopentyl, cyclooctyl, cyclopentenyl and cyclohexenyl. The cycloalkyl including a polybicycloalkyl ring system includes dicyclohexyl, dicyclopentyl and dicyclooctyl. For example,

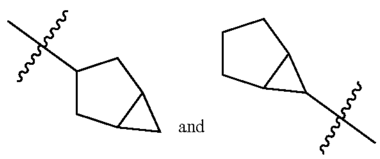 [SMILES: *C1CC2CC2C1 ; *C1C2CCCC12]

are dicyclohexyl.

The cycloalkyl and cycloalkyl also include partially saturated cyclic group where an aromatic ring is fused with a non-aromatic ring, and an attachment site may be at a non-aromatic carbon atom or an aromatic carbon atom. For example, 1,2,3,4-tetrahydronaphthalen-5-yl and 5,6,7,8-tetrahydronaphthalen-5-yl.

The term "unsaturated" means that the group or molecule includes carbon-carbon double bond, carbon-carbon triple bond, carbon-oxygen double bond, carbon-sulfur double bond, carbon-nitrogen triple bond, etc. The unsaturated carbocyclic herein includes or excludes aryl groups, and the unsaturated heterocyclic includes or excludes heteroaryl groups, as the skilled in the art may freely choose.

The alkenyl refers to a straight or branched hydrocarbon group having 2-10 carbon atoms, 2-6 carbon atoms or 2-4 carbon atoms, and having at least one vinyl unsaturated site (>C═C<). For example, $C_{a-b}$ alkenyl is an alkenyl with a-b carbon atoms, such as vinyl, propenyl, isopropenyl and 1,3-butadienyl.

The alkynyl is a linear monovalent hydrocarbon radical or a branched monovalent hydrocarbon radical containing at least one triple bond. The term "alkynyl" includes those alkyl having a triple bond and a double bond. For example, $C_{2-6}$ alkynyl includes ethynyl and propargyl.

The halogen is fluorine, chlorine, bromine or iodine.

The terms "haloalkyl" and "halogen-substituted alkyl" refer to alkyl in which the hydrogen atom may be replaced with one or more halogen atoms. For example, halogen-substituted $C_{1-4}$ alkyl refers to alkyl containing 1-4 carbon atoms with hydrogen atoms substituted by one or more halogen atoms, as well as monofluoromethyl, difluoromethyl and trifluoromethyl.

The heterocycloalkyl, heterocyclic, heterocyclic alkane indicate a saturated ring or a non-aromatic partially saturated ring containing at least one heteroatom and having a single ring or multiple rings (dense and bridged). The heteroatom includes nitrogen (N), oxygen and sulfur. For example, monovalent saturated or partially unsaturated monocyclic or bicyclic ring systems of a plurality of ring atoms, which includes 1, 2 or 3 ring heteroatoms selected from the group consisting of N, O and S, and the remaining ring atoms are carbon. Bicycles represent a chain consisting of two rings with two ring atoms in common, that is, a bridge separating the two rings is either a single bond or one or two ring atoms. The monocyclic saturated heterocyclic alkyl includes oxetanyl, azetidinyl, pyrrolidinyl, 2-oxo-pyrrolidin-3-yl, tetrahydropyranyl, tetrahydro-thienyl, pyrazolidinyl, imidazolidinyl, thiazolidinyl, piperidinyl, tetrahydropyranyl, tetrahydrothiopyranyl, piperazinyl, morpholinyl,

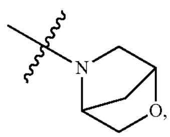 [SMILES: *N1CC2CC1CO2]

thiomorpholinyl, 1,1-dioxo-thiomorpholin-4-yl, azepanyl, diazepanyl, homopiperazinyl and oxazepanyl. The bicyclic saturated heterocycloalkyl includes 8-azabicyclo[3.2.1]octan, quinuclidinyl, 8-oxa-3-azabicyclo[3.2.1]octan and 9-azabicyclo[3.3.1]nonane. The partially unsaturated heterocycloalkyl includes dihydrofuranyl, imidazolinyl, tetrahydro-pyridyl and dihydropyranyl. The heterocycloalkyl also includes a partially saturated cyclic group formed by an association of an aromatic ring including at least one heteroatom with a non-aromatic ring, in which a linkage site is located at a non-aromatic carbon atom, an aromatic carbon atom or a heteroatom, such as , , , , and .

The aryl group and aromatic ring refers to an aromatic group with multiple carbon atoms. The aryl is usually a monocyclic, bicyclic or tricyclic aryl having a plurality of carbon atoms, such as benzene ring, naphthyl and tetrahydronaphthyl.

The heteroaromatic ring is an aromatic unsaturated ring containing at least one heteroatom. The heteroatom is nitrogen atoms, oxygen atoms, sulfur atoms, etc. For example, aromatic monocyclic or bicyclic hydrocarbons with a plurality of ring atoms and one or more of the ring atoms being selected from the group consisting of O, N and S. Preferably, there are 1-3 heteroatoms. The heteroaromatic ring includes pyridinyl, indolyl, quinoxalinyl, quinolinyl, isoquinolinyl, benzothienyl, benzofuranyl, benzothienyl, benzothiopyranyl, benzothiopyranyl, furanyl, pyrrolyl, thiazolyl, oxazolyl, isoxazolyl, triazolyl, tetrazolyl, pyrazolyl, imidazolyl, thienyl, oxadiazolyl, benzimidazolyl, benzothiazolyl and benzoxazolyl.

The stereoisomer includes enantiomer and diastereoisomer.

The —OR and —NRR indicate that the R group is connected to the O or N atom by a single bond.

The —C(O)R and —$S(O)_2$R indicate that the O is connected to the C or S atom by a double bond, and the R is connected to the C or S atom by a single bond.

The ═O and ═S indicate that the oxygen and sulfur atoms are connected to a substitution position by a double bond.

The --- and

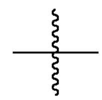

are indicate the substitution position of groups.

The deuterated compound refers to a substitution of one or more hydrogen atoms in a molecule or group by deuterium atoms, where the percentage of deuterium atoms is greater than an abundance of deuterium in nature.

The limitation "pharmacologically acceptable" refers to a carrier, delivery agent, diluent, excipient, and/or salt are generally chemically or physically compatible with the other ingredients including a pharmaceutical dosage form, and are physiologically compatible with the receptor.

The terms "salt" and "medicinal salt" refer to the acid and/or base salts formed by the above compounds or their stereoisomers with inorganic and/or organic acids and bases. It includes amphoteric salts (internal salts) and quaternary ammonium salts such as alkyl ammonium salts. The salts can be directly obtained in a final isolation and purification of the compound, or obtained by mixing the above compounds or their stereoisomers with an appropriate amount of acid or base (e.g. in equivalent amounts). The salts may be collected by filtration as precipitates in solution, recovered by evaporation of the solvent, or freeze-dried after reaction in aqueous media. The salt provided herein includes sodium, potassium, hydrochloride, sulfate, citrate, benzenesulfonate, hydrobromide, hydrofluorate, phosphate, acetate, propionate, succinate, oxalate, malate, succinate, fumarate, maleate, tartarate and trifluoroacetate of the compound.

In some embodiments, one or more compounds of the present disclosure may be used in combination with each other. Optionally, the compounds may also be used in combination with any other active agent for the preparation of drugs or pharmaceutical compositions that modulate cellular function or treat disease. If a group of compounds is used, the compounds may be administered to the subject simultaneously, separately or in an ordered manner.

Described above are merely illustrative of the disclosure, and are not intended to limit the disclosure. Those skilled in the art could still make modifications and changes to the disclosure based on the content disclosed herein.

The disclosure will be described in detail below with reference to the embodiments, but is not limited thereto. It should be understood that any changes, replacements and modifications made by those skilled in the art without departing from the spirit of the disclosure shall fall within the scope of the present disclosure defined by the appended claims.

DETAILED DESCRIPTION OF EMBODIMENTS

Figure 1:
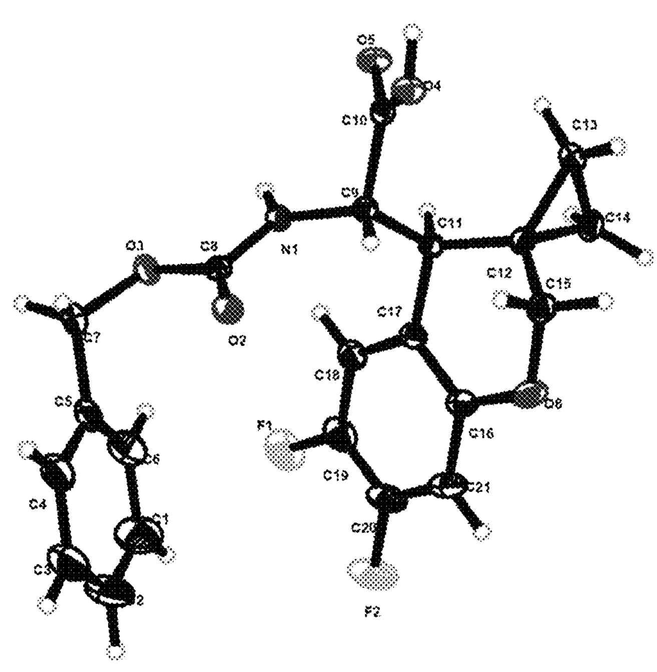
FIG. 1 is a single-crystal X-ray diffraction image of an intermediate Z12.
Figure 2A:
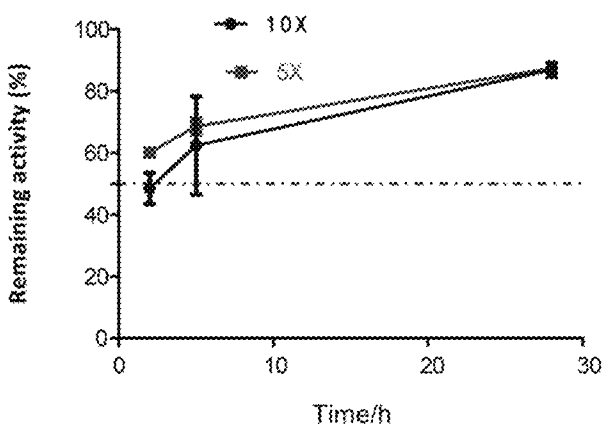
FIGS. 2A-2D show inhibition of several compounds prepared in Examples of the disclosure on IL17A/IL17RA (coating) after jump dilution, where 2A: positive control compound; 2B: compound 26; 2C: compound 43, and 2D: compound 47.
Figure 2B:
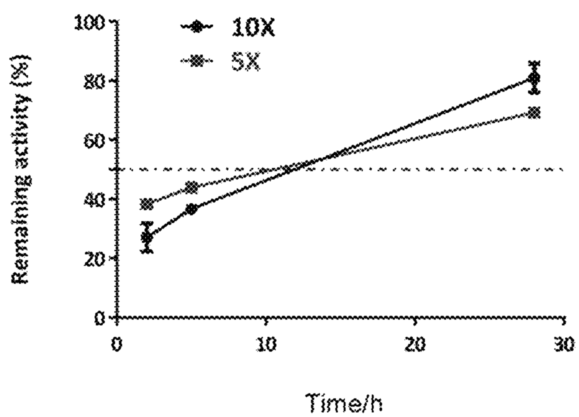
Figure 2C:
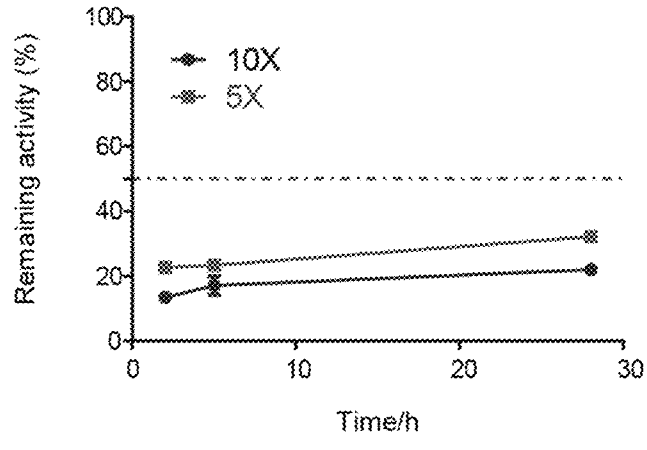
Figure 2D:
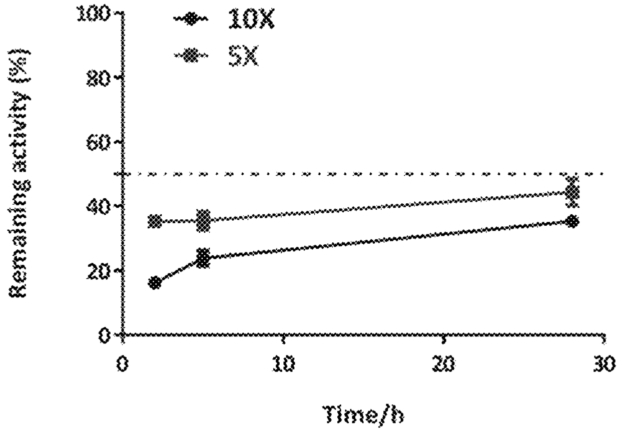

The structure of compound is determined by nuclear magnetic resonance (NMR) and mass spectrometry (MS). A displacement in NMR is 1-6 (ppm). NMR equipment is Bruker AvanceIII 400 and Bruker Avance 300. A solvent includes dimethyl sulfoxide-d6 (DMSO-d6), deuterated chloroform (CDCl3) and deuterated methanol ($CD_3OD$). An internal standard substance is tetramethylsilane (TMS)

Liquid chromatograph mass spectrometry (LC-MS) adopted Shimadzu LC-MS 2020 (ESI). High performance liquid chromatography (HPLC) adopted Shimadzu LC-20A. Medium pressure preparative liquid chromatography (MPLC) adopted Gilson GX-281 reversed-phase chromatograph. A silica gel plate adopted antai Huanghai HSGF254 or Qingdao GF254 silica gel plate. A size of a product for thin layer chromatography is 0.4-0.5 mm. A column chromatography adopted Yantai Huanghai silica gel 200-300 mesh silica gel as the carrier.

A raw material can be synthesized using methods known in the art, or can be purchased from companies such as Anegis Chemical, Chengdu Kolon Chemical, Shaoyuan Chemical Technology, J&K Scientific Technology, etc.

Unless otherwise specified, reaction was carried out under a nitrogen atmosphere, a solution is an aqueous solution, a temperature of the reaction is room temperature, and M is moles per liter.

TEA or $Et_3N$ is triethylamine. DIPEA is N,N-diisopropylethylamine. HOBt is 1-hydroxybenzotriazole. DCM is dichloromethane. PE is petroleum ether. EA or EtOAc is ethyl acetate. THE is tetrahydrofuran. DMF is N,N-dimethylformamide. NMP is N-methylpyrrolidone. NMO is N-methylmorpholine oxide. MeOH is methanol. EtOH is ethanol. DMSO is dimethyl sulfoxide. TAF is trifluoroacetic acid. $NaBH_4$ is sodium borohydride. MsCl is methyl sulfonyl chloride. DIBAL is diisobutylaluminium hydride. NBS is N-bromosuccinimide. NCS is N-chlorosuccinimide. DMS is dimethyl sulfide. CbzOSu is N-(benzyloxycarbonyloxy) succinimide. $ZnEt_2$ is diethylzinc. Pd/C is palladium on carbon. DIAD is diisopropyl azodicarboxylate. DEAD is diethyl azodicarboxylate. $PPh_3$ is triphenylphosphorus. $(COCl)_2$ is oxalyl chloride. n-BuLi is n-butyllithium. $Ti(OEt)_4$ is ethyl titanate. TMSCN is trimethylsilyl cyanide. CsF is cesium fluoride. MTBE is methyl tert-butyl ether. $H_2O_2$ is hydrogen peroxide. $(Boc)_2O$ is di-tert-butyl dicarbonate. SEMCl is 2-(trimethylsilyl)ethoxymethyl chloride. NaH is sodium hydrogen. $ICH_2Cl$ is chloroiodomethane. $PBr_3$ is phosphorus tribromide. $(CH_2O)n$ is paraformaldehyde. TFA. PrNH is diisopropylamine trifluoroacetate. HATU is O-(7-Azabenzotriazol-1-yl)-N,N,N',N'-tetramethyluronium hexafluorophosphate. HOAt is 1-hydroxy-7-azobenzotriazole. HBTU is O-(nenzotriazol-1-yl)-N,N,N',N'-tetramethyluronium Hexafluorophosphate. CDI is N,N'-carbonyldiimidazole. T3P is 1-propylphosphonic anhydride. PyBOP is 1H-benzotriazol-1-yloxytripyrrolidinophosphonium hexafluorophosphate. DCC is dicyclohexylcarbodiimide. EDC or EDCI is N-(3-dimethylaminopropyl)-N'-ethylcarbodiimide hydrochloride. Fmoc-Osu is N-(9-fluorenylmethoxycarbonyloxy)-succinimide.

Preparation of Intermediate Z1 (Method A)

A preparation of intermediate Z1 is illustrated as follows:

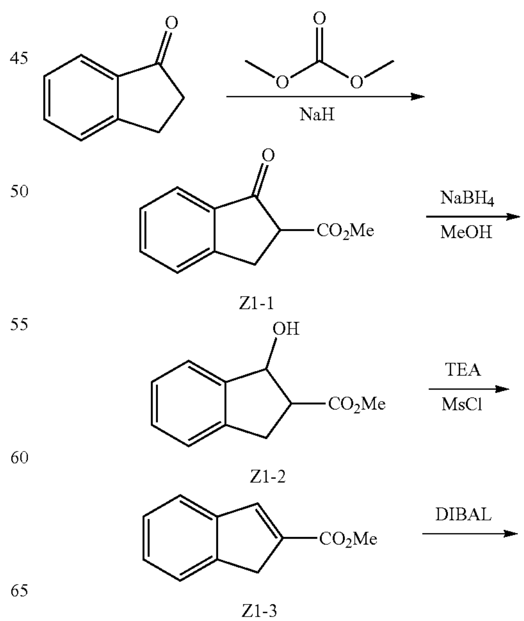

Z1-1

Z1-2

Z1-3

-continued

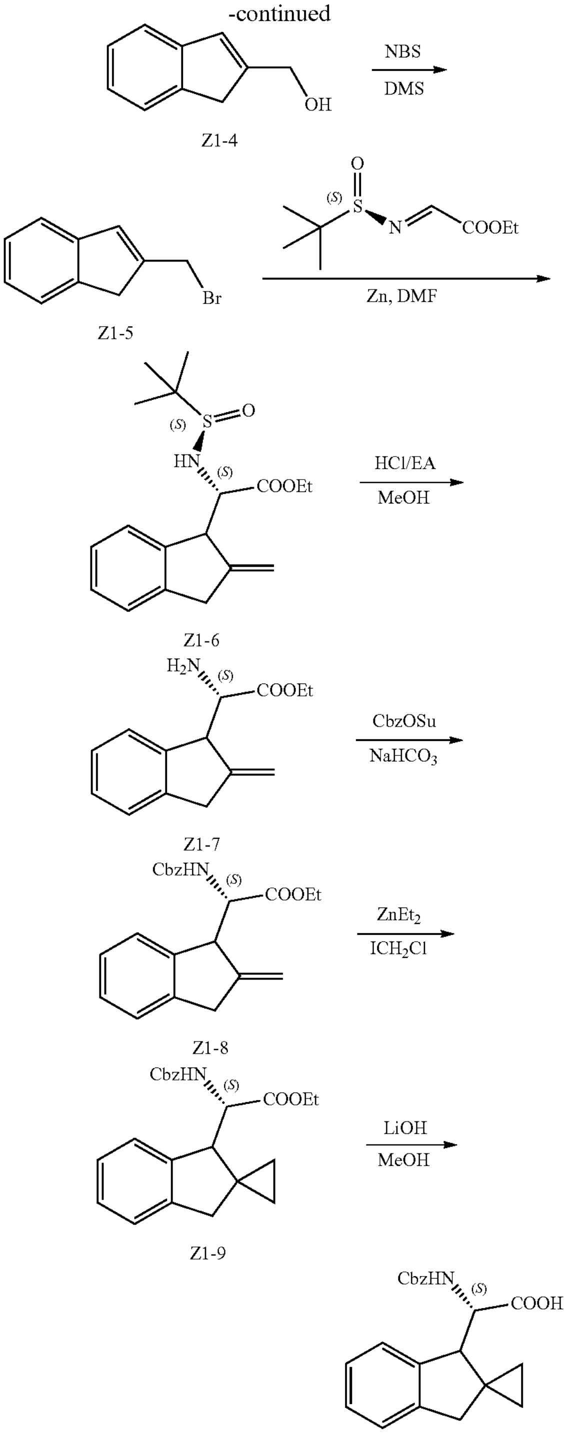

Z1-4

Z1-5

Z1-6

Z1-7

Z1-8

Z1-9

Z1

(S1) Preparation of Intermediate Z1-1

17 g (189 mmol) of dimethyl carbonate and 80 mL of THF were added to a 250 mL three-necked flask, 3.18 g (79.4 mmol) of 60% w/w NaH were added under stirring with protection of nitrogen displacement. A THE (40 mL) solution of 1-indanone (5 g, 37.8 mmol) was dropwise added into the reaction mixture by using a dropping funnel, and heated and refluxed for 2 h. After the reaction was confirmed by thin-layer chromatography (TCL) to be complete, the reaction mixture was decanted into a mixture of 1 M hydrogen chloride (HCl) and ice, and subjected to extraction for 3 times by 100 mL of ethyl acetate (EA) to obtain an EA layer. The EA layer was dried and spin-dried to obtain 7.11 g of a black oil-like substance as intermediate Z1-1 (yield: 99%).

(S2) Preparation of Intermediate Z1-2

7.11 g (37.8 mmol) of intermediate Z1-1 and 100 mL of MeOH were added into a 250 mL single-necked flask for dissolving. 1.58 g (41.6 mmol) of $NaBH_4$ were added in portions with ice bath cooling. The reaction mixture was slowly heated to room temperature and reacted for 1 h. After the reaction was confirmed by TCL to be complete, the reaction mixture was subjected to vacuum spin to remove MeOH. The residue was added with 100 mL of water, and then extracted with 100 mL of EA for 3 times to obtain an EA layer. The EA layer was dried and spin-dried to obtain 7.18 g of a brown oil-like substance as intermediate Z1-2 (yield: 99%). MS m/z: 193 $(M+1)^+$.

(S3) Preparation of Intermediate Z1-3

7.18 g (37.8 mmol) of intermediate Z1-2 and 100 mL of DCM were added into a 250 mL single-necked flask for dissolving, and then added with 15.7 mL (113.4 mmol) of TEA. 4.4 mL (56.7 mmol) of methylsulfonyl chloride were added in portions with ice bath cooling. The reaction mixture was slowly heated to room temperature and reacted overnight. After the reaction was confirmed by TCL to be complete, the reaction mixture was washed by 100 mL of water, and a DCM layer was collected. The DCM layer was dried, spin-dried and purified by column chromatography (with 100-200 mesh silica gel, and gradient elution with 100% PE to PE:EA=10:1) to obtain 6.04 g of a yellow solid as intermediate Z1-3 (yield: 92.8%). MS m/z: 175 $(M+1)^+$.

(S4) Preparation of Intermediate Z1-4

6.04 g (35.1 mmol) of intermediate Z1-3 and 60 mL of THF were added into a 250 mL single-necked flask for dissolving. The reaction mixture was cooled to −78° C. by a dry ice-ethanol bath, dropwise added with 70.2 g (70.2 mmol) of a 1 M toluene solution of DIBAL, and then slowly heated to room temperature and reacted overnight. After the reaction was confirmed by TCL to be complete, the reaction mixture was decanted into 1 M HCl, stirred at room temperature for 30 min, and extracted by 100 mL of EA for 3 times to collect an EA layer. The EA layer was dried, spin-dried and purified by column chromatography (with 100-200 mesh silica gel, and gradient elution with PE:EA=10:1 to PE:EA=5:1) to obtain 2.3 g of a yellow oil-like substance as intermediate Z1-4 (yield: 45.3%).

(S5) Preparation of Intermediate Z1-5

3.15 g (17.7 mmol) of NBS and 50 mL of DCM were added into a 250 mL three-necked flask. The reaction mixture was cooled to −30° C. under a nitrogen atmosphere, dropwise added with 1.23 mL (16.9 mmol) of methyl sulfide and reacted at −30° C. for 30 min to obtain a light yellow suspension. The light yellow suspension was dropwise added with a DCM (15 mL) solution of intermediate Z1-4 (2.35 g, 16.1 mmol), slowly heated to room temperature and reacted for 2 h. After a product generation was confirmed by TCL, the reaction mixture was transferred to a single-necked flask and spun to remove DCM. The residue was added with water and 50 mL of ethyl ether for dissolving to obtain a first ethyl ether layer and a water layer. The water layer was extracted with 50 mL of ethyl ether 2 times to obtain a second ethyl ether layer. The first ethyl ether layer and the second ethyl ether layer were combined, dried and spin-dried to obtain 3.36 g of light brown liquid as intermediate Z1-5 (yield: 100%).

(S6) Preparation of Intermediate Z1-6

A DMF (50 mL) solution of ethyl (S)-2-((tert-butylsulfinyl)imino)acetate (3.30 g, 16.1 mmol) and 1.05 g (16.1 mmol) of zinc dust were added into a 250 mL single-necked flask under protection of nitrogen displacement. A DMF (10 mL) solution of intermediate Z1-5 (3.36 g, 16.1 mmol) were added into the reaction mixture, and reacted under room temperature overnight. After the reaction was confirmed by liquid chromatograph mass spectrometry (LCMS) to be complete, the reaction mixture was decanted into a mixture of water and EA (100 mL) for filtration to remove insoluble matters. The filtrate was divided int a first EA layer and a water layer. The water layer was extracted by 50 mL of EA 2 times to obtain a second EA layer. The first EA layer and the second EA layer were combined, dried, spin-dried and purified by column chromatography (with 100-200 mesh silica gel, gradient elution with PE:EA=5:1 to PE:EA=2:1 and coloration by iodine) to obtain 1.53 g of a light yellow oil-like substance as intermediate Z1-6 (yield: 28.4%). MS m/z: 336 $(M+1)^+$.

$^1$H NMR (400 MHz, Chloroform-d) δ 7.38-7.29 (m, 5H), 5.11 (s, 2H), 4.48 (dd, J=9.7, 6.1 Hz, 1H), 4.22-4.06 (m, 2H), 2.64-2.46 (m, 1H), 2.03 (d, J=8.5 Hz, 1H), 2.00-1.75 (m, 3H), 1.75-1.62 (m, 3H), 1.27 (t, 3H), 0.92 (s, 3H), 0.30-0.09 (m, 4H).

(S7) Preparation of Intermediate Z1-7

1.53 g (4.57 mmol) of intermediate Z1-6 and 20 mL of MeOH were added into a 100 mL single-necked flask for dissolving. An ethyl acetate solution of hydrogen chloride (4 M, 2.3 mL, 9.13 mmol) were added into the reaction mixture under stirring, and the reaction mixture was reacted at room temperature for 2 h. After the reaction was confirmed by LCMS to be complete, a solution of intermediate Z1-7 was obtained. MS m/z: 231 $(M+1)^+$.

(S8) Preparation of Intermediate Z1-8

The solution of intermediate Z1-7 was added with 1.15 g (13.7 mmol) of sodium bicarbonate ($NaHCO_3$) and 1.37 g (5.48 mmol) of CbzOSu, and stirred for reaction overnight. After the reaction was confirmed by LCMS to be complete, the reaction mixture was subjected to vacuum spin. The residue was dissolved by water and EA (30 mL) to obtain a first EA layer and a water layer. The water layer was extracted by EA (30 mL) 2 times to collect a second EA layer. The first EA layer and the second EA layer were combined, dried, spin-dried and purified by column chromatography (with 100-200 mesh silica gel, gradient elution with PE:EA=10:1 to PE:EA=5:1 and coloration by potassium permanganate) to obtain 1.67 g of a light yellow solid as intermediate Z1-8 (yield: 100%). MS m/z: 366 $(M+1)^+$.

(S9) Preparation of Intermediate Z1-9

Diethylzinc (2 M toluene solution, 6.86 mL, 13.7 mmol) and 50 mL of anhydrous DCM were added into a 250 mL single-necked flask, cooled to −10° C., and dropwise added with 2 mL (27.5 mmol) of chloroiodomethane to react under stirring for 30 min, so as to obtain a white suspension. 1.67 g (4.58 mmol) of intermediate Z1-8 were dissolved in 10 mL of anhydrous DCM to obtain an intermediate Z1-8 solution. The intermediate Z1-8 solution was dropwise added in the white suspension, and then slowly heated to room temperature to react overnight. After the reaction was confirmed by LCMS to be complete, the reaction mixture was decanted into 80 mL of saturated ammonium chloride ($NH_4Cl$) solution to stir for 30 min to obtain a first DCM layer and a water layer. The water layer was extracted by 50 mL of DCM 2 times to obtain a second DCM layer. The first DCM layer and the second DCM layer were combined, dried and spin-dried to obtain 1.73 g of a yellow oil-like substance as intermediate Z1-9 (yield: 100%). MS m/z: 380 $(M+1)^+$.

(S10) Preparation of Intermediate Z1-10

1.73 g (4.56 mmol) of intermediate Z1-9, 20 mL of ethanol and 2 mL of water were added into a 100 mL single-necked flask to stir to obtain a transparent solution. The transparent solution was added with 575 mg (13.7 mmol) of lithium hydroxide monohydrate and heated to 50° C. to react overnight. After the reaction was confirmed by LCMS to be complete, the reaction mixture was spin-dried. The residue was adjusted to weak acidity by adding 1 M HCl, and extracted by 20 mL of EA for 3 times to collect an EA layer. The EA layer was purified by MPLC (gradient elution with by methyl cyanide (MeCN)–0.05% HCOOH aqueous solution, with showing a product peak at 55% MeCN) to obtain 540 mg of a light yellow solid Z1 (yield: 33.8%). MS m/z: 352 $(M+1)^+$.

Preparation of Intermediate Z2

A preparation of intermediate Z2 is illustrated as follows:

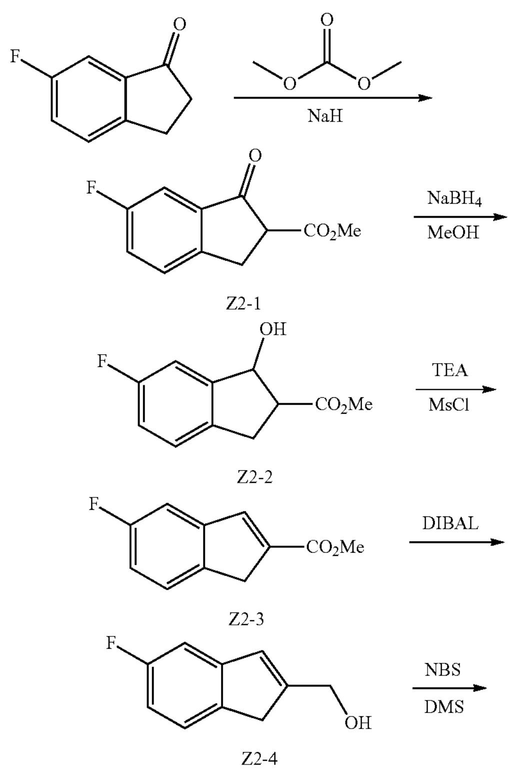

Z2-1
Z2-2
Z2-3
Z2-4

-continued
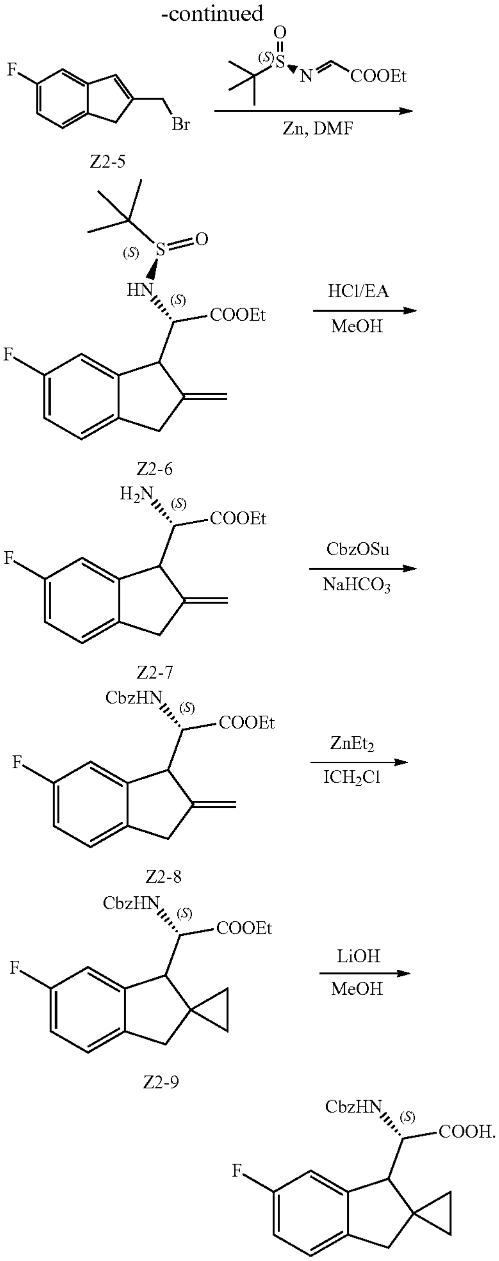
Z2-5
Z2-6
Z2-7
Z2-8
Z2-9
Z2
The preparation of intermediate Z2 was performed according to steps (S1)-(S10) of the method A of preparing intermediate Z1, in which the 1-indanone in step (S1) was replaced with 6-fluoro-1-indanone. MS m/z: 370 $(M+1)^+$.
Preparation of Intermediate Z3
A preparation of intermediate Z3 is illustrated as follows:
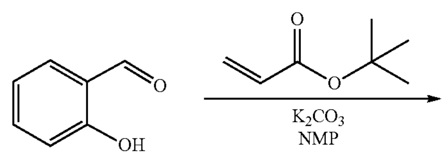
-continued
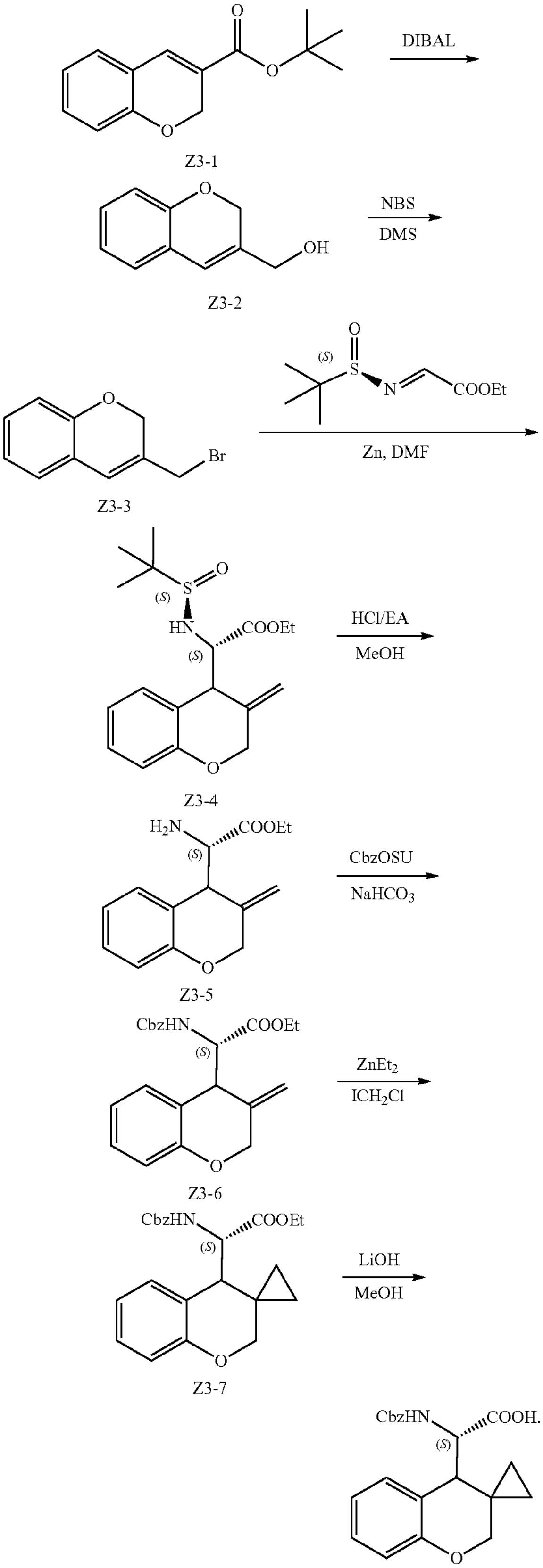
Z3-1
Z3-2
Z3-3
Z3-4
Z3-5
Z3-6
Z3-7
Z3

(S1) Preparation of Intermediate Z3-1

10 g (82.0 mmol) of salicylic aldehyde, 15.7 g (122.6 mmol) of tert-Butyl acrylate and 80 mL of NMP were added into a 250 mL single-necked flask for dissolving. The reaction mixture was added with 11.3 g (81.9 mmol) of potassium carbonate, and heated to 130° C. to react for 4 h. After the reaction was confirmed by TCL to be complete, the reaction mixture was decanted into water, and extracted by 100 mL of EA for 3 times to collect an EA layer. The EA layer was dried, spin-dried and purified by column chromatography (with 100-200 mesh silica gel, and gradient elution with PE:EA=20:1 to PE:EA=10:1) to obtain 12 g of a yellow oil-like substance as intermediate Z3-1 (yield: 63%).

(S2) Preparation of Intermediate Z3

The rest steps were performed according to steps (S4)-(S10) of the method A of preparing intermediate Z1 to obtain the intermediate Z3, in which the intermediate Z1-3 in step (S4) was replaced with intermediate Z3-1. MS m/z: 368 $(M+1)^+$. A chiral purity was 98%.

Preparation of Intermediate Z4

A structure of intermediate Z4 is shown as follows:

Z4

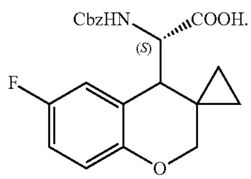

A preparation of intermediate Z4 is performed according to the preparation of intermediate Z3, in which 5-fluoro-salicylaldehyde was taken as a raw material.

Similarly, the intermediate Z4 can be prepared according to a preparation of intermediate Z8 (method B) shown as follows, in which p-fluorophenol was taken as a raw material. MS m/z: 368 $(M+1)^+$.

$^1$H NMR (400 MHz, Methanol-$d_4$) δ 7.37-7.23 (m, 5H), 6.86 (qd, J=9.9, 9.2, 3.1 Hz, 2H), 6.76 (dd, J=8.9, 4.9 Hz, 1H), 5.09-4.95 (m, 2H), 4.66 (dd, J=11.3, 2.0 Hz, 1H), 4.62-4.52 (m, 1H), 3.26 (dd, J=11.4, 1.8 Hz, 1H), 2.41 (dd, J=7.6, 1.6 Hz, 1H), 0.89 (dt, J=9.2, 5.6 Hz, 1H), 0.69 (dt, J=9.3, 5.5 Hz, 1H), 0.59 (ddd, J=9.6, 5.8, 4.3 Hz, 1H), 0.42 (qd, J=6.0, 3.3 Hz, 1H).

Data of the optical rotation is as follows. A temperature was 25° C.; a concentration was 0.002 g/mL; a solvent was methanol; a specific rotation was −128.8°; and a chiral purity was 98%.

Preparation of Intermediate Z5

A preparation of intermediate Z5 is illustrated as follows:

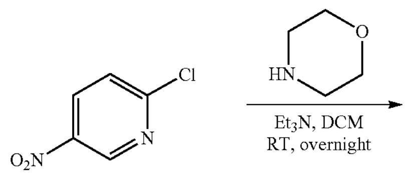

-continued

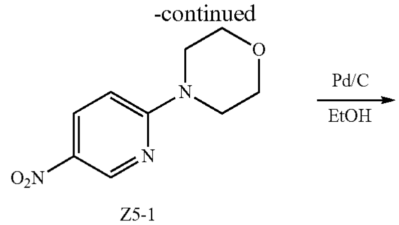

Z5-1

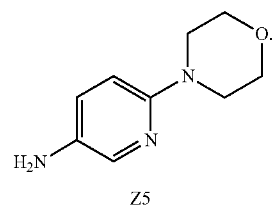

Z5

(S1) Preparation of Intermediate Z5-1

1.98 g (22.71 mmol) of morpholine were added into a DCM (95 mL) solution of 2-chloro-5-nitropyridine (3.0 g, 18.92 mmol) to stir at room temperature overnight. After the reaction was complete, the reaction mixture was quenched with water, and extracted with DCM to collect an organic phase. The organic phase was dried by anhydrous sodium sulfate, filtered, spin-dried and purified by column chromatography to obtain 3.6 g (18.92 mmol) of a yellow solid as intermediate Z5-1 (yield: 91%). MS m/z: 210 $(M+1)^+$.

(S1) Preparation of Intermediate Z5

An ethanol (60 mL) solution of intermediate Z5-1 (3.6 g, 18.92 mmol) was added with 450 mg of Pd/C, and reacted under stirring under a hydrogen atmosphere overnight. After the reaction was complete, the reaction mixture was filtered to remove Pd/C. The filtrate was spin-dried to obtain 3.1 g (18.9 mmol) of intermediate Z5 (yield: 100%). MS m/z: 180 $(M+1)^+$.

Preparation of Intermediate Z7

A structure of intermediate Z7 is shown as follows:

Z7

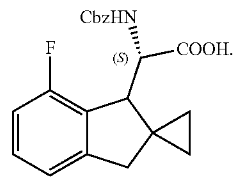

The preparation of intermediate Z7 was performed according to steps (S1)-(S10) of the method A of preparing intermediate Z1, in which the 1-indanone in step (S1) was replaced with 7-fluoro-1-indanone. MS m/z: 370 $(M+1)^+$.

Preparation of Intermediate Z8

A structure of intermediate Z8 is shown as follows:

Z8

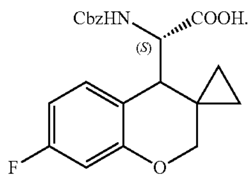

The preparation of intermediate Z8 was performed according to the method A of preparing intermediate Z1, in which 4-fluorosalicylaldehyde was taken as a raw material. MS m/z: 368 $(M+1)^+$. A chiral purity was 98%.

$^1$H NMR (400 MHz, Methanol-$d_4$) δ 7.30 (q, J=7.7, 6.6 Hz, 5H), 7.02 (dd, J=8.5, 6.6 Hz, 1H), 6.52 (dd, J=10.6, 2.6 Hz, 1H), 6.44 (td, J=8.5, 2.7 Hz, 1H), 5.06 (d, J=12.5 Hz, 1H), 4.96 (d, J=12.6 Hz, 1H), 4.68 (dd, J=11.3, 2.0 Hz, 1H), 4.54 (d, J=7.6 Hz, 1H), 3.27 (d, J=1.8 Hz, 1H), 2.38 (d, J=7.5 Hz, 1H), 0.94-0.79 (m, 2H), 0.75-0.64 (m, 1H), 0.63-0.53 (m, 2H), 0.46-0.35 (m, 1H).

The intermediate Z8 can be prepared through method B, which is shown as follows:

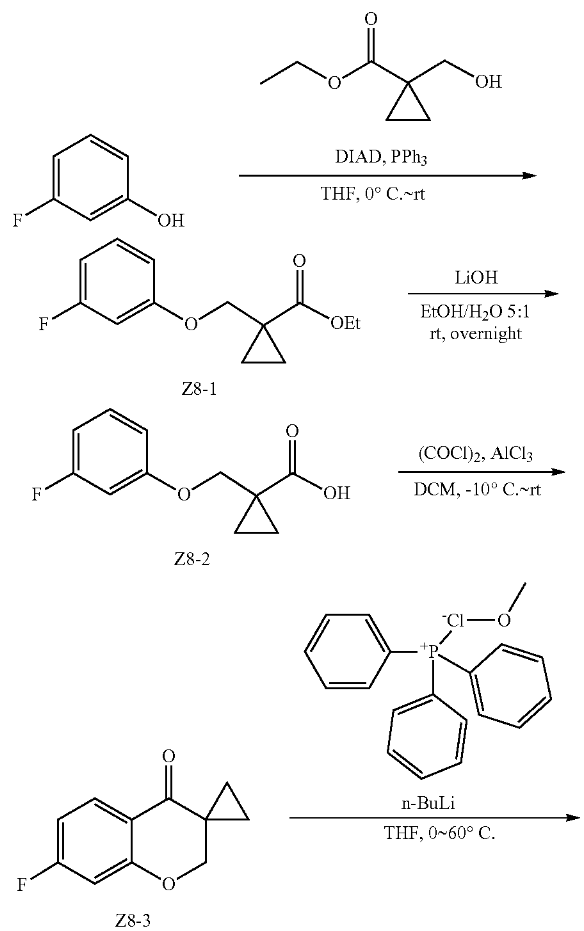

Z8-1

Z8-2

Z8-3

-continued

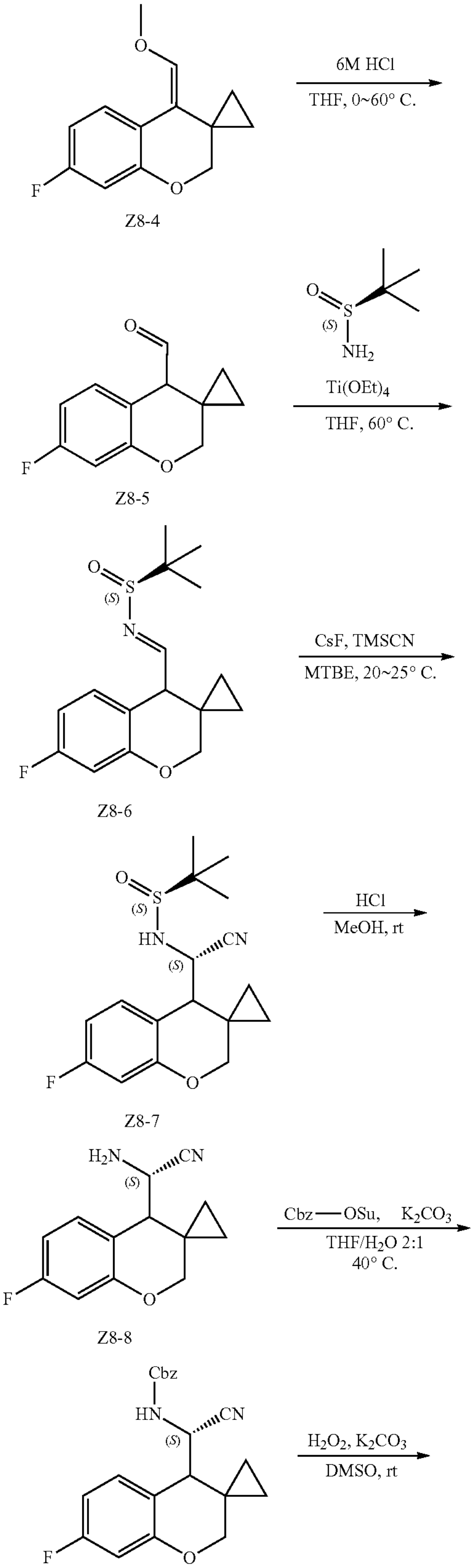

Z8-4

Z8-5

Z8-6

Z8-7

Z8-8

Z8-9

-continued

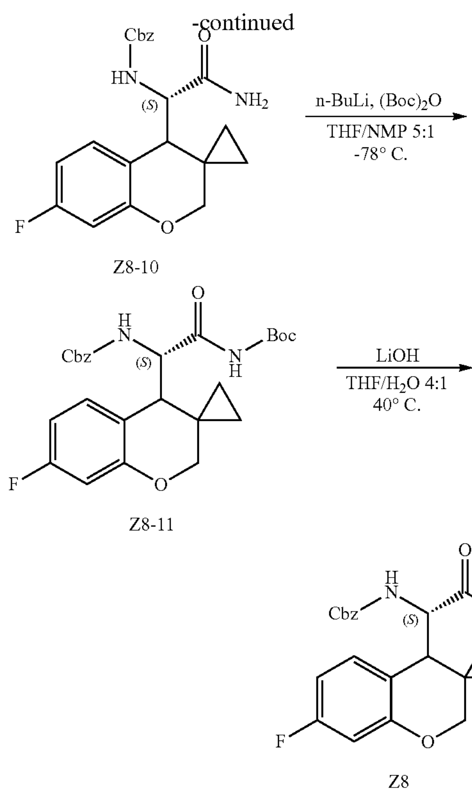

Z8-10

Z8-11

Z8

(S1) Preparation of Intermediate Z8-1

1063 g (9.49 mol) of 3-fluorophenol, 1435 g (9.96 mol) of ethyl 1-(hydroxymethyl)cyclopropanecarboxylate and a THF (15 L) solution of $PPh_3$ (2741 g, 10.46 mol) were mixed at 0° C. to obtain a mixed solution. The mixed solution was dropwise added with 2099 g (10.39 mol) DIAD at 0° C., and then naturally heated to room temperature to react overnight. After the reaction was confirmed by LCMS to be complete, the reaction mixture was concentrated to dry, added with 12 L of a solution with PE:EA=15:1, stirred for 30 min to precipitate a large amount of solid, and passed through a short silica gel column. A silica layer was subjected to drip washing with 15 L of a solution with PE:EA=15:1. The filtrate was concentrated to dry to obtain intermediate Z8-1, which was considered as purify of 100%. MS m/z: 239 $(M+1)^+$.

(S2) Preparation of Intermediate Z8-2

A 95% EtOH (8 L)/$H_2O$ (1.6 L) solution of intermediate Z8-1 (9.49 mol) was added with 988.4 g (23.72 mol) of lithium hydroxide (LiOH) for reaction under stirring at room temperature for 12 h. After the reaction was complete, the reaction mixture was concentrated, diluted by water, adjusted to pH 3-4 with HCl (conc.), and extracted by DCM to obtain an organic phase. The organic phase was washed with water 3 times and then with saturated salt solution 3 time, dried with sodium sulfate, filtered, concentrated to dry, added with petroleum ether to stir for 30 min and filtered to collect a solid. The solid was washed by petroleum ether, and dried to obtain 1495 g (7.12 mol) of intermediate Z8-2 (two-step yield: 75%). MS m/z: 209 $(M+1)^+$. The intermediate Z8-2 required no purification for the next step.

(S3) Preparation of Intermediate Z8-3

1365.2 g of (10.75 mol) $(COCl)_2$ were dropwise added into a DCM (10 L)/DMF (50 mL) solution of intermediate Z8-2 (1505 g 7.16 mol) at 0° C. The reaction mixture was stirred at 0° C. for 3 h under a nitrogen atmosphere, followed by cooling to −10° C. and addition of 1904.56 g (14.32 mol) of $AlCl_3$ in batches. The reaction mixture was slowly heated to room temperature and reacted under stirring for 1 h. The reaction mixture was slowly decanted into ice water to obtain a first organic phase and a water phase. The water phase was extracted by DCM for 3 times to obtain a second organic phase. The first organic phase and the second organic phase were combined, washed with water for 3 times, washed with a saturated sodium bicarbonate solution to weakly alkaline, washed with saturated salt solution for 2 times, dried with anhydrous sodium sulfate, filtered, and concentrated to obtain 1200 g (6.25 mol) of intermediate Z8-3 (yield: 85.3%). The intermediate Z8-3 required no purification for the next step.

(S4) Preparation of Intermediate Z8-4

271 mL (0.677 mol) of n-BuLi (2.5 M in hexane) were dropwise added into an anhydrous THF (1000 mL) solution of (methoxymethyl)triphenylphosphonium chloride (0.677 mol, 232.1 g) under ice bath and nitrogen atmosphere. The reaction mixture was stirred at 0° C. for 1 h until it turned dark brown, followed by dropwise adding with a THF solution of the intermediate Z8-3 (100 g, 0.521 mol). The reaction mixture was heated to 60° C. for reaction under stirring for 4 h. After the reaction was complete, the reaction mixture was cooled to room temperature, quenched by a 30% $NH_4Cl$ aqueous solution, extracted with ethyl acetate to collect an organic phase. The organic phase was dried with anhydrous sodium sulfate, filtered and spin-dried to obtain a crude product. The crude product was subjected to separation and purification by using a silica gel column (0-10%, PE/EA) to obtain 114.74 g (0.521 mol) of a clarified oil-like substance as intermediate Z8-4 (yield: 100%).

(S5) Preparation of Intermediate Z8-5

A THF (570 mL) solution of intermediate Z8-4 (114 g, 0.518 mmol) was cooled to 0° C., and added with 6 M HCl (570 mL) at a temperature controlled at 10° C. The reaction mixture was heated to 60° C. and reacted under stirring for 5 h. After the reaction was complete, the reaction mixture was extracted with ethyl acetate to collect an organic phase. The organic phase was washed by a 10% sodium bicarbonate aqueous solution for 1 time, washed by a saturated sodium chloride solution for one time, dried by anhydrous sodium sulfate and concentrated to obtain 106.8 g (0.518 mol) of an oil-like substance as intermediate Z8-5 (yield: 100%). The intermediate Z8-5 required no purification for the next step.

(S6) Preparation of Intermediate Z8-6

106.8 g (0.518 mol) of intermediate Z8-5, 62.78 g (0.518 mol) of (S)-(+)-tert-butylsulfinamide, 1000 mL of anhydrous THF and 236.3 g (1.036 mol) of $(EtO)_4Ti$ were mixed in a 2000 mL single-necked flask under a nitrogen atmosphere. The reaction mixture was heated to 60° C. and reacted under stirring for 5 h. Then the reaction mixture was cooled to room temperature, added with water and ethyl acetate and filtered to remove an insoluble matter. The filtrate was subjected to stratification. A water layer was collected and extracted with ethyl acetate for 2 times. Organic phases were combined, concentrated to obtain a brown oil-like substance. The brown oil-like substance was subjected to separation and purification by silica gel column (eluent: PE/EA 0-50%) to obtain 128 g (0.414 mol) of a light yellow solid as intermediate Z8-6 (yield: 80%). MS m/z: 310 $(M+1)^+$.

(S7) Preparation of Intermediate Z8-7

A MTBE (2560 mL) solution of intermediate Z8-6 (128 g, 0.414 mol) was added with 125.78 g (0.828 mol) of CsF and 82.1 g (0.828 mol) of TMSCN at room temperature. The reaction mixture was reacted under stirring at 20-25° C. overnight. After the reaction was complete, large amounts of solids were precipitated. The reaction mixture was filtered to collect the solids. The solids were dissolved with water and ethyl acetate, subjected to stratification to obtain a first organic phase and a water phase. The water phase was extracted with ethyl acetate 2 times to obtain a second organic phase. The first organic phase and the second organic phase were combined, dried with anhydrous sodium sulfate and filtered. The filtrate was spin-dried to obtain a crude product. The crude product was added with MTBE (5 v/m), heated to reflux beating for 1 hour, cooled to room temperature, stirred for 2 h and filtered to obtain 37.6 g (0.112 mol) of a white solid as intermediate Z8-7 (yield: 27%). MS m/z: 337 $(M+1)^+$.

(S8) Preparation of Intermediate Z8-8

A MeOH (376 mL) solution of intermediate Z8-7 (37.6 g, 0.112 mol) was dropwise added with HCl/EA (4 M, 56 ml, 0.224 mol). The reaction mixture was reacted under stirring for 2 h. After the reaction was complete, the reaction mixture was concentrated to obtain a crude product. The crude product was washed with MTBE under beating 1 time, filtered and dried to obtain 25.52 g (0.110 mol) of intermediate Z8-8 (yield: 98%). MS m/z: 233 $(M+1)^+$.

(S9) Preparation of Intermediate Z8-9

A THF (153 mL)/$H_2O$ (77 mL) solution of intermediate Z8-8 (25.52 g, 0.110 mol) was added with 45.6 g (0.330 mol) of $K_2CO_3$ and 54.82 g (0.220 mol) of Cbz-Osu for reaction under stirring at 40° C. overnight. After the reaction was complete, the reaction mixture was extracted with ethyl acetate to collect an organic phase. The organic phase was concentrated to obtain a crude product. The crude product was subjected to separation and purification by MPLC to obtain 38.66 g (0.106 mol) of an oil-like substance as intermediate Z8-9 (yield: 96.02%). MS m/z: 367 $(M+1)^+$.

(S10) Preparation of Intermediate Z8-10

A dimethyl sulfoxide (DMSO) (387 mL) solution of intermediate Z8-9 (38.66 g, 0.106 mol) was added with 14.65 g (0.106 mol) of $K_2CO_3$, and dropwise added with 24 g (0.212 mol) of $H_2O_2$ (30%). The reaction mixture was reacted under stirring at 25° C. for 2 h. After the reaction was complete, the reaction mixture was diluted with plenty of water to precipitate a large amount of white solid. The white solid was filtered. The filter cake was fully drenched with water, dissolved by an appropriate amount of ethyl acetate, washed with water by 1 time, washed with a saturated salt solution 1 time, dried with anhydrous sodium sulfate and filtered. The filtrate was concentrated to obtain 39.93 g (0.104 mol) of a solid as intermediate Z8-10 (yield: 98%). MS m/z: 385 $(M+1)^+$.

(S11) Preparation of Intermediate Z8-11

An anhydrous THF (400 mL)/NMP (80 mL) solution of intermediate Z8-10 (39.93 g, 0.104 mol) was dropwise added with n-BuLi (96 mL, 0.239 mol, 2.5 M in hexane) at −78° C. under a nitrogen atmosphere. The reaction mixture was reacted under stirring at −78° C. for 1 h, and added with a THF solution of (Boc)2O (29.06 g, 0.135 mol) followed by reaction under stirring for 1 h. After the reaction was complete, the reaction mixture was quenched with a cooled 30% $NH_4Cl$ aqueous solution, extracted with ethyl acetate, followed by concentrated extraction to obtain 50.4 g (0.104 mol) of intermediate Z8-11 (yield: 100%). The intermediate Z8-11 required no purification for the next step. MS m/z: 485 $(M+1)^+$.

(S12) Preparation of Intermediate Z8-12

A THF (806 mL)/NMP (201 mL) solution of intermediate Z8-11 (50.4 g, 0.104 mol) was added with 8.67 g (0.208 mol) of LiOH monohydrate. The reaction mixture was heated to 40° C. and reacted under stirring overnight. After the reaction was complete, a first water layer was adjusted to pH=3-4 by 2 M HCl, subjected to stratification to obtain a second water layer and a first organic layer. The second water layer was extracted with ethyl acetate 2 times to collect a second organic layer. The first organic layer and the second organic layer were combined, washed by a saturated salt solution 1 time, dried with anhydrous sodium sulfate, filtered and subjected to vacuum distillation to remove a solvent to obtain a crude product. The crude product was dissolved in ethyl acetate, dropwise added with 12.6 g (0.125 mol) of diisopropylamine under stirring at room temperature, followed by reaction under stirring for 2 h and filtration to obtain a white solid. The white solid was dissolved by an appropriate amount of water and ethyl acetate to collect a water layer. The water layer was adjusted to pH=3-4 by 2 M HCl, and subjected to stratification to collect a first organic phase. The first organic phase was washed by a saturated salt solution, dried by anhydrous sodium and filtered to collect a second organic phase. The second organic phase was subjected to concentrated to dry to obtain 27 g (70 mmol) of pure intermediate Z8 (two-step yield: 67.3%). MS m/z: 368 $(M+1)^+$.

$^1$H NMR (400 MHz, Methanol-$d_4$) δ 7.30 (q, J=7.7, 6.6 Hz, 5H), 7.02 (dd, J=8.5, 6.6 Hz, 1H), 6.52 (dd, J=10.6, 2.6 Hz, 1H), 6.44 (td, J=8.5, 2.7 Hz, 1H), 5.06 (d, J=12.5 Hz, 1H), 4.96 (d, J=12.6 Hz, 1H), 4.68 (dd, J=11.3, 2.0 Hz, 1H), 4.54 (d, J=7.6 Hz, 1H), 3.27 (d, J=1.8 Hz, 1H), 2.38 (d, J=7.5 Hz, 1H), 0.94-0.79 (m, 2H), 0.75-0.64 (m, 1H), 0.63-0.53 (m, 2H), 0.46-0.35 (m, 1H).

Data of the optical rotation is as follows. A temperature was 25° C.; a concentration was 0.002 g/100 mL; a solvent was methanol; a specific rotation was −132.8°; and a chiral purity was 98%.

Preparation of Intermediate Z9

A structure of the intermediate Z9 is as follows:

Z9

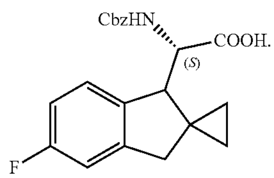

The preparation of intermediate Z9 was performed according to steps (S1)-(S10) of the method A of preparing intermediate Z1, in which the 1-indanone in step (S1) was replaced with 5-fluoro-1-indanone. MS m/z: 370 $(M+1)^+$.

Preparation of Intermediate Z10

A preparation of intermediate Z10 is illustrated as follows:

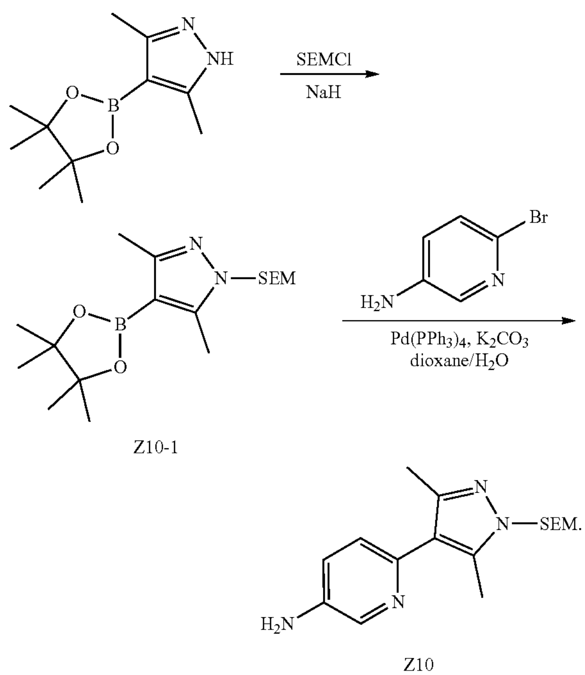

Z10-1

Z10

(S1) Preparation of Intermediate Z10-1

A DMF (800 mL) solution of 3,5-dimethylpyrazole-4-boronic acid pinacol ester (50 g, 225.13 mmol) was added with 13.51 g (337.70 mmol) of NaH (purity of 60%) under an ice bath. The reaction mixture was stirred at 0° C. for 1 h, dropwise added with 39.48 g (236.39 mmol) of SEMCl, and then heated to room temperature for reaction under stirring for 20 h. The reaction mixture was quenched by slowly adding water, extracted with ethyl acetate, washed by a salt solution and dried with anhydrous sodium sulfate. An organic phase was combined and subjected to spin dry to obtain a crude product. The crude product was subjected to separation and purification by a silica gel column to obtain 73.5 g (208.60 mmol) of intermediate Z10-1 (yield: 92.66%). MS m/z: 353 $(M+1)^+$.

(S2) Preparation of Intermediate Z10

A dioxane (75 mL)/$H_2O$ (15 mL) solution of 6-bromo-3-aminopyridine (3 g, 17.34 mmol) was added with 10.47 g (20.81 mmol) of intermediate Z10-1, 4.79 g (34.68 mmol) of $K_2CO_3$ and 1.20 g (1.04 mmol) of tetrakis(triphenylphosphine)palladium ($Pd(PPh_3)_4$). The reaction mixture was heated to 90° C. for reaction under stirring under a nitrogen atmosphere overnight. After the reaction was complete, the reaction mixture was quenched by a salt solution, extracted with ethyl acetate to collect an organic phase. The organic phase was washed by a saturated salt solution, dried with anhydrous sodium sulfate and filtered. The filtrate was concentrated to obtain a crude product. The crude product was subjected to separation and purification by a silica gel column (EtOAc/Pet.ether/DCM=1/2/1, v/v) to obtain 5.1 g (12.81 mmol) of intermediate Z10-1 (yield: 73.88%, purity: 80%). MS m/z: 391 $(M+1)^+$.

$^1H$ NMR (400 MHz, Chloroform-d) δ 8.32 (s, 1H), 7.16 (d, 2H), 5.40 (s, 2H), 3.62 (t, J=8.9, 7.6 Hz, 2H), 2.44 (s, 3H), 2.33 (s, 3H), 0.93 (t, 2H).

Preparation of Intermediate Z11

A structure of the intermediate Z11 is as follows:

Z11

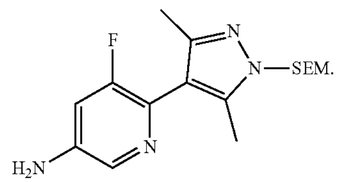

The preparation of intermediate Z11 was performed according to steps (S1)-(S2) of the preparation of intermediate Z10, in which the 6-bromo-3-aminopyridine in step (S2) was replaced with 5-amino-2-bromo-3-fluoropyridine. MS m/z: 337 $(M+1)^+$.

$^1H$ NMR (400 MHz, Chloroform-d) δ 8.18 (s, 1H), 6.92 (d, J=10.7 Hz, 1H), 5.40 (s, 2H), 3.63 (t, 2H), 2.33 (s, 3H), 2.24 (s, 3H), 0.92 (t, 2H), 0.00 (s, 9H).

Preparation of Intermediate Z12

A preparation of intermediate Z12 is illustrated as follows:

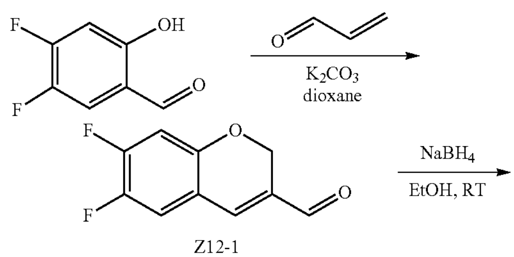

Z12-1

-continued

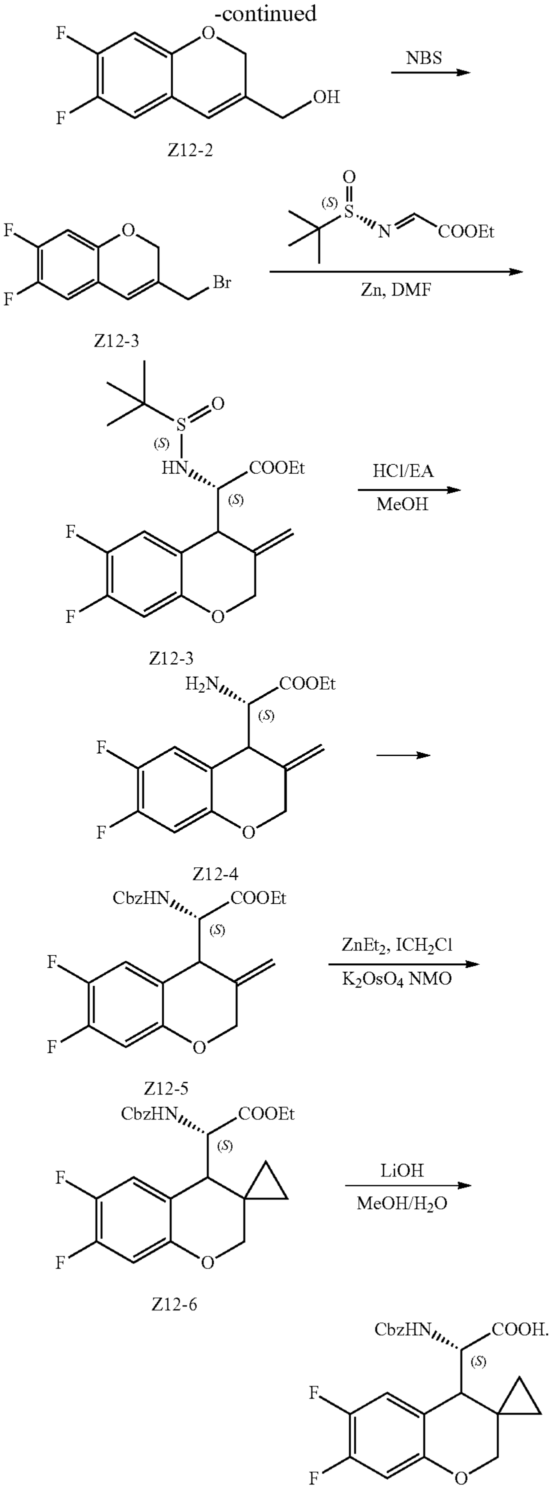

Z12-2, Z12-3, Z12-3, Z12-4, Z12-5, Z12-6, Z12

(S1) Preparation of Intermediate Z12-1

A dioxane (230 mL) solution of 2-hydroxy-4,5-difluorobenzaldehyde (30 g, 190 mmol) was successively added with 28.9 g (209 mmol) of $K_2CO_3$ and 14.9 g (266 mmol) of acrolein. The reaction mixture was heated for reflux reaction for 8 h. After the reaction was complete, the reaction mixture was cooled to room temperature, diluted with water and extracted with ethyl acetate to collect an organic phase. The organic phase was dried with anhydrous sodium sulfate and concentrated to obtain a crude product of intermediate Z12-1 (30 g, 153 mmol). The intermediate Z12-1 required no purification for the next step.

(S2) Preparation of Intermediate Z12-2

An ethanol (400 mL) solution of the intermediate Z12-1 (30 g, 153 mmol) was added in batches with 6.95 g (183.5 mmol) of $NaBH_4$. The reaction mixture was reacted under stirring for 20 min. After the reaction was complete, the reaction mixture was diluted with ethyl acetate, quenched with 1N HCl (50 mL) and water (100 mL), and separated to collect an organic phase. The organic phase was dried with anhydrous sodium sulfate and concentrated to obtain a crude product. The crude product was subjected to separation and purification by using a silica gel column to obtain 22.1 g (111.6 mmol) of intermediate Z12-2. MS m/z: 199.0 $(M+1)^+$.

(S3)-(S8) Preparation of Intermediate Z12

Steps (S3)-(S2) of the preparation of intermediate Z12 was performed according to steps (S5)-(S10) of the method A of preparing intermediate Z1, in which the intermediate Z1-4 in step (S5) was replaced with intermediate Z12-2.

$^1$H NMR (400 MHz, Methanol-$d_4$) δ 7.29 (q, J=7.1, 6.6 Hz, 5H), 6.97 (dd, J=11.2, 9.0 Hz, 1H), 6.67 (dd, J=12.0, 7.0 Hz, 1H), 5.07 (d, J=12.6 Hz, 1H), 4.98 (d, J=12.5 Hz, 1H), 4.66 (dd, J=11.4, 2.0 Hz, 1H), 4.55 (d, J=7.8 Hz, 1H), 3.28 (d, J=10.7 Hz, 1H), 2.37 (d, J=7.7 Hz, 1H), 0.89 (dt, J=9.3, 5.6 Hz, 1H), 0.70 (dt, J=10.9, 5.6 Hz, 1H), 0.59 (dt, J=9.8, 5.3 Hz, 1H), 0.42 (s, 1H).

Data of the optical rotation is as follows. A temperature was 25° C.; a concentration was 0.002 g/100 mL; a solvent was methanol; a specific rotation was −142.8°; and a chiral purity was 98%.

Preparation of Intermediate Z12 (Method B)

A method B for preparing of intermediate Z12 is illustrated as follows:

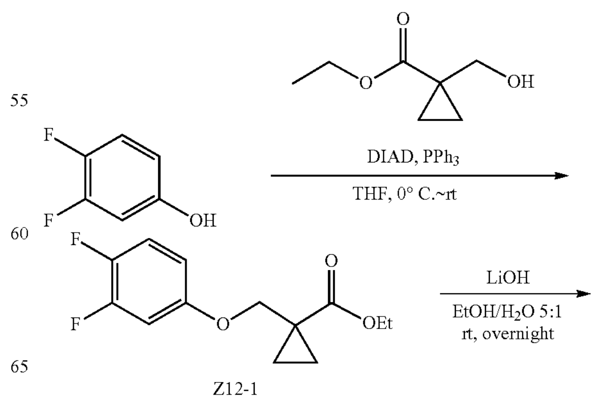

Z12-1

-continued

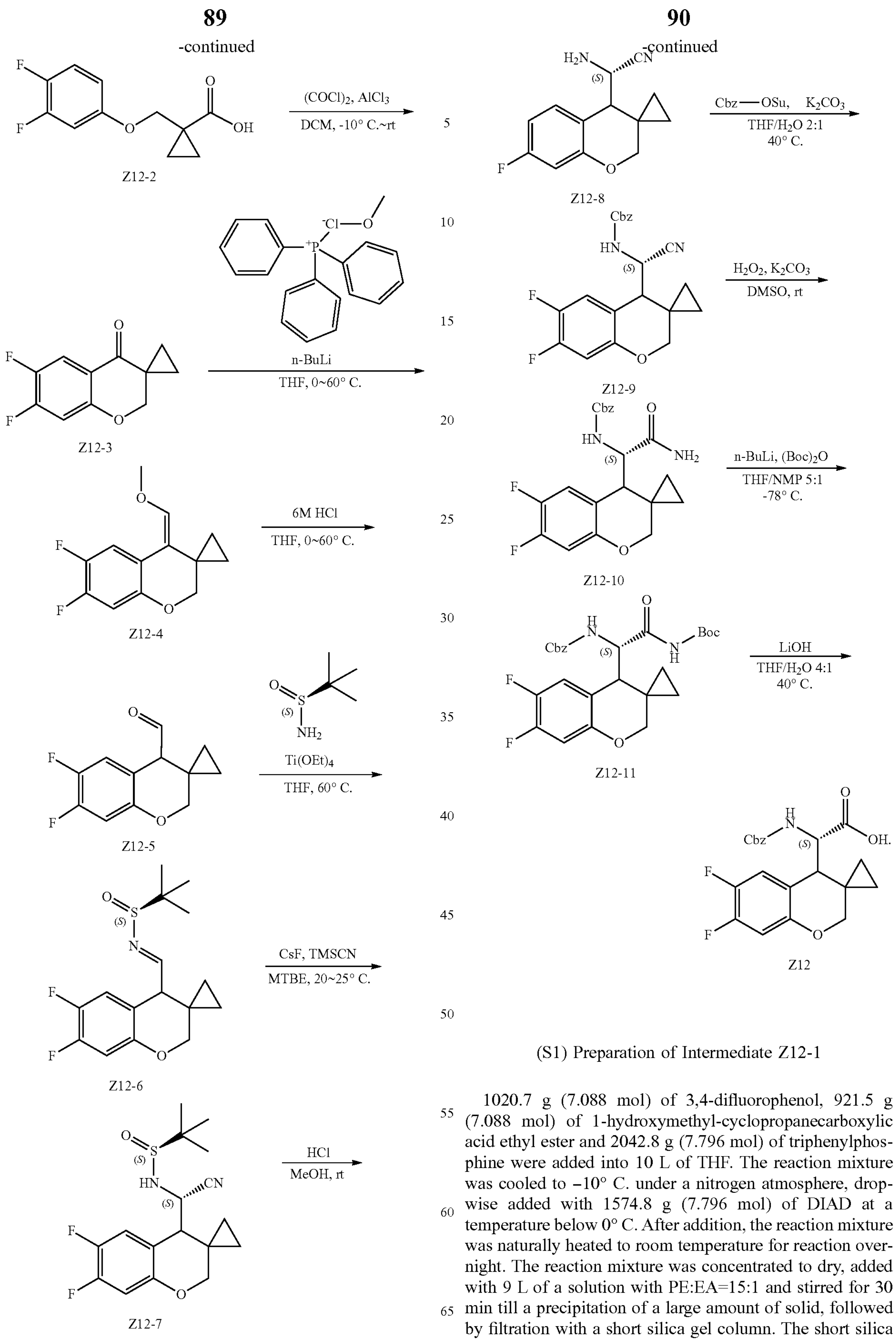

Z12-2

Z12-3

Z12-4

Z12-5

Z12-6

Z12-7

-continued

Z12-8

Z12-9

Z12-10

Z12-11

Z12

(S1) Preparation of Intermediate Z12-1

1020.7 g (7.088 mol) of 3,4-difluorophenol, 921.5 g (7.088 mol) of 1-hydroxymethyl-cyclopropanecarboxylic acid ethyl ester and 2042.8 g (7.796 mol) of triphenylphosphine were added into 10 L of THF. The reaction mixture was cooled to −10° C. under a nitrogen atmosphere, dropwise added with 1574.8 g (7.796 mol) of DIAD at a temperature below 0° C. After addition, the reaction mixture was naturally heated to room temperature for reaction overnight. The reaction mixture was concentrated to dry, added with 9 L of a solution with PE:EA=15:1 and stirred for 30 min till a precipitation of a large amount of solid, followed by filtration with a short silica gel column. The short silica gel column was drenched with 12 L of a solution with PE:EA=15:1. The filtrate was concentrated to dry to obtain the intermediate Z12-1, which was considered as purify of 100%. MS m/z: 257 $(M+1)^+$.

(S2) Preparation of Intermediate Z12-2

7.088 mol of the intermediate Z12-1 was added into a solution having 6 L of 95% ethanol and 1.2 L of water. The reaction mixture was added with 738.2 g (17.72 mol) of LiOH and reacted under stirring at room temperature overnight. Then the reaction mixture was subjected to vacuum concentration to dry, and dissolved with 10 L of water. The reaction mixture was extracted by a solution with PE:EA=1:1 to obtain a first organic phase and a water phase. The water phase was adjusted to pH=3 by a concentrated hydrochloric acid solution, and extracted with ethyl acetate 3 times to obtain a second organic phase. The first organic phase and the second organic phase was combined, washed by water for 3 times, washed by saturated salt solution for 3 times, dried with sodium sulfate, filtered and concentrated to dry to obtain a mixture. The mixture was added into 3 L of petroleum ether to stir for 30 min and filtered to collect a solid. The solid was washed with petroleum ether and dried to obtain 1272.1 g (5.5747 mol) of intermediate Z12-2 (two-step yield: 78.4%). MS m/z: 227 $(M+1)^+$.

(S3) Preparation of Intermediate Z12-3

1271.1 g (5.578 mol) of intermediate Z12-2 were added in 5 L of DCM. The reaction mixture was cooled to −10° C. under a nitrogen atmosphere, and dropwise added with 1062.6 g (8.36 mol) of oxalyl chloride. The reaction mixture was controlled below 0° C., reacted for 3 h, cooled to −10° C., and added in batches with 1483.8 g (11.156 mol) of aluminum trichloride. Then the reaction mixture was naturally heated to room temperature for reaction overnight. After the reaction was complete, the reaction mixture was slowly decanted into ice water to obtain a first organic phase and a water phase. The water phase was extracted 3 times with DCM to collect a second organic phase. The first organic phase and the second organic phase was combined, washed 3 times with water, washed with a saturated sodium bicarbonate solution to weakly alkaline, washed with a saturated salt solution for 2 times, dried with sodium sulfate, filtered and concentrated to obtain 1100 g (5.234 mol) of intermediate Z12-3 (yield: 93.9%).

(S4) Preparation of Intermediate Z12-4

207 mL of n-BuLi (2.5 M in hexane, 517.76 mmol) were dropwise added into an anhydrous THF (800 mL) solution of (methoxymethyl)triphenylphosphonium chloride (196 g, 517.76 mmol) under ice bath and nitrogen atmosphere. The reaction mixture was reacted under stirring at 0° C. for 1 h. After the reaction mixture turned dark brown, an anhydrous THF solution of the intermediate Z12-3 (80 g, 380.63 mmol) was dropwise added into the reaction mixture. After the reaction was complete, the reaction mixture was cooled to room temperature, quenched with a 30% $NH_4Cl$ aqueous solution and extracted with ethyl acetate to collect an organic phase. The organic phase was dried with anhydrous sodium sulfate, filtered and spin-dried to obtain a crude product. The crude product was purified by passing a column with PE:EA=10:1 to obtain 72.1 g (302.84 mmol) of a clarified oil-like substance as intermediate Z12-4 (yield: 79.56%). MS m/z: 239 $(M+1)^+$.

(S5) Preparation of Intermediate Z12-5

6 M HCl (350 mL) were added into a THE (350 mL) solution of the intermediate Z12-4 (72.1 g, 302.84 mmol). The reaction mixture was heated to 60° C. for reaction under stirring for 5 h. After the reaction was complete, the reaction mixture was extracted with ethyl acetate to collect an organic phase. The organic phase was dried and concentrated to obtain 64.5 g (287.69 mol) of an oil-like substance as intermediate Z12-5 (yield: 95.0%). The intermediate Z12-5 required no purification for the next step.

(S6) Preparation of Intermediate Z12-6

70 g (312.22 mmol) of the intermediate Z12-5, 37.8 g (311.88 mmol) of (S)-(+)-tert-butylsulfinamide, 700 mL of THE and 214.0 g (938.59 mmol) of $Ti(OEt)_4$ were mixed to dissolve in a 2 L single-necked flask under a nitrogen atmosphere. The reaction mixture was heated to 60° C. for reaction under stirring for 5 h. Then the reaction mixture was cooled to room temperature, added with water and ethyl acetate and filtered to remove an insoluble matter. The filtrate was subjected to stratification to collect an organic phase. The organic phase was concentrated to obtain a brown oil-like substance. The brown oil-like substance was purified by passing a silica gel column (eluent: PE/EA 0-50%) to obtain 67.7 g (206.79 mmol) of a light yellow solid as intermediate Z12-6 (yield: 66.23%). MS m/z: 328 $(M+1)^+$.

(S7) Preparation of Intermediate Z12-7

84.0 g (556.29 mmol) of CsF were added into a tert-butyl methyl ether (TBME) solution (1.8 L) of the intermediate Z12-6 (91 g, 277.96 mmol). 67.5 g (556.93 mmol) of TMSCN were dropwise added into the reaction mixture under a nitrogen atmosphere. The reaction mixture heated to room temperature to react under stirring overnight. After the reaction was complete, the reaction mixture was filtered. A filter cake was extracted with ethyl acetate and water to collect an organic phase. The organic phase was concentrated to dry, added with 500 mL of TBME and purified under beating to obtain 39.97 g (112.78 mmol) of a white solid as intermediate Z12-7 (yield: 40.57%). MS m/z: 355 $(M+1)^+$.

(S8) Preparation of Intermediate Z12-8

77 mL of HCl/EA (4 M, 308 mmol) were added into a MeOH (500 mL) solution of the intermediate Z12-7 (36.5 g, 102.99 mmol). The reaction mixture was reacted under stirring at room temperature for 2 h. After the reaction was complete, the reaction mixture was concentrated to obtain a crude product. The crude product was washed under beating with 300 mL PE/EA=10/1, filtered and dried to obtain 29 g (101.22 mmol) of intermediate Z12-8 (yield: 92.28%). MS m/z: 251 $(M+1)^+$.

(S9) Preparation of Intermediate Z12-9

28.94 g (209.41 mmol) of $K_2CO_3$ and 34.79 g (139.61 mmol) of CbzOSu were added into a THE (200 mL)/$H_2O$ (100 mL) solution of the intermediate Z12-8 (20 g, 69.81 mmol). The reaction mixture was reacted at 40° C. under stirring overnight. After the reaction was complete, the reaction mixture was extracted with ethyl acetate to collect an organic phase. The organic phase was concentrated to obtain a crude product. The crude product was purified by PE/EA=5/1 to obtain 25.52 g (66.31 mmol) of an oil-like substance as intermediate Z12-9 (yield: 95.00%). MS m/z: 385 $(M+1)^+$.

(S10) Preparation of Intermediate Z12-10

A DMSO (200 mL) solution of the intermediate Z12-9 (25 g, 64.96 mmol) were added with 8.89 g (64.98 mmol) of $K_2CO_3$, and then dropwise added with 30% $H_2O_2$ (4.72 g, 129.92 mmol). The reaction mixture was reacted at room temperature under stirring overnight. After the reaction was complete, the reaction mixture was diluted with water and extracted with ethyl acetate to collect an organic phase. The organic phase was concentrated and purified by PE/EA=5/1 to obtain 17.33 g (43.07 mmol) of a solid as intermediate Z12-10 (yield: 66.30%). MS m/z: 403 $(M+1)^+$.

(S11) Preparation of Intermediate Z12-11

46.8 mL of n-BuLi (117.0 mmol, 2.5 M in hexane) were dropwise added into an anhydrous THE (200 mL)/NMP (40 mL) solution of the intermediate Z12-10 (21.4 g, 53.18 mmol) at −78° C. under a nitrogen atmosphere. The reaction mixture was reacted at −78° C. under stirring for 1 h, and then added with an anhydrous THF solution of $(Boc)_2O$ (14.88 g, 69.14 mmol) for reaction under stirring for 1 h. After the reaction was complete, the reaction mixture was quenched with 30% $NH_4Cl$ aqueous solution, extracted with ethyl acetate and subjected to concentrated extraction to obtain intermediate Z12-11. MS m/z: 503 $(M+1)^+$. A yield of the intermediate Z12-11 was considered as 100% for the next step.

(S12) Preparation of Intermediate Z12

4.43 g (106.33 mmol) of lithium hydroxide monohydrate ($LiOH \cdot H_2O$) were added int a THF (400 mL)/$H_2O$ (100 mL) solution of the intermediate Z12-11 (26.72 g, 53.18 mmol). The reaction mixture was heated to 40° C. to react under stirring overnight. After the reaction was complete, the reaction mixture was subjected to vacuum distillation to remove a solvent to obtain a crude product. The crude product was dissolved with water. The solution was adjusted to weakly acidic with hydrochloric acid, extracted with ethyl acetate, concentrated to dry and purified by MPLC to obtain 19.09 g (47.33 mmol) of intermediate Z12 (yield: 89.0%). MS m/z: 404 $(M+1)^+$.

$^1H$ NMR (400 MHz, Methanol-$d_4$) δ 7.29 (q, J=7.1, 6.6 Hz, 5H), 6.97 (dd, J=11.2, 9.0 Hz, 1H), 6.67 (dd, J=12.0, 7.0 Hz, 1H), 5.07 (d, J=12.6 Hz, 1H), 4.98 (d, J=12.5 Hz, 1H), 4.66 (dd, J=11.4, 2.0 Hz, 1H), 4.55 (d, J=7.8 Hz, 1H), 3.28 (d, J=10.7 Hz, 1H), 2.37 (d, J=7.7 Hz, 1H), 0.89 (dt, J=9.3, 5.6 Hz, 1H), 0.70 (dt, J=10.9, 5.6 Hz, 1H), 0.59 (dt, J=9.8, 5.3 Hz, 1H), 0.42 (s, 1H).

Data of the optical rotation is as follows. A temperature was 25° C.; a concentration was 0.002 g/100 mL; a solvent was methanol; a specific rotation was −142.8°; and a chiral purity was 98%.

Preparation of Intermediate Z13 (Method A)

A preparation of intermediate Z13 (method A) is illustrated as follows:

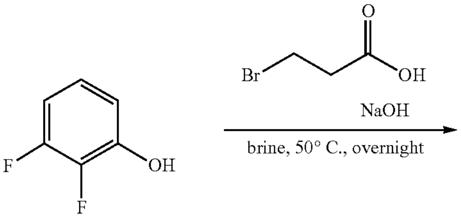

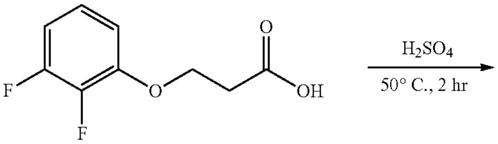

Z13-1

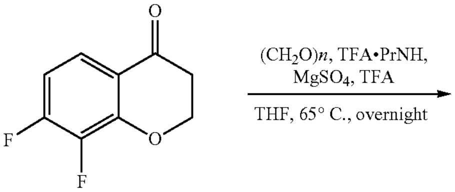

Z13-2

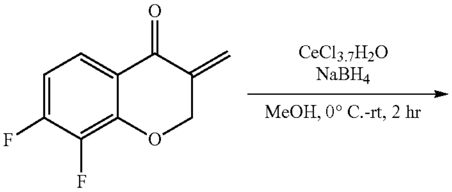

Z13-3

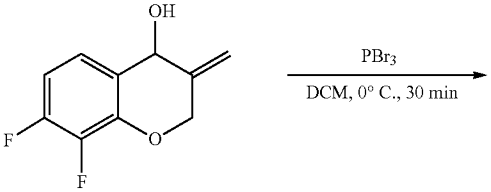

Z13-4

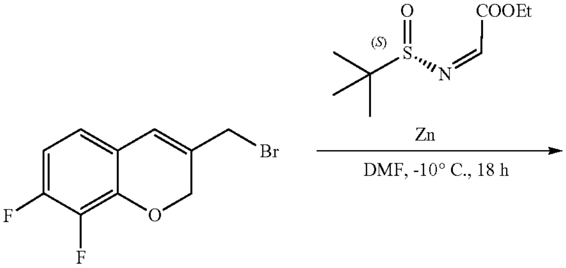

Z13-5

-continued

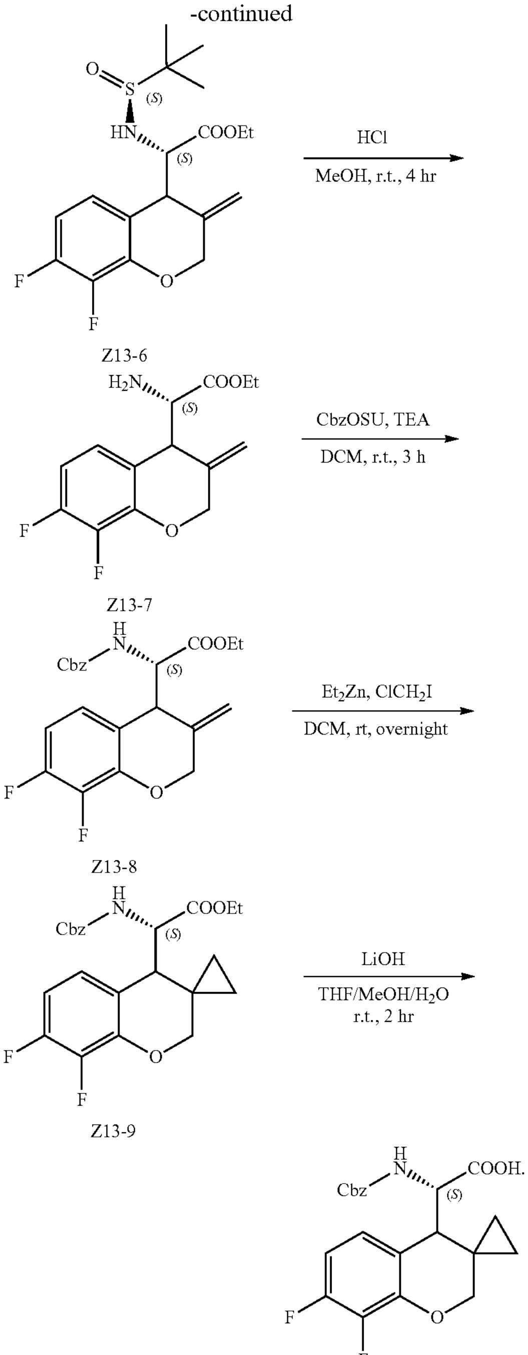

Z13-6

Z13-7

Z13-8

Z13-9

Z13

(S1) Preparation of Intermediate Z13-1

14.76 g (368.97 mmol) of sodium hydroxide (NaOH) were dissolved with 60 mL of a saturated salt solution. The reaction mixture was added with 15 g (115.30 mmol) of 2,3-difluorophenol at 0° C. and slowly dropwise added with 22.93 g (149.89 mmol) of 3-bromopropionic acid. After addition, the reaction mixture was heated to 50° C. for reaction under stirring overnight. After the reaction was complete, the reaction mixture was adjusted to pH=4 with 6N HCl and extracted with ethyl acetate to collected an organic phase. The organic phase was washed with a saturated salt solution, dried with anhydrous sodium sulfate, filtered and spin-dried to obtain a crude product. The crude product was purified by using a silica gel column (PE:EA=5:1) to obtain 8 g (39.57 mmol) of intermediate Z13-1 (yield: 34.32%). MS m/z: 203 $(M+1)^+$.

$^1$H NMR (400 MHz, Chloroform-d) δ 6.90 (m, 1H), 6.71 (m, 2H), 4.25 (t, J=6.3 Hz, 2H), 2.83 (t, J=6.3 Hz, 2H).

(S2) Preparation of Intermediate Z13-2

8 g (39.57 mmol) of the intermediate Z13-1 were slowly added to a concentrated sulfuric acid solution (13 mL) in batches under ice bath. The reaction mixture was slowly heated to room temperature for reaction under stirring for 1.5 h, and then cooled to 0° C. and decanted into ice water for quenching. Then the reaction mixture was extracted with ethyl acetate (50 mL×2) to collect an organic phase. The organic phase was washed with 80 mL of a saturated salt solution, dried with anhydrous sodium sulfate, filtered and concentrated to obtain a crude product. The crude product was purified by using a silica gel column (PE:EA=8:1) to obtain 3 g (16.29 mmol) of intermediate Z13-2 (yield: 41.17%). MS m/z: 185 $(M+1)^+$.

$^1$H NMR (400 MHz, DMSO-d6) δ 7.63 (ddd, J=8.6, 6.0, 2.2 Hz, 1H), 7.12 (ddd, J=10.1, 9.0, 6.7 Hz, 1H), 4.71 (t, J=6.4 Hz, 2H), 2.87 (t, J=6.4 Hz, 2H).

(S3) Preparation of Intermediate Z13-3

6.51 g (195.50 mmol) of $(CH_2O)_n$, 2.93 g (24.44 mmol) of $MgSO_4$ and 10.52 g (48.88 mmol) of TFA·PrNH were successively added into a THF (120 mL) solution of the intermediate Z13-2 (4.5 g, 24.44 mmol). The reaction mixture was reacted at room temperature under stirring for 5 min, added with 5.57 g (48.88 mmol) of TFA and heated to 65° C. for reaction under stirring overnight. After the reaction was complete, the reaction mixture was diluted with 50 mL of water and extracted with ethyl acetate (2×80 mL) to collect an organic phase. The organic phase was washed with a saturated salt solution, dried with anhydrous sodium sulfate, filtered and concentrated to obtain a crude product. The crude product was purified by using a silica gel column (PE:EA=20:1) to obtain 3.69 g (18.79 mmol) of intermediate Z13-3 (yield: 76.87%).

(S4) Preparation of Intermediate Z13-4

6.98 g (18.76 mmol) of cerium chloride heptahydrate ($CeCl_3·7H_2O$) were added into a MeOH (94 mL) solution of the intermediate Z13-3 (3.68 g, 18.76 mmol) at 0° C. The reaction mixture was stirred at 0° C. for 8 min, added in batches with 2.13 g (56.28 mmol) of $NaBH_4$ and then reacted under stirring at room temperature for 1.5 h. After the reaction was complete, the reaction mixture was quenched with a saturated ammonium chloride aqueous solution and extracted with ethyl acetate (80 mL×2) to collect an organic phase. The organic phase was washed with a salt solution, dried with anhydrous sodium sulfate, filtered and concentrated to obtain a crude product. The crude product was purified with a silica gel column (PE:EA=5:1) to obtain 2.86 g (14.45 mmol) of intermediate Z13-4 (yield: 77.01%). MS m/z: 199 $(M+1)^+$.

$^1$H NMR (400 MHz, DMSO-$d_6$) δ 7.24-7.15 (m, 1H), 7.02-6.87 (m, 1H), 5.97 (d, J=6.2 Hz, 1H), 5.36 (dt, J=21.0, 1.6 Hz, 2H), 5.11 (d, J=6.1 Hz, 1H), 4.84-4.71 (m, 2H).

(S5) Preparation of Intermediate Z13-5

A DCM (30 mL) solution of PBr3 (5.11 g, 18.89 mmol) was dropwise added into a DCM (90 mL) solution of intermediate Z13-4 (4.68 g, 23.61 mmol) at −10° C. The reaction mixture was reacted at −10° C. under stirring for 1 h. After the reaction was complete, the reaction mixture was quenched with 80 mL of water and extracted with 50 mL of DCM to collect an organic phase. The organic phase was washed with a saturated $NaHCO_3$ solution and a saturated salt solution successively, dried with anhydrous sodium sulfate, filtered, and concentrated to obtain 5.8 g (22.22 mmol) of crude intermediate Z13-5 (yield: 94.11%). The crude intermediate Z13-5 required no purification for the next step. MS m/z: 262 $(M+1)^+$.

(S6)-(S10) Preparation of Intermediate Z13

The rest steps were performed according to steps (S6)-(S10) of the method A of preparing intermediate Z1 to obtain the intermediate Z13, in which the intermediate Z1-5 in step (S5) was replaced with intermediate Z13-5. MS m/z: 404 $(M+1)^+$.

$^1H$ NMR (400 MHz, Methanol-$d_4$) δ 7.31 (q, J=7.4, 6.6 Hz, 5H), 6.80 (ddd, J=8.3, 5.8, 2.2 Hz, 1H), 6.61-6.49 (m, 1H), 5.11-4.95 (m, 2H), 4.73 (dd, J=11.2, 1.9 Hz, 1H), 4.56 (d, J=7.6 Hz, 1H), 3.43 (d, J=11.3 Hz, 1H), 2.43 (d, J=7.7 Hz, 1H), 0.92 (dt, J=9.4, 5.7 Hz, 1H), 0.74 (dt, J=10.8, 5.7 Hz, 1H), 0.62 (dt, J=9.8, 5.2 Hz, 1H), 0.43 (p, J=5.1 Hz, 1H).

Data of the optical rotation is as follows. A temperature was 25° C.; a concentration was 0.002 g/mL; a solvent was methanol; specific rotation was −115.3°; and a chiral purity was 98%.

Preparation of Intermediate Z13 (Method B)

Similarly, the intermediate Z13 can be prepared according to the preparation of intermediate Z8 (method B), in which 2,3-difluorophenol was taken as a raw material. MS m/z: 404 $(M+1)^+$.

$^1H$ NMR (400 MHz, Methanol-$d_4$) δ 7.31 (q, J=7.4, 6.6 Hz, 5H), 6.80 (ddd, J=8.3, 5.8, 2.2 Hz, 1H), 6.61-6.49 (m, 1H), 5.11-4.95 (m, 2H), 4.73 (dd, J=11.2, 1.9 Hz, 1H), 4.56 (d, J=7.6 Hz, 1H), 3.43 (d, J=11.3 Hz, 1H), 2.43 (d, J=7.7 Hz, 1H), 0.92 (dt, J=9.4, 5.7 Hz, 1H), 0.74 (dt, J=10.8, 5.7 Hz, 1H), 0.62 (dt, J=9.8, 5.2 Hz, 1H), 0.43 (p, J=5.1 Hz, 1H).

Data of the optical rotation is as follows. A temperature was 25° C.; a concentration was 0.002 g/mL; a solvent was methanol; a specific rotation was −115.3°; and a chiral purity was 98%.

Preparation of Intermediate Z14 (Method B)

A preparation of intermediate Z14 (method B) is illustrated as follows:

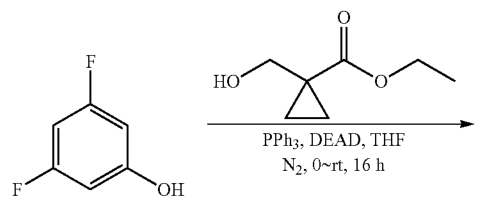

-continued

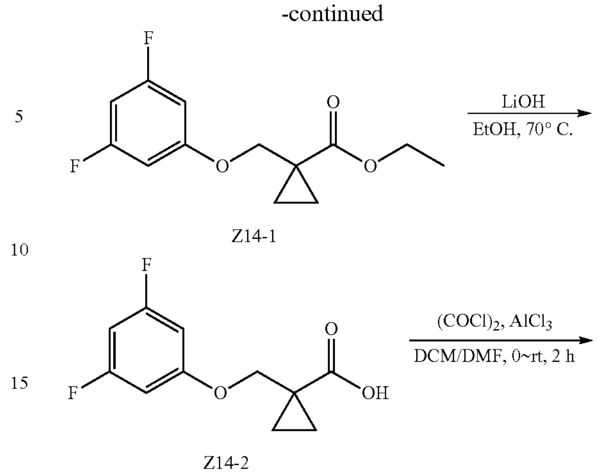

Z14-1

Z14-2

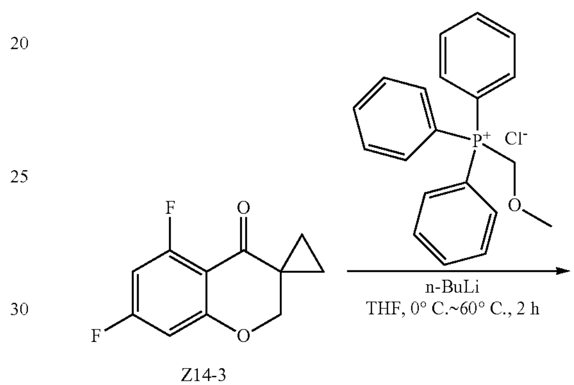

Z14-3

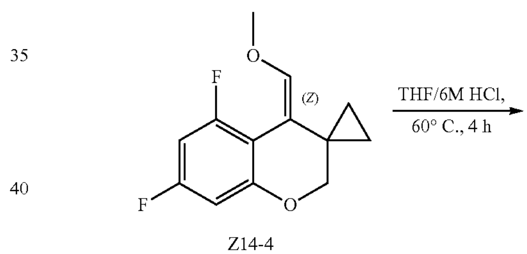

Z14-4

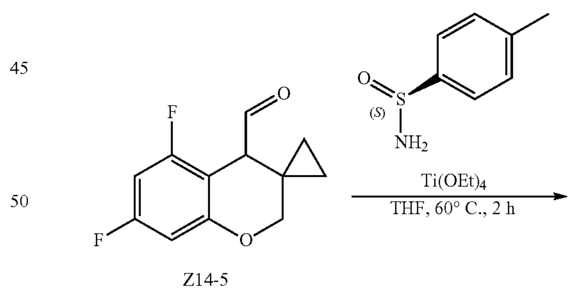

Z14-5

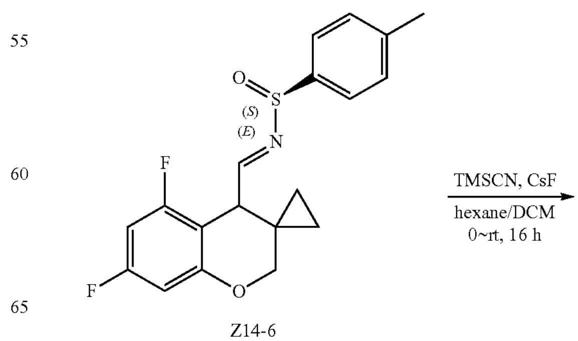

Z14-6

-continued

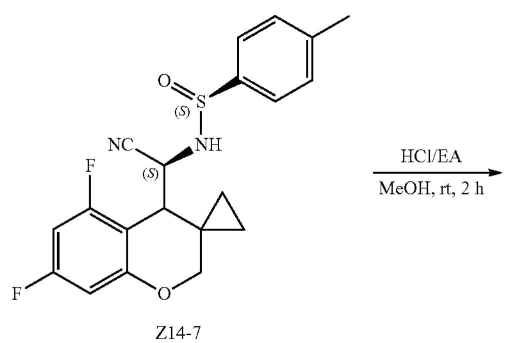

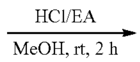

Z14-7

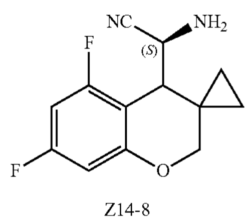

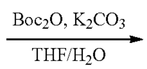

Z14-8

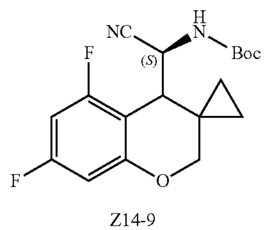

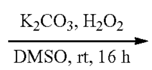

Z14-9

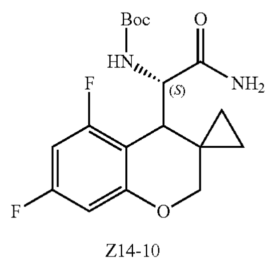

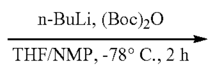

Z14-10

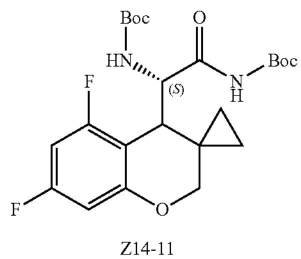

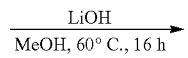

Z14-11

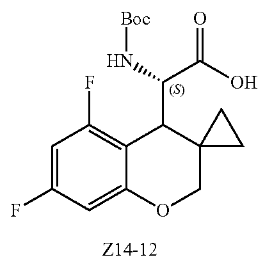

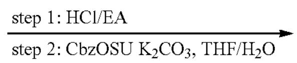

Z14-12

-continued

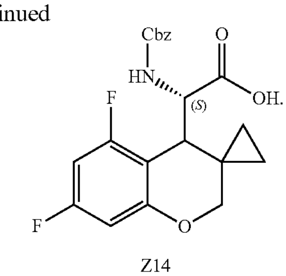

Z14

(S1) Preparation of Intermediate Z14-1

2,5-difluorophenol (27.1 g, 208.31 mmol), ethyl 1-(hydroxymethyl)cyclopropanecarboxylate (30.03 g, 208.31 mmol), $PPh_3$ (60.10 g, 229.15 mmol) and THF (1000 mL) were mixed at 0° C., and then dropwise added with 46.29 g (229.15 mmol) of DIAD. The reaction mixture was reacted at room temperature under stirring for 12 h. After the reaction was complete, the reaction mixture was concentrated, diluted with water and extracted with ethyl acetate to collected an organic phase. The organic phase was washed with water and a saturated salt solution successively, dried with anhydrous sodium sulfate, filtered and concentrated to obtain a crude product. The crude product was purified by using a silica gel column (PE/EA=10/1) to obtain 35.8 g (139.71 mmol) of intermediate Z14-1 (yield: 67.07%). MS m/z: 257 $(M+1)^+$.

(S2) Preparation of Intermediate Z14-2

24.96 g (624.01 mmol) LiOH were added into a EtOH (300 mL)/$H_2O$ (30 mL) solution of the intermediate Z14-2 (53.3 g, 208.00 mmol). The reaction mixture was heated to 60° C. for reaction under stirring for 12 h. After the reaction was complete, the reaction mixture was concentrated, diluted with water, adjusted to pH=3-4 by dropwise adding HCl (conc.) and extracted with DCM to collect an organic phase. The organic phase was concentrated to obtain 47.4 g (207.72 mmol) of intermediate Z14-2 (yield: 99.86%). MS m/z: 227 $(M+1)^+$. The intermediate Z14-2 required no purification for the next step.

(S3) Preparation of Intermediate Z14-3

52.76 g (415.44 mmol) of $(COCl)_2$ were dropwise added into a DCM (600 mL)/DMF (5 mL) solution of the intermediate Z14-2 (47.4 g, 207.72 mmol) at 0° C. under a nitrogen atmosphere. The reaction mixture was reacted at 0° C. under stirring for 1 h and added with 55.39 g (415.44 mmol) of $AlCl_3$, and then slowly heated to room temperature for reaction under stirring for 1 h. After the reaction was complete, the reaction mixture was diluted by slowly adding with water, and then extracted with ethyl acetate to collect an organic phase. The organic phase was washed with a $NaHCO_3$ (aq.) solution, water and a salt solution successively, dried with anhydrous sodium sulfate, filtered and concentrated to obtain 37.4 g (177.95 mmol) of a crude intermediate Z14-3 (yield: 85.67%). The intermediate Z14-3 required no purification for the next step.

(S4) Preparation of Intermediate Z14-4

17 mL of n-BuLi (2.5 M in hexane, 40.68 mmol) were dropwise added into an anhydrous THF (120 mL) solution of (methoxymethyl)triphenylphosphonium chloride (196 g, 517.76 mmol) under ice bath and nitrogen atmosphere. The reaction mixture was stirred at 0° C. for 1 h until it turned dark brown, followed by dropwise adding with an anhydrous THF solution of the intermediate Z12-3 (80 g, 380.63 mmol). The reaction mixture was heated to 60° C. for reaction under stirring for 4 h. After the reaction was complete, the reaction mixture was cooled to room temperature, quenched by a 30% $NH_4Cl$ aqueous solution, extracted with ethyl acetate to collect an organic phase. The organic phase was dried with anhydrous sodium sulfate, filtered and spin-dried to obtain a crude product. The crude product was subjected to separation and purification by using a silica gel column (PE:EA=10:1) to obtain 72.1 g (302.84 mmol) of a clarified oil-like substance as intermediate Z14-4 (yield: 89.77%). MS m/z: 239 $(M+1)^+$.

(S5) Preparation of Intermediate Z14-5

A THF (30 mL) solution of intermediate Z14-4 (5.7 g, 23.93 mmol) was added with 6 M HCl (30 mL). The reaction mixture was heated to 60° C. and reacted under stirring for 5 h. After the reaction was complete, the reaction mixture was extracted with ethyl acetate to collect an organic phase. The organic phase was dried to obtain 4.93 g (21.99 mmol) of an oil-like substance as intermediate Z14-5 (yield: 91.90%). The intermediate Z14-5 required no purification for the next step.

(S6) Preparation of Intermediate Z14-6

The intermediate Z14-5 (4.93 g, 21.99 mmol), (s)-4-methylbenzenesulfonamide (3.41 g, 21.99 mmol), THE (50 mL) and $(EtO)_4Ti$ (15.05 g, 65.97 mmol) were mixed in a 250 mL single-necked flask for dissolving under a nitrogen atmosphere. The reaction mixture was heated to 60° C. and reacted under stirring for 5 h. Then the reaction mixture was cooled to room temperature, added with water and ethyl acetate and filtered to remove an insoluble matter. The filtrate was subjected to stratification. An organic phase was collected and concentrated to obtain a brown oil-like substance. The brown oil-like substance was subjected to separation and purification by silica gel column (eluent: PE/EA 0-50%) to obtain 2.5 g (6.92 mmol) of a light yellow solid as intermediate Z14-6 (yield: 31.5%). MS m/z: 362 $(M+1)^+$.

(S7) Preparation of Intermediate Z14-7

2.32 g (15.27 mmol) of CsF were added into a n-hexane (70 mL)/DCM (7 mL) solution of the intermediate Z14-6 (2.5 g, 6.92 mmol). The reaction mixture was cooled to 0° C. under a nitrogen atmosphere, and then injected with 1.52 g (15.27 mmol) of TMSCN by using a syringe. Then the reaction mixture was heated to room temperature for reaction under stirring overnight. After the reaction was complete, the reaction mixture was diluted with water and extracted with ethyl acetate to obtain an organic phase. The organic phase was subjected to separation and purification with a silica gel column to obtain 1.37 g (3.53 mmol) of a white solid as intermediate Z14-7 (yield: 51%). MS m/z: 389 $(M+1)^+$.

(S8) Preparation of Intermediate Z14-8

HCl/EA (4 M) was added into a MeOH (10 mL) solution of the intermediate Z14-7 (1.37 g, 3.53 mmol). The reaction mixture was reacted at room temperature under stirring for 2 h. After the reaction was complete, the reaction mixture was concentrated, washed under beating with petroleum ether several times, filtered and dried to obtain 967 mg (3.53 mmol) of intermediate Z14-8 (purity: 90%). The intermediate Z14-8 required no purification for the next step. MS m/z: 251 $(M+1)^+$.

(S9) Preparation of Intermediate Z14-9

$K_2CO_3$ (1.60 g, 11.59 mmol) and $(Boc)_2O$ (1.25 g, 5.80 mmol) were added into a THE (10 mL)/$H_2O$ (10 mL) solution of the intermediate Z14-8 (967 mg, 3.53 mmol) at room temperature. The reaction mixture was reacted at 25° C. under stirring for 2 h. After the reaction was complete, the reaction mixture was extracted with ethyl acetate to collect an organic phase. The organic phase was concentrated to obtain a crude product. The crude product was purified through MPLC to obtain 1.3 g (3.71 mmol) of an oil-like substance as intermediate Z14-9 (yield: 96.02%). MS m/z: 351 $(M+1)^+$.

(S10) Preparation of Intermediate Z14-10

$K_2CO_3$ (512.79 mg, 3.71 mmol) and $H_2O_2$ (252.39 mg, 7.42 mmol) were successively added into a DMSO (20 mL) solution of the intermediate Z14-9 (1.3 g, 3.71 mmol). The reaction mixture was reacted at 25° C. under stirring overnight. After the reaction was complete, the reaction mixture was extracted with ethyl acetate to collect an organic phase. The organic phase was concentrated to obtain 1.37 g (3.72 mmol) of a solid as intermediate Z14-10 (yield: 100%). MS m/z: 369 $(M+1)^+$.

(S11) Preparation of Intermediate Z14-11

500.31 mg of n-BuLi (7.81 mmol, 2.5 M in hexane) were dropwise added into a THF (40 mL)/NMP (8 mL) solution of the intermediate Z14-10 (1.37 g, 3.72 mmol) at −78° C. under a nitrogen atmosphere. The reaction mixture was reacted at −78° C. under stirring for 1 h, then added with a THF solution of $(Boc)_2O$ (880.37 mg, 4.09 mmol) for reaction under stirring for 1 h. After the reaction was complete, the reaction mixture was quenched with 30% $NH_4Cl$ aqueous solution, extracted with ethyl acetate, and subjected to concentrated extraction to obtain 1.74 g (3.71 mmol) intermediate Z14-11 (yield: 100%). The intermediate Z14-11 required no purification for the next step. MS m/z: 469 $(M+1)^+$.

(S12) Preparation of Intermediate Z14-12

266.86 mg (11.14 mmol) of LiOH were added into a MeOH (10 mL)/$H_2O$ (2 mL) solution of the intermediate Z14-11 (1.74 g, 3.71 mmol). The reaction mixture was heated to 60° C. for reaction under stirring overnight. After the reaction was complete, the reaction mixture was subjected to vacuum distillation to remove a solvent to obtain a crude product. The crude product was dissolved with water to obtain a solution. The solution was extracted with ethyl acetate to collect an organic phase. The organic phase was concentrated to obtain a solid. The solid was purified through MPLC to obtain 570 mg (1.54 mmol) of intermediate Z14-12 (yield: 41.55%). MS m/z: 370 $(M+1)^+$.

(S13) Preparation of Intermediate Z14

1 mL (4.0 M) of HCl/EA were added into an ethyl acetate (3 mL) solution of the intermediate Z14-12 (570 mg, 1.54 mmol). The reaction mixture was reacted under stirring at room temperature for 1 h. After the reaction was complete, the reaction mixture was spin-dried to remove a solvent to obtain a crude product. The crude product was dissolved with a $THF/H_2O$ (5 mL/2 mL) solution. The mixed solution was successively added with $K_2CO_3$ (878 mg, 6.35 mmol) and CbzOSU (528 mg, 2.12 mmol) to react at room temperature under stirring for 3 h. After the reaction was complete, the mixed solution was diluted with water and extracted with ethyl acetate to collected an organic phase. The organic phase was washed with water, washed with a saturated salt solution and dried with anhydrous sodium sulfate to obtain a crude product. The crude product is separated through a supercritical fluid chromatography (SFC) column to obtain a target isomer (intermediate Z14). MS m/z: 404 $(M+1)^+$.

$^1H$ NMR (400 MHz, Methanol-$d_4$) δ 7.29 (dddd, J=17.5, 11.1, 6.0, 4.3 Hz, 5H), 6.48-6.27 (m, 2H), 5.07 (d, J=12.6 Hz, 1H), 4.95 (d, J=12.4 Hz, 1H), 4.73 (dd, J=11.5, 2.0 Hz, 1H), 4.63 (d, J=6.4 Hz, 1H), 3.35 (s, 1H), 2.73 (d, J=6.3 Hz, 1H), 1.03-0.89 (m, 2H), 0.79-0.68 (m, 1H), 0.69-0.53 (m, 1H), 0.53-0.38 (in, 3H).

Data of the optical rotation is as follows. A temperature was 25° C.; a concentration was 0.002 g/mL; a solvent was methanol; a specific rotation was 109.3; and a chiral purity was 984.

Preparation of Intermediates Z15-Z19

The preparation of intermediates Z15-Z19 was performed according to the method A of preparing intermediate Z13, in which 2,3-difluorophenol in step (S) was replaced with a starting phenol from the following table.

| Intermediate number | Starting phenol | Structure of intermediate | Optical rotation | $^1$HNMR or MS m/z |
|---|---|---|---|---|
| Z15 | 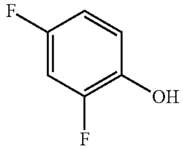 | 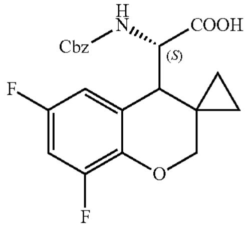 Z15 | / | (ESI)m/z = 404 $(M + 1)^+$ |
| Z16 | 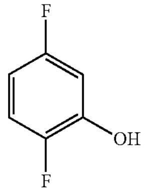 | 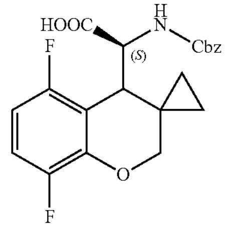 Z16 | Temperature of 25° C., a concentration of 0.002 g/mL, solvent of methanol and specific rotation of −90.8°. | $^1H$ NMR (400 MHz, Methanol-$d_4$) δ 7.43-7.11 (m, 6H), 6.95 (td, J = 9.8, 5.1 Hz, 1H), 6.50 (dtd, J = 12.7, 9.4, 4.1 Hz, 1H), 5.05 (d, J = 12.7 Hz, 1H), 4.96 (d, J = 12.3 Hz, 2H), 4.75 (d, J = 11.5 Hz, 1H), 4.68 (d, J = 6.2 Hz, 1H), 3.42 (d, J = 11.5 Hz, 1H), 2.80 (d, J = 6.2 Hz, 1H), 1.06-0.89 (m, 1H), 0.84-0.70 (m, 1H), 0.69-0.56 (m, 1H), 0.56-0.41 (m, 4H). (ESI)m/z = 404$(M + 1)^+$ and a chiral purity of 98%. |
| Z17 | 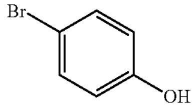 | 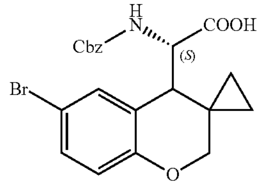 Z17 | / | (ESI)m/z = 446/448 |

-continued

| Intermediate number | Starting phenol | Structure of intermediate | Optical rotation | $^1$HNMR or MS m/z |
|---|---|---|---|---|
| Z18 | 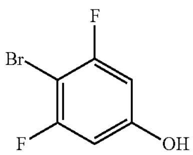 | 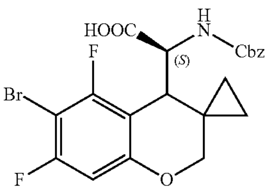 Z18 | / | (ESI)m/z = 482/484 |
| Z19 | 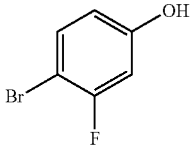 | 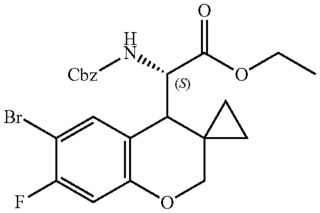 Z19 | / | (ESI)m/z = 492/494 |

Preparation of Intermediate Z20

A preparation of intermediate Z20 is illustrated as follows:

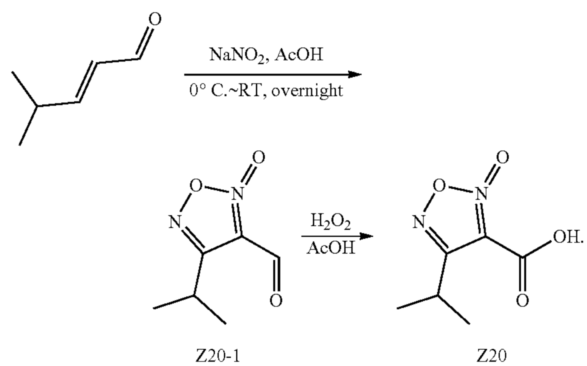

Z20-1 Z20

(S1) Preparation of Intermediate Z20-1

A water (30 mL) solution of sodium nitrite ($NaNO_2$) (12.65 g, 183.4 mol) was dropwise added into an acetic acid (HOAc) (10 mL) solution of 4-methyl-2-pentanol (5 g, 50.59 mmol) under ice bath. The reaction mixture was slowly heated to room temperature for reaction under stirring overnight. After the reaction was complete, the reaction mixture was diluted with water and extracted with DCM to collect an organic phase. The organic phase was dried with anhydrous sodium sulfate and filtered. The filtrate was spin-dried to obtain a crude product. The crude product was separated and purified through a silica gel column to obtain 2.23 g (14.26 mmol) of intermediate Z20-1 (yield: 28%). MS m/z: 157 $(M+1)^+$.

(S2) Preparation of Intermediate Z20

4.36 g (38.43 mmol) of 30% $H_2O_2$ were added into a HOAc (10 mL) solution of the intermediate Z20-1 (3.00 g, 19.21 mmol) under ice salt bath. The reaction mixture was reacted at room temperature under stirring overnight. After the reaction was complete, the reaction mixture was concentrated to obtain a crude product. The crude product was separated and purified through MPLC (TFA/MeCN/$H_2O$) to obtain 1.5 g (8.71 mmol) of intermediate Z20 (yield: 45.35%). MS m/z: 173 $(M+1)^+$.

Preparation of Intermediate Z21

A preparation of intermediate Z21 is illustrated as follows:

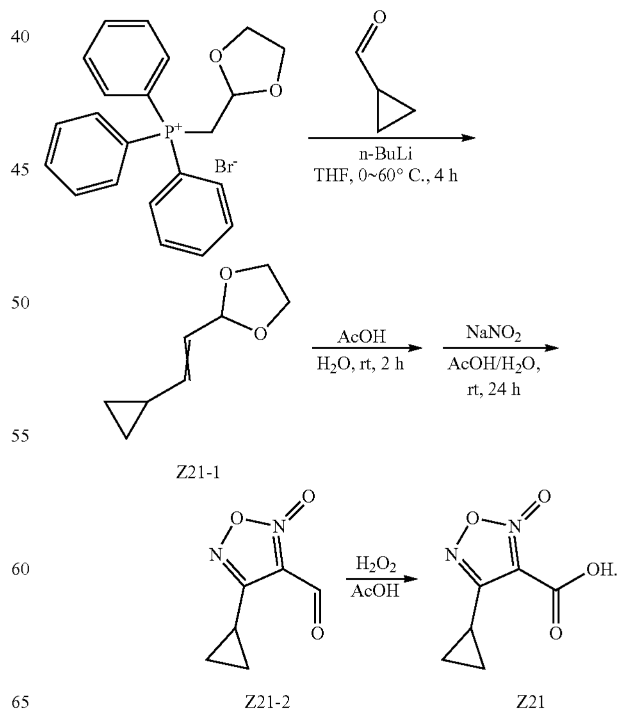

Z21-1

Z21-2 Z21

(S1) Preparation of Intermediate Z21-1

200 mL of n-BuLi (2.5 M in THF, 500 mmol) were slowly added into a THF (1000 mL) solution of cyclopropanecarbaldehyde (27.2 g, 388.07 mmol) at 0° C. The reaction mixture was reacted at 0° C. under stirring for 1 h, added with 199.91 g of (465.69 mmol) (1,3-dioxolan-2-yl)methyltriphenylbromide and heated to 60° C. Then the reaction mixture was reacted at 60° C. under stirring for 4 h. After the reaction was complete, the reaction mixture was diluted with a $NaHCO_3$ (aq) solution and extracted with ethyl acetate to collect an organic phase. The organic phase was wash with water and a saturated salt solution, dried with anhydrous sodium sulfate and concentrated to obtain a crude product. The crude product was subjected to separation and purification by using a silica gel column (PE/EA=5/1) to obtain 15.2 g (98.57 mmol) of intermediate Z21-1 (yield: 25.40%).

(S2) Preparation of Intermediate Z21-2

15.2 g (98.57 mmol) of the intermediate Z21-1 were dissolved into an AcOH (100 mL)/H2O (20 mL) solution. The reaction mixture was reacted at room temperature under stirring for 1 h, added with 13.60 g (197.14 mmol) of $NaNO_2$ and then reacted at room temperature under stirring for 72 h. After the reaction was complete, the reaction mixture was concentrated to obtain 13.5 g (97.74 mmol) of a crude intermediate Z21-2 (yield: 99.16%). The intermediate Z21-2 required no purification for the next step. MS m/z: 155.2 $(M+1)^+$.

(S3) Preparation of Intermediate Z21

11.38 g (334.48 mmol) of $H_2O_2$ were added into an AcOH (100 mL) solution of the intermediate Z21-2 (15.4 g, 111.49 mmol). The reaction mixture was reacted at room temperature under stirring for 12 h. After the reaction was complete, the reaction mixture was concentrated to obtain a crude product. The crude product was subjected to separation and purification by a silica gel column (DCM/MeOH=5/1, v/v) to obtain 10 g (64.88 mmol) of intermediate Z21 (yield: 58.19%). MS m/z: 171.2 $(M+1)^+$.

Preparation of Intermediate Z22

The preparation of intermediate Z22 was performed according to step (S2), illustrated as follows:

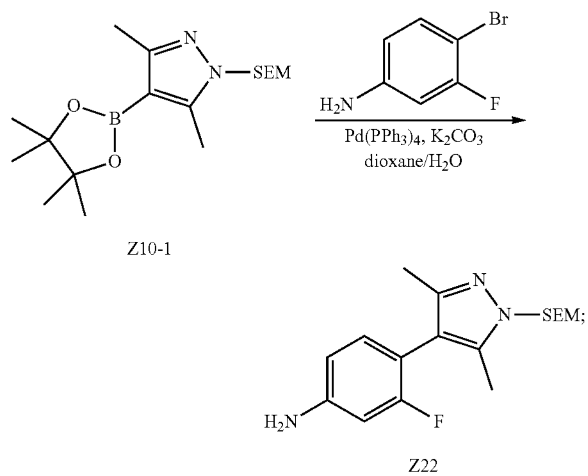

Z10-1

Z22 where 6-bromo-3-aminopyridine was replaced with 4-bromo-3-fluoroaniline. MS m/z: 336 $(M+1)^+$.

Preparation of Intermediate Z23

A preparation of intermediate Z23 is illustrated as follows:

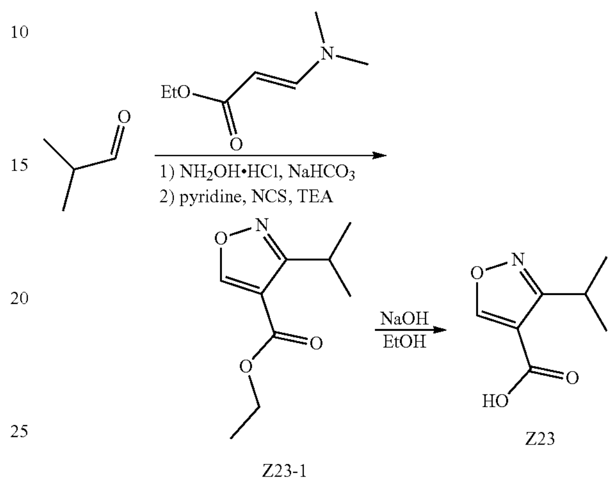

Z23-1

Z23

(S1) Preparation of Intermediate Z23-1

$NaHCO_3$ (75.49 g, 898.68 mmol) and hydroxylamine hydrochloride (31.23 g, 449.34 mmol) were added into a DCM (500 mL) solution of isobutyraldehyde (10.8 g, 149.78 mmol) at room temperature. The reaction mixture was reacted at room temperature under stirring for 12 h and added with water to collect an organic phase. The organic phase was dried with anhydrous sodium sulfate and filtered. The filtrate was successively added with pyridine (2 mL) and NCS (20.00 g, 149.78 mmol). Then the filtrate was heated to 40° C. to stir for 1 h and cooled to room temperature, then added with ethyl N,N-dimethylaminoacrylate (32.17 g, 224.67 mmol) and TEA (45.47 g, 449.34 mmol, 62.67 mL) for reaction at room temperature under stirring for 1 h. After the reaction was complete, the reaction mixture was concentrated to obtain a crude product. The crude product was separated and purified by using a silica gel column (PE/EA=5/1, v/v) to obtain 27 g (147.38 mmol) of intermediate Z23-1 (yield: 98.40%, purity: 80%). MS m/z: 184.3 $(M+1)^+$.

(S2) Preparation of Intermediate Z23

5.90 g (147.38 mmol) of NaOH were added into an EtOH (200 mL) solution of the intermediate Z23-1 (13.5 g, 73.69 mmol). The reaction mixture was reacted at room temperature under stirring for 2 h. After the reaction was complete, the reaction mixture was concentrated, diluted with water and washed with EtOAc to collect a water phase. The water phase was adjusted to pH=3-4 by using HCl (6 M), extracted with EtOAc to collect an organic phase. The organic phase was concentrated to obtain 4.8 g (30.94 mmol) of intermediate Z12-1 (yield: 41.98%). MS m/z: 156.2 $(M+1)^+$.

Preparation of Intermediate Z24

The preparation of intermediate Z24 was performed according to steps (S1)-(S2) of the preparation of intermediate Z23, in which in step (S1), isobutyraldehyde was replaced with cyclopropanecarbaldehyde.

Preparation of Intermediate Z25

A preparation of intermediate Z25 is illustrated as follows:

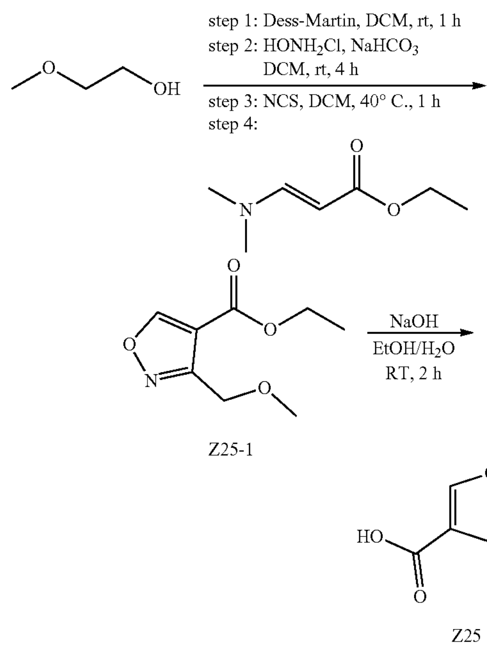

Z25-1

Z25

(S1) Preparation of Intermediate Z25-1

58.25 g (137.33 mmol) of Dess-Martin periodinane were added into a DCM (182.12 mL) solution of ethylene glycol methyl ether (9.5 g, 124.85 mmol). The reaction mixture was reacted at room temperature under stirring for 1 h, and successively added with $NaHCO_3$ (73.41 g, 873.92 mmol) and hydroxylamine hydrochloride (26.03 g, 374.54 mmol), followed by reaction at room temperature under stirring for 4 h and filtration by diatomite. The filtrate was successively added with pyridine (1 mL) and NCS (16.67 g, 124.85 mmol), and heated to 40° C. to stir for 2 h. The mixture was then cooled to room temperature, added with ethyl 3-(N,N-dimethylamino)acrylate (21.45 g, 149.81 mmol) and TEA (37.90 g, 374.54 mmol, 52.24 mL), and then reacted under stirring overnight. After the reaction was complete, the mixture was concentrated and purified through MPLC (MTBE/PE=0-30%) to obtain 1.5 g (8.10 mmol) of an oil-like substance as intermediate Z25-1 (yield: 6.49%). MS m/z: 186 $(M+1)^+$.

(S2) Preparation of Intermediate Z25

648.03 mg (16.20 mmol) of NaOH were added into an EtOH (15 mL)/$H_2O$ (5 mL) solution of the intermediate Z25-1 (1.5 g, 8.10 mmol). The reaction mixture was reacted at room temperature under stirring for 2 h. After the reaction was complete, the reaction mixture was concentrated, diluted with water and EA and adjusted to pH=3-4 with 2 M HCl to collect an organic phase. The organic phase was concentrated to obtain a crude product. The crude product was purified through MPLC to obtain 300 mg (1.91 mmol) of an oil-like substance as intermediate Z25 (yield: 23.57%).

Preparation of Intermediate Z26

The preparation of intermediate Z26 was performed according to steps (S1)-(S2) of the preparation of intermediate Z25, in which in step (S1), ethylene glycol methyl ether was replaced with propylene glycol methyl ether, illustrated as follows:

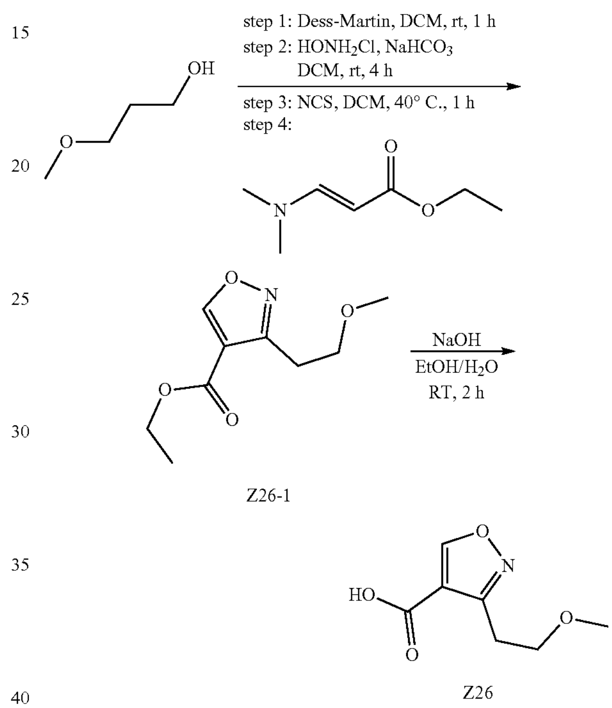

Z26-1

Z26

Preparation of Intermediate Z27

The preparation of intermediate Z27 is illustrated as follows:

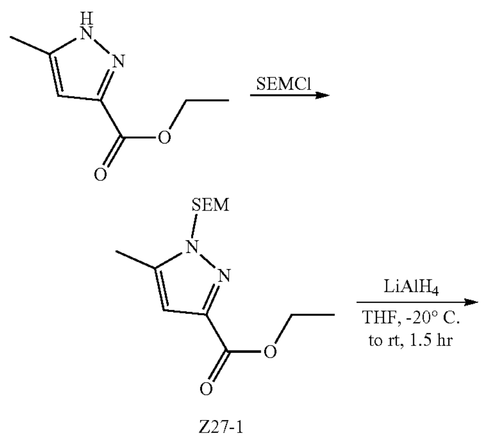

Z27-1

-continued

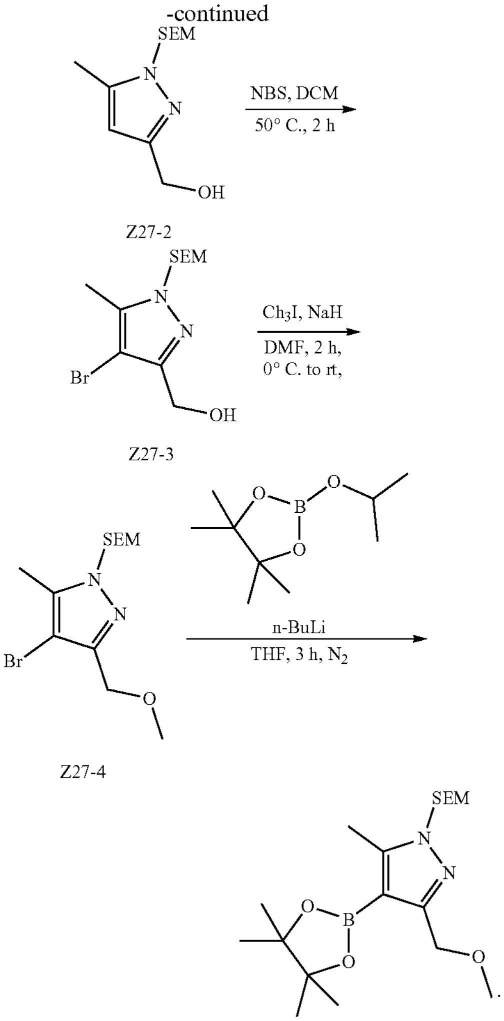

Z27-2

Z27-3

Z27-4

Z27

(S1) Preparation of Intermediate Z27-1

7.01 g (291.89 mmol) of NaH were added into a DMF (500 mL) solution of ethyl 3-methylpyrazole-5-carboxylate (30 g, 194.60 mmol) at −10° C. under a nitrogen atmosphere. The reaction mixture was reacted at room temperature under stirring for 1 h, dropwise added with SEMCl (34.06 g, 204.33 mmol), and then slowly heated to room temperature for reaction under stirring for 2 h. After the reaction was complete, the reaction mixture was decanted into ice water, stirred at −10° C. under stirring and extracted with ethyl acetate to collect an organic phase. The organic phase was washed with a saturated salt solution, dried with anhydrous sodium sulfate and filtered. The filtrate was concentrated and purified with a silica gel column to obtain 50 g (175.79 mmol) of intermediate Z27-1 (yield: 90.34%) (a TLC plate showing two dots, LCMS showing two peaks, (trimethylsilyl)ethoxymethyl (SEM) protects a mixture of structural isomers). MS m/z: 285 $(M+1)^+$.

(S2) Preparation of Intermediate Z27-2

8.67 g (228.53 mmol) of lithium aluminum hydride ($LiAlH_4$) were added into a THF (900 mL) solution of the intermediate Z27-1 (50 g, 175.79 mmol) at −30° C. under a nitrogen atmosphere. The reaction mixture was slowly heated to −20° C. for reaction under stirring under a nitrogen atmosphere. After the reaction was complete, the reaction mixture was dropwise added with $H_2O$ (10 mL) at −20° C. for quench and continued to stir for 10 min. Then the reaction mixture was successively added with a 15% NaOH (10 mL) aqueous solution and $H_2O$ (30 mL), stirred at −20° C. for 15 min and filtered. The filtrate was extracted with ethyl acetate to collect an organic phase. The organic phase was washed with a saturated salt solution, dried with anhydrous sodium sulfate and filtered, followed by vacuum concentration to obtain 41.88 g (172.78 mmol) of intermediate Z27-2 (yield: 98.29%). The intermediate Z27-2 required no purification for the next step. MS m/z: 243 $(M+1)^+$.

(S3) Preparation of Intermediate Z27-3

61.68 g (346.55 mmol) of NBS were added into a DCM (800 mL) solution of the intermediate Z27-2 (41.88 g, 172.78 mmol) at room temperature. The reaction mixture was reacted at 50° C. under stirring for 2 h. After the reaction was complete, the reaction mixture was concentrated to obtain a crude product. The crude product was subjected to separation and purification by a silica gel column (PE:EA=9:1, v/v) to obtain 44 g (136.95 mmol) of intermediate Z27-3 (yield: 79.04%). MS m/z: 322 $(M+1)^+$.

(S4) Preparation of Intermediate Z27-4

25 g (77.81 mmol) of the intermediate Z27-3 were dissolved in DMF (500 mL). The reaction mixture was stirred at −10° C. under stirring for 10 min, and then slowly added with NaH (2.80 g, 116.72 mmol) in batches. The reaction mixture was then stirred at −10° C. under stirring for 2 h, slowly added with $CH_3I$ (12.15 g, 85.59 mmol), followed by reaction at room temperature under stirring overnight. The reaction mixture was decanted into a saturated ammonium chloride aqueous solution and extracted with ethyl acetate to collect an organic phase. The organic phase was washed with a saturated salt solution, dried with anhydrous sodium sulfate, filtered and concentrated to obtain a crude product. The crude product was purified by using a silica gel column (PE:EA=25:1, v/v) to obtain 18.8 g (56.07 mmol) of intermediate Z27-4 (yield: 72.05%). MS m/z: 336 $(M+1)^+$.

(S5) Preparation of Intermediate Z27

18.8 g (56.07 mmol) of the intermediate Z27-4 were dissolved in THF (430 mL) at −78° C. under a nitrogen atmosphere. The reaction mixture was dropwise added with n-BuLi (84.10 mmol, 34 mL), and then added with isopropoxyboronic acid pinacol ester (15.65 g, 84.10 mmol) for reaction at room temperature under stirring for 2 h. After the reaction was complete, the reaction mixture was decanted into a saturated ammonium chloride aqueous solution for quench and extracted with ethyl acetate to collect an organic phase. The organic phase was washed with a saturated salt solution, dried with anhydrous sodium sulfate, filtered and concentrated to obtain a crude product. The crude product was purified with a silica gel column (PE:EA=20:1) to obtain 17 g (44.46 mmol) of intermediate Z27 (yield: 79.30%). MS m/z: 383 $(M+1)^+$.

Preparation of Intermediate Z28

A preparation of the intermediate Z9 is illustrated as follows:

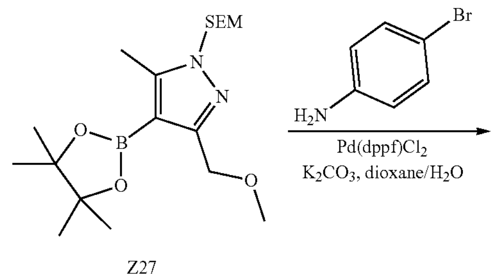

Z27

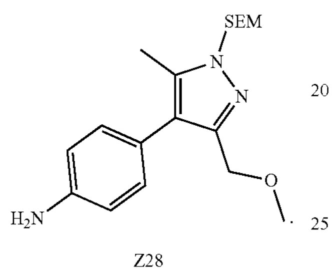

Z28 p-bromoaniline and $K_2CO_3$ (216.54 mg, 1.57 mmol) were added into a dioxane (10 mL)/$H_2O$ (1 mL) of the intermediate Z27 (200 mg, 523.04 μmol) at room temperature. The reaction mixture was subjected to nitrogen replacement several times and addition of 1,1'-bis(diphenylphosphino) ferrocene]dichloropalladium (II) (Pd(dppf)$Cl_2$) (76.47 mg, 104.61 μmol). Then the reaction mixture was slowly heated to 80° C. under a nitrogen atmosphere and reacted under stirring overnight. After the reaction was complete, the reaction mixture was quenched with water, and extracted with ethyl acetate to collect an organic phase. The organic phase was washed with a saturated salt solution, dried with anhydrous sodium sulfate, filtered, and concentrated to obtain a crude product. The crude product was purified through MPLC to obtain 43 mg (0.12 mmol) of intermediate Z28 (yield: 24%). MS m/z: 348 $(M+1)^+$.

General Route A for Preparation of Target Compounds

The general route A is illustrated as follows:

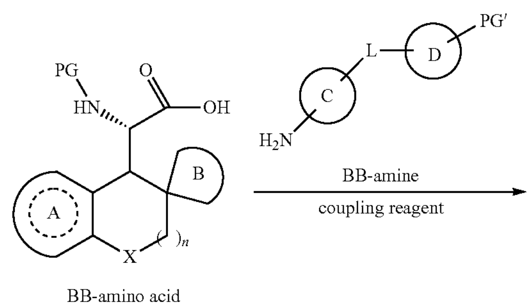

BB-amino acid

-continued

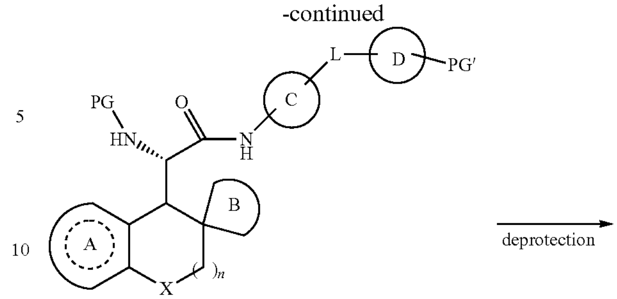

Int 1

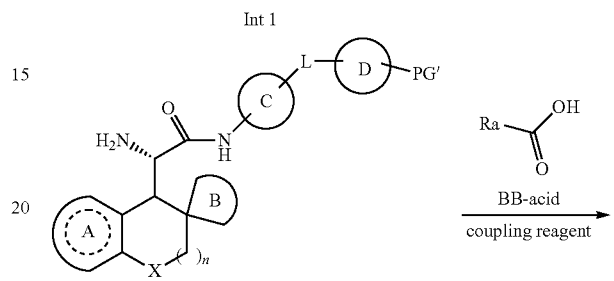

Int 2

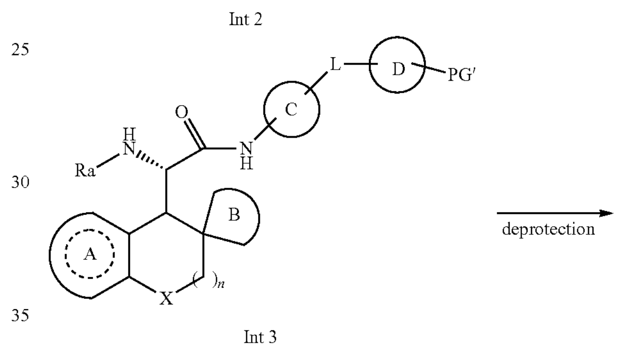

Int 3

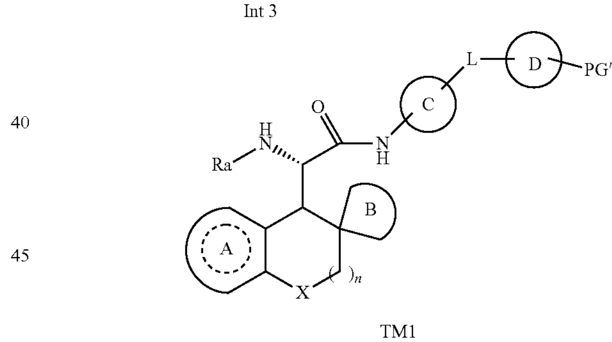

TM1

A homemade chiral amino acid intermediate BB-amino acid performed condensation with homemade or commercially available amines of a general formula BB-amino, so as to obtain intermediate Int 1 in the presence of alkali and suitable solvent. A coupling agent included HATU, HBTU, CDI, T3P, PyBOP, DCC and EDC. The alkali included DIPEA, TEA and pyridine. The solvent included DMF, DCM and $CH_3CN$.

Protective groups PG on the Int 1, such as Boc, Cbz and Fomc, can be selectively removed by methods known to those skilled in the art, thereby preparing intermediate Int 2.

The Int 2 performed condensation with acid with general formula BB-acid in the presence of a coupling agent, and then reacted with alkali in the presence of suitable solvent to obtain intermediate Int 3. The coupling agent included HATU, HBTU, CDI, T3P, PyBOP, DCC and EDC. The alkali included DIPEA, TEA and pyridine. The solvent included DMF, DCM and $CH_3CN$.

Protective groups PG' on the Int 3, such as SEM, can be removed by methods known to those skilled in the art, such as the removal of SEM by trifluoroacetic acid, to prepare a target molecule of general formula TM1.

General Route B for Preparation of Target Compounds

The general route B is illustrated as follows:

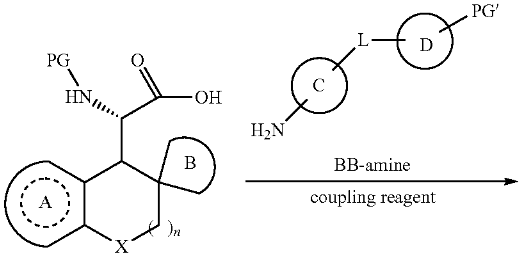

BB-amino acid

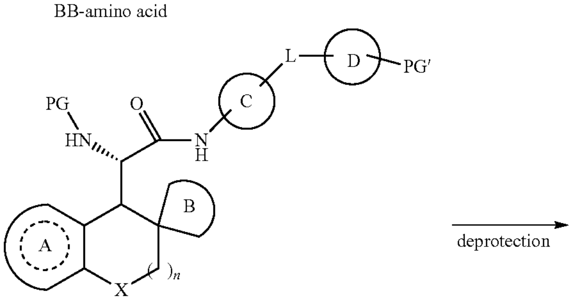

Int 1

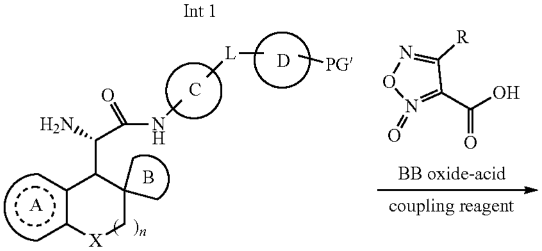

Int 2

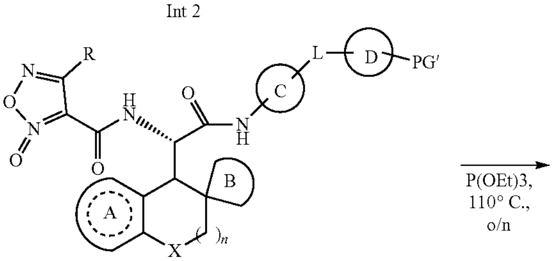

Int 3'

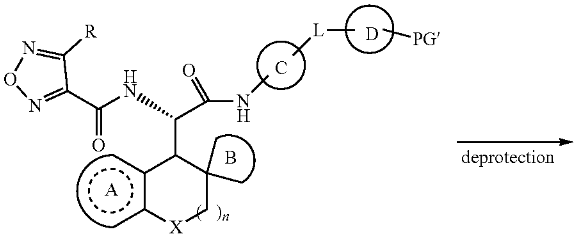

Int 4

-continued

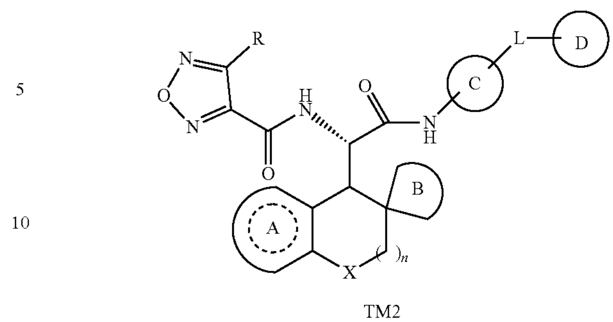

TM2

A preparation of the Int 2 was performed according to the general route A. The Int 2 performed condensation with furazan acid with general formula BB oxide-acid in the presence of a coupling agent, and then reacted with alkali in the presence of suitable solvent to obtain intermediate Int 3'. The coupling agent included HATU, HBTU, CDI, T3P, PyBOP, DCC and EDC. The alkali included DIPEA, TEA and pyridine. The solvent included DMF, DCM and $CH_3CN$.

The Int 3' was dissolved in triethyl phosphite, heated to 110° C., and subjected to reduction reaction under stirring overnight to obtain intermediate Int 4.

Protective group PG' on intermediate Int 4, such as SEM, can be removed by methods known to those skilled in the art, such as the removal of SEM by trifluoroacetic acid, to prepare a target molecule of general formula TM2.

Example 1 Preparation of Compound 1 (General Rout A)

A preparation of compound 1 is illustrated as follows:

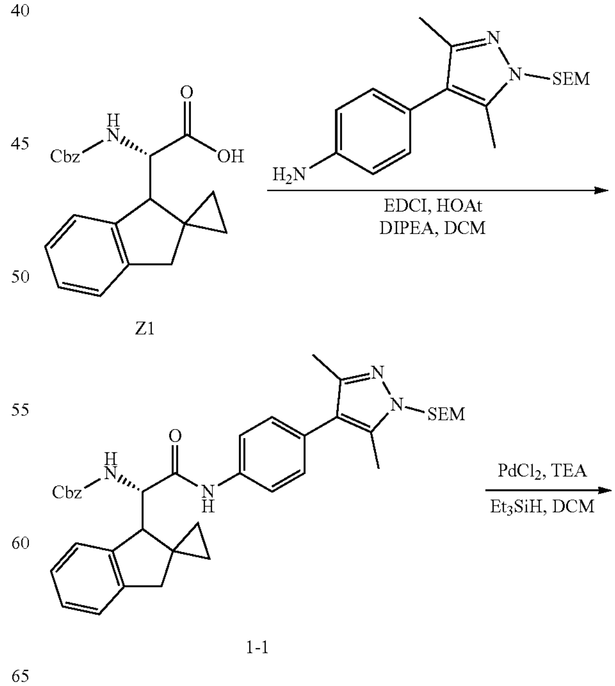

Z1

1-1

-continued

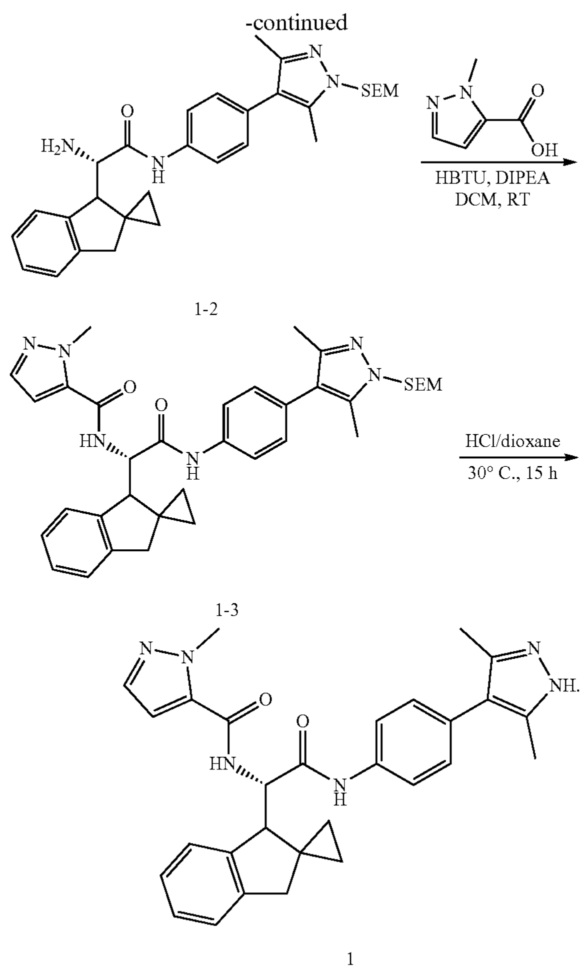

1-2

1-3

1

(S1) Preparation of Compound 1-1

360 mg (1.02 mmol) of intermediate Z1, 390 mg (1.23 mmol) of 4-(3,5-dimethyl-1-{(2-(trimethylsilyl)ethoxy) methyl}-1H-pyrazolyl)aniline and 15 mL of DCM were added into a 100 mL single-necked flask to obtain a light brown clarified solution. The solution was successively added with DIPEA (0.51 mL, 2.907 mmol), HOAt (158 mg, 1.162 mmol) and EDCI (223 mg, 1.162 mmol) for acylation at room temperature under stirring for 3 h. After the acylation was confirmed by LCMS to be complete, the solution was washed with water (20 mL), dried, and spin-dried. The residual was purified by column chromatography (with 100-200 mesh silica gel, PE:EA=2:1) to obtain 450 mg (0.69 mmol) of a yellow solid as compound 1-1 (yield: 67.5%). MS m/z: 651 $(M+1)^+$.

(S2) Preparation of Compound 1-2

450 mg (0.69 mmol) of the compound 1-1 and DCM (10 mL) were added into a 100 mL single-necked flask for dissolving. The reaction mixture was successively added with $PdCl_2$ (27 mg, 0.152 mmol) and TEA (0.073 mL, 0.531 mmol) under ice bath, dropwise added with triethylsilane $Et_3SiH$ (0.6 mL, 3.79 mmol) under stirring, and slowly heated to room temperature for reaction overnight. After the reaction was confirmed by LCMS to be complete, the reaction mixture was filtered to remove an insoluble matter, and spin-dried to obtain 358 mg of brown oil as compound 1-2 (yield: 100%). The compound 1-2 required no purification for the next step. MS m/z: 517 $(M+1)^+$.

(S3) Preparation of Compound 1-3

430 mg (0.83 mmol) of the compound 1-2 and DCM (10 mL) were added into a 100 mL single-necked flask to stir to obtain a light brown clarified solution. The solution was successively added with 1-methyl-5-pyrazolecarboxylic acid (126 mg, 1.0 mmol), DIPEA (0.4 mL, 2.0 mmol) and HBTU (373 mg, 0.985 mmol) under stirring for reaction at room temperature under a nitrogen atmosphere overnight. After the reaction was confirmed by LCMS to be complete, the solution was washed with water (20 mL) and separated to collect a DCM layer. The DCM layer was dried and spin-dried. The residual was purified by column chromatography to obtain 471 mg (0.73 mmol) of a light yellow oil as compound 1-3 (yield: 88%). MS m/z: 625 $(M+1)^+$.

(S4) Preparation of Compound 1

4.0 M of HCl/dioxane (1.5 mL, 6 mmol) were added into a methanol (5 mL) solution of the compound 1-3 (364 mg, 0.74 mmol). The reaction mixture was heated to 30° C. and reacted under stirring for 15 h. After the reaction was complete, the reaction mixture was neutralized with a saturated $NaHCO_3$ aqueous solution, and extracted with DCM to collect an organic phase. The organic phase was subjected to vacuum concentration. The residual was purified by a MPLC reversed-phase column to obtain 250 mg (0.5 mmol) of compound 1 (yield: 69%). MS m/z: 495 $(M+1)^+$.

$^1H$ NMR (400 MHz, DMSO-$d_6$) δ 10.46 (s, 1H), 8.67 (d, J=8.9 Hz, 1H), 7.83-7.68 (m, 2H), 7.47 (d, J=2.1 Hz, 1H), 7.35 (d, J=7.4 Hz, 1H), 7.33-7.20 (m, 6H), 7.16 (td, J=7.4, 1.2 Hz, 1H), 7.06 (t, J=7.4 Hz, 1H), 7.02 (d, J=2.1 Hz, 1H), 4.65 (t, J=9.3 Hz, 1H), 3.93 (s, 3H), 3.57 (d, J=15.7 Hz, 1H), 3.13 (d, J=9.7 Hz, 1H), 2.30 (d, J=15.9 Hz, 1H), 2.23 (s, 6H), 0.85-0.75 (m, 1H), 0.65-0.55 (m, 2H), 0.45-0.34 (m, 2H).

Example 2 Preparation of Compound 2

A structure of compound 2 is shown as follows:

2

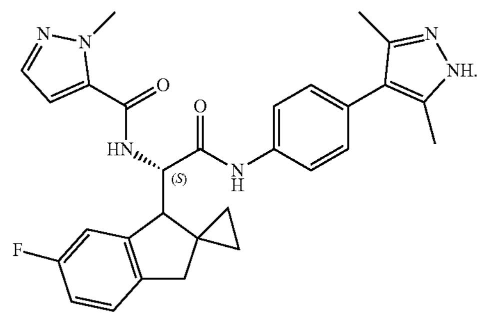

The preparation of compound 2 was performed according to the preparation of compound 1 (general route A) in Example 1, in which the intermediate Z2 was taken as a raw material. MS m/z: 513 $(M+1)^+$.

Example 3 Preparation of Compound 3

A structure of compound 3 is shown as follows:

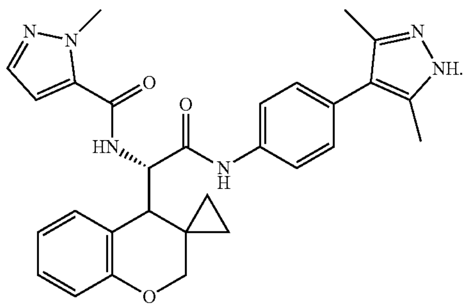

3

The preparation of compound 3 was performed according to the preparation of compound 1 (general route A) in Example 1, in which the intermediate Z3 was taken as a raw material. MS m/z: 511 $(M+1)^+$.

Example 4 Preparation of Compound 4

A structure of compound 4 is shown as follows:

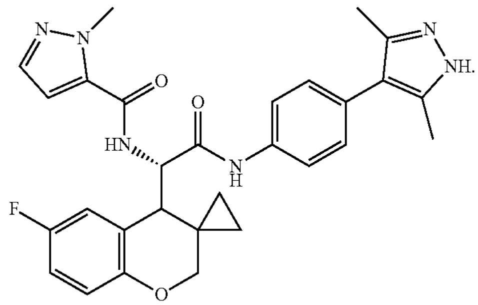

4

The preparation of compound 4 was performed according to the preparation of compound 1 (general route A) in Example 1, in which the intermediate Z4 was taken as a raw material. MS m/z: 529 $(M+1)^+$.

Example 5 Preparation of Compound 5

A preparation of compound 5 is illustrated as follows:

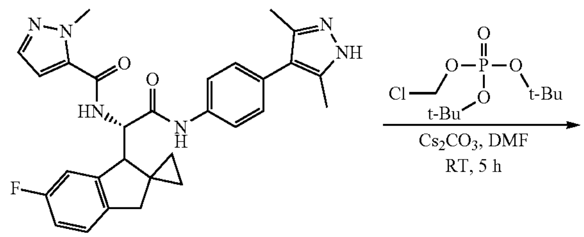

2

-continued

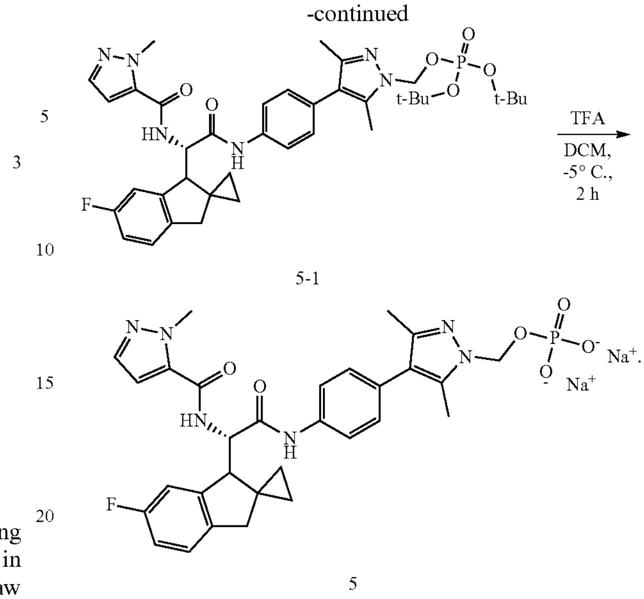

5-1

5

(S1) Preparation of Compound 5-1

Caesium carbonate ($Cs_2CO_3$) (71 mg, 0.21 mmol) and di-tert-butyl chloromethyl phosphate (54 mg, 0.21 mmol) were added into a DMSO (2 mL) solution of the compound 2 (72 mg, 0.14 mmol). The reaction mixture was stirred at room temperature for 5 h, and then purified by a reversed phase column to obtain 37 mg (0.14 mmol) of compound 5-1. Alkali method MS m/z: 735 $(M+1)^+$.

(S2) Preparation of Compound 5-2

0.5 mL of TFA were added into dry DCM (5 mL) of the compound 5-1 (120 mg, 0.16 mmol) at −5° C. The reaction mixture was stirred at −5° C. under a nitrogen atmosphere for 2 h, and spun to remove a solvent under vacuum. The residue was adjusted to pH greater than 8 with 1N of NaOH aqueous solution. The mixed solution was stirred for 10 min, added with MeCN (5 mL) until there as white solid precipitation, and filtered. The filter cake was dried under vacuum to obtain 65 mg of compound 5 (yield: 59%). Alkali method MS m/z: 623 $(M+1)^+$.

Example 6 Preparation of Compound 6

A preparation of compound 6 is illustrated as follows:

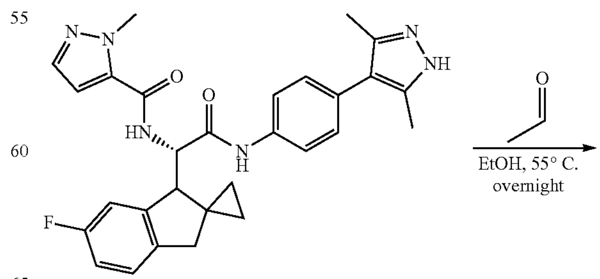

2

-continued

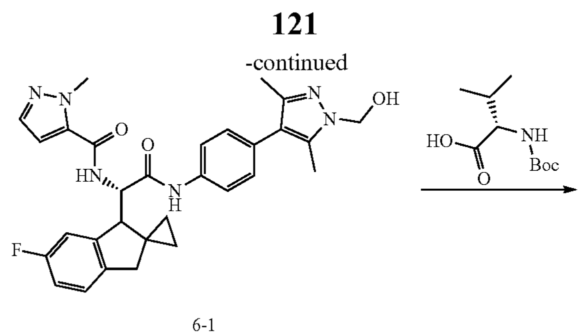

6-1

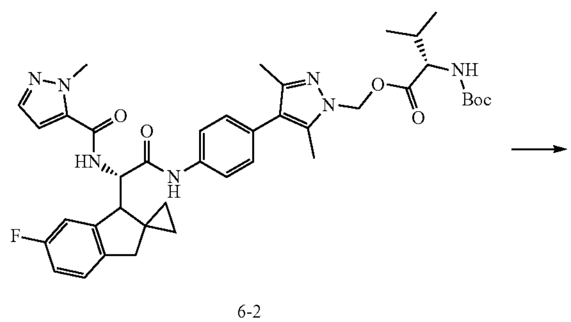

6-2

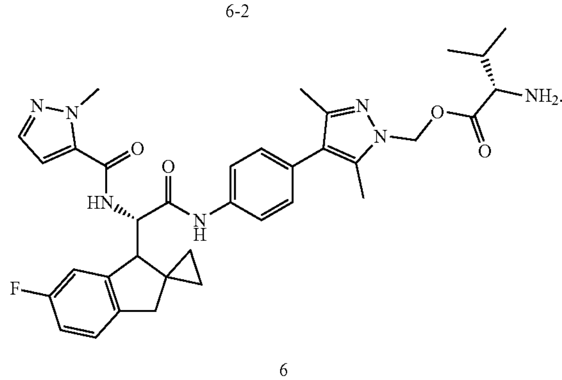

6

(S1) Preparation of Compound 6-1

An EtOH (7 mL) solution of the compound 2 (220 mg, 0.43 mmol) was added with a saturated acetaldehyde aqueous solution (99 μL, 1.29 mmol) under a nitrogen atmosphere. The mixture was heated to 55° C. to stir under a nitrogen atmosphere overnight. The mixture was cooled to room temperature, and subjected to vacuum distillation and spin to remove a solvent. The residual was dried in a vacuum drying oven at 30° C. overnight to obtain 215 mg (0.43 mmol) of compound 6-1 (yield: 92%). MS m/z: 543 $(M+1)^+$.

(S2) Preparation of Compound 6-2

(S)-2-(tert-butoxycarbonylamino-methyl)-butyric acid (103 mg, 0.47 mmol) and N, N-diisopropylcarbodiimide (DIC) (112 mg, 0.72 mmol) were added into a DCM (5 mL)/NMP (1 mL) solution of the compound 6-1 (215 mg, 0.43 mmol). The reaction mixture was stirred at room temperature for 2 h, and spin-dried to remove a solvent. The residual was purified with Pre.HPLC to obtain 220 mg (0.3 mmol) of compound 6-2 (yield: 75%). MS m/z: 742 $(M+1)^+$.

(S3) Preparation of Compound 6

0.3 mL of HCl/dioxane (4N, 1.2 mmol) were added into a DCM (2 mL) solution of the compound 6-2 (220 mg, 0.3 mmol). The reaction mixture was reacted at room temperature under stirring for 15 min. After the reaction was complete, the reaction mixture was spin-dried to remove a solvent to obtain 129 mg (0.2 mmol) of compound 6 (yield: 60%). MS m/z: 642 $(M+1)^+$.

Example 7 Preparation of Compound 7

A structure of compound 7 is shown as follows:

7

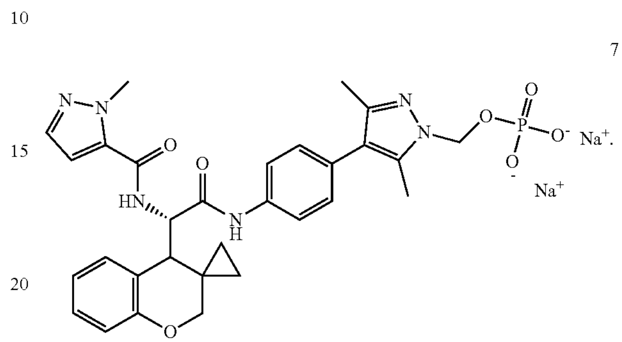

The preparation of compound 7 was performed according to the preparation of compound 5, in which the compound 3 was taken as a raw material. MS m/z: 621 $(M+1)^+$.

Example 8 Preparation of Compound 8

A structure of compound 8 is shown as follows:

8

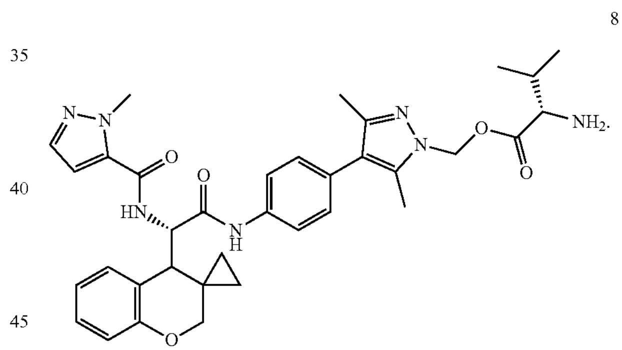

The preparation of compound 8 was performed according to the preparation of compound 6, in which the compound 3 was taken as a raw material. MS m/z: 621 $(M+1)^+$.

Example 9 Preparation of Compound 9

A preparation of compound 9 is illustrated as follows:

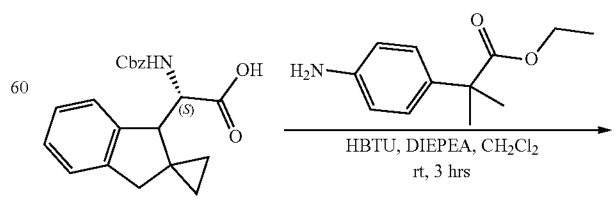

1

-continued

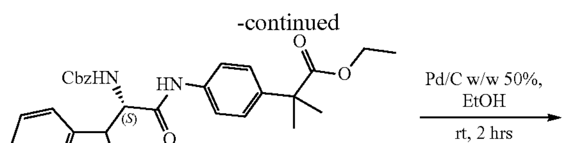

9-1

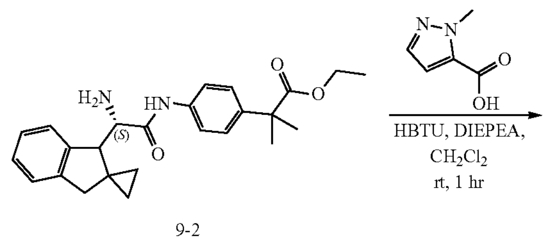

9-2

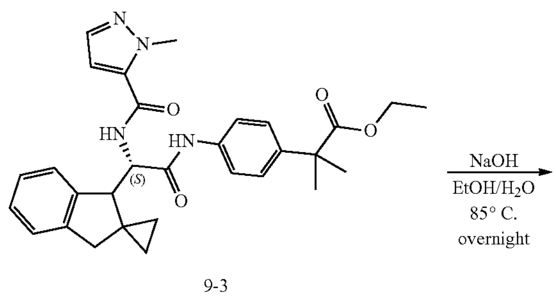

9-3

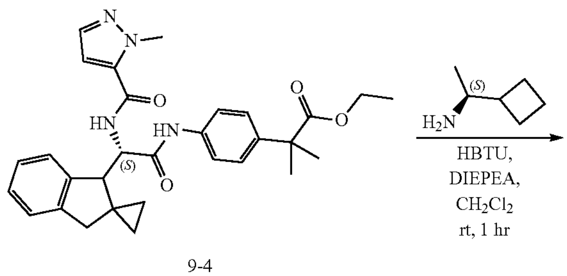

9-4

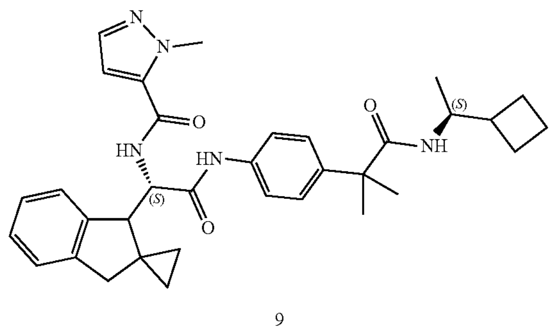

9

(S1) Preparation of Intermediate 9-1

The intermediate Z1 (500 mg, 1.42 mmol), HBTU (647.86 mg, 1.70 mmol), DIPEA (549.54 mg, 4.26 mmol) and $CH_2Cl_2$ (14 mL) were added into a 100 mL single-necked flask for dissolving. The reaction mixture was stirred at room temperature for 10 min, added with ethyl 2-(4-aminophenyl)-2-methylpropanoate (351.9 mg, 1.70 mmol), and stirred at room temperature for 3 h. Then the reaction mixture was added with 30 mL of water, and extracted with $CH_2Cl_2$ (30 mL×2) to collect an organic phase. The organic phase was washed with a saturated salt solution (30 mL×2), dried with anhydrous sodium sulfate, filtered, followed by vacuum concentration to dry. The residue was purified by a silica gel column separation to obtain 559.76 mg (1.04 mmol) of intermediate 9-1 (yield: 73%), MS m/z: 541 $(M+1)^+$.

(S2) Preparation of Intermediate 9-2

The intermediate 9-1 (559.76 mg, 1.04 mmol) and EtOH (20 mL) were added into a 100 mL single-necked flask. The reaction mixture was added with Pd/C (168 mg, w/w 50%) at room temperature under stirring and a nitrogen atmosphere. Then the reaction mixture was reacted at room temperature under stirring and a hydrogen atmosphere for 2 h. The reaction mixture was filtered, and subjected to vacuum concentration to dry to obtain 392.68 mg (0.97 mmol) of intermediate 9-2 (yield: 93%). MS m/z: 407 $(M+1)^+$.

(S3) Preparation of Intermediate 9-3

1-methyl-1H-pyrazole-5-carboxylic acid (122.22 mg, 0.97 mmol), HBTU (441.16 mg, 1.16 mmol), DIPEA (375.39 mg, 2.91 mmol) and $CH_2Cl_2$ (10 mL) were added into a 100 mL single-necked flask for dissolving. The reaction mixture was stirred at room temperature for 10 min, and added with the intermediate 9-2 (392.68 mg, 0.97 mmol), then reacted at room temperature under stirring for 1 h. The reaction mixture was added with 30 mL of water, extracted with $CH_2Cl_2$ (30 mL×2) to collect an organic phase. The organic phase was washed with a saturated salt solution (30 mL×2), dried with anhydrous sodium sulfate, filtered, and subjected to vacuum concentration to dry. The residue was purified by silica gel column separation to obtain 373.94 mg (0.73 mmol) of intermediate 9-3 (yield: 75%). MS m/z: 515 $(M+1)^+$.

(S4) Preparation of Intermediate 9-4

The intermediate 9-3 (373.94 mg, 0.73 mmol), EtOH (4 mL) and $H_2O$ (0.4 mL) were added into a 50 mL single-necked flask for dissolving. The reaction mixture was added with NaOH (146 mg, 3.65 mmol) under stirring at room temperature, heated to 85° C. for reaction under stirring over night. Then the reaction mixture was cooled, diluted with 30 mL of water, adjusted to pH=4 with 6N HCl, and extracted with ethyl acetate (30 mL×2) to collect an organic phase. The organic phase was washed with a saturated salt solution (30 mL×2), dried with anhydrous sodium sulfate, filtered, and subjected to vacuum concentration to dry, so as to obtain 326.40 mg (0.67 mmol) of intermediate 9-4 (yield: 92%). MS m/z: 487 $(M+1)^+$.

(S5) Preparation of Compound 9

The intermediate 9-4 (30.00 mg, 0.062 mmol), HBTU (28.05 mg, 0.074 mmol), DIPEA (23.99 mg, 0.186 mmol) and $CH_2Cl_2$ (2 mL) were added into a 25 mL single-necked flask for dissolving. The reaction mixture was stirred at room temperature for 10 min, added with (s)-1-cyclobutylethylamine (7.33 mg, 0.074 mmol) for reaction under stirring at room temperature for 1 h. Then the reaction mixture was added with 10 mL of water, and extracted with $CH_2Cl_2$ (10 mL×2) to collect an organic phase. The organic phase was washed with a saturated salt solution (10 mL×2), dried with anhydrous sodium sulfate, filtered, and subjected to vacuum concentration to dry. The residue was purified through MPLC (ACN/$H_2O$, 0.05% FA) to obtain 18.28 mg (0.032 mmol) of compound 9 (yield: 52%). MS m/z: 568 $(M+1)^+$.

Example 10 Preparation of Compound 10

A preparation of compound 10 is shown as follows:

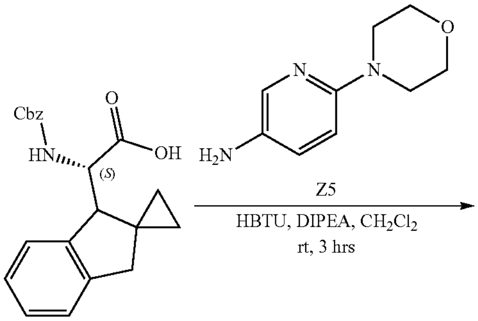

Z1

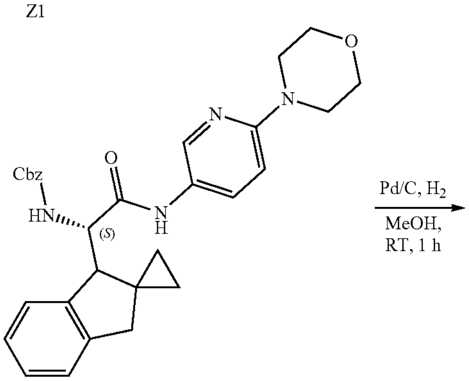

10-1

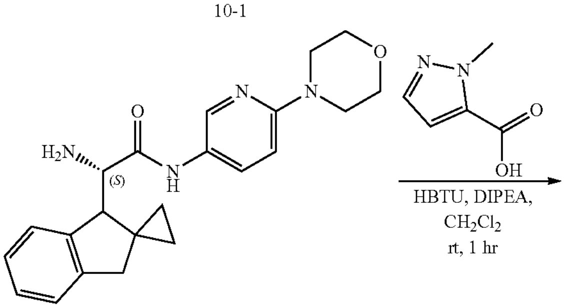

10-2

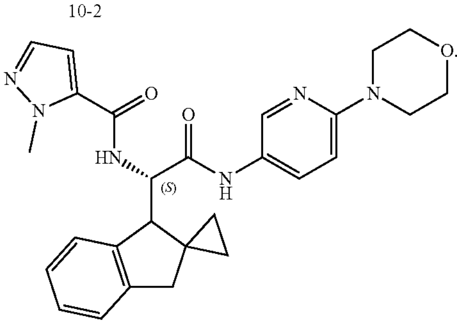

10

The preparation of compound 10 was performed according to the steps (S1)-(S3) of Example 9, in which in the step (S1), ethyl 2-(4-aminophenyl)-2-methylpropanoate was replaced with the intermediate Z5. MS m/z: 487 $(M+1)^+$.

$^1$H NMR (400 MHz, Methanol-$d_4$) δ 8.36 (dd, J=2.7, 0.6 Hz, 1H), 7.88 (dd, J=9.1, 2.7 Hz, 1H), 7.46 (d, J=2.2 Hz, 1H), 7.34-7.21 (m, 3H), 7.19-7.10 (m, 2H), 6.87 (dd, J=9.2, 0.7 Hz, 1H), 6.61 (d, J=2.1 Hz, 1H), 4.92 (d, J=6.8 Hz, 1H), 4.01 (s, 3H), 3.87-3.76 (m, 4H), 3.50-3.40 (m, 5H), 3.26 (d, J=6.7 Hz, 1H), 2.43 (d, J=16.0 Hz, 1H), 1.02-0.91 (m, 1H), 0.78-0.68 (m, 1H), 0.68-0.58 (m, 2H), 0.61-0.51 (m, 2H).

Example 13 Preparation of Compound 13

A structure of compound 13 is shown as follows:

13

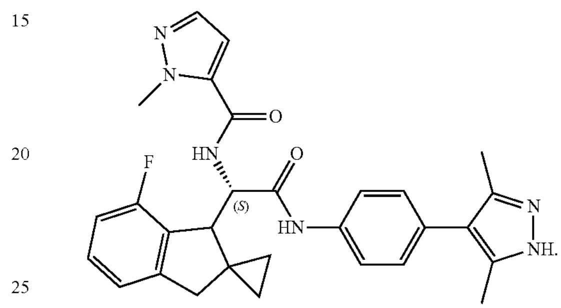

The preparation of compound 13 was performed according to the preparation of compound 1 in Example 1, in which in step (S1), the intermediate Z7 replaced the intermediate Z1 as a raw material. MS m/z: 513 $(M+1)^+$.

$^1$H NMR (400 MHz, Methanol-d4) δ 7.76-7.69 (m, 2H), 7.45 (d, J=2.1 Hz, 1H), 7.37-7.30 (m, 2H), 7.31-7.21 (m, 1H), 7.15-7.08 (m, 2H), 6.93-6.83 (m, 2H), 6.67 (d, J=2.1 Hz, 1H), 5.01 (d, J=7.5 Hz, 1H), 4.01 (s, 3H), 3.57-3.47 (m, 2H), 3.50-3.43 (m, 2H), 2.42 (d, J=16.1 Hz, 1H), 2.33 (s, 6H), 1.33-1.27 (m, 3H), 1.07-0.97 (m, 1H), 0.81-0.71 (m, 1H), 0.69-0.59 (m, 1H), 0.58-0.48 (m, 1H).

Example 14 Preparation of Compound 14

A structure of compound 14 is shown as follows:

14

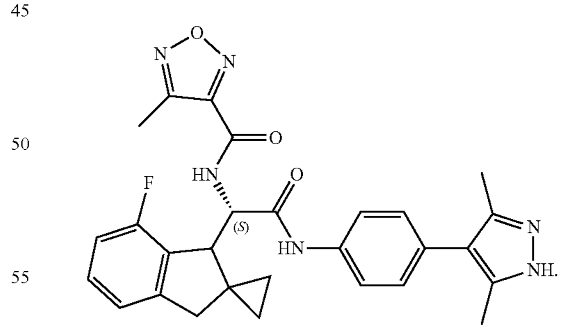

The preparation of compound 14 was performed according to the preparation of compound 1 in Example 1, in which in step (S1), the intermediate Z7 replaced the intermediate Z1 as a raw material, and 4-methylfurazan-3-carboxylic acid replaced 1-methyl-5-pyrazolecarboxylic acid in step (S3). MS m/z: 515 $(M+1)^+$.

$^1$H NMR (400 MHz, Methanol-d4) δ 7.74-7.65 (m, 2H), 7.36-7.24 (m, 3H), 7.12 (d, J=7.4 Hz, 1H), 6.96-6.84 (m, 3H), 5.08 (d, J=6.1 Hz, 1H), 3.57-3.49 (m, 2H), 2.48 (s, 6H), 2.33 (s, 6H), 1.39-1.25 (m, 1H), 1.11-0.98 (m, 1H), 0.83-0.72 (m, 1H), 0.75-0.64 (m, 2H), 0.62-0.51 (m, 1H).

Example 15 Preparation of Compound 15

A structure of compound 15 is shown as follows:

15

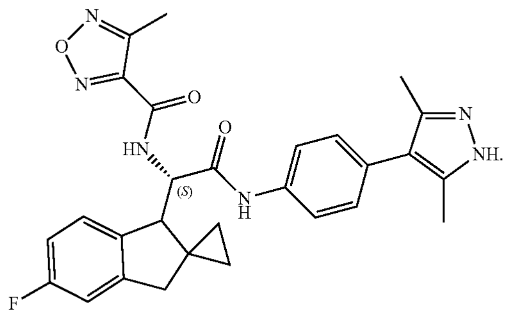

The preparation of compound 15 was performed according to the preparation of compound 1 in Example 1, in which in step (S1), the intermediate Z9 replaced the intermediate Z1 as a raw material, and 4-methylfurazan-3-carboxylic acid replaced 1-methyl-5-pyrazolecarboxylic acid in step (S3). MS m/z: 515 $(M+1)^+$.

$^1$H NMR (400 MHz, Methanol-$d_4$) δ 7.70-7.62 (m, 2H), 7.28 (dd, J=8.5, 1.5 Hz, 2H), 7.21 (dd, J=8.4, 5.2 Hz, 1H), 7.02 (d, J=9.0 Hz, 1H), 6.87 (t, J=8.9 Hz, 1H), 4.98 (d, J=6.4 Hz, 1H), 3.47 (d, J=16.3 Hz, 1H), 2.56-2.36 (m, 4H), 2.25 (s, 6H), 1.40-1.21 (m, 1H), 1.00 (dt, J=9.8, 5.4 Hz, 1H), 0.78-0.56 (m, 3H).

Example 16 Preparation of Compound 16

A structure of compound 16 is shown as follows:

16

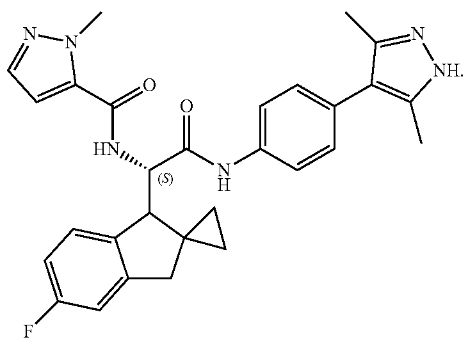

The preparation of compound 16 was performed according to the preparation of compound 1 in Example 1, in which in step (S1), the intermediate Z9 replaced the intermediate Z1 as a raw material. MS m/z: 513 $(M+1)^+$.

$^1$H NMR (400 MHz, Methanol-d4) δ 7.69 (d, J=8.6 Hz, 2H), 7.47 (d, J=2.1 Hz, 1H), 7.34-7.18 (m, 3H), 7.03 (dd, J=9.1, 2.4 Hz, 1H), 6.88 (td, J=8.9, 2.5 Hz, 1H), 6.68 (d, J=2.1 Hz, 1H), 4.95 (d, J=7.1 Hz, 1H), 4.02 (s, 3H), 3.46 (d, J=16.3 Hz, 1H), 3.22 (d, J=7.1 Hz, 1H), 2.43 (d, J=16.3 Hz, 1H), 2.26 (s, 6H), 1.07-0.97 (m, 1H), 0.79-0.69 (m, 1H), 0.69-0.52 (m, 2H).

Example 17 Preparation of Compound 17

A structure of compound 17 is shown as follows:

17

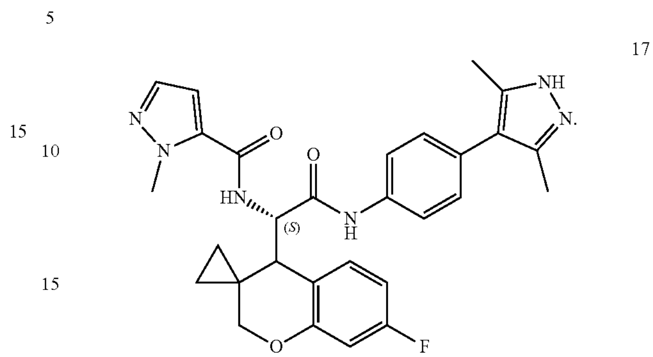

The preparation of compound 17 was performed according to the preparation of compound 1 in Example 1, in which in step (S1), the intermediate Z8 replaced the intermediate Z1 as a raw material. MS m/z: 529 $(M+1)^+$.

$^1$H NMR (400 MHz, Methanol-d4) δ 7.68 (d, J=8.4 Hz, 2H), 7.46 (d, J=2.2 Hz, 1H), 7.32-7.23 (m, 2H), 7.14-7.06 (m, 1H), 6.80 (d, J=2.2 Hz, 1H), 6.58-6.51 (m, 1H), 6.49-6.39 (m, 1H), 5.09 (d, J=9.8 Hz, 1H), 5.01-4.94 (m, 1H), 3.89 (s, 3H), 3.34 (s, 7H), 2.24 (s, 6H), 1.36-1.21 (m, 8H), 1.01-0.82 (m, 5H), 0.72-0.56 (m, 2H), 0.48-0.36 (m, 1H).

Example 18 Preparation of Compound 18

A structure of compound 18 is shown as follows:

18

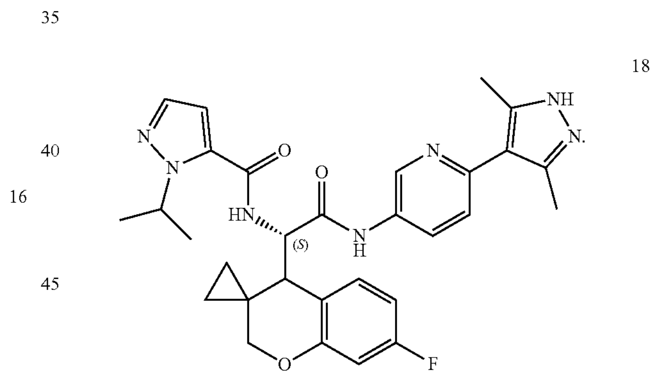

The preparation of compound 18 was performed according to the preparation of compound 1 in Example 1, in which in step (S1), the intermediate Z9 replaced the intermediate Z1, and 4-(3,5-dimethyl-1-{(2-(trimethylsilyl)ethoxy) methyl}-1H-pyrazolyl)aniline was replaced with intermediate Z10; and in step (S3), 1-methyl-5-pyrazolecarboxylic acid was replaced with 1-isopropyl-5-pyrazole carboxylic acid. MS m/z: 558 $(M+1)^+$.

$^1$H NMR (400 MHz, Methanol-d4) δ 9.24 (d, J=2.5 Hz, 1H), 8.45 (dd, J=8.8, 2.6 Hz, 1H), 7.83 (d, J=8.8 Hz, 1H), 7.49 (d, J=2.0 Hz, 1H), 7.10 (dd, J=8.5, 6.6 Hz, 1H), 6.70 (d, J=2.1 Hz, 1H), 6.56 (dd, J=10.5, 2.6 Hz, 1H), 6.47 (td, J=8.4, 2.6 Hz, 1H), 5.13 (d, J=9.8 Hz, 1H), 5.04 (p, J=6.7 Hz, 1H), 4.96 (dd, J=11.4, 2.0 Hz, 1H), 3.42 (dd, J=11.5, 1.7 Hz, 1H), 2.69-2.61 (m, 1H), 2.40 (s, 6H), 1.34 (dd, J=12.0, 6.6 Hz, 6H), 0.92-0.84 (m, 1H), 0.70-0.59 (m, 2H), 0.45 (d, J=9.5 Hz, 1H).

Example 19 Preparation of Compound 19

A structure of compound 19 is shown as follows:

19

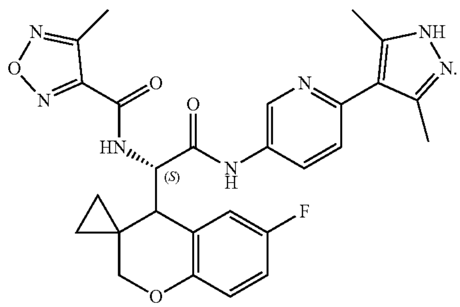

The preparation of compound 19 was performed according to the preparation of compound 1 in Example 1, in which in step (S1), the intermediate Z4 replaced the intermediate Z1, and 4-(3,5-dimethyl-1-{(2-(trimethylsilyl)ethoxy) methyl}-1H-pyrazolyl)aniline was replaced with intermediate Z10; and in step (S3), 1-methyl-5-pyrazole carboxylic acid was replaced with 4-methylfurazan-3-carboxylic acid. MS m/z: 532 $(M+1)^+$.

$^1H$ NMR (400 MHz, Methanol-d4) δ 8.86 (s, 1H), 8.22 (dd, J=8.6, 2.5 Hz, 1H), 7.46 (d, J=8.6 Hz, 1H), 7.02-6.70 (m, 3H), 5.18 (d, J=9.8 Hz, 1H), 5.00-4.91 (m, 1H), 3.38 (dd, J=11.5, 1.8 Hz, 1H), 2.65 (d, J=9.7, 1.6 Hz, 1H), 2.35 (d, J=6.9 Hz, 9H), 0.99-0.84 (m, 1H), 0.73-0.56 (m, 2H), 0.51-0.37 (m, 1H).

Example 20 Preparation of Compound 20

A structure of compound 20 is shown as follows:

20

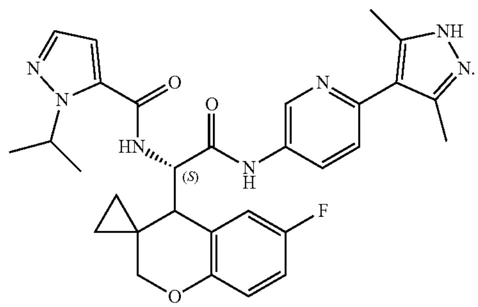

The preparation of compound 20 was performed according to the preparation of compound 1 in Example 1, in which in step (S1), the intermediate Z4 replaced the intermediate Z1, and 4-(3,5-dimethyl-1-{(2-(trimethylsilyl)ethoxy) methyl}-1H-pyrazolyl)aniline was replaced with intermediate Z10; and in step (S3), 1-methyl-5-pyrazolecarboxylic acid was replaced with 1-isopropyl-5-pyrazolecarboxylic acid. MS m/z: 558 $(M+1)^+$.

$^1H$ NMR (400 MHz, Methanol-$d_4$) δ 8.95 (d, J=2.6 Hz, 1H), 8.32-8.20 (m, 1H), 7.58-7.51 (m, 1H), 7.49 (d, J=2.1 Hz, 1H), 6.95-6.83 (m, 2H), 6.83-6.74 (m, 1H), 6.71 (d, J=2.1 Hz, 1H), 5.16 (d, J=10.0 Hz, 1H), 5.08-4.98 (m, 1H), 4.98-4.91 (m, 1H), 3.43-3.35 (m, 1H), 2.69-2.58 (m, 1H), 2.36 (s, 7H), 1.39-1.31 (m, 6H), 1.17-1.09 (m, 1H), 0.90 (dt, J=7.9, 4.4 Hz, 1H), 0.71-0.58 (m, 2H), 0.49-0.40 (m, 1H).

Example 21 Preparation of Compound 21

A structure of compound 21 is shown as follows:

21

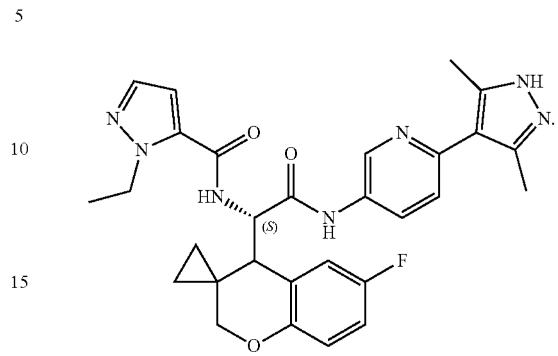

The preparation of compound 21 was performed according to the preparation of compound 1 in Example 1, in which in step (S1), the intermediate Z4 replaced the intermediate Z1, and 4-(3,5-dimethyl-1-{(2-(trimethylsilyl)ethoxy) methyl}-1H-pyrazolyl)aniline was replaced with intermediate Z10; and in step (S3), 1-methyl-5-pyrazolecarboxylic acid was replaced with 1-ethyl-5-pyrazolecarboxylic acid. MS m/z: 544 $(M+1)^+$.

$^1H$ NMR (400 MHz, Methanol-$d_4$) δ 8.86 (d, J=2.6 Hz, 1H), 8.25-8.15 (m, 1H), 7.51-7.41 (m, 2H), 6.93-6.81 (m, 2H), 6.81-6.73 (m, 2H), 5.15 (d, J=10.0 Hz, 1H), 4.99-4.92 (m, 2H), 4.45-4.32 (m, 1H), 4.32-4.20 (m, 1H), 3.42-3.35 (m, 1H), 2.65-2.57 (m, 1H), 2.35 (s, 7H), 1.26-1.20 (m, 3H), 0.97-0.86 (m, 1H), 0.71-0.57 (m, 2H), 0.48-0.39 (m, 1H).

Example 22 Preparation of Compound 22

A structure of compound 22 is shown as follows:

22

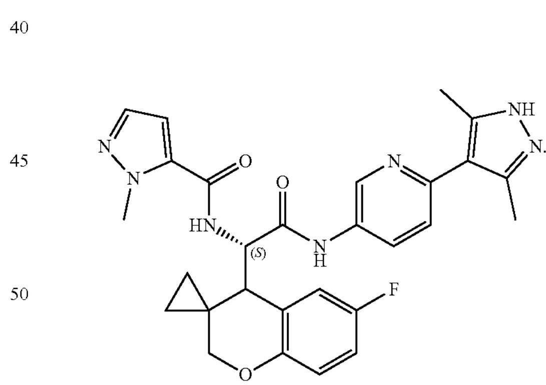

The preparation of compound 22 was performed according to the preparation of compound 1 in Example 1, in which in step (S1), the intermediate Z4 replaced the intermediate Z1, and 4-(3,5-dimethyl-1-{(2-(trimethylsilyl)ethoxy) methyl}-1H-pyrazolyl)aniline was replaced with intermediate Z10. MS m/z: 530 $(M+1)^+$.

$^1H$ NMR (400 MHz, Methanol-d4) δ 8.88-8.83 (m, 1H), 8.25-8.15 (m, 1H), 7.49-7.43 (m, 2H), 6.92-6.83 (m, 2H), 6.81-6.76 (m, 2H), 5.14 (d, J=9.9 Hz, 1H), 4.97-4.92 (m, 1H), 3.89 (s, 3H), 3.41-3.36 (m, 1H), 2.67-2.56 (m, 1H), 2.35 (s, 6H), 1.32-1.25 (m, 1H), 0.94-0.87 (m, 1H), 0.70-0.58 (m, 2H).

Example 23 Preparation of Compound 23

A structure of compound 23 is shown as follows:

23

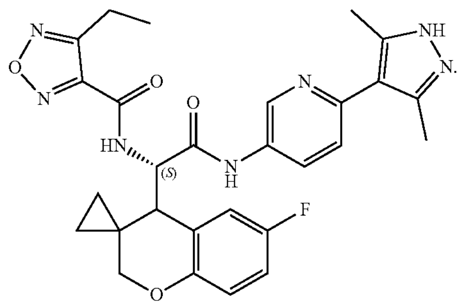

The preparation of compound 23 was performed according to the preparation of compound 1 in Example 1, in which in step (S1), the intermediate Z4 replaced the intermediate Z1, and 4-(3,5-dimethyl-1-{(2-(trimethylsilyl)ethoxy) methyl}-1H-pyrazolyl)aniline was replaced with intermediate Z10; and in step (S3), 1-methyl-5-pyrazolecarboxylic acid was replaced with 4-ethylfurazan-3-carboxylic acid. MS m/z: 546 $(M+1)^+$.

$^1H$ NMR (400 MHz, Methanol-$d_4$) δ 9.24 (d, J=2.3 Hz, 1H), 8.46 (dd, J=8.9, 2.6 Hz, 1H), 7.84 (d, J=8.7 Hz, 1H), 7.12 (dd, J=8.5, 6.6 Hz, 1H), 6.55 (dd, J=10.5, 2.6 Hz, 1H), 6.44 (td, J=8.4, 2.6 Hz, 1H), 5.18 (d, J=9.6 Hz, 1H), 4.93 (dd, J=11.5, 2.0 Hz, 1H), 3.42 (dd, J=11.6, 1.7 Hz, 1H), 2.80 (q, J=7.5 Hz, 2H), 2.69 (d, J=9.9 Hz, 1H), 2.41 (s, 6H), 1.19 (t, J=7.5 Hz, 3H), 0.94-0.83 (m, 1H), 0.71-0.60 (m, 2H), 0.52-0.42 (m, 1H).

Example 24 Preparation of Compound 24

A preparation of compound 24 is illustrated as follows:

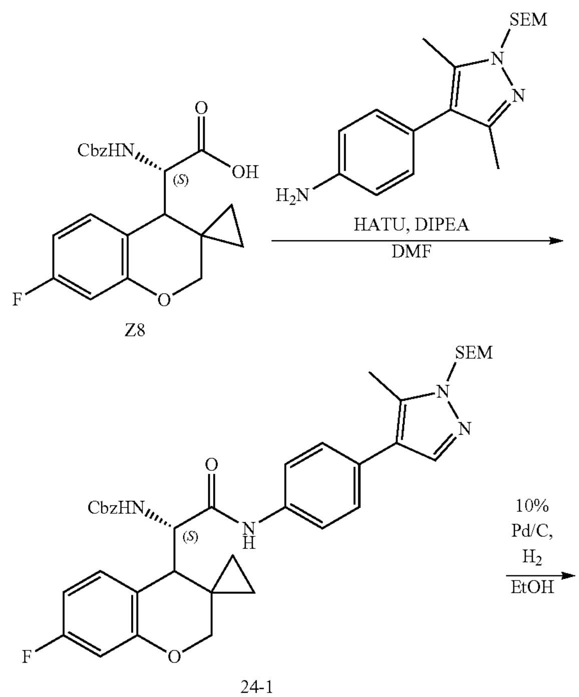

Z8

24-1

-continued

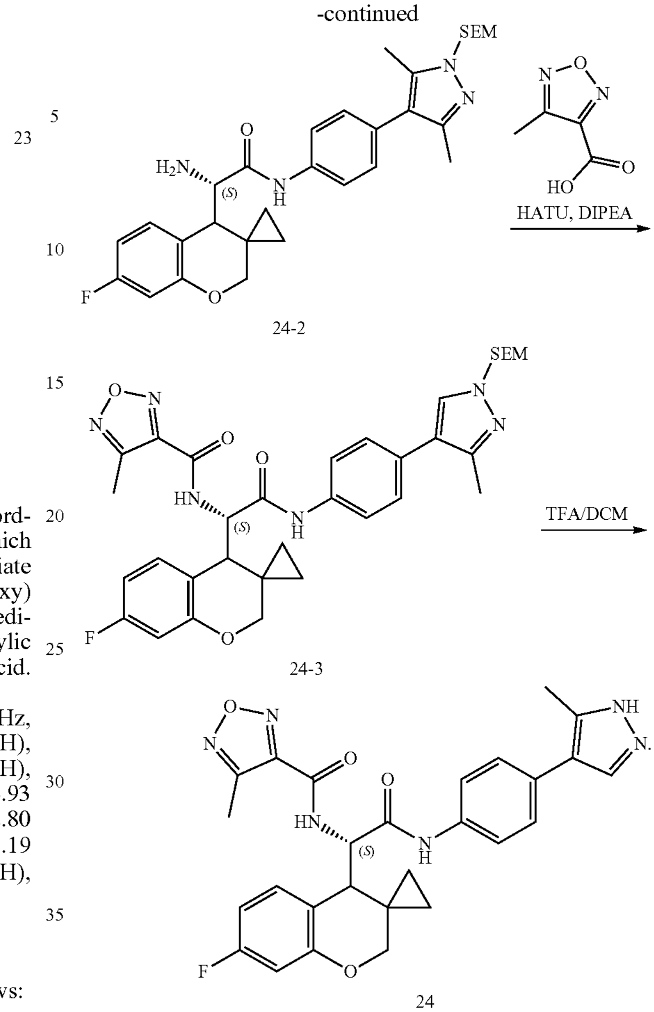

24-2

24-3

24

(S1) Preparation of Intermediate 24-1

The intermediate Z8 (2.0 g, 5.19 mmol) and DMF (25 mL) were successively added into a 100 mL single-necked flask. The reaction mixture was successively added with HATU (2.57 g, 6.75 mmol) and DIPEA (2.68 g, 20.78 mmol, 3.69 mL) under stirring and ice bath, and then reacted under stirring and ice bath for 10 min. The reaction mixture was added with 4-(3,5-dimethyl-1-{(2-(trimethylsilyl)ethoxy) methyl}-1H-pyrazolyl)aniline (1.97 g, 6.23 mmol), heated to room temperature for reaction under stirring for 1 h. After the reaction was confirmed by LC-MS to be complete, the reaction mixture was added with 100 mL of ethyl acetate, and washed with a saturated salt solution (100 mL×2) to collect an organic phase. The organic phase was dried with anhydrous sodium sulfate, filtered, subjected to vacuum concentration to dry, and then purified by column chromatography to obtain 3.96 g (5.91 mmol) of intermediate 24-1 (yield: 86%). MS m/z: 671 $(M+1)^+$.

(S2) Preparation of Intermediate 24-2

The intermediate 24-1 (3.96 g, 5.91 mmol) and EtOH (100 mL) were successively added into a 250 mL single-necked flask. The mixture was added with 10% Pd/C (1.19 g, w/w 30%) under a nitrogen atmosphere. Then the mixture was subjected to hydrogen replacement three times under stirring, followed by reaction under stirring and hydrogen atmosphere at room temperature for 3 h. After the reaction was complete, the mixture was filtered with diatomite by Brønsted funnel, and washed with ethanol. The filtrate was combined, and subjected to vacuum concentration to dry to obtain 3.02 g (5.49 mmol) of intermediate 24-2 (yield: 95%). MS m/z: 551 $(M+1)^+$.

(S3) Preparation of Intermediate 24-3

The intermediate 24-2 (450 mg, 0.82 mmol), 4-methyl-1,2,5-oxadiazole-3-carboxylic acid (136 mg, 1.06 mmol) and DCM (6 mL) were successively added into a 50 mL single-necked flask. Then, HBTU (402 mg, 1.07 mmol) and DIPEA (421 mg, 3.28 mmol, 0.58 mL) were successively added into the 50 mL single-necked flask under stirring and ice bath. The reaction mixture was reacted under stirring and ice bath for 10 min, and then heated to room temperature for reaction under stirring for 1 h. After the reaction was confirmed by LC-MS to be complete, the reaction mixture was added with 50 mL of dichloromethane, and washed with a saturated salt solution (50 mL×2) to collect an organic phase. The organic phase was dried with anhydrous sodium sulfate, and filtered. The filtrate was subjected to vacuum concentration to dry, and purified by column chromatography to obtain 460 mg (0.71 mmol) of intermediate 24-3 (yield: 86%). MS m/z: 647 $(M+1)^+$.

(S4) Preparation of Compound 24

The intermediate 24-3 (460 mg, 0.71 mmol) and $CH_2Cl_2$ (5 mL) were successively added into a 50 mL single-necked flask. 5 mL of TFA were added into the 50 mL single-necked flask under stirring and ice bath. The reaction mixture was heated to room temperature, and reacted under stirring for 3 h. After the reaction was confirmed by LC-MS to be complete, the reaction mixture was subjected to vacuum concentration to dry, purified with reversed-phase MPLC ($CH_3CN/H_2O$, 0.05% TFA), concentrated, and subjected to vacuum freeze drying to obtain 77 mg (0.71 mmol) of compound 24 (yield: 77%). MS m/z: 531 $(M+1)^+$.

$^1$H NMR (400 MHz, Methanol-$d_4$) δ 7.75 (d, J=8.2 Hz, 2H), 7.34 (d, J=8.3 Hz, 2H), 7.13 (dd, J=8.4, 6.7 Hz, 1H), 6.54 (dd, J=10.5, 2.6 Hz, 1H), 6.44 (td, J=8.4, 2.7 Hz, 1H), 5.12 (d, J=9.8 Hz, 1H), 4.96 (dd, J=11.5, 1.9 Hz, 1H), 3.40 (dd, J=11.6, 1.9 Hz, 1H), 2.62 (d, J=9.6 Hz, 1H), 2.39-2.30 (m, 9H), 0.94 (dt, J=8.2, 4.6 Hz, 1H), 0.63 (tq, J=9.4, 4.9, 4.5 Hz, 2H), 0.47-0.40 (m, 1H).

Example 25 Preparation of Compound 25

A structure of compound 25 is shown as follows:

25

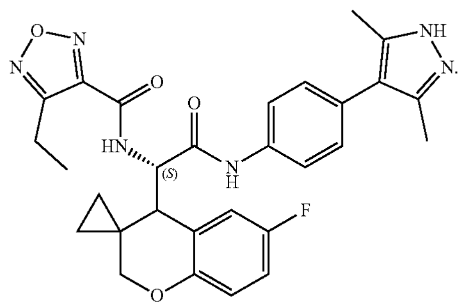

The preparation of compound 25 was performed according to the preparation of compound 1 in Example 1, in which in step (S1), the intermediate Z4 replaced the intermediate Z1; and in step (S3), 1-methyl-5-pyrazolecarboxylic acid was replaced with 4-ethylfurazan-3-carboxylic acid. MS m/z: 545 $(M+1)^+$.

$^1$H NMR (400 MHz, Methanol-$d_4$) δ 7.68 (d, J=8.4 Hz, 2H), 7.28 (d, J=8.5 Hz, 2H), 6.92 (dt, J=9.2, 3.3 Hz, 1H), 6.85 (td, J=8.4, 3.1 Hz, 1H), 6.77 (dd, J=9.0, 4.9 Hz, 1H), 5.17 (dd, J=9.8, 2.5 Hz, 1H), 4.95 (d, J=11.5 Hz, 1H), 3.37 (dd, J=11.5, 1.8 Hz, 1H), 2.85-2.74 (m, 2H), 2.61 (d, J=9.8 Hz, 1H), 2.24 (s, 6H), 1.19 (tt, J=7.6, 1.5 Hz, 3H), 0.95 (dt, J=9.3, 5.1 Hz, 1H), 0.71-0.56 (m, 2H), 0.47-0.40 (m, 1H).

Example 26 Preparation of Compound 26

A structure of compound 26 is shown as follows:

26

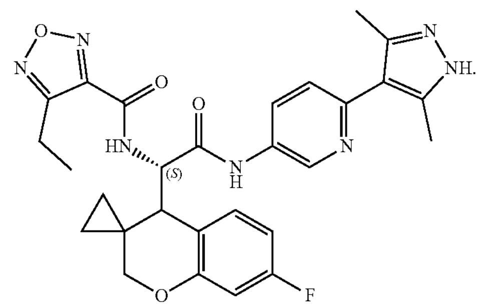

A preparation of compound 26 is illustrated as follows:

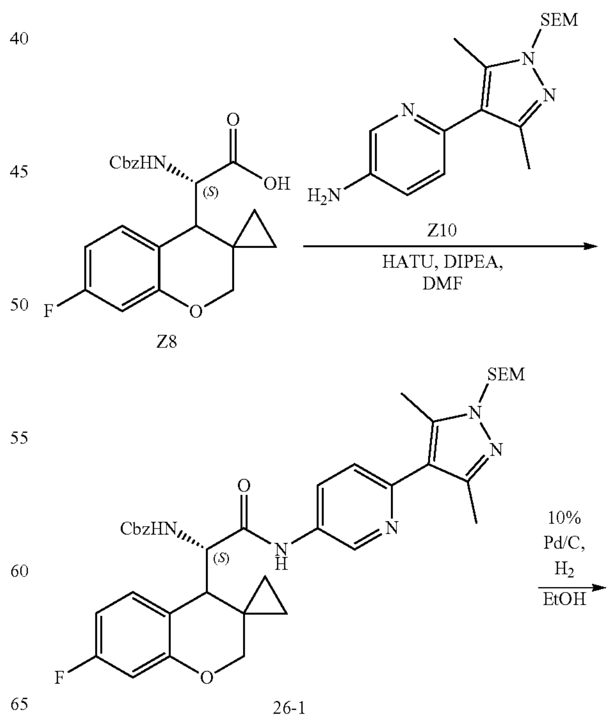

Z10

Z8

26-1

-continued

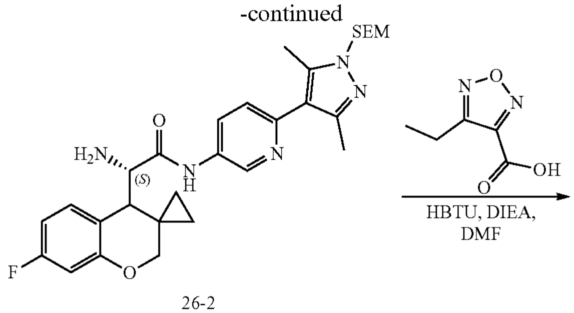

26-2

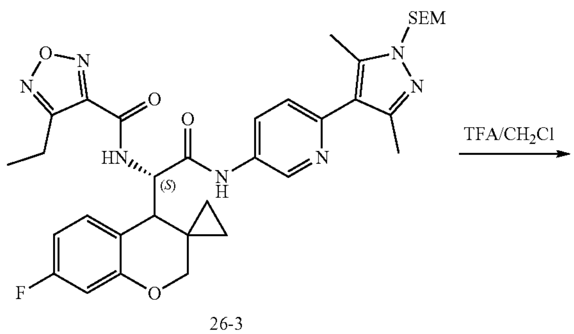

26-3

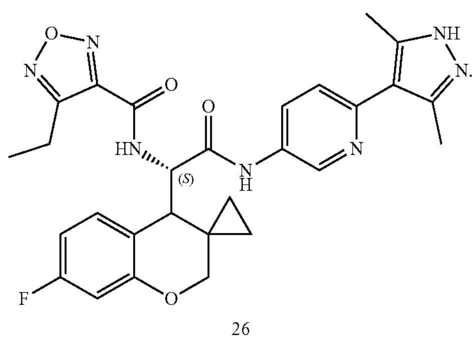

26

(S1) Preparation of Intermediate 26-1

The intermediate Z8 (25.0 g, 64.94 mmol) and DMF (200 mL) were successively added into a 500 mL single-necked flask. 32.08 g (84.42 mmol) of HATU were added into the 500 mL single-necked flask under stirring and ice bath. The reaction mixture was successively added with the intermediate Z10 (8.65 g, 27.30 mmol) and DIPEA (33.51 g, 259.76 mmol, 42.85 mL), heated to 60° C. for reaction under stirring for 2 h. After the reaction was confirmed by LC-MS to be complete, the reaction mixture was decanted into 800 mL of ice water, extracted with ethyl acetate, and washed with a saturated salt solution (200 mL×2) to collect an organic phase. The organic phase was dried with anhydrous sodium sulfate, filtered, and subjected to vacuum concentration to dry and column chromatography for purification, so as to obtain 43.2 g (63.03 mmol) of intermediate 26-1 (yield: 97%). MS m/z: 686 $(M+1)^+$.

(S2) Preparation of Intermediate 26-2

The intermediate 26-1 (20 g, 29.18 mmol) and 95% EtOH (200 mL) were successively added into a 500 mL single-necked flask. 6.0 g 10% Pd/C (w/w 30%) were added into the 500 mL single-necked flask under a nitrogen atmosphere. The reaction mixture was subjected to hydrogen replacement three times under stirring. Then, the reaction mixture was reacted at room temperature under stirring and hydrogen atmosphere for 2 h, filtered with diatomite by Brønsted funnel, and washed with ethanol. The filtrate was combined, and subjected to vacuum concentration to dry to obtain 14.92 g (27.04 mmol) of intermediate 26-2 (yield: 92.6%), MS m/z: 552 $(M+1)^+$.

(S3) Preparation of Intermediate 26-3

The intermediate 26-2 (14.92 g, 27.04 mmol), 4-ethyl-1,2,5-oxadiazole-3-carboxylic acid (5.76 g, 40.56 mmol) and DMF (100 mL) were successively added into a 250 mL single-necked flask. HBTU (15.37 g, 40.56 mmol) and DIPEA (10.46 g, 81.12 mmol, 13.4 mL) were successively added into the 250 mL single-necked flask under stirring and ice bath. The reaction mixture was stirred to react under ice bath for 10 min, and heated to room temperature to react under stirring for 1 h. After the reaction was confirmed by LC-MS to be complete, the reaction mixture was decanted into 500 mL of ice water, extracted with ethyl acetate, and washed with a saturated salt solution (200 mL×2) to collect an organic phase. The organic phase was dried with anhydrous sodium sulfate, filtered, and subjected to vacuum concentration to dry and column chromatography for purification, so as to obtain 6.2 g (9.18 mmol) of intermediate 26-3 (yield: 61.5%). MS m/z: 676 $(M+1)^+$.

(S4) Preparation of Compound 26

The intermediate 26-3 (6.2 g, 9.18 mmol) and $CH_2Cl_2$ (25 mL) were successively added into a 250 mL single-necked flask. 25 mL of TFA were added into the 250 mL single-necked flask under stirring and ice bath. The reaction mixture was heated to room temperature to react under stirring for 3 h. After the reaction was confirmed by LC-MS to be complete, the reaction mixture was subjected to vacuum concentration to dry, reversed-phase MPLC for purification ($CH_3CN/H_2O$, 0.05% TFA), concentration and vacuum freeze drying to obtain 3.01 g (5.52 mmol) of compound 26 (yield: 60.1%). MS m/z: 546 $(M+1)^+$.

$^1H$ NMR (400 MHz, Methanol-$d_4$) δ 9.24 (d, J=2.3 Hz, 1H), 8.46 (dd, J=8.9, 2.6 Hz, 1H), 7.84 (d, J=8.7 Hz, 1H), 7.12 (dd, J=8.5, 6.6 Hz, 1H), 6.55 (dd, J=10.5, 2.6 Hz, 1H), 6.44 (td, J=8.4, 2.6 Hz, 1H), 5.18 (d, J=9.6 Hz, 1H), 4.93 (dd, J=11.5, 2.0 Hz, 1H), 3.42 (dd, J=11.6, 1.7 Hz, 1H), 2.80 (q, J=7.5 Hz, 2H), 2.69 (d, J=9.9 Hz, 1H), 2.41 (s, 6H), 1.19 (t, J=7.5 Hz, 3H), 0.94-0.83 (m, 1H), 0.71-0.60 (m, 2H), 0.52-0.42 (m, 1H).

Example 27 Preparation of Compound 27

A structure of compound 27 is shown as follows:

27

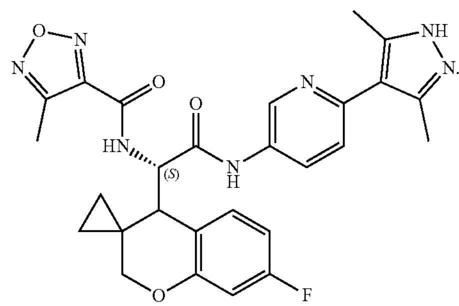

The preparation of compound 27 was performed according to the preparation of compound 1 in Example 1, in which in step (S1), the intermediate Z8 replaced the intermediate Z1, and 4-(3,5-dimethyl-1-{(2-(trimethylsilyl)ethoxy) methyl}-1H-pyrazolyl)aniline was replaced with intermediate Z10; and in step (S3), 1-methyl-5-pyrazolecarboxylic acid was replaced with 4-methylfurazan-3-carboxylic acid. MS m/z: 532 $(M+1)^+$.

$^1$H NMR (400 MHz, Methanol-$d_4$) δ 9.20 (d, J=2.5 Hz, 1H), 8.43 (dd, J=8.8, 2.6 Hz, 1H), 7.80 (d, J=8.8 Hz, 1H), 7.13 (dd, J=8.6, 6.6 Hz, 1H), 6.55 (dd, J=10.5, 2.6 Hz, 1H), 6.46 (td, J=8.4, 2.6 Hz, 1H), 5.17 (d, J=9.6 Hz, 1H), 4.93 (dd, J=11.5, 2.1 Hz, 1H), 3.41 (dd, J=11.6, 1.8 Hz, 1H), 2.69 (dd, J=9.7, 1.6 Hz, 1H), 2.40 (s, 6H), 2.37 (s, 3H), 0.93-0.87 (m, 1H), 0.70-0.60 (m, 2H), 0.50-0.44 (m, 1H).

Example 28 Preparation of Compound 28 (General Route B)

A preparation of compound 28 (general route B) is illustrated as follows:

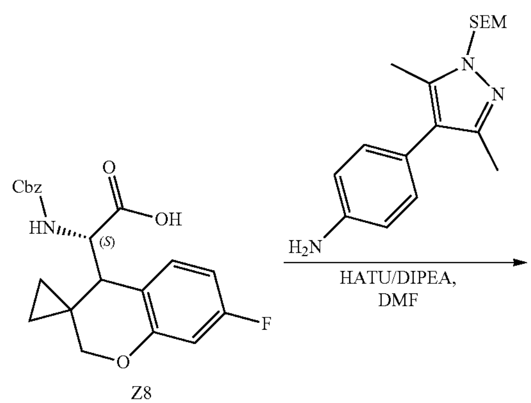

Z8

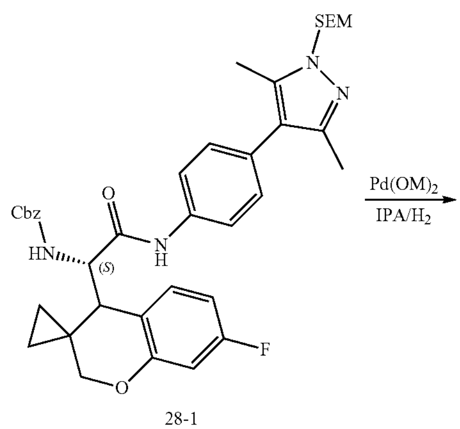

28-1

-continued

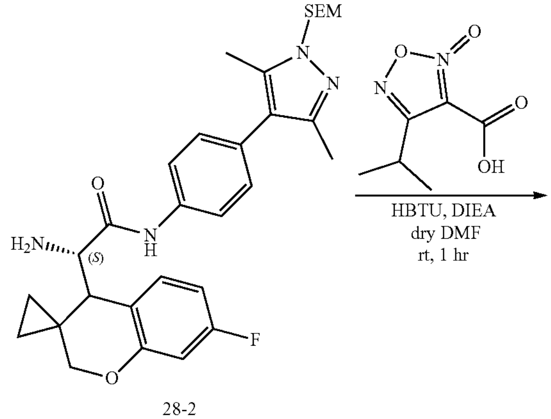

28-2

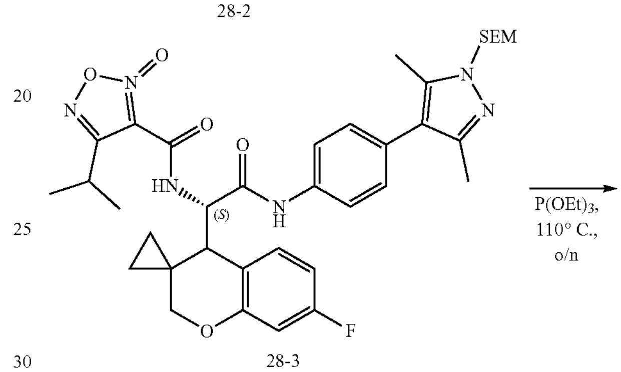

28-3

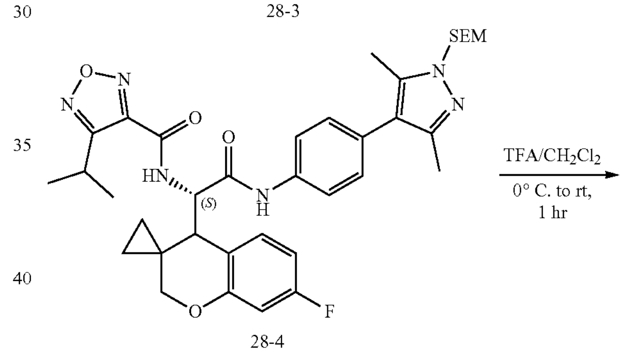

28-4

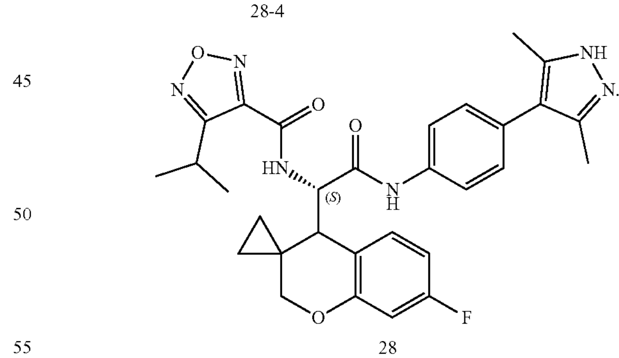

28

(S1)-(S3) Preparation of Intermediate 28-3

The steps (S1)-(S3) for preparing intermediate 28-3 were performed according to the steps (S1)-(S3) of the preparation of compound 1 in Example 1, in which in step (S1), the intermediate Z1 was replaced with intermediate Z8; and in step (S3), 1-methyl-5-pyrazolecarboxylic acid was replaced with the intermediate Z20. MS m/z: 546 $(M+1)^+$.

(S4) Preparation of Intermediate 28-4

23 mg (32.63 μmol) of the intermediate 28-3 were dissolved in 0.7 mL of $P(OEt)_3$. The reaction mixture was heated to 110° C. for reaction under stirring overnight. After the reaction was complete, the reaction mixture was subjected to vacuum concentration, and C-18 reversed-phase medium pressure-high performance liquid chromatography (M-HPLC) ($ACN/H_2O$, 0.05% TFA) for purification to obtain 18 mg (26.13 μmol) of intermediate 28-4 (yield: 80.08%), MS m/z: 689 $(M+1)^+$.

(S5) Preparation of Compound 28

0.5 mL of TFA were added into a DCM (0.5 mL) solution of the intermediate 28-4 (18 mg, 26.13 μmol) at 0° C. The reaction mixture was reacted at room temperature under stirring for 2 h. After the reaction was complete, the reaction mixture was concentrated, and purified by C-18 reversed-phase M-HPLC ($ACN/H_2O$, 0.05% TFA) to obtain 9 mg (15.97 μmol) of compound 28 (yield: 61.10%, purity: 99.1%). MS m/z: 559 $(M+1)^+$.

$^1H$ NMR (400 MHz, Methanol-$d_4$) δ 7.74 (d, J=8.5 Hz, 2H), 7.33 (d, J=8.6 Hz, 2H), 7.11 (dd, J=8.5, 6.6 Hz, 1H), 6.54 (dd, J=10.5, 2.6 Hz, 1H), 6.43 (td, J=8.5, 2.6 Hz, 1H), 5.14 (d, J=9.8 Hz, 1H), 4.97 (dd, J=11.5, 2.0 Hz, 1H), 3.40 (dd, J=11.5, 1.8 Hz, 1H), 3.28-3.20 (m, 1H), 2.61 (d, J=9.9 Hz, 1H), 2.33 (s, 6H), 1.23 (dd, J=24.5, 6.9 Hz, 6H), 0.98-0.89 (in, 1H), 0.71-0.56 (m, 2H), 0.48-0.38 (in, 1H).

Examples 29-104 Preparations of Compounds 28-104

Corresponding compounds were prepared according to the general route A, such as the steps of Example 1, in which in step (S1), the intermediate Z1 was replaced by BB-amino acid shown at the following table, 4-(3,5-dimethyl-1-{(2-(trimethylsilyl)ethoxy)methyl}-1H-pyrazolyl)aniline was replaced with BB-amine shown at the following table; and in step (S3), 1-methyl-5-pyrazolecarboxylic acid was replaced with BB-acid shown at the following table.

Corresponding compounds were prepared according to the general route B, such as the steps of Example 28, in which in step (S1), the intermediate Z8 was replaced with BB-amino acid shown at the following table, 4-(3,5-dimethyl-1-{(2-(trimethylsilyl)ethoxy)methyl}-1H-pyrazolyl) aniline was replaced with BB-amine shown at the following table; and in step (S3), intermediate Z20 was replaced with BB-acid shown at the following table.

| Compound | General route | BB-amino acid | BB-amine | BB-acid | Structural formula | $^1$HNMR and/or LCMS: |
|---|---|---|---|---|---|---|
| 29 | A | 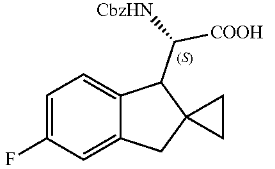 Z9 | 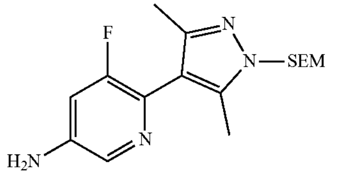 Z11 | 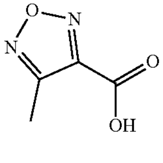 | 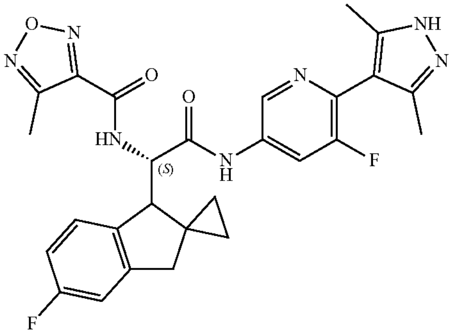 | $^1$H NMR (400 MHz, Methanol-$d_4$) δ 8.63 (d, J = 1.9 Hz, 1H), 8.25 (dd, J = 11.6, 2.1 Hz, 1H), 7.21 (dd, J = 8.4, 5.2 Hz, 1H), 7.02 (dd, J = 9.0, 2.4 Hz, 1H), 6.87 (td, J = 8.9, 2.5 Hz, 1H), 5.03-4.98 (m, 1H), 3.46 (d, J = 16.3 Hz, 1H), 2.48 (s, 3H), 2.26 (s, 6H), 1.01-0.83 (m, 3H), 0.77-0.65 (m, 2H), 0.64-0.57 (m, 1H). (ESI) m/z: 534 $[M + 1]^+$ |
| 30 | A | 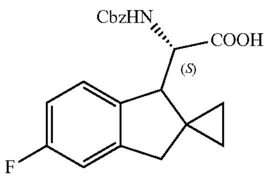 Z9 | 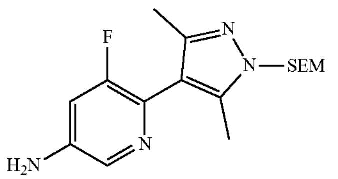 Z11 | 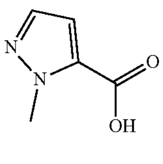 | 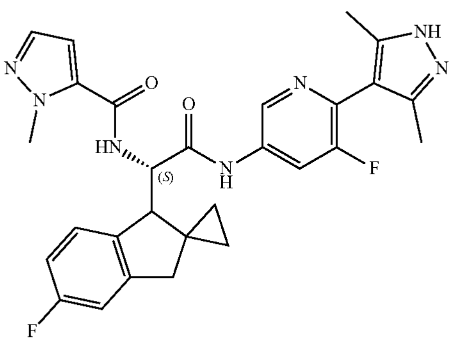 | $^1$H NMR (400 MHz, Methanol-$d_4$) δ 8.66 (d, J = 2.3 Hz, 1H), 8.28 (dd, J = 11.6, 2.1 Hz, 1H), 7.46 (d, J = 2.1 Hz, 1H), 7.21 (dd, J = 8.4, 5.2 Hz, 1H), 7.02 (dd, J = 9.0, 2.4 Hz, 1H), 6.86 (td, J = 8.9, 2.5 Hz, 1H), 6.67 (d, J = 2.1 Hz, 1H), 4.94 (dd, J = 7.2, 2.8 Hz, 1H), 4.01 (s, |

-continued
| Compound | General route | BB-amino acid | BB-amine | BB-acid | Structural formula | $^1$HNMR and/or LCMS: |
|---|---|---|---|---|---|---|
| | | | | | | 3H), 3.44 (d, J = 16.3 Hz, 1H), 3.23 (d, J = 7.2 Hz, 1H), 2.43 (d, J = 16.4 Hz, 1H), 2.29 (s, 6H), 0.99-0.89 (m, 1H), 0.78-0.68 (m, 1H), 0.67-0.60 (m, 1H), 0.60-0.52 (m, 1H). (ESI) m/z: 532 $[M + 1]^+$ |
| 31 | A | 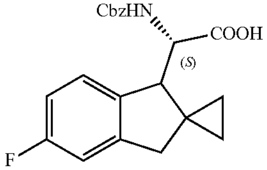 Z9 | 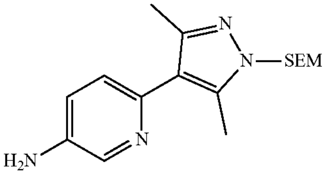 Z10 | 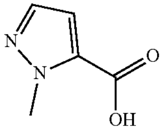 | 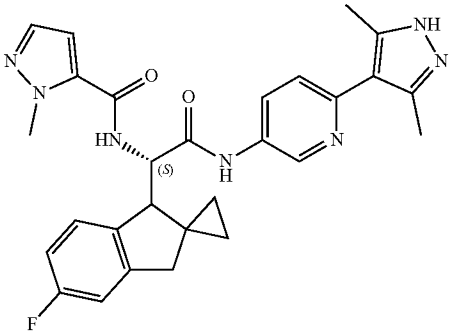 | $^1$H NMR (400 MHz, Methanol-$d_4$) δ 9.27 (d, J = 2.5 Hz, 1H), 8.46 (dd, J = 8.8, 2.6 Hz, 1H), 7.85 (d, J = 8.8 Hz, 1H), 7.46 (d, J = 2.2 Hz, 1H), 7.26 (dd, J = 8.8, 5.2 Hz, 1H), 7.01-6.93 (m, 2H), 6.66 (d, J = 2.2 Hz, 1H), 4.98 (dd, J = 7.4, 2.8 Hz, 1H), 4.00 (s, 3H), 3.40 (d, J = 15.8 Hz, 1H), 3.27 (s, 1H), 2.40 (s, 7H), 0.93 (dt, J = 10.4, 5.6 Hz, 1H), 0.74 (dt, J = 9.6, 5.7 Hz, 1H), 0.68-0.60 (m, 1H), 0.60-0.53 (m, 1H). (ESI) m/z: 514 $[M + 1]^+$ |

-continued
| Compound | General route | BB-amino acid | BB-amine | BB-acid | Structural formula | $^1$HNMR and/or LCMS: |
|---|---|---|---|---|---|---|
| 32 | A | 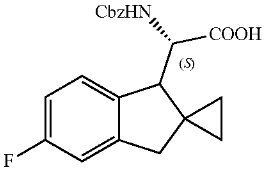 Z9 | 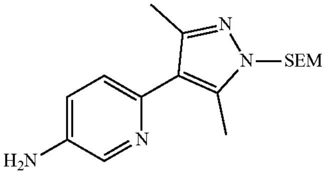 Z10 | 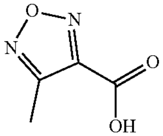 | 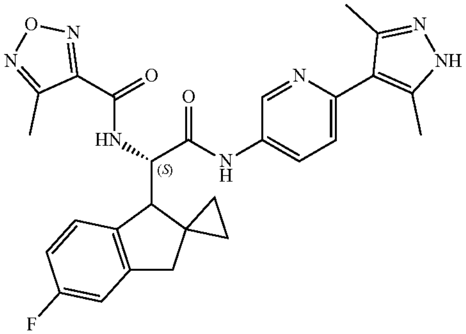 | $^1$H NMR (400 MHz, Methanol-$d_4$) δ 9.20 (d, J = 2.5 Hz, 1H), 8.41 (dd, J = 8.8, 2.5 Hz, 1H), 7.81 (d, J = 8.7 Hz, 1H), 7.21 (dd, J = 8.4, 5.2 Hz, 1H), 7.03 (dd, J = 9.0, 2.4 Hz, 1H), 6.87 (td, J = 8.9, 2.5 Hz, 1H), 5.02 (d, J = 6.4 Hz, 1H), 3.53-3.42 (m, 1H), 3.33 (d, J = 6.5 Hz, 1H), 2.47 (s, 4H), 2.40 (s, 6H), 0.96 (dt, J = 9.7, 5.4 Hz, 1H), 0.78-0.65 (m, 2H), 0.61 (ddd, J = 9.8, 5.9, 3.7 Hz, 1H). (ESI) m/z: 516 $[M + 1]^+$ |
| 33 | A | 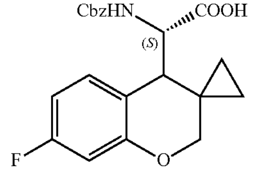 Z8 | 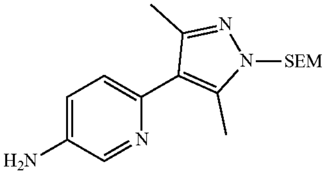 Z10 | 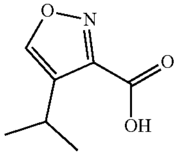 | 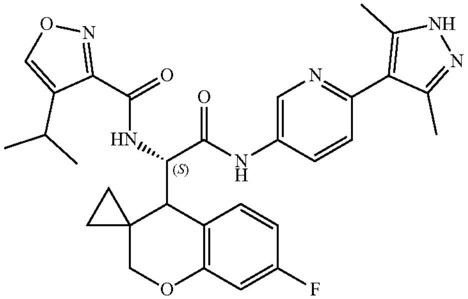 | $^1$H NMR (400 MHz, Methanol-$d_4$) δ 9.05 (d, J = 2.5 Hz, 1H), 8.54 (d, J = 0.8 Hz, 1H), 8.33 (dd, J = 8.7, 2.6 Hz, 1H), 7.65 (d, J = 8.7 Hz, 1H), 7.12 (dd, J = 8.6, 6.6 Hz, 1H), 6.54 (dd, J = 10.5, 2.6 Hz, 1H), 6.45 (td, J = 8.4, 2.6 |

-continued
| Compound | General route | BB-amino acid | BB-amine | BB-acid | Structural formula | $^1$HNMR and/or LCMS: |
|---|---|---|---|---|---|---|
| | | | | | | Hz, 1H), 5.15 (d, J = 9.4 Hz, 1H), 4.93 (dd, J = 11.4, 2.0 Hz, 1H), 3.40 (dd, J = 11.5, 1.8 Hz, 1H), 3.08-2.93 (m, 1H), 2.68-2.60 (m, 1H), 2.38 (s, 6H), 1.13 (dd, J = 22.2, 6.9 Hz, 6H), 0.94-0.85 (m, 1H), 0.72-0.58 (m, 2H), 0.52-0.40 (m, 1H). (ESI) m/z = 559 $[M + 1]^+$ |
| 34 | A | 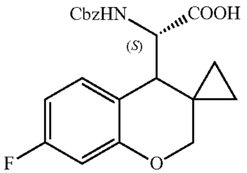 Z8 | 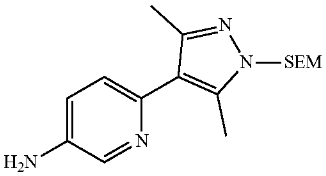 Z10 | 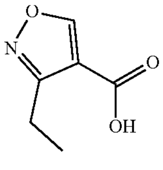 | 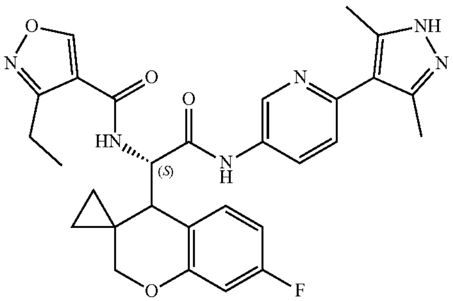 | $^1$H NMR (400 MHz, Methanol-$d_4$) δ 9.16 (t, J = 2.7 Hz, 1H), 9.02 (s, 1H), 8.40 (dd, J = 8.7, 2.6 Hz, 1H), 7.76 (dd, J = 8.7, 4.2 Hz, 1H), 7.09 (dd, J = 8.5, 6.6 Hz, 1H), 6.54 (dd, J = 10.5, 2.6 Hz, 1H), 6.48 (td, J = 8.4, 2.6 Hz, 1H), 5.12 (d, J = 9.8 Hz, 1H), 4.94 (dd, J = 11.4, 2.0 Hz, 1H), 3.41 (dd, J = 11.5, 1.7 Hz, 1H), 2.73 (q, J = 7.5 Hz, 2H), 2.60 (d, J = 9.6 Hz, 1H), 2.39 (s, 6H), 1.12 (t, J = |

-continued
| Compound | General route | BB-amino acid | BB-amine | BB-acid | Structural formula | $^1$HNMR and/or LCMS: |
|---|---|---|---|---|---|---|
| | | | | | | 7.5 Hz, 3H), 0.93-0.82 (m, 1H), 0.70-0.59 (m, 2H), 0.48-0.40 (m, 1H). (ESI) m/z = 545(M + 1)$^+$ |
| 35 | A | 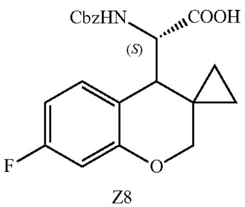 Z8 | 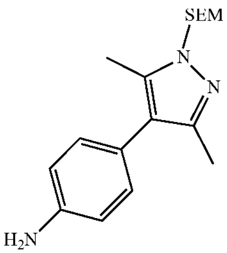 | 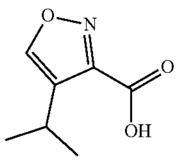 | 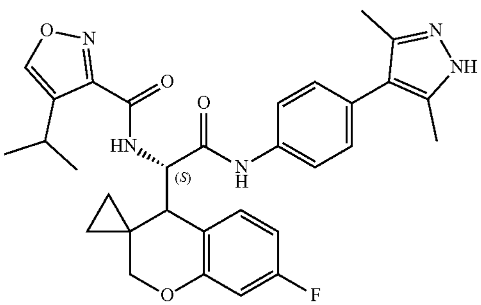 | $^1$H NMR (400 MHz, Methanol-$d_4$) δ 8.54 (s, 1H), 7.73 (d, J = 8.2 Hz, 2H), 7.33 (d, J = 8.2 Hz, 2H), 7.12 (dd, J = 8.5, 6.6 Hz, 1H), 6.54 (dd, J = 10.5, 2.6 Hz, 1H), 6.43 (td, J = 8.4, 2.6 Hz, 1H), 5.13 (d, J = 9.4 Hz, 1H), 3.39 (d, J = 11.5 Hz, 1H), 3.01 (p, J = 7.0 Hz, 1H), 2.59 (d, J = 9.5 Hz, 1H), 2.33 (s, 6H), 1.28 (dd, J = 12.2, 5.7 Hz, 1H), 1.16 (d, J = 6.9 Hz, 3H), 1.10 (d, J = 6.9 Hz, 3H), 1.01-0.89 (m, 1H), 0.74-0.57 (m, 2H), 0.44 (d, J = 8.1 Hz, 1H). (ESI) m/z = 558 (M + 1)$^+$ |

-continued
| Compound | General route | BB-amino acid | BB-amine | BB-acid | Structural formula | $^1$HNMR and/or LCMS: |
|---|---|---|---|---|---|---|
| 36 | A | 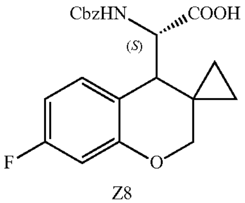 Z8 | 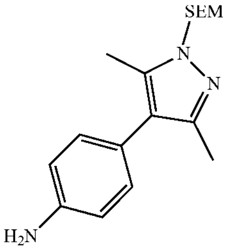 | 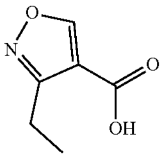 | 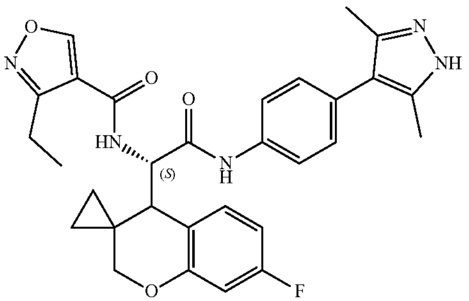 | $^1$H NMR (400 MHz, Methanol-$d_4$) δ 9.02 (s, 1H), 7.72 (d, J = 8.5 Hz, 2H), 7.32 (d, J = 8.5 Hz, 2H), 7.07 (dd, J = 8.5, 6.6 Hz, 1H), 6.60-6.38 (m, 2H), 5.08 (d, J = 9.8 Hz, 2H), 2.73 (q, J = 7.5 Hz, 2H), 2.54 (d, J = 9.9 Hz, 1H), 2.31 (s, 6H), 1.37-1.21 (m, 1H), 1.12 (t, J = 7.5 Hz, 3H), 0.98-0.87 (m, 1H), 0.71-0.56 (m, 2H), 0.41 (d, J = 8.6 Hz, 1H). (ESI) m/z = 544 $(M + 1)^+$ |
| 37 | A | 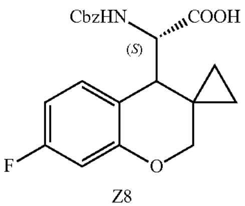 Z8 | 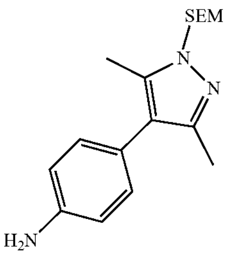 [SMILES: Cc1nn(COCC[Si](C)(C)C)c(C)c1-c1ccc(N)cc1] | 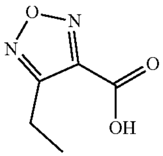 | 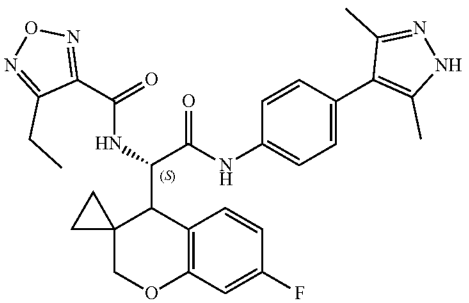 | $^1$H NMR (400 MHz, Methanol-$d_4$) δ 7.74 (d, J = 8.4 Hz, 2H), 7.33 (d, J = 8.3 Hz, 2H), 7.12 (dd, J = 8.6, 6.6 Hz, 1H), 6.54 (dd, J = 10.5, 2.6 Hz, 1H), 6.43 (td, J = 8.5, 2.7 Hz, 1H), 5.13 (d, J = 9.8 Hz, 1H), 4.99-4.95 (m, 1H), 3.44-3.38 (m, 1H), 2.81 (q, J = 7.5 Hz, 2H), |

-continued
| Compound | General route | BB-amino acid | BB-amine | BB-acid | Structural formula | $^1$HNMR and/or LCMS: |
|---|---|---|---|---|---|---|
| | | | | | | 2.62 (d, J = 9.8 Hz, 1H), 2.32 (s, 6H), 1.20 (t, J = 7.5 Hz, 3H), 1.00-0.89 (m, 1H), 0.71-0.58 (m, 2H), 0.43 (d, J = 8.6 Hz, 1H). (ESI) m/z = 545 $(M + 1)^+$ |
| 38 | A | 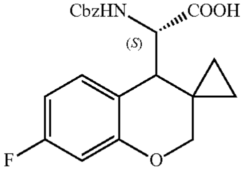 Z8 | 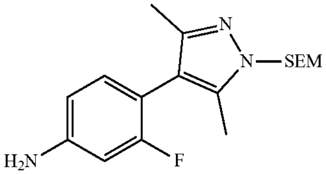 Z22 | 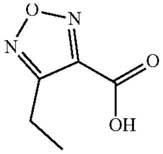 | 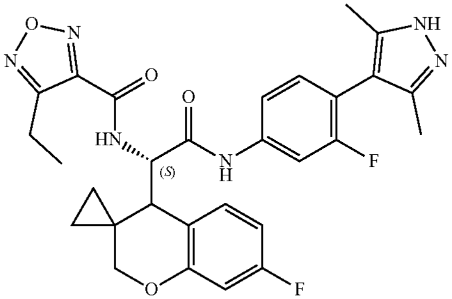 | $^1$H NMR (400 MHz, Methanol-$d_4$) δ 7.75 (dd, J = 12.0, 2.1 Hz, 1H), 7.44 (dd, J = 8.4, 2.1 Hz, 1H), 7.29 (t, J = 8.3 Hz, 1H), 7.12 (dd, J = 8.6, 6.6 Hz, 1H), 6.54 (dd, J = 10.5, 2.6 Hz, 1H), 6.43 (td, J = 8.4, 2.6 Hz, 1H), 5.12 (d, J = 9.8 Hz, 1H), 4.95 (dd, J = 11.5, 2.0 Hz, 1H), 3.40 (dd, J = 11.5, 1.7 Hz, 1H), 2.81 (q, J = 7.5 Hz, 2H), 2.62 (d, J = 9.8 Hz, 1H), 2.23 (s, 6H), 1.20 (t, J = 7.5 Hz, 3H), 0.96-0.84 (m, 1H), 0.69-0.58 (m, 2H), 0.48-0.40 (m, 1H). (ESI)m/z = 563 $(M + 1)^+$ |

-continued
| Compound | General route | BB-amino acid | BB-amine | BB-acid | Structural formula | $^1$HNMR and/or LCMS: |
|---|---|---|---|---|---|---|
| 39 | B | 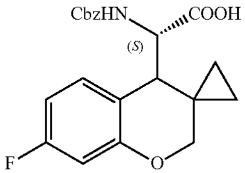 Z8 | 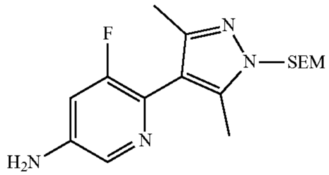 Z11 | 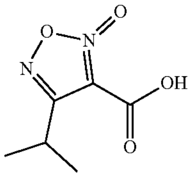 Z20 | 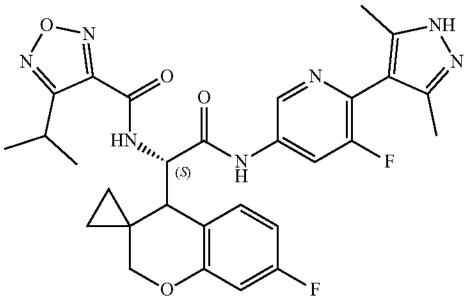 | $^1$H NMR (400 MHz, Methanol-$d_4$) δ 8.65 (d, J = 2.0 Hz, 1H), 8.28 (dd, J = 11.6, 2.1 Hz, 1H), 7.11 (dd, J = 8.6, 6.6 Hz, 1H), 6.54 (dd, J = 10.5, 2.7 Hz, 1H), 6.44 (td, J = 8.4, 2.6 Hz, 1H), 5.16 (d, J = 9.8 Hz, 1H), 4.95 (dd, J = 11.4, 2.0 Hz, 1H), 3.41 (dd, J = 11.6, 1.7 Hz, 1H), 3.28-3.20 (m, 1H), 2.27 (s, 6H), 1.26 (d, J = 6.9 Hz, 3H), 1.20 (d, J = 6.9 Hz, 3H), 0.93-0.84 (m, 1H), 0.71-0.59 (m, 2H), 0.50-0.40 (m, 1H). (ESI)m/z = 578 $(M + 1)^+$ |
| 40 | B | 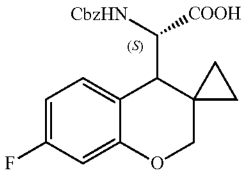 Z8 | 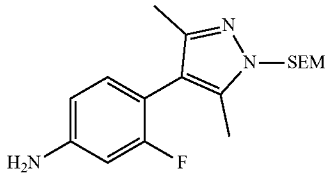 Z22 | 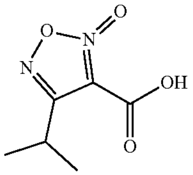 Z20 | 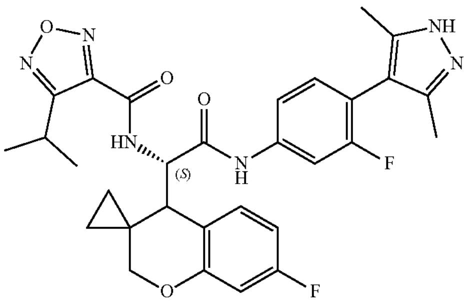 | $^1$H NMR (400 MHz, Methanol-$d_4$) δ 7.74 (dd, J = 12.1, 2.1 Hz, 1H), 7.43 (dd, J = 8.4, 2.1 Hz, 1H), 7.29 (t, J = 8.3 Hz, 1H), 7.11 (dd, J = 8.5, 6.6 Hz, 1H), 6.54 (dd, J = 10.5, 2.6 Hz, 1H), 6.43 (td, J = 8.4, 2.7 Hz, 1H), 5.13 |

-continued
| Compound | General route | BB-amino acid | BB-amine | BB-acid | Structural formula | $^1$HNMR and/or LCMS: |
| --- | --- | --- | --- | --- | --- | --- |
| | | | | | | (d, J = 9.8 Hz, 1H), 4.96 (dd, J = 11.5, 2.0 Hz, 1H), 3.40 (dd, J = 11.6, 1.7 Hz, 1H), 3.28-3.18 (m, 1H), 2.62 (d, J = 10.0 Hz, 1H), 2.23 (s, 6H), 1.23 (dd, J = 24.5, 6.9 Hz, 6H), 0.96-0.86 (m, 1H), 0.70-0.56 (m, 2H), 0.48-0.40 (m, 1H). (ESI)m/z = 577 (M + 1)$^+$ |
| 41 | B | 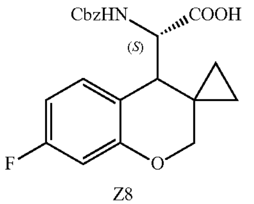 Z8 | 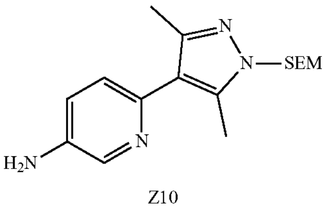 [SMILES: Cc1nn(COCC[Si](C)(C)C)c(C)c1-c1ccc(N)cn1] Z10 | 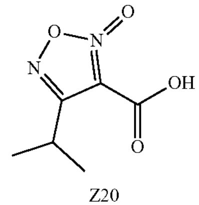 Z20 | 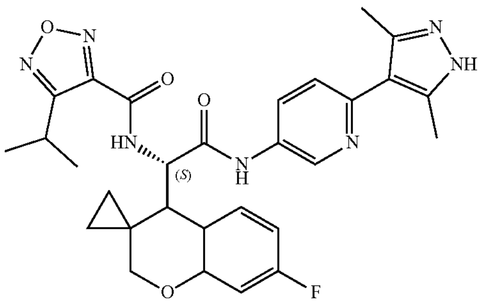 | $^1$H NMR (400 MHz, Methanol-d$_4$) δ 9.20 (d, J = 2.5 Hz, 1H), 8.42 (dd, J = 8.7, 2.6 Hz, 1H), 7.80 (d, J = 8.8 Hz, 1H), 7.11 (dd, J = 8.5, 6.6 Hz, 1H), 6.55 (dd, J = 10.5, 2.6 Hz, 1H), 6.45 (td, 1H), 5.18 (d, J = 9.7 Hz, 1H), 4.94 (dd, 2H), 3.42 (dd, J = 11.6, 1.7 Hz, 1H), 3.28-3.20 (m, 1H), 2.40 (s, 6H), 1.26 (d, J = 7.0 Hz, 3H), 1.20 (d, J = 7.0 Hz, 3H), 0.95-0.86 (m, 1H), 0.72-0.60 (m, 2H), 0.51- |

-continued
| Compound | General route | BB-amino acid | BB-amine | BB-acid | Structural formula | $^{1}$HNMR and/or LCMS: |
|---|---|---|---|---|---|---|
| | | | | | | 0.42 (m, 1H). (ESI)m/z = 560 $(M + 1)^+$ |
| 42 | A | 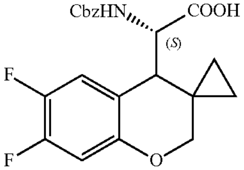 Z12 | 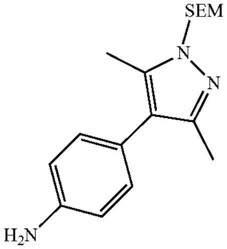 | 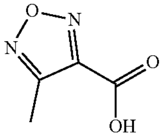 | 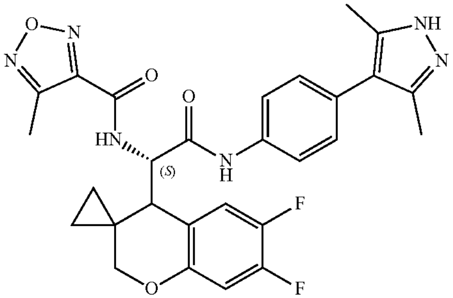 | $^{1}$H NMR (400 MHz, Methanol-d4) δ 7.76-7.68 (m, 2H), 7.36-7.28 (m, 2H), 7.09 (dd, J = 11.2, 9.1 Hz, 1H), 6.70 (dd, J = 12.0, 7.1 Hz, 1H), 5.13 (d, J = 9.9 Hz, 1H), 4.93 (dd, J = 11.5, 2.0 Hz, 1H), 3.39 (dd, J = 11.5, 1.7 Hz, 1H), 2.63-2.55 (m, 1H), 2.39 (s, 3H), 2.30 (s, 6H), 0.95 (dt, J = 9.0, 4.9 Hz, 1H), 0.64 (dtd, J = 18.6, 9.4, 5.3 Hz, 2H), 0.45 (dd, J = 5.7, 3.7 Hz, 1H). (ESI) m/z = 549 $(M + 1)^+$ |

-continued
| Compound | General route | BB-amino acid | BB-amine | BB-acid | Structural formula | $^1$HNMR and/or LCMS: |
|---|---|---|---|---|---|---|
| 43 | A | 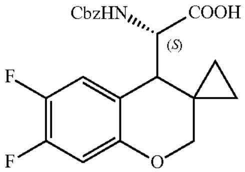 Z12 | 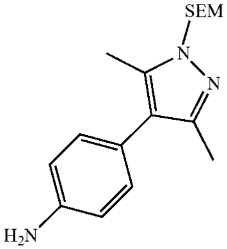 | 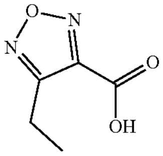 | 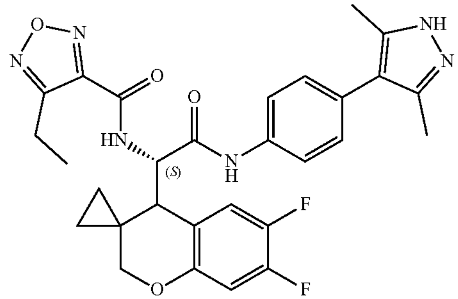 | $^1$H NMR (400 MHz, Methanol-d4) δ 7.77-7.69 (m, 2H), 7.37-7.29 (m, 2H), 7.07 (dd, J = 11.2, 9.0 Hz, 1H), 6.69 (dd, J = 11.9, 7.1 Hz, 1H), 5.15 (d, J = 9.9 Hz, 1H), 4.94 (dd, J = 11.5, 2.0 Hz, 1H), 3.39 (dd, J = 11.5, 1.7 Hz, 1H), 2.83 (q, J = 7.5 Hz, 2H), 2.63-2.55 (m, 1H), 2.32 (s, 6H), 1.20 (t, J = 7.5 Hz, 3H), 0.94 (dt, J = 8.9, 4.9 Hz, 1H), 0.65 (dtd, J = 13.3, 9.4, 4.8 Hz, 2H), 0.44 (dd, J = 5.6, 3.6 Hz, 1H). (ESI) m/z = 563 $(M + 1)^+$ |
| 44 | B | 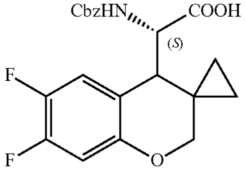 Z12 | 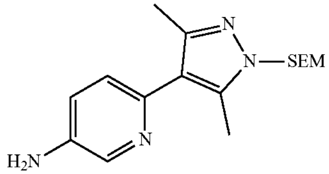 Z10 | 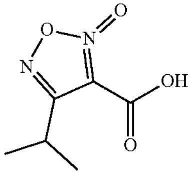 Z20 | 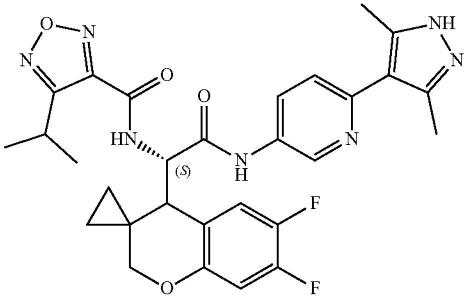 | $^1$H NMR (400 MHz, Methanol-d4) δ 9.16 (d, J = 2.5 Hz, 1H), 8.40 (dd, J = 8.7, 2.6 Hz, 1H), 7.76 (d, J = 8.8 Hz, 1H), 7.06 (dd, J = 11.2, 9.0 Hz, 1H), 6.70 (dd, J = 11.9, 7.1 Hz, 1H), 5.20 (d, J = 9.9 Hz, 1H), 4.92 (dd, |

-continued
| Compound | General route | BB-amino acid | BB-amine | BB-acid | Structural formula | $^1$HNMR and/or LCMS: |
|---|---|---|---|---|---|---|
| | | | | | | J = 11.4, 2.0 Hz, 1H), 3.41 (dd, J = 11.6, 1.7 Hz, 1H), 3.28-3.22 (m, 1H), 2.65 (d, J = 9.8 Hz, 1H), 2.40 (s, 6H), 1.27 (d, J = 6.9 Hz, 3H), 1.20 (d, J = 6.9 Hz, 3H), 0.89 (dt, J = 7.5, 4.2 Hz, 1H), 0.66 (tq, J = 8.2, 4.3 Hz, 2H), 0.47 (d, J = 9.1 Hz, 1H). (ESI) m/z = 578 $(M + 1)^+$ |
| 45 | B | 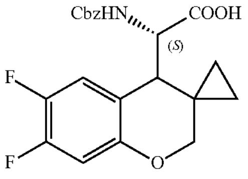 Z12 | 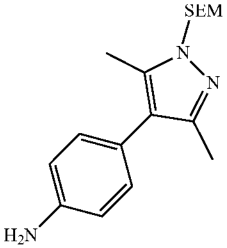 [SMILES: Cc1nn(COCC[Si](C)(C)C)c(C)c1-c1ccc(N)cc1] | 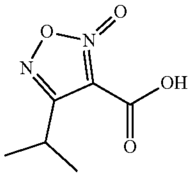 Z20 | 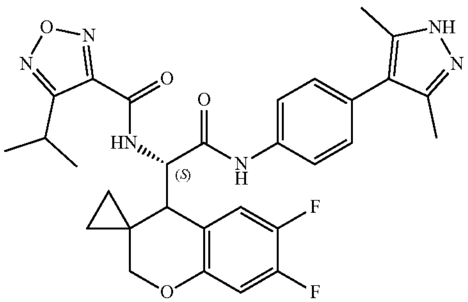 | $^1$H NMR (400 MHz, Methanol-d4) δ 7.78-7.68 (m, 2H), 7.36-7.29 (m, 2H), 7.06 (dd, J = 11.2, 9.0 Hz, 1H), 6.69 (dd, J = 11.9, 7.1 Hz, 1H), 5.16 (d, J = 10.0 Hz, 1H), 4.95 (dd, J = 11.5, 2.0 Hz, 1H), 3.40 (dd, J = 11.5, 1.7 Hz, 1H), 3.29-3.24 (m, 1H), 2.59 (d, J = 10.0 Hz, 1H), 2.33 (s, 6H), 1.27 (d, J = 7.0 Hz, 3H), 1.21 (d, J = 6.9 Hz, 3H), 0.94 (dt, J = 8.9, 4.9 Hz, 1H), 0.63 (ddt, J = 18.4, 9.3, 4.6 Hz, |

-continued
| Compound | General route | BB-amino acid | BB-amine | BB-acid | Structural formula | $^1$HNMR and/or LCMS: |
|---|---|---|---|---|---|---|
| | | | | | | 2H), 0.44 (dd, J = 5.7, 3.7 Hz, 1H). (ESI) m/z = 577 $(M + 1)^+$ |
| 46 | B | 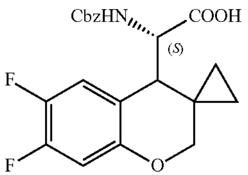 Z12 | 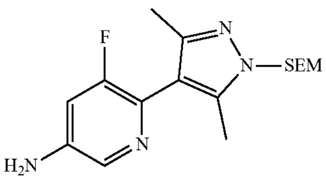 Z11 | 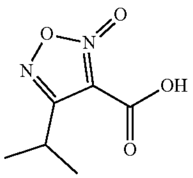 Z20 | 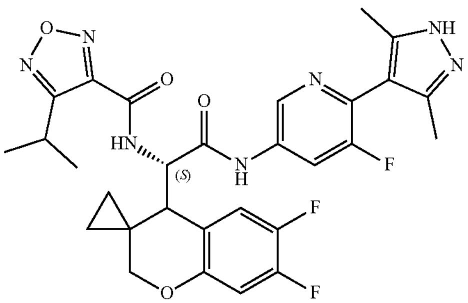 | $^1$H NMR (400 MHz, Methanol-d4) δ 8.66 (d, J = 2.0 Hz, 1H), 8.28 (dd, J = 11.6, 2.1 Hz, 1H), 7.06 (dd, J = 11.2, 9.0 Hz, 1H), 6.70 (dd, J = 11.9, 7.1 Hz, 1H), 5.17 (d, J = 9.9 Hz, 1H), 4.92 (dd, J = 11.5, 2.0 Hz, 1H), 3.41 (dd, J = 11.5, 1.7 Hz, 1H), 3.28-3.21 (m, 1H), 2.63 (d, J = 9.8 Hz, 1H), 2.28 (d, J = 1.0 Hz, 6H), 1.27 (d, J = 6.9 Hz, 3H), 1.21 (d, J = 6.9 Hz, 3H), 0.88 (dt, J = 7.8, 4.3 Hz, 1H), 0.64 (tq, J = 9.5, 4.6 Hz, 2H), 0.46 (d, J = 7.2 Hz, 1H). (ESI) m/z = 596 $(M + 1)^+$ |

-continued
| Compound | General route | BB-amino acid | BB-amine | BB-acid | Structural formula | $^1$HNMR and/or LCMS: |
|---|---|---|---|---|---|---|
| 47 | A | 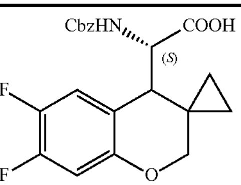 Z12 | 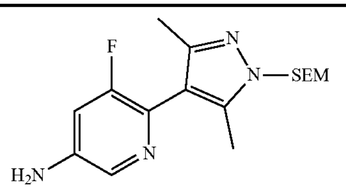 Z11 | 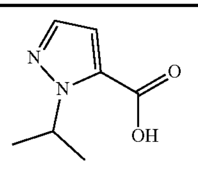 | 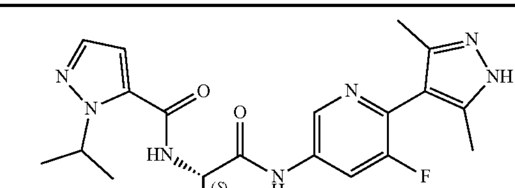 | $^1$H NMR (400 MHz, Methanol-$d_4$) δ 8.68 (d, J = 2.2 Hz, 1H), 8.29 (dd, J = 11.6, 2.1 Hz, 1H), 7.51 (d, J = 2.1 Hz, 1H), 7.03 (dd, J = 11.2, 9.0 Hz, 1H), 6.76-6.64 (m, 2H), 5.13 (d, J = 10.0 Hz, 1H), 5.04 (p, J = 6.7 Hz, 1H), 4.94 (dd, J = 11.4, 1.9 Hz, 1H), 3.41 (dd, J = 11.5, 1.7 Hz, 1H), 2.60 (d, 1H), 2.34-2.25 (m, 6H), 1.37 (d, J = 6.6 Hz, 3H), 1.33 (d, J = 6.7 Hz, 3H), 0.91-0.82 (m, 1H), 0.69-0.59 (m, 2H), 0.49-0.42 (m, 1H). (ESI) m/z = 594 $(M + 1)^+$ |
| 48 | A | 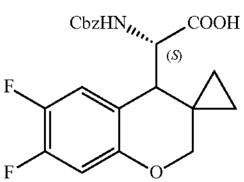 Z12 | 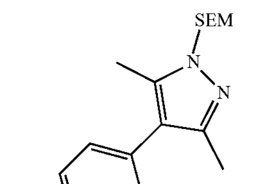 | 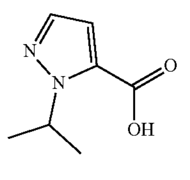 | 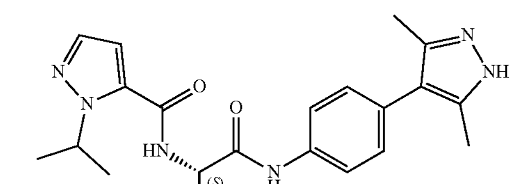 | $^1$H NMR (400 MHz, Methanol-$d_4$) δ 7.75 (d, J = 8.5 Hz, 2H), 7.51 (s, 1H), 7.40-7.28 (m, 2H), 7.05 (t, J = 10.1 Hz, 1H), 6.80-6.63 (m, 2H), 5.12 (d, J = 10.0 Hz, 1H), 5.08-4.96 (m, 2H), 3.40 (d, J = |

-continued
| Compound | General route | BB-amino acid | BB-amine | BB-acid | Structural formula | $^1$HNMR and/or LCMS: |
|---|---|---|---|---|---|---|
| | | | | | | 11.5 Hz, 1H), 2.57 (d, J = 9.6 Hz, 1H), 2.34 (s, 6H), 1.36 (dd, J = 17.6, 6.6 Hz, 6H), 1.01-0.86 (m, 1H), 0.72-0.56 (m, 2H), 0.49-0.37 (m, 1H). (ESI) m/z = 575 $(M + 1)^+$ |
| 49 | B | 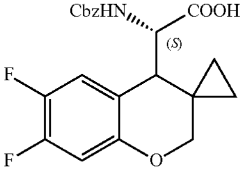 Z12 | 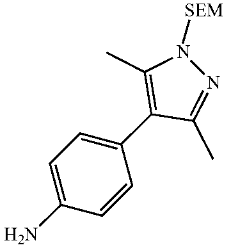 | 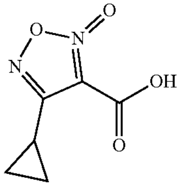 Z21 | 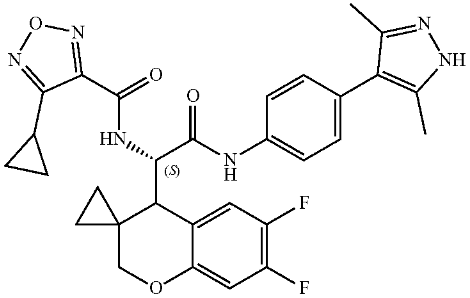 | $^1$H NMR (400 MHz, Methanol-$d_4$) δ 7.75 (d, J = 8.5 Hz, 2H), 7.40-7.29 (m, 2H), 7.14-7.03 (m, 1H), 6.77-6.63 (m, 1H), 5.17 (d, J = 9.9 Hz, 1H), 4.95 (dd, J = 11.4, 1.9 Hz, 1H), 3.41 (dd, J = 11.5, 1.7 Hz, 1H), 2.61 (d, J = 9.9 Hz, 1H), 2.34 (s, 6H), 2.23-2.12 (m, 1H), 1.13-0.89 (m, 5H), 0.72-0.59 (m, 2H), 0.51-0.41 (m, 1H). (ESI) m/z = 575 $(M + 1)^+$ |

-continued
| Compound | General route | BB-amino acid | BB-amine | BB-acid | Structural formula | $^1$HNMR and/or LCMS: |
|---|---|---|---|---|---|---|
| 50 | A | 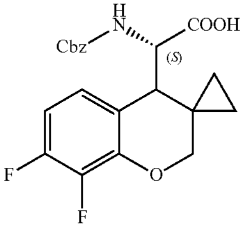 Z13 | 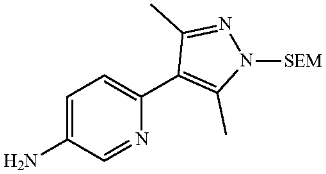 Z10 | 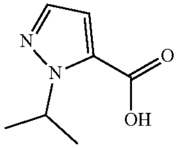 | 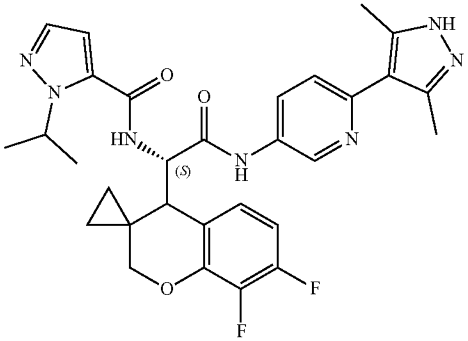 | $^1$H NMR (400 MHz, Methanol-$d_4$) 7.74 (d, J = 8.5 Hz, 2H), 7.33 (d, J = 8.6 Hz, 2H), 7.11 (dd, J = 8.5, 6.6 Hz, 1H), 6.54 (dd, J = 10.5, 2.6 Hz, 1H), 6.43 (td, J = 8.5, 2.6 Hz, 1H), 5.14 (d, J = 9.8 Hz, 1H), 4.97 (dd, J = 11.5, 2.0 Hz, 1H), 3.40 (dd, J = 11.5, 1.8 Hz, 1H), 3.28-3.20 (m, 1H), 2.61 (d, J = 9.9 Hz, 1H), 2.33 (s, 6H), 1.23 (dd, J = 24.5, 6.9 Hz, 6H), 0.98-0.89 (m, 1H), 0.71-0.56 (m, 2H), 0.48-0.38 (m, 1H). (ESI)m/z = 576 $(M + 1)^+$ |
| 51 | A | 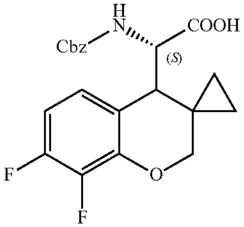 Z13 | 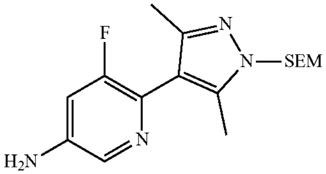 Z11 | 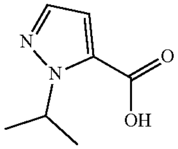 | 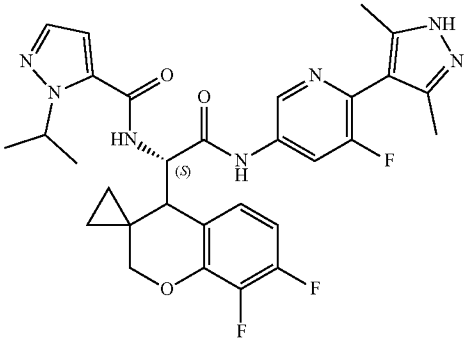 | $^1$H NMR (400 MHz, Methanol-$d_4$) δ 8.69 (t, J = 1.3 Hz, 1H), 8.30 (dd, J = 11.6, 2.2 Hz, 1H), 7.49 (d, J = 2.1 Hz, 1H), 6.88 (ddd, J = 8.5, 5.7, 2.2 Hz, 1H), 6.72 (d, J = 2.1 Hz, 1H), 6.64-6.53 (m, 1H), 5.14 (d, J = 9.9 Hz, 1H), |

-continued
| Compound | General route | BB-amino acid | BB-amine | BB-acid | Structural formula | $^1$HNMR and/or LCMS: |
|---|---|---|---|---|---|---|
| | | | | | | 5.10-4.97 (m, 2H), 3.55 (dd, J = 11.5, 1.7 Hz, 1H), 2.67 (d, J = 10.0 Hz, 1H), 2.30 (d, J = 1.0 Hz, 6H), 1.35 (dd, J = 14.6, 6.6 Hz, 6H), 0.95-0.83 (m, 1H), 0.75-0.61 (m, 2H), 0.50-0.43 (m, 1H). (ESI)m/z = 594 $(M + 1)^+$ |
| 52 | A | 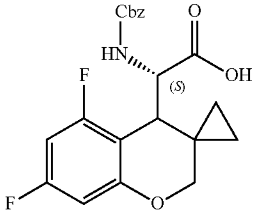 Z14 | 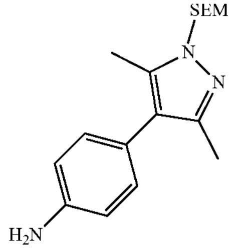 | 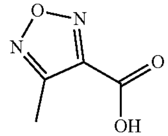 | 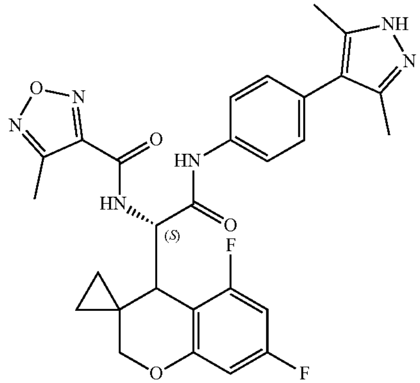 | $^1$H NMR (400 MHz, Methanol-d4) δ 7.77-7.69 (m, 2H), 7.36-7.26 (m, 2H), 6.48-6.34 (m, 2H), 5.18 (d, J = 9.5 Hz, 1H), 5.03 (dd, J = 11.6, 2.0 Hz, 1H), 3.47 (dd, J = 11.6, 1.8 Hz, 1H), 2.98 (d, J = 9.6 Hz, 1H), 2.40 (s, 3H), 2.32 (s, 6H), 0.96 (dt, J = 9.1, 5.4 Hz, 1H), 0.72 (dt, J = 10.7, 5.4 Hz, 1H), 0.63 (dt, J = 9.7, 5.1 Hz, 1H), 0.48 (s, 1H). (ESI)m/z = 549 $(M + 1)^+$ |

-continued
| Compound | General route | BB-amino acid | BB-amine | BB-acid | Structural formula | $^1$HNMR and/or LCMS: |
|---|---|---|---|---|---|---|
| 53 | A | 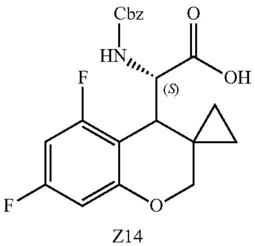 Z14 | 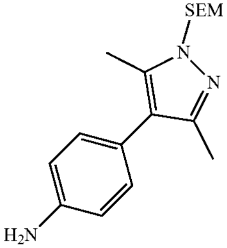 | 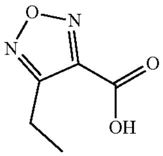 | 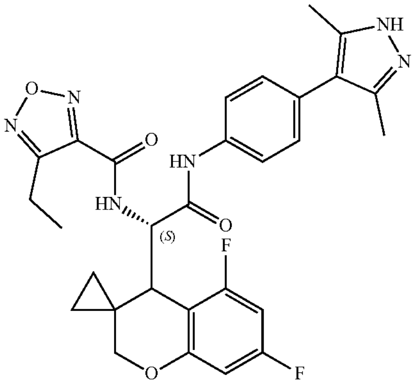 | $^1$H NMR (400 MHz, Methanol-d4) δ 7.77-7.68 (m, 2H), 7.36-7.28 (m, 2H), 6.44 (dt, J = 10.3, 2.1 Hz, 1H), 6.36 (td, J = 9.4, 2.6 Hz, 1H), 5.18 (d, J = 9.6 Hz, 1H), 5.04 (dd, J = 11.5, 2.0 Hz, 1H), 3.47 (dd, J = 11.8, 1.8 Hz, 1H), 2.97 (d, J = 9.6 Hz, 1H), 2.85 (q, J = 7.5 Hz, 2H), 2.31 (s, 6H), 1.21 (t, J = 7.5 Hz, 3H), 0.96 (dt, J = 9.1, 5.4 Hz, 1H), 0.72 (dt, J = 10.8, 5.5 Hz, 1H), 0.63 (dt, J = 9.6, 5.2 Hz, 1H), 0.48 (t, J = 4.9 Hz, 1H). (ESI)m/z = 563 $(M + 1)^+$ |

-continued
| Compound | General route | BB-amino acid | BB-amine | BB-acid | Structural formula | $^1$HNMR and/or LCMS: |
|---|---|---|---|---|---|---|
| 54 | A | 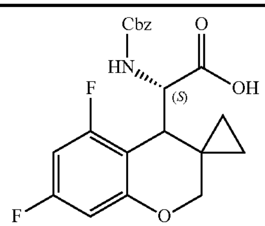 Z14 | 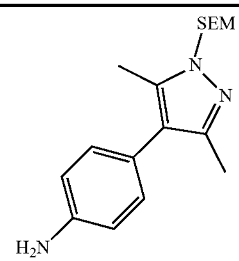 | 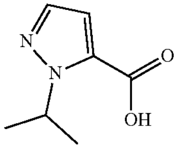 | 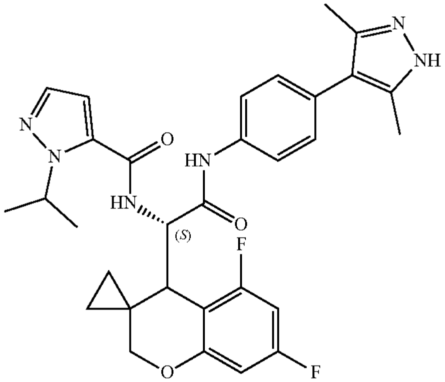 | $^1$H NMR (400 MHz, Methanol-$d_4$) δ 7.70-7.62 (m, 2H), 7.38 (d, J = 2.1 Hz, 1H), 7.28-7.21 (m, 2H), 6.61 (d, J = 2.1 Hz, 1H), 6.34 (dt, J = 10.3, 2.0 Hz, 1H), 6.27 (td, J = 9.5, 2.6 Hz, 1H), 5.11-4.92 (m, 3H), 3.37 (dd, J = 11.7, 1.8 Hz, 1H), 2.87 (d, J = 9.8 Hz, 1H), 2.25 (s, 6H), 1.25 (dd, J = 9.8, 6.6 Hz, 6H), 0.85 (dt, J = 10.0, 5.4 Hz, 1H), 0.60 (dt, J = 10.5, 5.3 Hz, 1H), 0.53 (dt, J = 9.6, 5.0 Hz, 1H), 0.37 (dd, J = 9.2, 5.3 Hz, 1H). (ESI)m/z = 575 $(M + 1)^+$ |
| 55 | A | 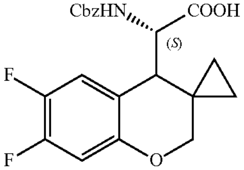 Z12 | 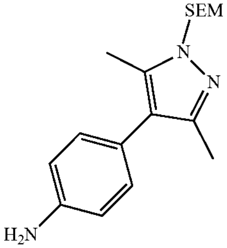 [SMILES: Cc1nn(COCC[Si](C)(C)C)c(C)c1-c1ccc(N)cc1] | 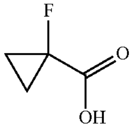 | 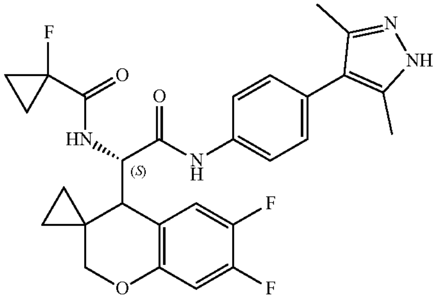 | $^1$H NMR (400 MHz, Methanol-d4) δ 7.63 (d, J = 8.3 Hz, 2H), 7.28-7.20 (m, 2H), 7.06-6.96 (m, 1H), 6.57 (dd, J = 12.0, 7.1 Hz, 1H), 4.93-4.86 (m, 1H), 4.80 (d, J = 1.8 Hz, 1H), 3.27 (dd, J = 11.5, |

-continued
| Compound | General route | BB-amino acid | BB-amine | BB-acid | Structural formula | $^1$HNMR and/or LCMS: |
|---|---|---|---|---|---|---|
| | | | | | | 1.7 Hz, 1H), 2.45 (d, J = 9.9 Hz, 1H), 2.24 (d, J = 1.2 Hz, 6H), 1.28-1.08 (m, 3H), 0.97-0.87 (m, 1H), 0.87-0.77 (m, 1H), 0.60-0.45 (m, 2H), 0.33 (d, J = 7.3 Hz, 1H). (ESI)m/z = 525 $(M + 1)^+$ |
| 56 | A | 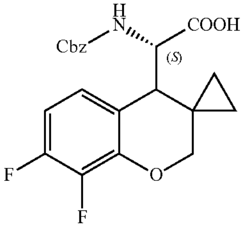 Z13 | 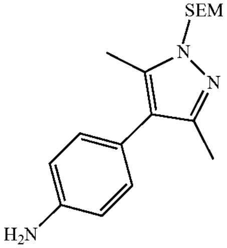 | 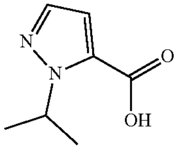 | 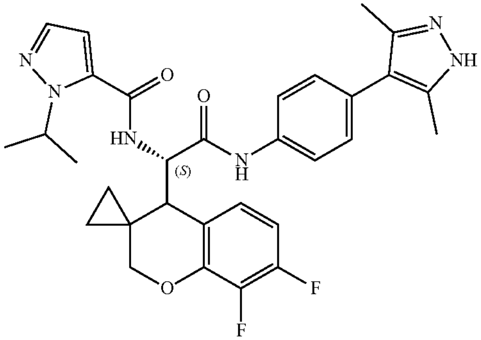 | $^1$H NMR (400 MHz, Methanol-$d_4$) δ 7.79-7.66 (m, 2H), 7.54-7.44 (m, 1H), 7.37-7.28 (m, 2H), 6.88 (s, 1H), 6.72 (t, J = 1.8 Hz, 1H), 6.58 (q, J = 8.6 Hz, 1H), 5.11 (d, J = 9.7 Hz, 1H), 5.04 (t, J = 8.3 Hz, 2H), 3.54 (d, J = 11.7 Hz, 1H), 2.62 (d, J = 10.0 Hz, 1H), 2.32 (t, J = 1.6 Hz, 6H), 2.15 (s, 1H), 1.42-1.19 (m, 10H), 1.02-0.81 (m, 2H), 0.77-0.58 (m, 2H). (ESI)m/z = 575 $(M + 1)^+$ |

-continued
| Compound | General route | BB-amino acid | BB-amine | BB-acid | Structural formula | $^1$HNMR and/or LCMS: |
|---|---|---|---|---|---|---|
| 57 | A | 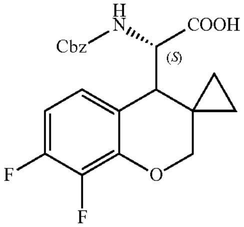 Z13 | 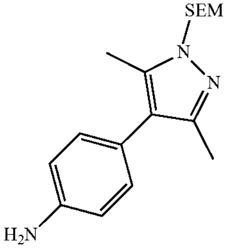 | 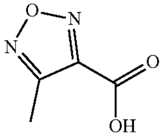 | 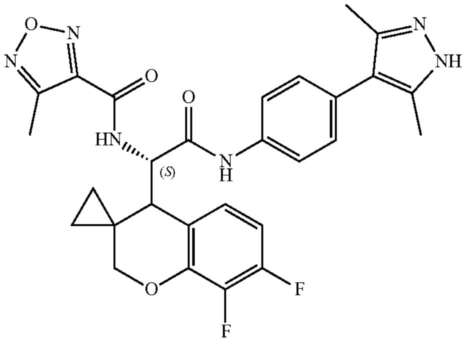 | $^1$H NMR (400 MHz, Methanol-$d_4$) δ 7.75 (d, J = 8.3 Hz, 2H), 7.34 (d, J = 8.3 Hz, 2H), 6.92 (ddd, J = 8.6, 5.8, 2.1 Hz, 1H), 6.65-6.50 (m, 1H), 5.15 (d, J = 9.9 Hz, 1H), 5.02 (dd, J = 11.6, 1.9 Hz, 1H), 3.54 (dd, J = 11.6, 1.6 Hz, 1H), 2.66 (d, J = 10.0 Hz, 1H), 2.38 (s, 3H), 2.33 (s, 6H), 0.97 (dt, J = 9.0, 4.9 Hz, 1H), 0.68 (dtd, J = 18.6, 9.4, 5.2 Hz, 2H), 0.53-0.35 (m, 1H). (ESI)m/z = 549 $(M + 1)^+$ |
| 58 | A | 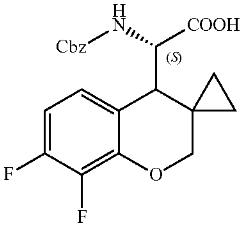 Z13 | 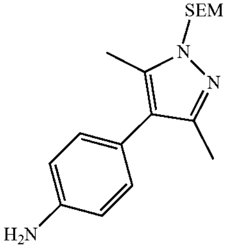 [SMILES: Cc1nn(COCC[Si](C)(C)C)c(C)c1-c1ccc(N)cc1] | 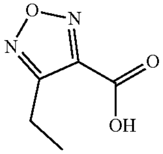 | 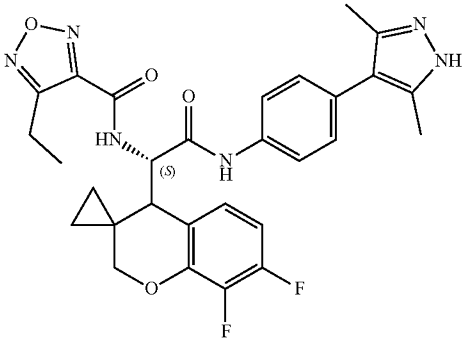 | $^1$H NMR (400 MHz, Methanol-$d_4$) δ 7.77-7.71 (m, 2H), 7.37-7.30 (m, 2H), 6.91 (ddd, J = 8.3, 5.7, 2.2 Hz, 1H), 6.61-6.49 (m, 1H), 5.16 (d, J = 9.9 Hz, 1H), 5.02 (dd, J = 11.5, 2.0 Hz, 1H), 3.54 (dd, J = 11.5, 1.7 Hz, 1H), 2.82 (q, J = 7.5 Hz, 2H), 2.66 (d, J = |

-continued
| Compound | General route | BB-amino acid | BB-amine | BB-acid | Structural formula | $^1$HNMR and/or LCMS: |
|---|---|---|---|---|---|---|
| | | | | | | 10.1 Hz, 1H), 2.32 (s, 6H), 1.20 (t, J = 7.5 Hz, 3H), 0.97 (dt, J = 9.2, 5.0 Hz, 1H), 0.75-0.61 (m, 2H), 0.46 (dq, J = 7.7, 4.0 Hz, 1H). (ESI)m/z = 563 $(M + 1)^+$ |
| 59 | A | 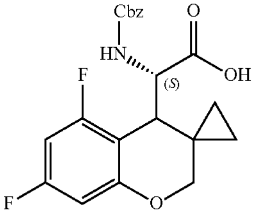 Z14 | 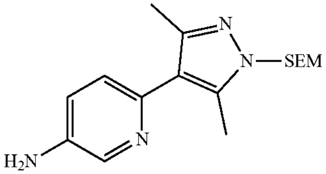 Z10 | 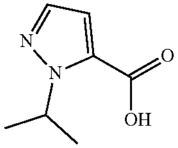 | 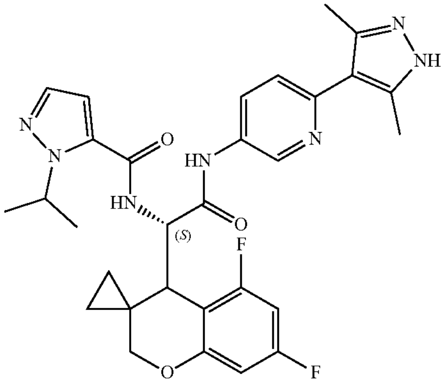 | $^1$H NMR (400 MHz, DMSO-$d_6$) δ 10.75 (s, 1H), 8.88 (d, J = 2.6 Hz, 1H), 8.63 (d, J = 9.2 Hz, 1H), 8.15 (dd, J = 8.7, 2.6 Hz, 1H), 7.58-7.40 (m, 2H), 6.86 (d, J = 2.0 Hz, 1H), 6.67-6.45 (m, 4H), 5.21-4.93 (m, 4H), 3.50 (dd, J = 11.5, 1.7 Hz, 1H), 2.93 (d, J = 9.6 Hz, 1H), 2.33 (s, 8H), 1.29 (d, J = 6.6 Hz, 3H), 1.23 (d, J = 6.6 Hz, 3H), 0.86-0.76 (m, 2H), 0.70-0.60 (m, 2H), 0.61-0.51 (m, 2H), 0.48-0.39 (m, 1H). (ESI)m/z = 576 $(M + 1)^+$ |

-continued
| Compound | General route | BB-amino acid | BB-amine | BB-acid | Structural formula | $^1$HNMR and/or LCMS: |
|---|---|---|---|---|---|---|
| 60 | A | 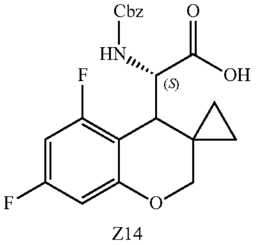 Z14 | 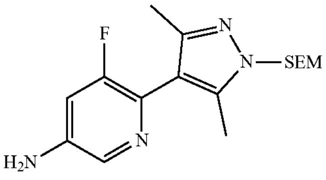 Z11 | 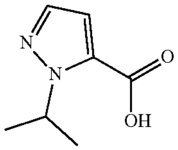 | 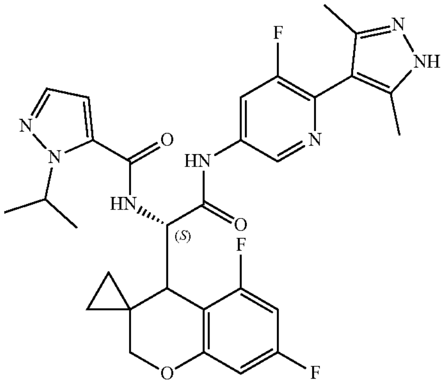 | $^1$H NMR (400 MHz, DMSO-$d_6$) δ 10.94 (s, 1H), 8.67 (s, 2H), 8.14 (dd, J = 12.1, 2.1 Hz, 1H), 7.45 (d, J = 2.0 Hz, 1H), 7.25-6.93 (m, 1H), 6.86 (d, J = 2.0 Hz, 1H), 6.56 (dd, J = 9.8, 7.7 Hz, 2H), 5.20-4.90 (m, 3H), 3.01-2.91 (m, 1H), 2.16 (s, 7H), 1.29 (d, J = 6.6 Hz, 4H), 1.23 (d, J = 6.6 Hz, 3H), 0.80 (dd, J = 9.8, 5.1 Hz, 1H), 0.70-0.61 (m, 1H), 0.61-0.54 (m, 1H), 0.44 (s, 1H). (ESI)m/z = 594 $(M + 1)^+$ |

-continued
| Compound | General route | BB-amino acid | BB-amine | BB-acid | Structural formula | $^1$HNMR and/or LCMS: |
|---|---|---|---|---|---|---|
| 61 | B | 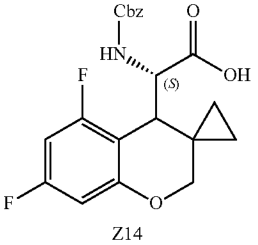 Z14 | 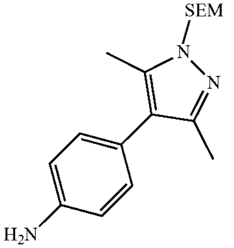 | 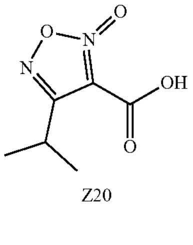 Z20 | 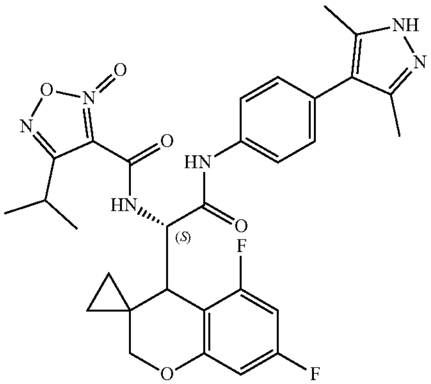 | $^1$H NMR (400 MHz, Methanol-d4) δ 7.78-7.67 (m, 2H), 7.37-7.30 (m, 2H), 6.44 (dt, J = 10.3, 2.1 Hz, 1H), 6.35 (td, J = 9.5, 2.6 Hz, 1H), 5.20 (d, J = 9.6 Hz, 1H), 5.04 (dd, J = 11.6, 2.0 Hz, 1H), 3.48 (dd, J = 11.7, 1.7 Hz, 1H), 3.31 (q, J = 1.8 Hz, 1H), 2.97 (d, J = 9.5 Hz, 1H), 2.33 (s, 6H), 1.28 (d, J = 6.9 Hz, 3H), 1.21 (d, J = 6.9 Hz, 3H), 0.95 (dt, J = 9.2, 5.5 Hz, 1H), 0.72 (dt, J = 9.3, 5.4 Hz, 1H), 0.63 (dt, J = 9.7, 5.0 Hz, 1H), 0.47 (s, 1H). (ESI)m/z = 577 $(M + 1)^+$ |

-continued
| Compound | General route | BB-amino acid | BB-amine | BB-acid | Structural formula | $^1$HNMR and/or LCMS: |
|---|---|---|---|---|---|---|
| 62 | A | 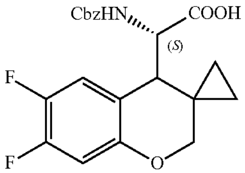 Z12 | 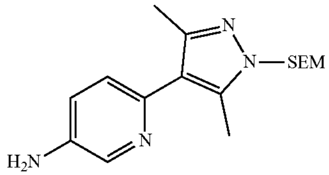 Z10 | 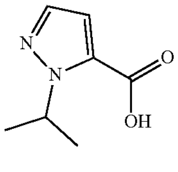 | 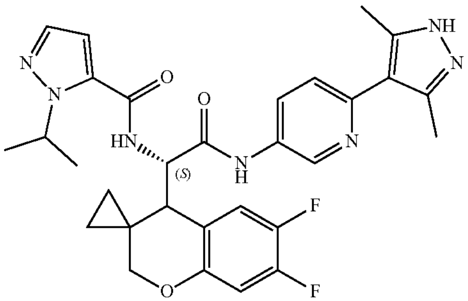 | $^1$H NMR (400 MHz, Methanol-d4) δ9.19-9.11 (m, 1H), 8.81 (d, J = 9.3 Hz, 0H), 8.39 (tt, J = 5.9, 2.6 Hz, 1H), 7.74 (t, J = 7.5 Hz, 1H), 7.51 (d, J = 1.9 Hz, 1H), 7.04 (dd, J = 11.2, 9.0 Hz, 1H), 6.76-6.66 (m, 2H), 5.15 (dt, J = 9.8, 4.7 Hz, 1H), 5.11-4.98 (m, 1H), 4.94 (dd, J = 11.5, 1.9 Hz, 1H), 3.41 (dd, J = 11.5, 1.7 Hz, 1H), 2.62 (d, J = 10.0 Hz, 1H), 2.39 (s, 6H), 1.35 (dd, J = 18.3, 6.6 Hz, 6H), 0.93-0.82 (m, 1H), 0.72-0.59 (m, 2H), 0.50-0.42 (m, 1H). (ESI)m/z = 576 $(M + 1)^+$. |

-continued
| Compound | General route | BB-amino acid | BB-amine | BB-acid | Structural formula | $^1$HNMR and/or LCMS: |
|---|---|---|---|---|---|---|
| 63 | B | 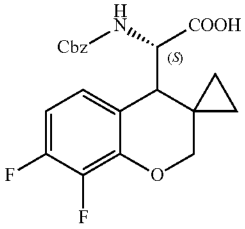 Z13 | 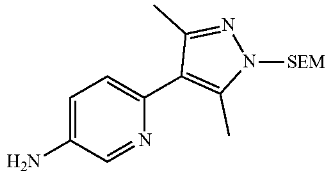 Z10 | 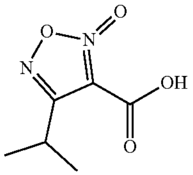 Z20 | 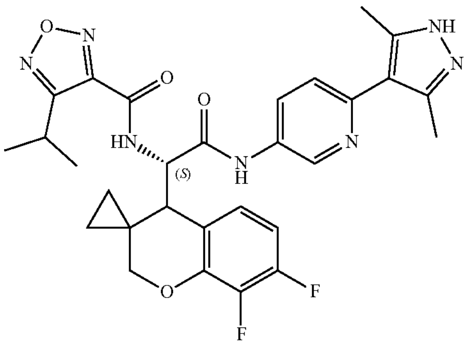 | $^1$H NMR (400 MHz, Methanol-$d_4$) δ 9.19 (d, J = 2.6 Hz, 1H), 8.42 (dd, J = 8.8, 2.7 Hz, 1H), 7.79 (d, J = 8.7 Hz, 1H), 6.91 (ddd, J = 8.5, 5.8, 2.2 Hz, 1H), 6.57 (td, J = 9.6, 7.3 Hz, 1H), 5.20 (d, J = 9.9 Hz, 1H), 5.00 (dd, J = 11.5, 2.0 Hz, 1H), 3.56 (dd, J = 11.5, 1.6 Hz, 1H), 3.28-3.19 (m, 1H), 2.72 (d, J = 9.7 Hz, 1H), 2.40 (s, 6H), 1.27 (d, J = 6.9 Hz, 3H), 1.20 (d, J = 6.9 Hz, 3H), 0.97-0.85 (m, 1H), 0.77-0.62 (m, 2H), 0.54-0.44 (m, 1H). (ESI)m/z = 578 $(M + 1)^+$ |

-continued
| Compound | General route | BB-amino acid | BB-amine | BB-acid | Structural formula | $^1$HNMR and/or LCMS: |
|---|---|---|---|---|---|---|
| 64 | B | 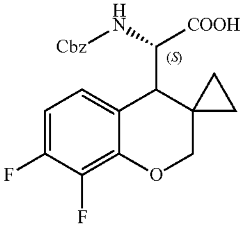 Z13 | 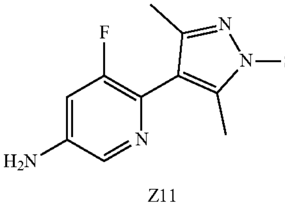 Z11 | 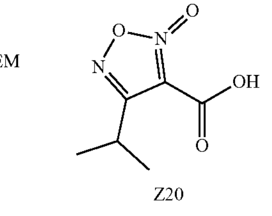 Z20 | 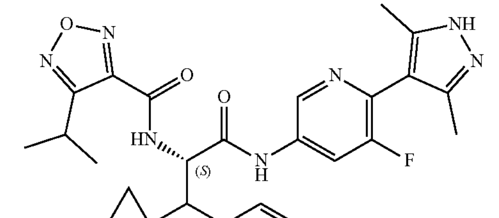 | $^1$H NMR (400 MHz, Methanol-$d_4$) δ 8.66 (s, 0H), 8.29 (dd, J = 11.6, 2.2 Hz, 1H), 6.91 (ddd, J = 8.4, 5.8, 2.1 Hz, 1H), 6.57 (td, J = 9.5, 7.2 Hz, 1H), 5.20-5.14 (m, 1H), 5.00 (dd, J = 11.5, 1.9 Hz, 1H), 3.55 (dd, J = 11.7, 1.7 Hz, 1H), 3.29-3.21 (m, 1H), 2.70 (d, J = 9.9 Hz, 1H), 2.29 (d, J = 1.0 Hz, 6H), 1.27 (d, J = 7.0 Hz, 3H), 1.20 (d, J = 6.9 Hz, 3H), 0.96-0.86 (m, 1H), 0.76-0.61 (m, 2H), 0.52-0.44 (m, 1H). (ESI)m/z = 596 $(M + 1)^+$ |
| 65 | B | 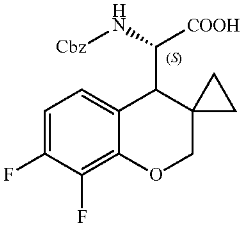 Z13 | 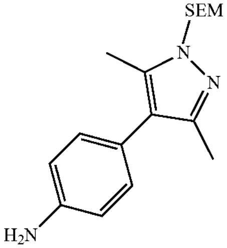 | 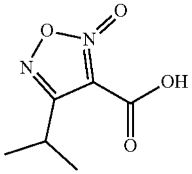 Z20 | 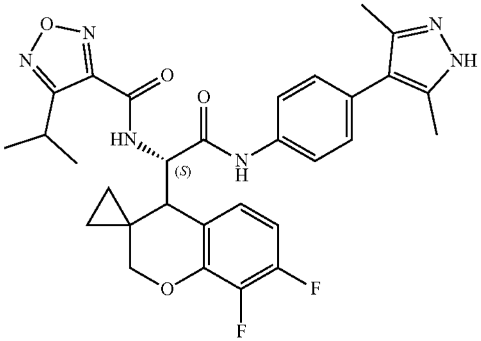 | $^1$H NMR (400 MHz, Methanol-$d_4$) δ 7.76-7.71 (m, 2H), 7.35-7.31 (m, 2H), 6.90 (ddd, J = 8.4, 5.8, 2.2 Hz, 1H), 6.55 (td, J = 9.7, 7.4 Hz, 1H), 5.16 (d, J = 10.0 Hz, 1H), 5.03 (dd, J = 11.6, 2.0 Hz, 1H), 3.54 (dd, J = 11.6, 1.6 Hz, 1H), |

-continued
| Compound | General route | BB-amino acid | BB-amine | BB-acid | Structural formula | $^1$HNMR and/or LCMS: |
|---|---|---|---|---|---|---|
| | | | | | | 3.26 (dd, J = 14.0, 7.0 Hz, 1H), 2.65 (d, J = 9.6 Hz, 1H), 2.32 (s, 6H), 1.27 (d, J = 6.9 Hz, 3H), 1.20 (d, J = 6.9 Hz, 3H), 0.99-0.92 (m, 1H), 0.74-0.60 (m, 2H), 0.50-0.42 (m, 1H). (ESI)m/z = 577 (M + 1)$^+$ |
| 66 | B | 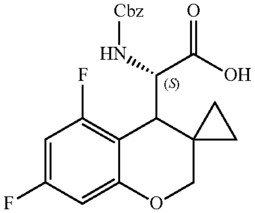 Z14 | 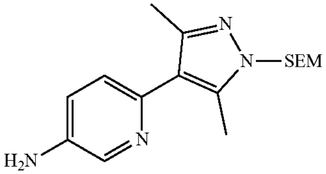 Z10 | 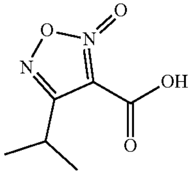 Z20 | 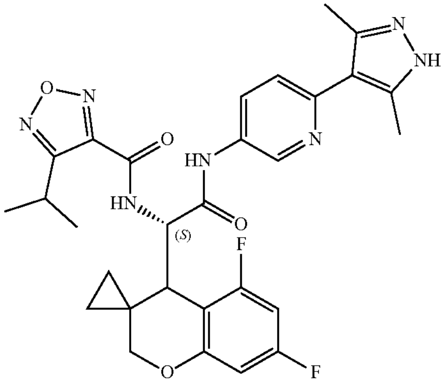 | $^1$H NMR (400 MHz, Methanol-d$_4$) δ 9.10 (d, J = 2.5 Hz, 1H), 8.36 (dd, J = 8.8, 12.6 Hz, 1H), 7.72 (d, J = 8.8 Hz, 1H), 6.52-6.29 (m, 2H), 5.24 (d, J = 9.1 Hz, 1H), 5.01 (d, J = 11.7 Hz, 1H), 3.48 (d, J = 11.1 Hz, 1H), 3.04 (d, J = 8.9 Hz, 1H), 2.39 (s, 6H), 1.42-1.32 (m, 1H), 1.28 (d, J = 6.9 Hz, 3H), 1.22 (d, J = 7.0 Hz, 3H), 1.01-0.90 (m, 1H), 0.80-0.69 (m, 1H), 0.69-0.61 (m, 1H), 0.56-0.45 (m, 1H). (ESI)m/z = 578 (M + 1)$^+$ |

-continued
| Compound | General route | BB-amino acid | BB-amine | BB-acid | Structural formula | $^1$HNMR and/or LCMS: |
|---|---|---|---|---|---|---|
| 67 | B | 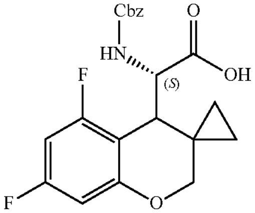 Z14 | 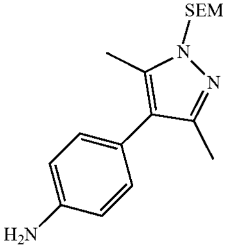 | 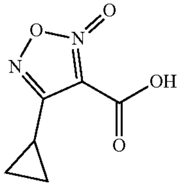 Z21 | 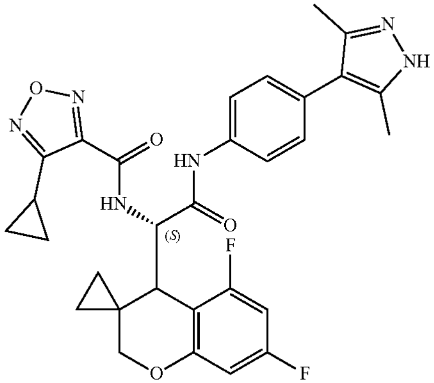 | $^1$H NMR (400 MHz, Methanol-$d_4$) δ 7.77-7.67 (m, 2H), 7.36-7.29 (m, 2H), 6.49-6.33 (m, 2H), 5.20 (d, J = 9.4 Hz, 1H), 5.04 (dd, J = 11.7, 2.0 Hz, 1H), 3.47 (dd, J = 11.7, 1.8 Hz, 1H), 2.98 (d, J = 9.4 Hz, 1H), 2.30 (s, 7H), 2.22 (tt, J = 8.4, 5.1 Hz, 1H), 1.15-1.01 (m, 3H), 1.05-0.92 (m, 4H), 0.78-0.67 (m, 1H), 0.68-0.58 (m, 1H), 0.53-0.42 (m, 1H). (ESI)m/z = 575 $(M + 1)^+$ |
| 68 | B | 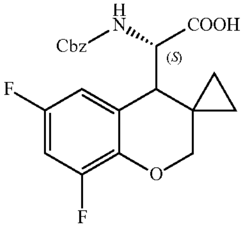 Z15 | 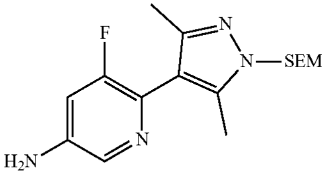 Z11 | 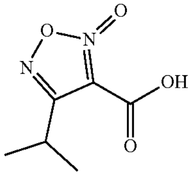 Z20 | 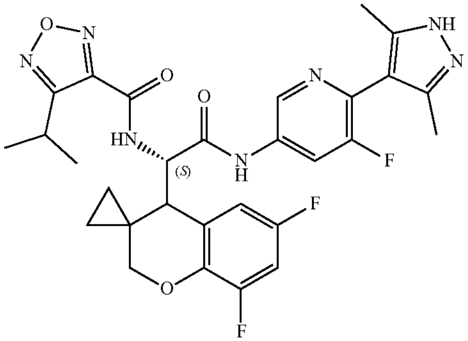 | (ESI)m/z = 596 $(M + 1)^+$ |

-continued
| Compound | General route | BB-amino acid | BB-amine | BB-acid | Structural formula | $^1$HNMR and/or LCMS: |
|---|---|---|---|---|---|---|
| 69 | A | 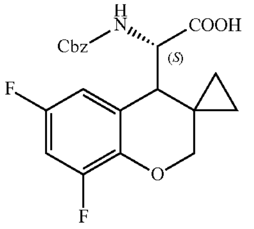 Z15 | 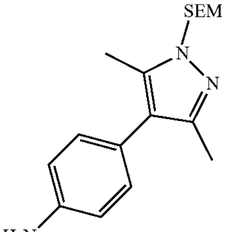 | 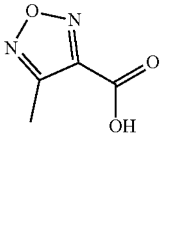 | 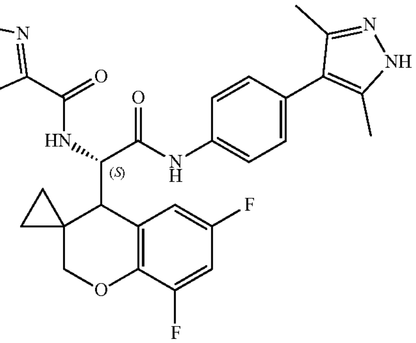 | $^1$H NMR (400 MHz, Methanol-$d_4$) δ 17.76 (d, J = 8.3 Hz, 2H), 7.34 (d, J = 8.2 Hz, 2H), 6.89-6.77 (m, 2H), 5.20 (d, J = 9.9 Hz, 1H), 5.00 (dd, J = 11.6, 1.9 Hz, 1H), 3.49 (d, J = 11.7 Hz, 1H), 2.68 (d, J = 9.8 Hz, 1H), 2.37 (d, J = 2.3 Hz, 3H), 2.35 (s, 6H), 0.97 (dt, J = 8.7, 4.9 Hz, 1H), 0.68 (qq, J = 9.3, 5.1 Hz, 2H), 0.46 (dd, J = 10.1, 4.8 Hz, 1H). (ESI)m/z = 549 (M + 1)$^+$ |
| 70 | A | 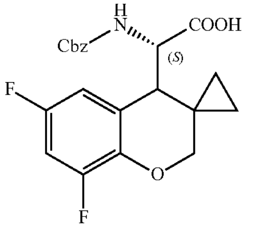 Z15 | 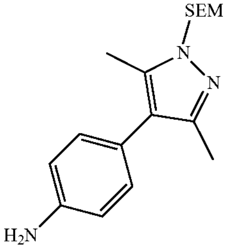 | 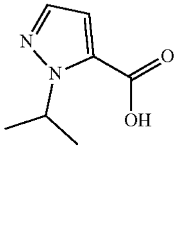 | 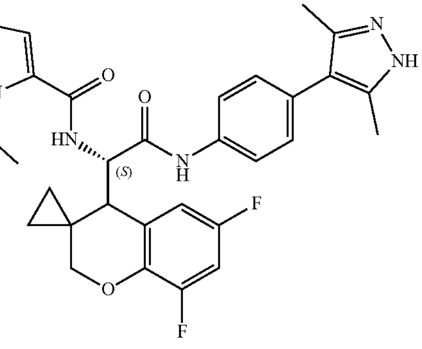 | $^1$H NMR (400 MHz, Methanol-$d_4$) δ 7.75 (d, J = 8.4 Hz, 2H), 7.53-7.46 (m, 2H), 7.37-7.30 (m, 2H), 6.83 (dt, J = 9.8, 2.5 Hz, 2H), 5.42 (dt, J = 19.7, 6.7 Hz, 1H), 5.16 (d, J = 10.1 Hz, 1H), 5.04-5.00 (m, 1H), 3.54-3.47 (m, 1H), 2.63 (d, J = 9.9 Hz, 1H), 2.33 (s, 6H), 1.39-1.33 (m, 6H), 0.95 (dt, J = |

-continued
| Compound | General route | BB-amino acid | BB-amine | BB-acid | Structural formula | $^1$HNMR and/or LCMS: |
|---|---|---|---|---|---|---|
| | | | | | | 8.6, 4.8 Hz, 1H), 0.68 (ddp, J = 14.1, 9.2, 4.3 Hz, 2H), 0.48-0.42 (m, 1H). (ESI)m/z = 575 (M + 1)$^+$ |
| 71 | A | 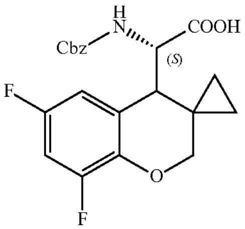 Z15 | 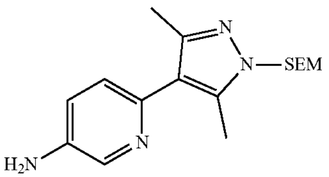 Z10 | 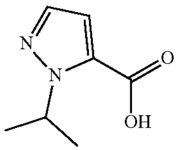 | 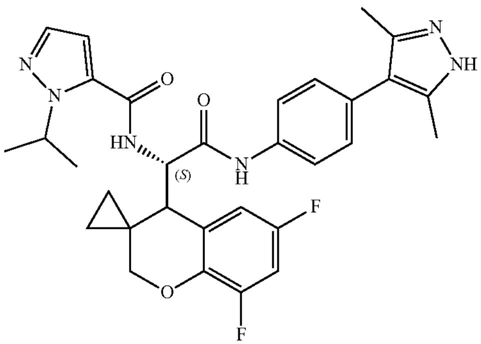 | $^1$H NMR (400 MHz, Methanol-d$_4$) δ 9.18 (s, 1H), 8.41 (d, J = 9.1 Hz, 1H), 7.77 (d, J = 8.8 Hz, 1H), 7.57-7.47 (m, 1H), 6.89-6.74 (m, 2H), 6.72-6.62 (m, 1H), 5.13-4.90 (m, 1H), 3.51 (d, J = 11.5 Hz, 1H), 2.67 (t, J = 10.2 Hz, 1H), 2.40-2.36 (m, 6H), 1.40 (ddd, J = 39.8, 15.7, 6.9 Hz, 7H), 0.91 (d, J = 9.1 Hz, 1H), 0.78-0.62 (m, 2H), 0.48 (d, J = 9.0 Hz, 1H), 0.10 (s, 1H). (ESI)m/z = 576 (M + 1)$^+$ |

-continued
| Compound | General route | BB-amino acid | BB-amine | BB-acid | Structural formula | $^1$HNMR and/or LCMS: |
|---|---|---|---|---|---|---|
| 72 | A | 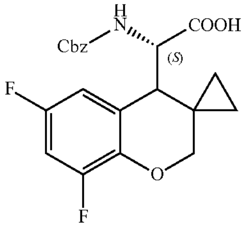 Z15 | 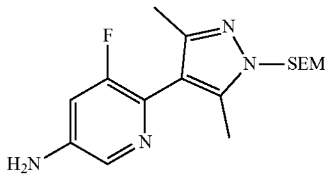 Z11 | 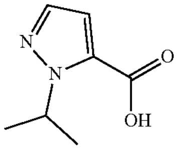 | 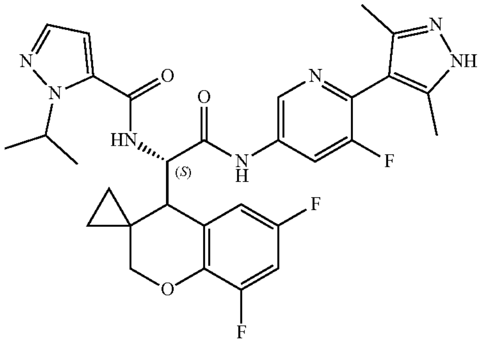 | $^1$H NMR (400 MHz, Methanol-$d_4$) δ 8.72-8.61 (m, 1H), 8.31 (dd, J = 11.7, 2.1 Hz, 1H), 7.57-7.48 (m, 1H), 6.89-6.79 (m, 1H), 6.78-6.69 (m, 1H), 6.59 (dd, J = 47.7, 8.8 Hz, 1H), 5.10-4.92 (m, 1H), 3.50 (d, J = 12.0 Hz, 1H), 2.67 (d, J = 10.1 Hz, 1H), 2.30 (d, J = 4.7 Hz, 6H), 1.48-1.27 (m, 7H), 1.19-1.06 (m, 1H), 0.93-0.86 (m, 1H), 0.67 (s, 1H), 0.47 (d, J = 8.9 Hz, 1H), 0.10 (s, 1H). (ESI)m/z = 594 $(M + 1)^+$ |
| 73 | B | 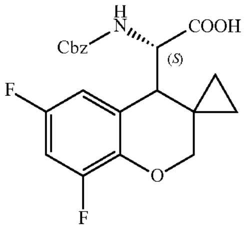 Z15 | 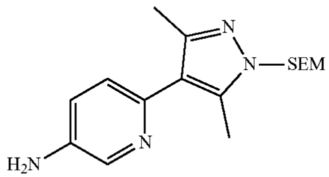 Z10 | 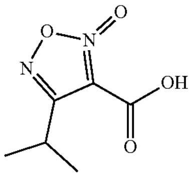 Z20 | 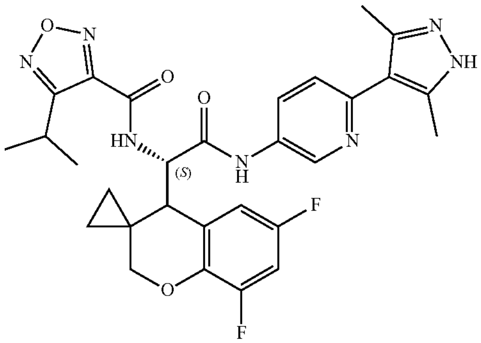 | $^1$H NMR (400 MHz, Methanol-$d_4$) δ 9.11-9.00 (m, 1H), 8.35 (dd, J = 8.6, 2.6 Hz, 1H), 7.74-7.58 (m, 1H), 6.89-6.74 (m, 1H), 6.56 (d, J = 8.9 Hz, 1H), 5.01-4.90 (m, 1H), 3.55-3.41 (m, 1H), 3.28-3.20 (m, 1H), 2.71 (d, J = 9.9 Hz, 1H), |

-continued
| Compound | General route | BB-amino acid | BB-amine | BB-acid | Structural formula | $^1HNMR$ and/or LCMS: |
|---|---|---|---|---|---|---|
| | | | | | | 2.49-2.33 (m, 6H), 1.48-1.01 (m, 8H), 0.93 (dt, J = 8.0, 4.4 Hz, 1H), 0.78-0.56 (m, 1H), 0.49 (d, J = 9.5 Hz, 1H). (ESI)m/z = 578 $(M + 1)^+$ |
| 74 | B | 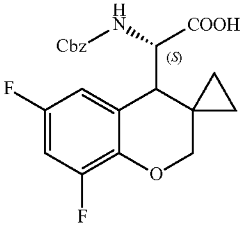 Z15 | 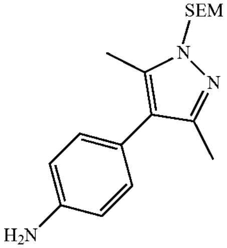 | 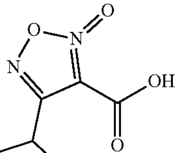 Z20 | 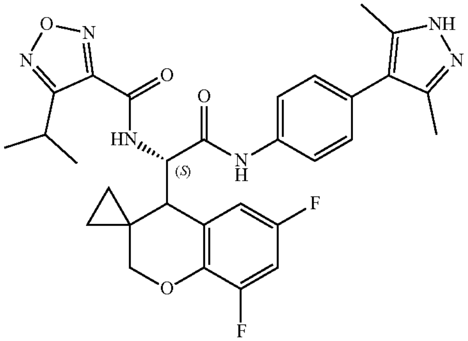 | (ESI)m/z = 577 $(M + 1)^+$ |

-continued
| Compound | General route | BB-amino acid | BB-amine | BB-acid | Structural formula | $^1$HNMR and/or LCMS: |
|---|---|---|---|---|---|---|
| 75 | A | 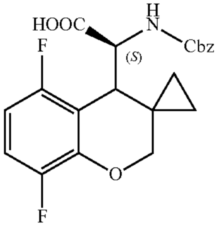 Z16 | 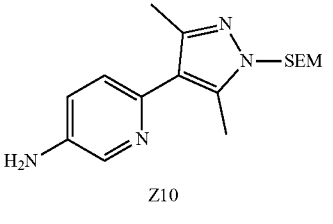 Z10 | 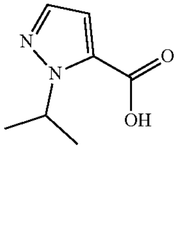 | 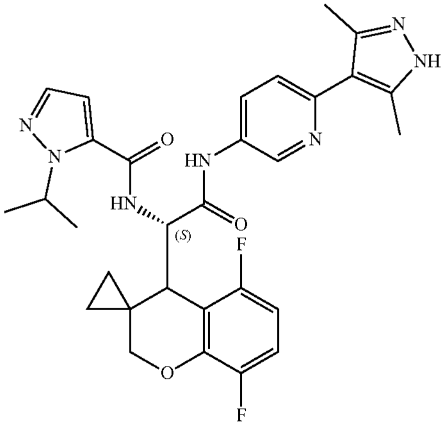 | $^1$H NMR (400 MHz, Methanol-$d_4$) δ 9.09 (d, J = 2.6 Hz, 1H), 8.41-8.32 (m, 2H), 7.69 (d, J = 8.7 Hz, 1H), 7.47 (d, J = 2.1 Hz, 1H), 7.03-6.92 (m, 2H), 6.73-6.67 (m, 2H), 6.56-6.44 (m, 2H), 5.28-5.20 (m, 2H), 5.16-5.10 (m, 1H), 5.11-5.05 (m, 2H), 5.07-4.99 (m, 1H), 3.60-3.49 (m, 1H), 3.50-3.46 (m, 1H), 3.16-3.12 (m, 1H), 3.13-3.05 (m, 2H), 2.38 (s, 6H), 1.45 (t, J = 6.8 Hz, 1H), 1.34 (dd, J = 12.4, 6.6 Hz, 7H), 1.01-0.91 (m, 1H), 0.77-0.63 (m, 2H), 0.57-0.48 (m, 1H). (ESI)m/z = 576 (M + 1)$^+$ |

-continued
| Compound | General route | BB-amino acid | BB-amine | BB-acid | Structural formula | $^1$HNMR and/or LCMS: |
|---|---|---|---|---|---|---|
| 76 | A | 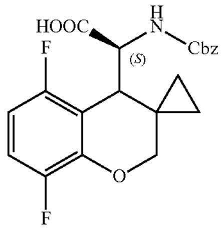 Z16 | 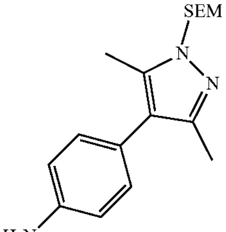 | 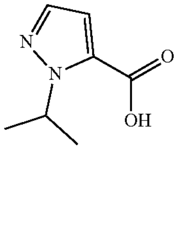 | 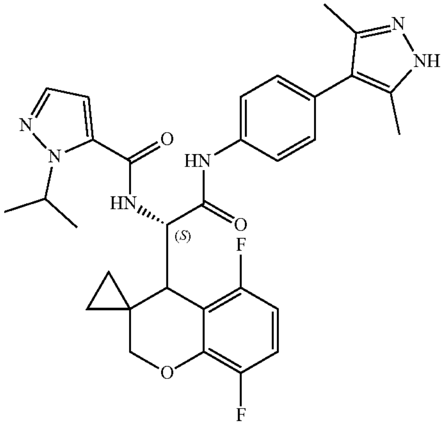 | $^1$H NMR (400 MHz, Methanol-$d_4$) δ 7.76 (d, J = 8.2 Hz, 2H), 7.47 (d, J = 2.1 Hz, 1H), 7.34 (d, J = 8.2 Hz, 2H), 7.02-6.91 (m, 1H), 6.71 (d, J = 2.1 Hz, 1H), 6.49 (m, J = 9.0, 3.5 Hz, 1H), 5.20 (d, J = 9.8 Hz, 1H), 5.11 (dd, J = 12.9, 6.8 Hz, 2H), 3.56 (d, J = 11.8 Hz, 1H), 3.03 (d, J = 9.8 Hz, 1H), 2.34 (s, 6H), 1.34 (dd, J = 11.4, 6.6 Hz, 6H), 1.02-0.92 (m, 1H), 0.78-0.69 (m, 1H), 0.69-0.60 (m, 1H), 0.52-0.44 (m, 1H). (ESI)m/z = 575 $(M + 1)^+$ |
| 77 | A | 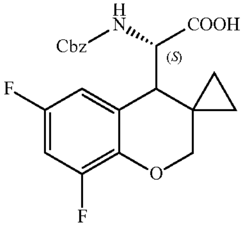 Z15 | 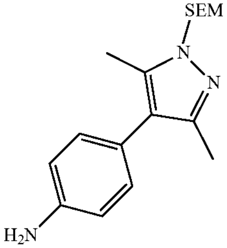 [SMILES: Cc1nn(COCC[Si](C)(C)C)c(C)c1-c1ccc(N)cc1] | 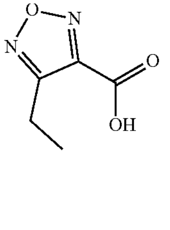 | 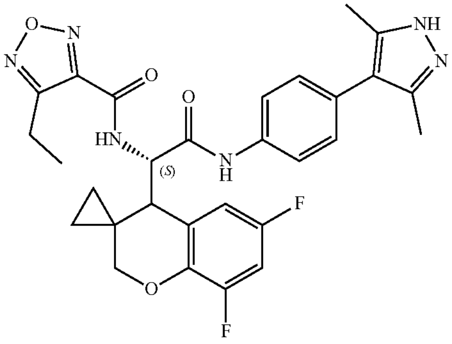 | $^1$H NMR (400 MHz, Methanol-$d_4$) δ 7.73 (d, J = 8.5 Hz, 2H), 7.32 (d, J = 8.4 Hz, 2H), 6.82 (ddt, J = 20.4, 11.2, 5.6 Hz, 2H), 5.19 (d, J = 10.0 Hz, 1H), 4.99 (dd, J = 11.5, 1.9 Hz, 1H), 3.53-3.46 (m, 1H), 2.81 (t, J = 7.6 |

-continued
| Compound | General route | BB-amino acid | BB-amine | BB-acid | Structural formula | $^1$HNMR and/or LCMS: |
|---|---|---|---|---|---|---|
| | | | | | | Hz, 2H), 2.66 (d, J = 10.0 Hz, 1H), 2.30 (s, 6H), 1.21 (t, J = 7.4 Hz, 3H), 0.97 (dt, J = 9.0, 4.9 Hz, 1H), 0.67 (dtd, J = 13.5, 9.3, 4.9 Hz, 2H), 0.46 (d, J = 5.8 Hz, 1H). (ESI)m/z = 563 $(M + 1)^+$ |
| 78 | A | 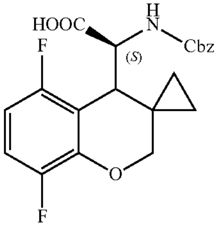 Z16 | 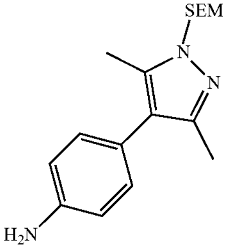 | 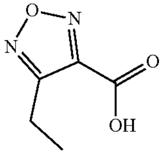 | 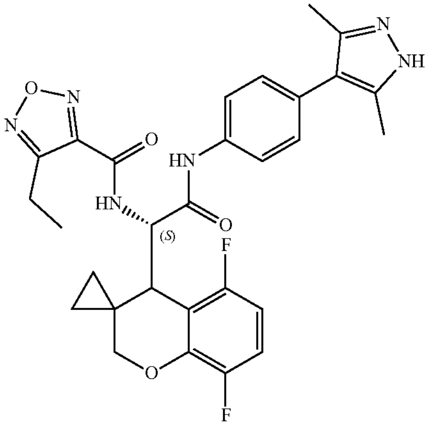 | $^1$H NMR (400 MHz, Methanol-$d_4$) δ 7.79-7.72 (m, 2H), 7.38-7.31 (m, 2H), 7.02-6.91 (m, 1H), 6.52-6.42 (m, 1H), 5.23 (d, J = 9.6 Hz, 1H), 5.07 (dd, J = 11.6, 2.0 Hz, 1H), 3.56 (dd, J = 11.6, 1.7 Hz, 1H), 3.08-2.95 (m, 1H), 2.82 (q, J = 7.6 Hz, 2H), 2.35 (s, 6H), 1.20 (t, J = 7.5 Hz, 3H), 1.02-0.92 (m, 1H), 0.80-0.61 (m, 2H), 0.50 (q, J = 4.9 Hz, 1H). (ESI)m/z = 563 $(M + 1)^+$ |

-continued
| Compound | General route | BB-amino acid | BB-amine | BB-acid | Structural formula | $^1$HNMR and/or LCMS: |
|---|---|---|---|---|---|---|
| 79 | B | 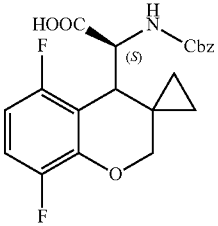 Z16 | 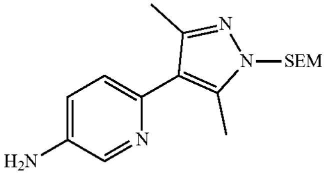 Z10 | 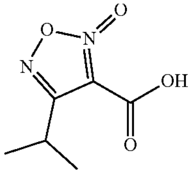 Z20 | 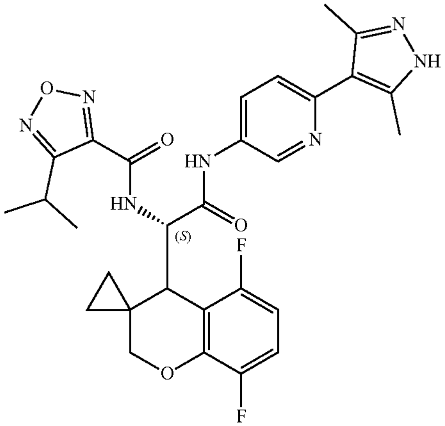 | $^1H$ NMR (400 MHz, Methanol-$d_4$) δ 7.79-7.72 (m, 2H), 7.38-7.31 (m, 2H), 7.02-6.91 (m, 1H), 6.52-6.42 (m, 1H), 5.23 (d, J = 9.6 Hz, 1H), 5.07 (dd, J = 11.6, 2.0 Hz, 1H), 3.56 (dd, J = 11.6, 1.7 Hz, 1H), 3.08-2.95 (m, 1H), 2.82 (q, J = 7.6 Hz, 2H), 2.35 (s, 6H), 1.20 (t, J = 7.5 Hz, 3H), 1.02-0.92 (m, 1H), 0.80-0.61 (m, 2H), 0.50 (q, J = 4.9 Hz, 1H). (ESI)m/z = 578 $(M + 1)^+$ |
| 80 | B | 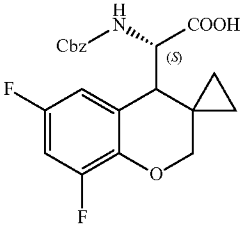 Z15 | 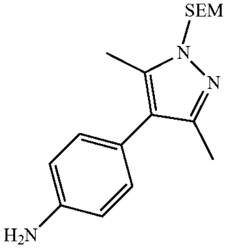 | 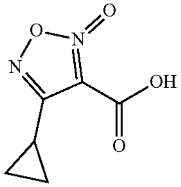 Z21 | 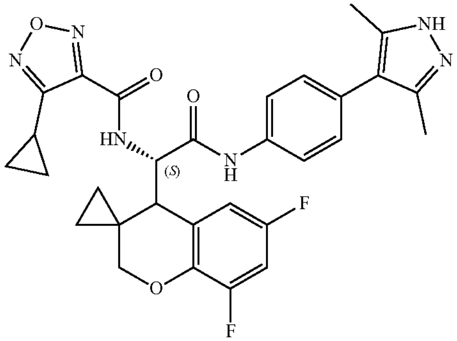 | (ESI)m/z = 575 $(M + 1)^+$ |

-continued
| Compound | General route | BB-amino acid | BB-amine | BB-acid | Structural formula | $^1$HNMR and/or LCMS: |
|---|---|---|---|---|---|---|
| 81 | A | 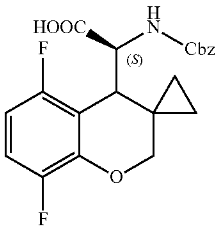 Z16 | 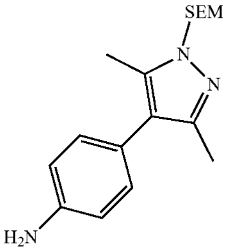 | 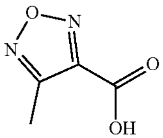 | 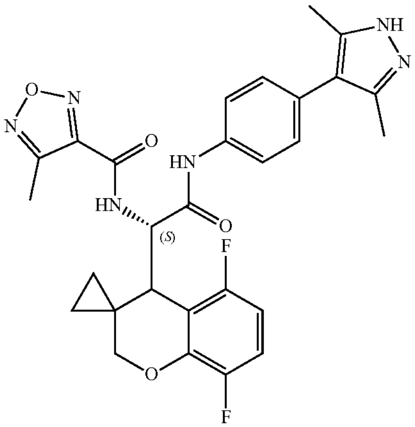 | $^1$H NMR (400 MHz, Methanol-$d_4$) δ 7.73 (d, J = 8.3 Hz, 2H), 7.33 (d, J = 8.5 Hz, 2H), 6.97 (td, J = 9.8, 5.1 Hz, 1H), 6.48 (td, J = 9.0, 3.6 Hz, 1H), 5.22 (d, J = 9.7 Hz, 1H), 5.07 (dd, J = 11.7, 2.0 Hz, 1H), 3.56 (dd, J = 11.7, 1.8 Hz, 1H), 3.04 (d, J = 9.6 Hz, 1H), 2.38 (s, 3H), 2.31 (s, 6H), 1.03-0.93 (m, 1H), 0.80-0.70 (m, 1H), 0.70-0.61 (m, 1H), 0.54-0.44 (m, 1H). (ESI)m/z = 549 $(M + 1)^+$ |

-continued
| Compound | General route | BB-amino acid | BB-amine | BB-acid | Structural formula | $^1$HNMR and/or LCMS: |
|---|---|---|---|---|---|---|
| 82 | B | 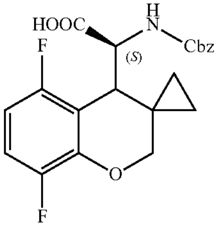 Z16 | 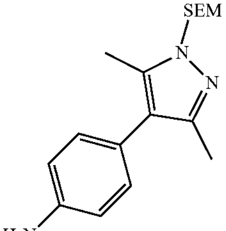 | 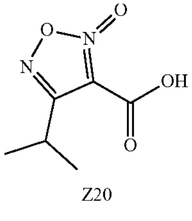 Z20 | 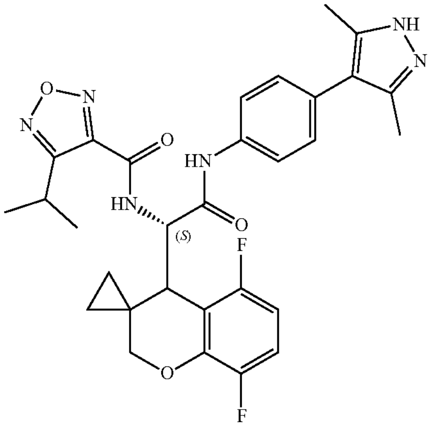 | $^1$H NMR (400 MHz, Methanol-$d_4$) δ 7.73 (d, J = 8.4 Hz, 2H), 7.33 (d, J = 8.5 Hz, 2H), 6.96 (td, J = 9.8, 5.1 Hz, 1H), 6.47 (td, J = 8.9, 3.6 Hz, 1H), 5.24 (d, J = 9.7 Hz, 1H), 5.08 (dd, J = 11.5, 2.0 Hz, 1H), 3.56 (dd, J = 11.5, 1.7 Hz, 1H), 3.04 (d, J = 9.7 Hz, 1H), 2.32 (s, 6H), 1.27 (d, J = 6.9 Hz, 3H), 1.20 (d, J = 6.9 Hz, 3H), 1.02-0.92 (m, 1H), 0.80-0.71 (m, 1H), 0.71-0.61 (m, 1H), 0.53-0.44 (m, 1H). (ESI)m/z = 577 $(M + 1)^+$ |

-continued
| Compound | General route | BB-amino acid | BB-amine | BB-acid | Structural formula | $^1$HNMR and/or LCMS: |
|---|---|---|---|---|---|---|
| 83 | A | 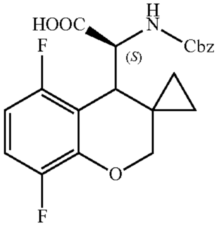 Z16 | 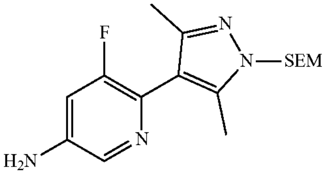 Z11 | 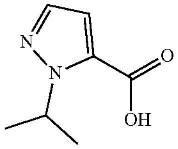 | 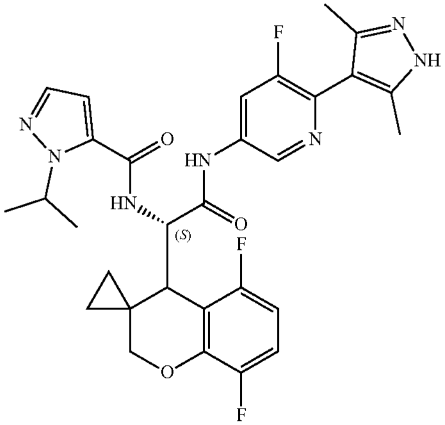 | 1H NMR (400 MHz, Methanol-d4) δ 8.66 (d, J = 2.0 Hz, 1H), 8.28 (dd, J = 11.6, 2.1 Hz, 1H), 7.47 (d, J = 2.0 Hz, 1H), 6.97 (td, J = 9.9, 5.1 Hz, 1H), 6.70 (d, J = 2.1 Hz, 1H), 6.49 (td, J = 8.9, 3.6 Hz, 1H), 5.27-5.19 (m, 1H), 5.14-5.02 (m, 2H), 3.56 (dd, J = 11.7, 1.7 Hz, 1H), 3.08 (d, J = 9.6 Hz, 1H), 2.27 (s, 6H), 1.36 (d, J = 6.6 Hz, 3H), 1.33 (d, J = 6.6 Hz, 3H), 0.95 (dt, J = 9.6, 5.2 Hz, 1H), 0.78-0.63 (m, 2H), 0.51 (s, 1H). (ESI)m/z = 594 $(M + 1)^+$ |

-continued
| Compound | General route | BB-amino acid | BB-amine | BB-acid | Structural formula | $^1$HNMR and/or LCMS: |
|---|---|---|---|---|---|---|
| 84 | B | 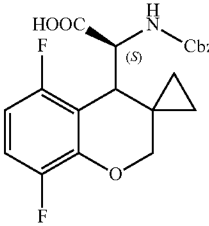 Z16 | 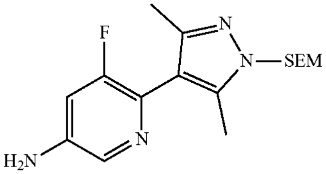 Z11 | 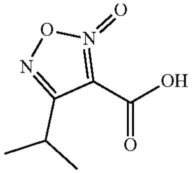 Z20 | 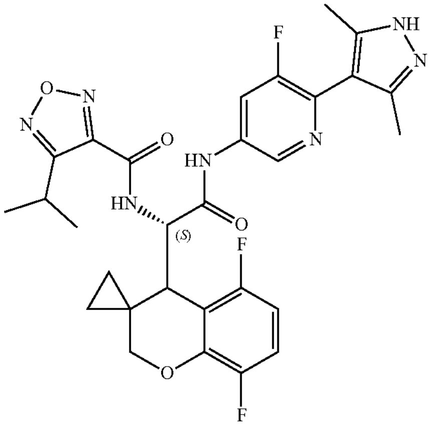 | $^1$H NMR (400 MHz, Methanol-d4) δ 8.64 (d, J = 2.0 Hz, 1H), 8.27 (dd, J = 11.5, 2.1 Hz, 1H), 6.97 (ddd, J = 10.7, 9.0, 5.2 Hz, 1H), 6.48 (td, J = 8.9, 3.6 Hz, 1H), 5.26 (d, J = 9.3 Hz, 1H), 5.05 (dd, J = 11.7, 2.0 Hz, 1H), 3.57 (dd, J = 11.6, 1.7 Hz, 1H), 3.28-3.24 (m, 1H), 3.09 (d, J = 9.3 Hz, 1H), 2.27 (s, 6H), 1.27 (d, J = 7.0 Hz, 3H), 1.20 (d, J = 6.9 Hz, 3H), 0.96 (dt, J = 9.8, 5.4 Hz, 1H), 0.71 (ddt, J = 33.3, 9.6, 5.4 Hz, 2H), 0.57-0.49 (m, 1H). (ESI)m/z = 596 (M + 1)$^+$ |

-continued
| Compound | General route | BB-amino acid | BB-amine | BB-acid | Structural formula | $^1$HNMR and/or LCMS: |
|---|---|---|---|---|---|---|
| 85 | A | 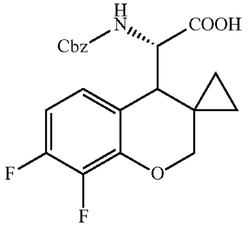 Z13 | 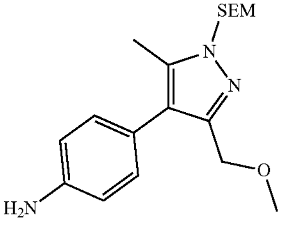 Z28 | 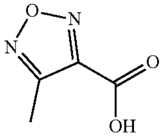 | 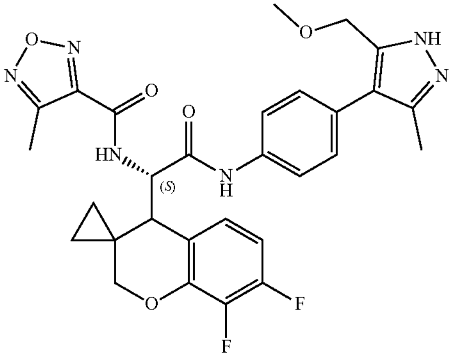 | $^1$H NMR (400 MHz, Methanol-$d_4$) δ 7.69 (dd, J = 8.7, 2.1 Hz, 2H), 7.39 (d, J = 8.5 Hz, 2H), 6.98-6.86 (m, 1H), 6.63-6.51 (m, 1H), 5.14 (d, J = 9.9 Hz, 1H), 5.04-5.00 (m, 2H), 4.39 (s, 2H), 3.65-3.55 (m, 1H), 3.57-3.51 (m, 2H), 3.51-3.44 (m, 1H), 3.34 (s, 3H), 2.69-2.61 (m, 2H), 2.38 (s, 3H), 2.32 (s, 3H), 1.35-1.27 (m, 1H), 1.22-1.13 (m, 1H), 1.02-0.92 (m, 2H), 0.76-0.60 (m, 3H), 0.51-0.41 (m, 1H). (ESI)m/z = 579 $(M + 1)^+$ |

-continued
| Compound | General route | BB-amino acid | BB-amine | BB-acid | Structural formula | $^1$HNMR and/or LCMS: |
|---|---|---|---|---|---|---|
| 86 | B | 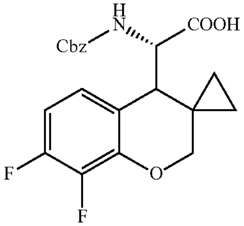 Z13 | 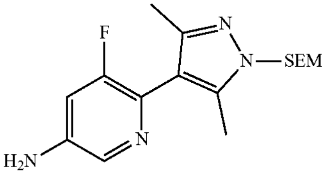 Z11 | 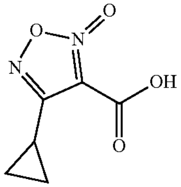 Z21 | 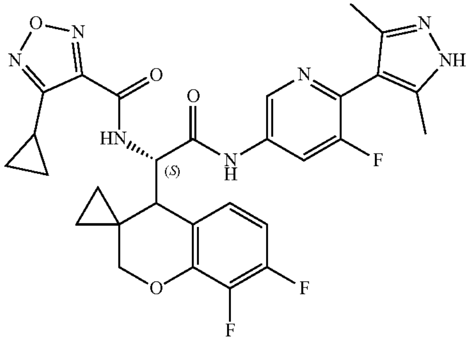 | $^1$H NMR (400 MHz, Methanol-$d_4$) δ 7.69 (dd, J = 8.7, 2.1 Hz, 2H), 7.39 (d, J = 8.5 Hz, 2H), 6.98-6.86 (m, 1H), 6.63-6.51 (m, 1H), 5.14 (d, J = 9.9 Hz, 1H), 5.04-5.00 (m, 2H), 4.39 (s, 2H), 3.65-3.55 (m, 1H), 3.57-3.51 (m, 2H), 3.51-3.44 (m, 1H), 3.34 (s, 3H), 2.69-2.61 (m, 2H), 2.38 (s, 3H), 2.32 (s, 3H), 1.35-1.27 (m, 1H), 1.22-1.13 (m, 1H), 1.02-0.92 (m, 2H), 0.76-0.60 (m, 3H), 0.51-0.41 (m, 1H). (ESI)m/z = 579 $(M + 1)^+$ |

-continued
| Compound | General route | BB-amino acid | BB-amine | BB-acid | Structural formula | $^1$HNMR and/or LCMS: |
|---|---|---|---|---|---|---|
| 87 | B | 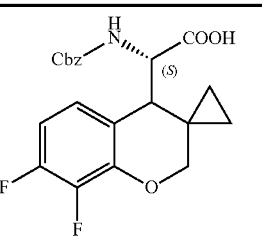 Z13 | 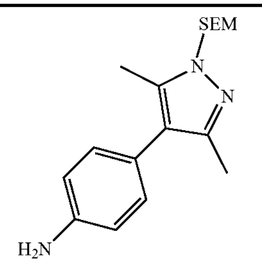 | 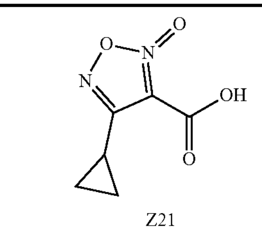 Z21 | 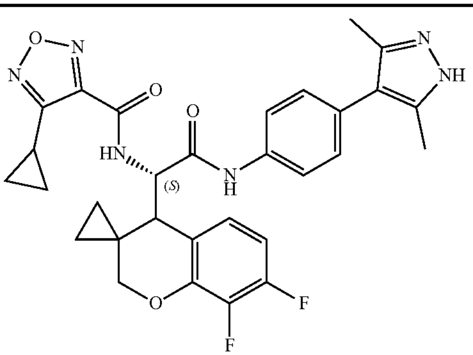 | $^1$H NMR (400 MHz, Methanol-$d_4$) δ 7.76 (d, J = 8.3 Hz, 2H), 7.38-7.31 (m, 2H), 6.96-6.86 (m, 1H), 6.64-6.52 (m, 1H), 5.17 (d, J = 9.9 Hz, 1H), 5.02 (dd, J = 11.5, 2.0 Hz, 1H), 3.54 (dd, J = 11.5, 1.7 Hz, 1H), 2.66 (d, J = 9.9 Hz, 1H), 2.34 (s, 6H), 2.22-2.10 (m, 1H), 1.11-1.03 (m, 2H), 1.02-0.92 (m, 3H), 0.75-0.60 (m, 2H), 0.46 (d, J = 6.9 Hz, 1H). (ESI)m/z = 575 $(M + 1)^+$ |
| 88 | A | 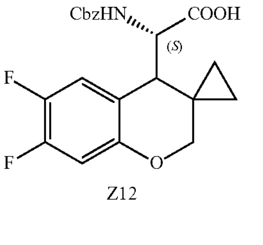 Z12 | 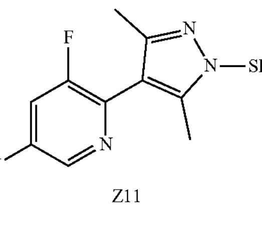 Z11 | 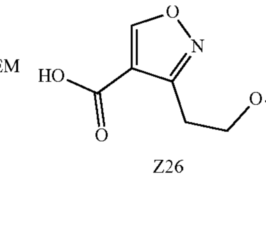 Z26 | 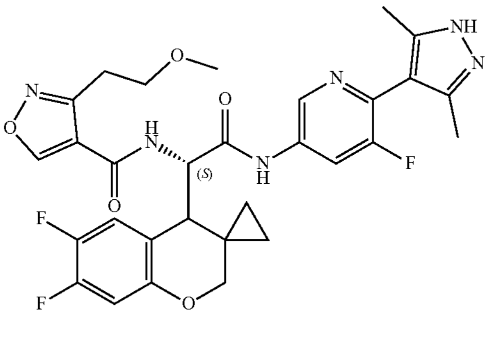 | $^1$H NMR (400 MHz, Methanol-$d_4$) δ 9.04 (s, 1H), 8.67 (d, J = 2.4 Hz, 1H), 8.28 (dd, J = 11.6, 2.2 Hz, 1H), 7.00 (dd, J = 11.1, 9.0 Hz, 1H), 6.72 (dd, J = 11.9, 7.1 Hz, 1H), 5.16 (d, J = 8.9 Hz, 1H), 4.89 (d, 1H), 3.56 (t, J = 6.5 Hz, 2H), 3.40 (dd, J = 11.5, 1.7 Hz, 1H), 3.26 (s, |

-continued
| Compound | General route | BB-amino acid | BB-amine | BB-acid | Structural formula | $^1$HNMR and/or LCMS: |
| --- | --- | --- | --- | --- | --- | --- |
| | | | | | | 3H), 3.01 (t, J = 6.5 Hz, 2H), 2.56 (d, J = 9.0 Hz, 1H), 2.29 (s, 7H), 0.97-0.85 (m, 1H), 0.73-0.58 (m, 3H), 0.52-0.44 (m, 1H). (ESI)m/z = 611 $(M + 1)^+$ |
| 89 | A | 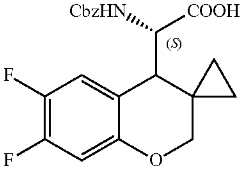 Z12 | 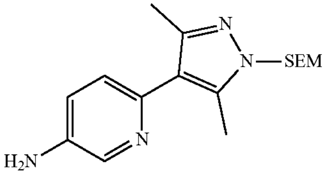 Z10 | 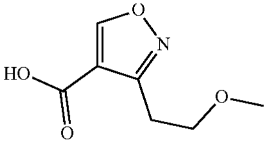 Z26 | 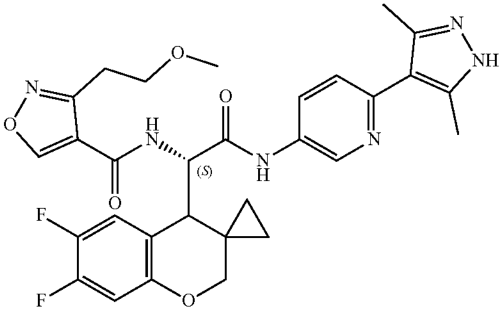 | $^1$H NMR (400 MHz, Methanol-$d_4$) δ 9.20 (d, J = 2.5 Hz, 1H), 9.04 (s, 1H), 8.42 (d, J = 2.6 Hz, 1H), 7.81 (d, J = 8.7 Hz, 1H), 7.00 (dd, J = 11.1, 9.0 Hz, 1H), 6.74 (dd, J = 11.9, 7.1 Hz, 1H), 5.19 (d, J = 8.6 Hz, 1H), 3.55 (td, J = 6.5, 2.3 Hz, 2H), 3.40 (dd, J = 11.8, 1.6 Hz, 1H), 3.25 (s, 3H), 3.01 (t, J = 6.5 Hz, 2H), 2.58 (d, J = 8.6 Hz, 1H), 2.40 (s, 6H), 0.97-0.90 (m, 1H), 0.73-0.61 (m, 2H), 0.53-0.46 (m, 1H). (ESI)m/z = 579 $(M + 1)^+$ |

-continued
| Compound | General route | BB-amino acid | BB-amine | BB-acid | Structural formula | $^1$HNMR and/or LCMS: |
|---|---|---|---|---|---|---|
| 90 | A | 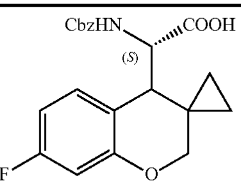 Z8 | 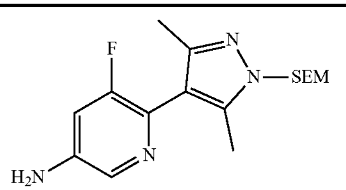 Z11 | 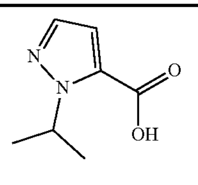 | 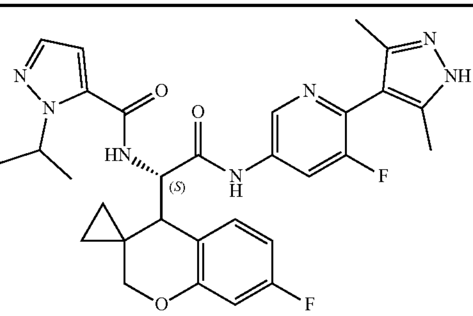 | $^1$H NMR (400 MHz, Methanol-$d_4$) δ 8.68 (d, 1H), 8.30 (dd, J = 11.6, 2.2 Hz, 1H), 7.49 (d, J = 2.1 Hz, 1H), 7.10 (dd, J = 8.5, 6.6 Hz, 1H), 6.71 (d, J = 2.1 Hz, 1H), 6.55 (dd, J = 10.5, 2.6 Hz, 1H), 6.46 (td, J = 8.4, 2.7 Hz, 1H), 5.11 (d, J = 9.9 Hz, 1H), 5.03 (p, J = 6.7 Hz, 1H), 4.96 (dd, J = 11.5, 2.0 Hz, 1H), 3.41 (dd, J = 11.6, 1.8 Hz, 1H), 2.63 (d, J = 9.9 Hz, 1H), 2.30 (d, J = 1.1 Hz, 6H), 1.34 (dd, J = 12.2, 6.7 Hz, 6H), 0.92-0.81 (m, 1H), 0.70-0.58 (m, 2H), 0.48-0.40 (m, 1H). (ESI)m/z = 577 $(M + 1)^+$ |

-continued
| Compound | General route | BB-amino acid | BB-amine | BB-acid | Structural formula | $^1$HNMR and/or LCMS: |
|---|---|---|---|---|---|---|
| 91 | B | 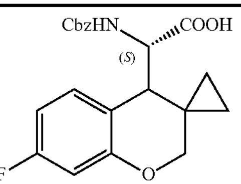 Z8 | 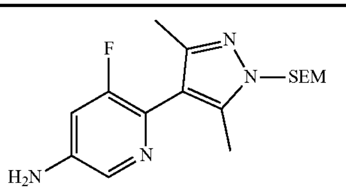 Z11 | 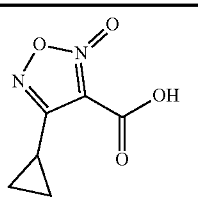 Z21 | 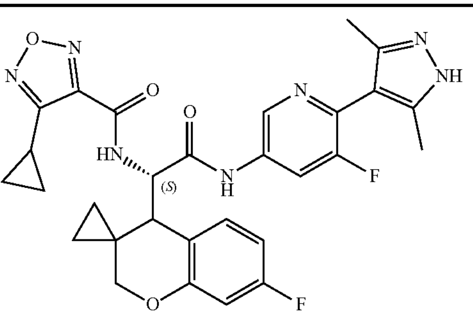 | $^1$H NMR (400 MHz, Methanol-$d_4$) δ 8.66 (d, J = 2.0 Hz, 1H), 8.32-8.24 (m, 1H), 7.17-7.08 (m, 1H), 6.59-6.51 (m, 1H), 6.51-6.42 (m, 1H), 5.17 (d, J = 9.7 Hz, 1H), 4.98-4.90 (m, 1H), 3.41 (dd, J = 11.5, 1.7 Hz, 1H), 2.66 (d, J = 9.6 Hz, 1H), 2.27 (s, 6H), 2.21-2.09 (m, 1H), 1.12-1.00 (m, 2H), 1.00-0.93 (m, 2H), 0.93-0.85 (m, 1H), 0.72-0.58 (m, 2H), 0.46 (d, J = 9.4 Hz, 1H). (ESI)m/z = 576 $(M + 1)^+$ |
| 92 | B | 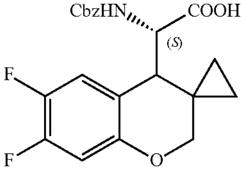 Z12 | 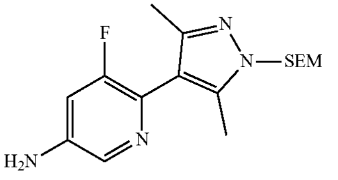 Z11 | 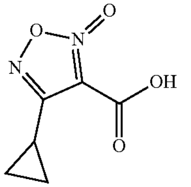 Z21 | 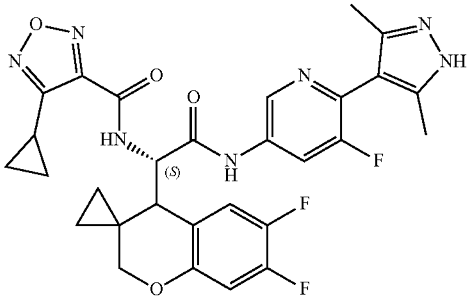 | $^1$H NMR (400 MHz, Methanol-$d_4$) δ 8.65 (d, J = 2.0 Hz, 1H), 8.27 (dd, J = 11.6, 2.1 Hz, 1H), 7.07 (dd, J = 11.2, 9.1 Hz, 1H), 6.70 (dd, J = 12.0, 7.1 Hz, 1H), 5.18 (d, J = 9.8 Hz, 1H), 4.92 (d, J = 12.1 Hz, 1H), 3.41 (d, J = 11.6 Hz, 1H), 2.64 (d, J = 9.8 |

-continued
| Compound | General route | BB-amino acid | BB-amine | BB-acid | Structural formula | $^1$HNMR and/or LCMS: |
|---|---|---|---|---|---|---|
| | | | | | | Hz, 1H), 2.26 (s, 6H), 2.17 (dd, J = 9.1, 4.6 Hz, 1H), 1.07 (d, J = 2.9 Hz, 1H), 1.01-0.95 (m, 2H), 0.90 (dd, J = 9.1, 4.9 Hz, 2H), 0.66 (dq, J = 8.4, 4.5 Hz, 2H), 0.47 (d, J = 8.1 Hz, 1H). (ESI)m/z = 594 $(M + 1)^+$ |
| 93 | A | 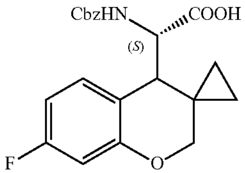 Z8 | 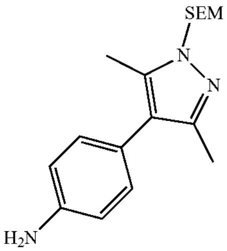 [SMILES: Cc1nn(COCC[Si](C)(C)C)c(C)c1-c1ccc(N)cc1] | 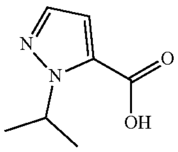 | 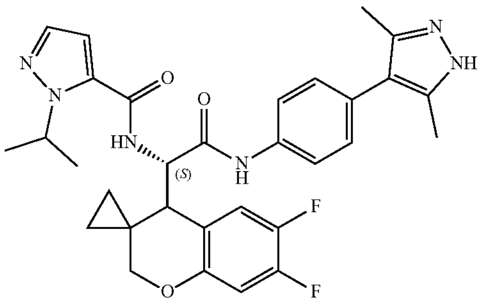 | $^1$H NMR (400 MHz, Methanol-$d_4$) δ 7.77-7.70 (m, 2H), 7.49 (d, J = 2.0 Hz, 1H), 7.36-7.29 (m, 2H), 7.09 (dd, J = 8.5, 6.6 Hz, 1H), 6.71 (d, J = 2.0 Hz, 1H), 6.55 (dd, J = 10.5, 2.6 Hz, 1H), 6.45 (td, J = 8.4, 2.7 Hz, 1H), 5.09 (d, J = 9.9 Hz, 1H), 5.06-4.95 (m, 2H), 3.40 (dd, J = 11.4, 1.7 Hz, 1H), 2.58 (d, J = 9.9 Hz, 1H), 2.32 (s, 6H), 1.36 (d, J = 6.7 Hz, 3H), 1.33 (d, J = 6.6 Hz, 3H), 0.92 (td, J = 9.1, 8.0, 4.7 Hz, 1H), 0.63 (qt, J = 9.3, 5.1 Hz, |

-continued
| Compound | General route | BB-amino acid | BB-amine | BB-acid | Structural formula | $^1$HNMR and/or LCMS: |
|---|---|---|---|---|---|---|
| | | | | | | 2H), 0.42 (t, J = 5.4 Hz, 1H). (ESI)m/z = 557 $(M + 1)^+$ |
| 94 | B | 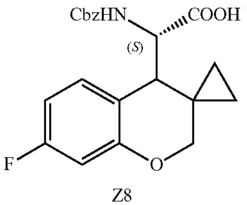 Z8 | 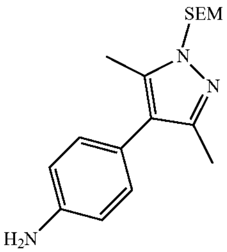 | 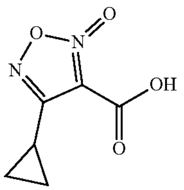 Z21 | 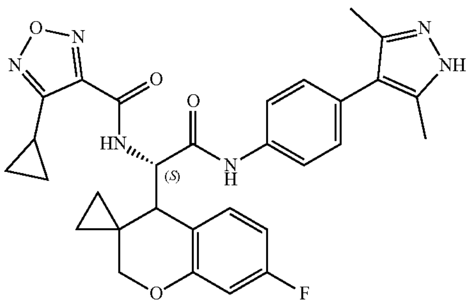 | $^1$H NMR (400 MHz, Methanol-$d_4$) δ 7.71 (d, J = 8.4 Hz, 2H), 7.30 (d, J = 8.4 Hz, 2H), 7.14-7.09 (m, 1H), 6.54 (dd, J = 10.6, 2.7 Hz, 1H), 6.46 (td, J = 8.3, 2.6 Hz, 1H), 5.14 (d, J = 9.7 Hz, 1H), 4.97 (d, J = 11.5 Hz, 1H), 3.40 (d, J = 11.5 Hz, 1H), 2.61 (d, J = 9.8 Hz, 1H), 2.28 (s, 6H), 2.22-2.12 (m, 1H), 1.08 (dd, J = 8.2, 3.0 Hz, 2H), 1.01-0.86 (m, 4H), 0.71-0.58 (m, 2H). (ESI)m/z = 557 $(M + 1)^+$ |

-continued
| Compound | General route | BB-amino acid | BB-amine | BB-acid | Structural formula | $^1$HNMR and/or LCMS: |
|---|---|---|---|---|---|---|
| 95 | B | 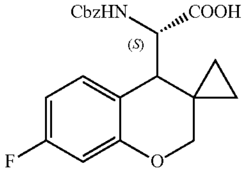 Z8 | 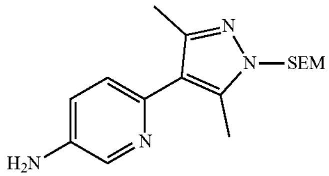 Z10 | 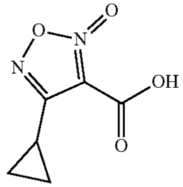 Z21 | 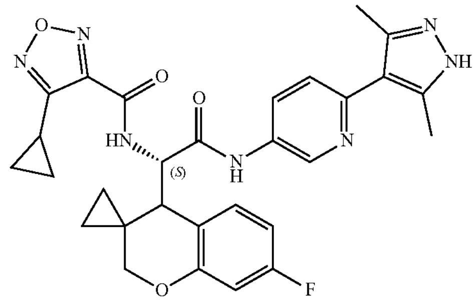 | $^1$H NMR (400 MHz, Methanol-$d_4$) δ 9.23 (d, J = 2.5 Hz, 1H), 8.45 (dd, J = 8.8, 2.6 Hz, 1H), 7.83 (d, J = 8.8 Hz, 1H), 7.12 (dd, J = 8.6, 6.6 Hz, 1H), 6.55 (dd, J = 10.5, 2.6 Hz, 1H), 6.47 (td, J = 8.4, 2.7 Hz, 1H), 5.19 (d, J = 9.6 Hz, 1H), 4.94 (dd, J = 11.6, 1.9 Hz, 1H), 3.42 (dd, J = 11.6, 1.7 Hz, 1H), 2.69 (d, J = 9.6 Hz, 1H), 2.41 (s, 6H), 2.22-2.08 (m, 1H), 1.11-1.04 (m, 2H), 1.01-0.94 (m, 2H), 0.93-0.86 (m, 1H), 0.74-0.59 (m, 2H), 0.53-0.44 (m, 1H). (ESI)m/z = 558 $(M + 1)^+$ |

-continued
| Compound | General route | BB-amino acid | BB-amine | BB-acid | Structural formula | $^1$HNMR and/or LCMS: |
|---|---|---|---|---|---|---|
| 96 | A | 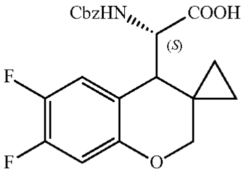 Z12 | 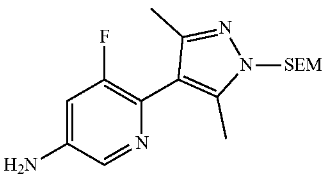 Z11 | 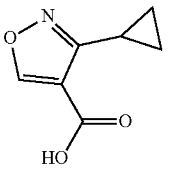 Z24 | 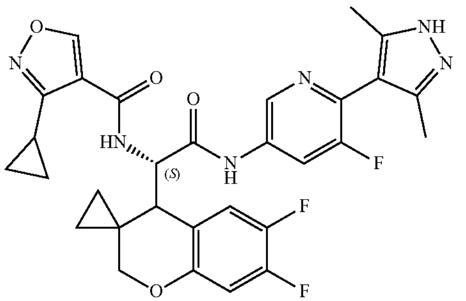 | $^1$H NMR (400 MHz, Methanol-$d_4$) δ 8.96 (s, 1H), 8.68 (d, J = 2.4 Hz, 1H), 8.29 (dd, J = 11.6, 2.1 Hz, 1H), 7.00 (dd, J = 11.2, 9.0 Hz, 1H), 6.70 (dd, J = 12.0, 7.1 Hz, 1H), 5.16 (d, J = 9.6 Hz, 1H), 4.91 (dd, J = 11.5, 1.9 Hz, 1H), 3.44-3.36 (m, 1H), 2.56 (d, J = 9.5 Hz, 1H), 2.30 (s, 6H), 2.10 (p, J = 6.9 Hz, 1H), 1.01-0.84 (m, 5H), 0.72-0.58 (m, 2H), 0.50-0.42 (m, 1H). (ESI)m/z = 593 $(M + 1)^+$ |
| 97 | A | 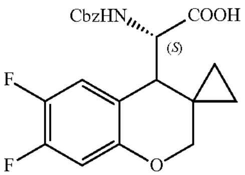 Z12 | 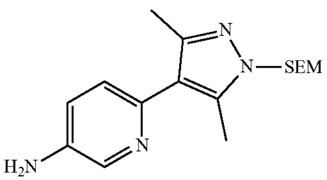 Z10 | 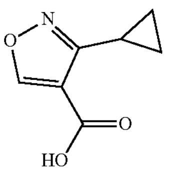 Z24 | 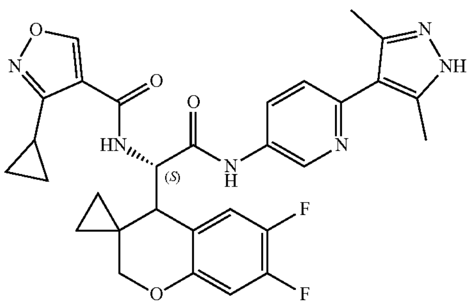 | $^1$H NMR (400 MHz, Methanol-$d_4$) δ 9.22 (d, J = 2.4 Hz, 1H), 8.95 (s, 1H), 8.44 (dd, 1H), 7.82 (d, J = 8.8 Hz, 1H), 7.01 (dd, J = 11.1, 9.0 Hz, 1H), 6.71 (dd, J = 12.0, 7.1 Hz, 1H), 5.18 (d, J = 9.4 Hz, 1H), 4.91 (d, J = 1.9 Hz, 1H), 3.40 (dd, J = 11.6, 1.7 Hz, 1H), 2.59 |

-continued
| Compound | General route | BB-amino acid | BB-amine | BB-acid | Structural formula | $^1$HNMR and/or LCMS: |
|---|---|---|---|---|---|---|
| | | | | | | (d, J = 9.5 Hz, 1H), 2.40 (s, 6H), 2.17-2.06 (m, 1H), 0.99-0.84 (m, 5H), 0.73-0.61 (m, 2H), 0.53-0.40 (m, 1H). (ESI)m/z = 575 $(M + 1)^+$ |
| 98 | A | 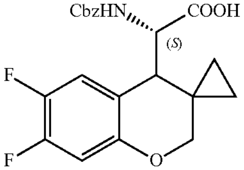 Z12 | 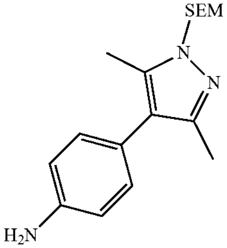 | 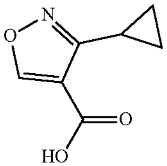 Z24 | 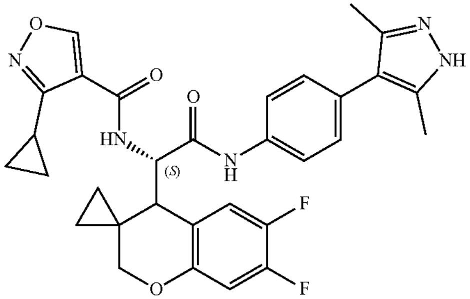 | $^1$H NMR (400 MHz, Methanol-$d_4$) δ 8.96 (s, 1H), 7.75 (d, J = 8.3 Hz, 2H), 7.34 (d, J = 8.5 Hz, 2H), 7.01 (dd, J = 11.2, 9.0 Hz, 1H), 6.69 (dd, J = 12.0, 7.1 Hz, 1H), 5.15 (d, J = 9.6 Hz, 1H), 4.93 (dd, J = 11.5, 1.9 Hz, 1H), 3.39 (dd, J = 11.4, 1.7 Hz, 1H), 2.53 (d, J = 9.5 Hz, 1H), 2.34 (s, 6H), 2.10 (p, J = 7.0, 6.6 Hz, 1H), 0.99-0.86 (m, 5H), 0.72-0.57 (m, 2H), 0.48-0.40 (m, 1H). (ESI)m/z = 688 $(M + 1)^+$ |

-continued
| Compound | General route | BB-amino acid | BB-amine | BB-acid | Structural formula | $^1$HNMR and/or LCMS: |
|---|---|---|---|---|---|---|
| 99 | A | 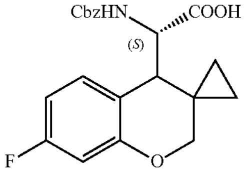 Z8 | 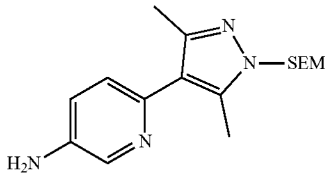 Z10 | 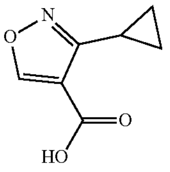 Z24 | 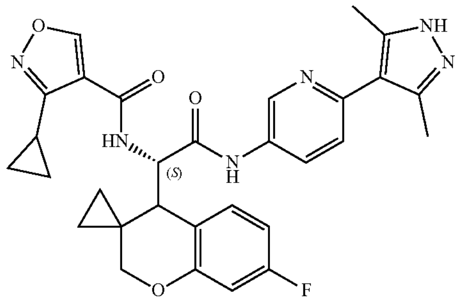 | $^1$H NMR (400 MHz, Methanol-$d_4$) δ 9.19 (d, J = 2.5 Hz, 1H), 8.96 (s, 1H), 8.42 (dd, J = 8.7, 2.5 Hz, 1H), 7.79 (d, J = 8.7 Hz, 1H), 7.09 (dd, J = 8.4, 6.6 Hz, 1H), 6.59-6.47 (m, 2H), 5.21-5.11 (m, 1H), 4.96-4.87 (m, 1H), 3.45-3.37 (m, 1H), 2.61 (d, J = 9.2 Hz, 1H), 2.40 (s, 6H), 2.15-2.03 (m, 1H), 0.96-0.87 (m, 5H), 0.72-0.59 (m, 2H), 0.46 (d, J = 9.0 Hz, 1H). (ESI)m/z = 671 $(M + 1)^+$ |
| 100 | A | 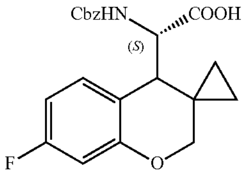 Z8 | 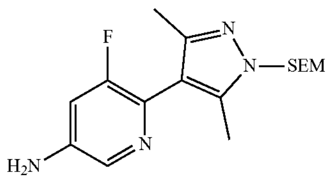 Z11 | 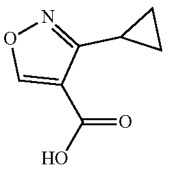 Z24 | 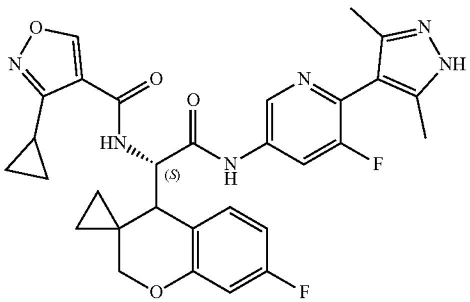 | $^1$H NMR (400 MHz, Methanol-$d_4$) δ 8.97 (s, 1H), 8.68 (d, J = 2.0 Hz, 1H), 8.28 (dd, J = 11.6, 2.1 Hz, 1H), 7.08 (dd, J = 8.4, 6.6 Hz, 1H), 6.52 (ddd, J = 16.9, 9.4, 2.6 Hz, 2H), 5.14 (d, J = 9.3 Hz, 1H), 4.92 (dd, J = 11.6, 2.0 Hz, 1H), 3.40 (d, J = 11.4 Hz, 1H), |

-continued
| Compound | General route | BB-amino acid | BB-amine | BB-acid | Structural formula | $^1$HNMR and/or LCMS: |
|---|---|---|---|---|---|---|
| | | | | | | 2.60 (d, J = 9.5 Hz, 1H), 2.29 (s, 6H), 2.14-2.03 (m, 1H), 0.99-0.83 (m, 5H), 0.71-0.58 (m, 2H), 0.49-0.42 (m, 1H). (ESI)m/z = 575 $(M + 1)^+$ |
| 101 | A | 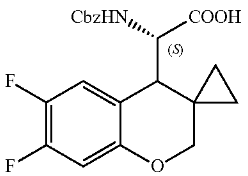 Z12 | 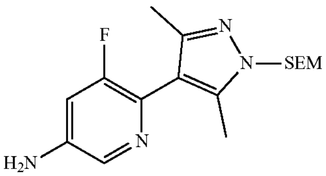 Z11 | 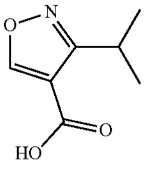 Z23 | 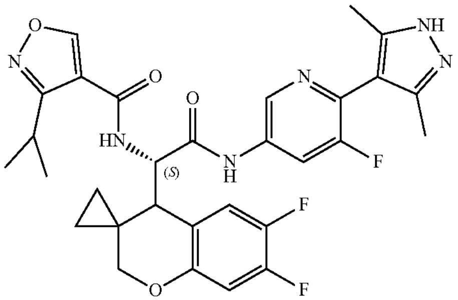 | $^1$H NMR (400 MHz, Methanol-$d_4$) δ 8.99 (s, 1H), 8.70-8.64 (m, 1H), 8.27 (dd, J = 11.6, 2.1 Hz, 1H), 7.00 (dd, J = 11.2, 9.0 Hz, 1H), 6.70 (dd, J = 12.0, 7.1 Hz, 1H), 5.13 (d, J = 10.0 Hz, 1H), 4.92 (dd, J = 11.5, 1.9 Hz, 1H), 3.40 (dd, J = 11.5, 1.7 Hz, 1H), 3.29-3.17 (m, 1H), 2.54 (d, J = 10.0 Hz, 1H), 2.29 (s, 6H), 1.22 (d, J = 6.9 Hz, 3H), 1.13 (d, J = 6.9 Hz, 3H), 0.91-0.80 (m, 1H), 0.71-0.57 (m, 2H), 0.49-0.40 (m, 1H). (ESI)m/z = 595 $(M + 1)^+$ |

-continued
| Compound | General route | BB-amino acid | BB-amine | BB-acid | Structural formula | $^1$HNMR and/or LCMS: |
|---|---|---|---|---|---|---|
| 102 | A | 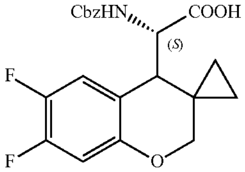 Z12 | 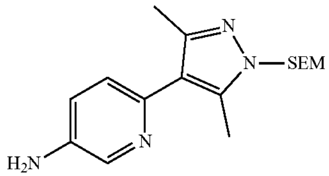 Z10 | 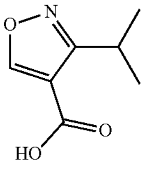 Z23 | 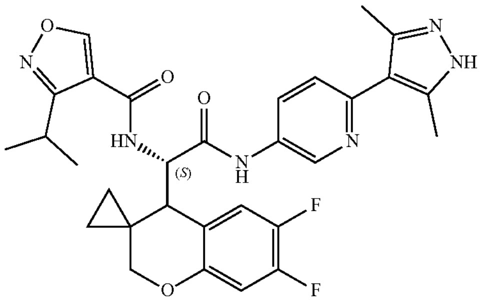 | $^1$H NMR (400 MHz, Methanol-$d_4$) δ 9.23 (d, J = 2.4 Hz, 1H), 8.98 (s, 1H), 8.45 (dd, J = 8.8, 2.6 Hz, 1H), 7.83 (d, J = 8.8 Hz, 1H), 7.01 (dd, J = 11.2, 9.0 Hz, 1H), 6.70 (dd, J = 11.9, 7.1 Hz, 1H), 5.16 (d, J = 9.9 Hz, 1H), 4.93 (d, J = 2.0 Hz, 1H), 3.41 (dd, J = 11.5, 1.7 Hz, 1H), 3.28-3.21 (m, 1H), 2.57 (d, J = 9.8 Hz, 1H), 2.40 (s, 6H), 1.22 (d, J = 6.9 Hz, 3H), 1.14 (d, J = 6.9 Hz, 3H), 0.92-0.84 (m, 1H), 0.72-0.59 (m, 2H), 0.50-0.42 (m, 1H). (ESI)m/z = 577 $(M + 1)^+$ |

-continued
| Compound | General route | BB-amino acid | BB-amine | BB-acid | Structural formula | $^1$HNMR and/or LCMS: |
| --- | --- | --- | --- | --- | --- | --- |
| 103 | A | 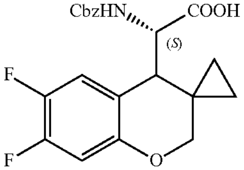 Z12 | 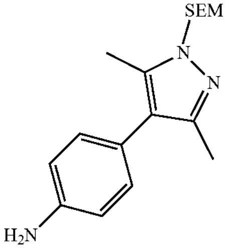 | 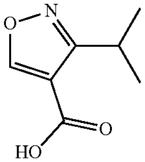 Z23 | 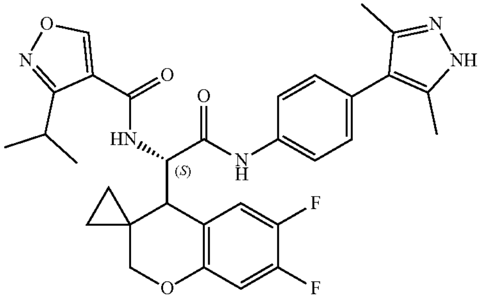 | $^1$H NMR (400 MHz, Methanol-$d_4$) δ 8.98 (s, 1H), 7.75 (d, J = 8.3 Hz, 2H), 7.34 (d, J = 8.3 Hz, 2H), 7.02 (dd, J = 11.2, 8.9 Hz, 1H), 6.69 (dd, J = 11.9, 7.1 Hz, 1H), 5.14 (d, J = 10.0 Hz, 1H), 4.95 (dd, J = 11.4, 2.0 Hz, 1H), 3.39 (dd, J = 11.5, 1.8 Hz, 1H), 2.52 (d, J = 10.0 Hz, 1H), 2.35 (s, 6H), 1.21 (d, J = 6.9 Hz, 3H), 1.13 (d, J = 6.9 Hz, 3H), 0.97-0.85 (m, 2H), 0.71-0.58 (m, 2H), 0.47-0.37 (m, 1H). (ESI)m/z = 576 $(M + 1)^+$ |
| 104 | A | 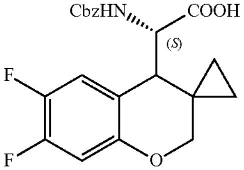 Z12 | 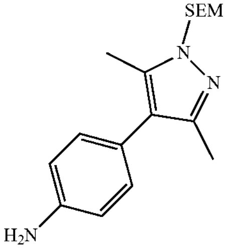 | 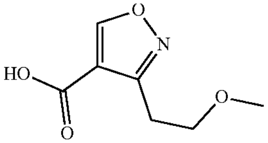 Z26 | 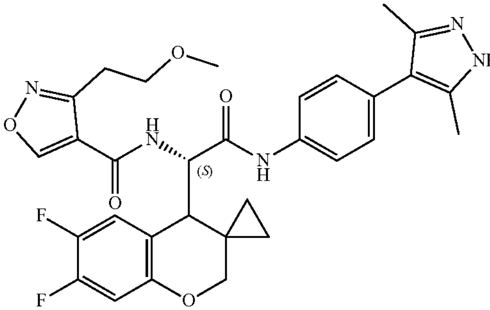 | $^1$H NMR (400 MHz, Methanol-$d_4$) δ 9.04 (s, 1H), 7.77-7.69 (m, 2H), 7.36-7.29 (m, 2H), 7.00 (dd, J = 11.2, 9.0 Hz, 1H), 6.71 (dd, J = 12.0, 7.0 Hz, 1H), 5.13 (dd, J = 9.2, 2.7 Hz, 1H), 4.90 (dd, J = 11.4, 1.9 Hz, 1H), 3.56 (t, J = |

-continued

| Compound | General route | BB-amino acid | BB-amine | BB-acid | Structural formula | $^1$HNMR and/or LCMS: |
|---|---|---|---|---|---|---|
| | | | | | | 6.5 Hz, 2H), 3.38 (dd, J = 11.4, 1.7 Hz, 1H), 3.26 (s, 3H), 3.02 (t, J = 6.5 Hz, 2H), 2.53 (d, J = 9.1 Hz, 1H), 2.31 (s, 6H), 1.01-0.91 (m, 1H), 0.72-0.57 (m, 2H). (ESI)m/z = 592 $(M + 1)^+$ |

Preparation of a part of compounds in the above table is described below.

Example 43 Preparation of Compound 43

A preparation of compound 43 is shown as follows:

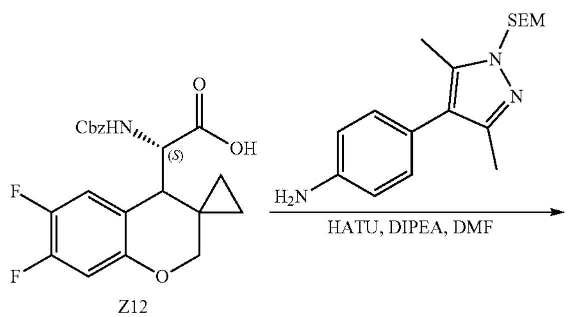

Z12

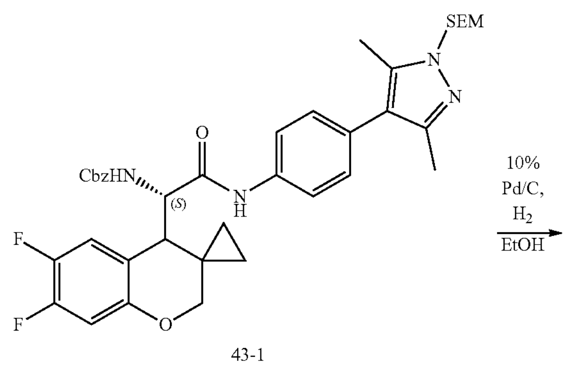

43-1

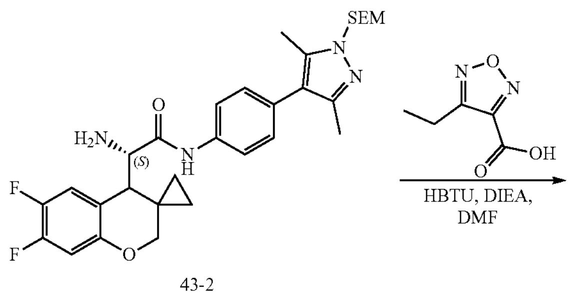

43-2

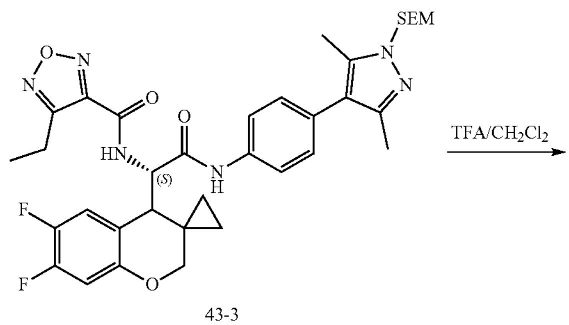

43-3

-continued

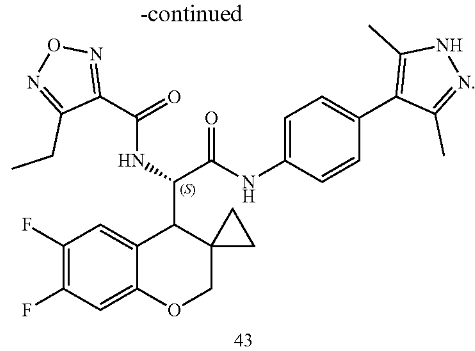

43

(S1) Preparation of Intermediate 43-1

The intermediate Z12 (10.0 g, 24.81 mmol) and DMF (100 mL) were successively added into a 250 mL single-necked flask. HATU (12.26 g, 32.26 mmol) and DIPEA (9.6 g, 74.44 mmol, 13.2 mL) were successively added into the 250 mL single-necked flask under stirring and ice bath. The reaction mixture was reacted under stirring and ice bath for 10 min, then added with 8.65 g (27.30 mmol) 4-(3,5-dimethyl-1-{(2-(trimethylsilyl)ethoxy)methyl}-1H-pyrazolyl)aniline, and heated to room temperature for reaction under stirring for 1 h. After the reaction was confirmed by LC-MS to be complete, the reaction mixture was added 200 mL of ethyl acetate, and washed with a saturated salt solution (200 mL×2) to collect an organic phase. The organic phase was dried with anhydrous sodium sulfate, filtered, and subjected to vacuum concentration to dry and column chromatography for purification to obtain 10.7 g (15.24 mmol) of intermediate 43-1 (yield: 61.4%). MS m/z: 703 $(M+1)^+$.

(S2) Preparation of Intermediate 43-2

The intermediate 43-1 (10.7 g, 15.24 mmol) and EtOH (150 mL) were successively added into a 500 mL single-necked flask. 3.1 g Pd/C (w/w 30%) were added into the 500 mL single-necked flask under a nitrogen atmosphere. The reaction mixture was subjected to hydrogen replacement 3 times under stirring, followed by reaction at room temperature under stirring and a hydrogen atmosphere for 3 h. The reaction mixture was filtered with diatomite by Brønsted funnel, and washed with ethanol. The filtrate was combined, and subjected to vacuum concentration to dry to obtain 8.3 g (14.61 mmol) of intermediate 43-2 (yield: 96%), MS m/z: 569 $(M+1)^+$.

(S3) Preparation of Intermediate 43-3

The intermediate 43-2 (8.0 g, 14.08 mmol), 4-ethyl-1,2,5-oxadiazole-3-carboxylic acid (2.87 g, 20.21 mmol) and DMF (70 mL) were successively added into a 250 mL single-necked flask. HBTU (6.9 g, 18.21 mmol) and DIPEA (5.45 g, 42.25 mmol, 7.5 mL) were successively added into the 250 mL single-necked flask under stirring and ice bath. The reaction mixture was stirred to react under ice bath for 10 min, and heated to room temperature to react under stirring for 1 h. After the reaction was confirmed by LC-MS to be complete, the reaction mixture was added with 180 mL of ethyl acetate, and washed with a saturated salt solution (180 mL×2) to collect an organic phase. The organic phase was dried with anhydrous sodium sulfate, filtered, and subjected to vacuum concentration to dry and column chromatography for purification, so as to obtain 7.5 g (10.59 mmol) of intermediate 43-3 (yield: 77%). MS m/z: 693 $(M+1)^+$.

(S4) Preparation of Compound 43

The intermediate 43-3 (7.2 g, 10.4 mmol) and $CH_2Cl_2$ (25 mL) were successively added into a 250 mL single-necked flask. 25 mL of TFA were added into the 250 mL single-necked flask under stirring and ice bath. The reaction mixture was heated to room temperature to react under stirring for 3 h. After the reaction was confirmed by LC-MS to be complete, the reaction mixture was subjected to vacuum concentration to dry, reversed-phase MPLC for purification ($CH_3CN/H_2O$, 0.05% TFA), concentration and vacuum freeze drying to obtain 4.6 g (8.19 mmol) of compound 43 (yield: 79%). MS m/z: 563 $(M+1)^+$.

$^1$H NMR (400 MHz, Methanol-d4) δ 7.77-7.69 (m, 2H), 7.37-7.29 (m, 2H), 7.07 (dd, J=11.2, 9.0 Hz, 1H), 6.69 (dd, J=11.9, 7.1 Hz, 1H), 5.15 (d, J=9.9 Hz, 1H), 4.94 (dd, J=11.5, 2.0 Hz, 1H), 3.39 (dd, J=11.5, 1.7 Hz, 1H), 2.83 (q, J=7.5 Hz, 2H), 2.63-2.55 (m, 1H), 2.32 (s, 6H), 1.20 (t, J=7.5 Hz, 3H), 0.94 (m, 1H), 0.65 (m, 2H), 0.44 (m, 1H).

Example 47 Preparation of Compound 47

A preparation of compound 47 is shown as follows:

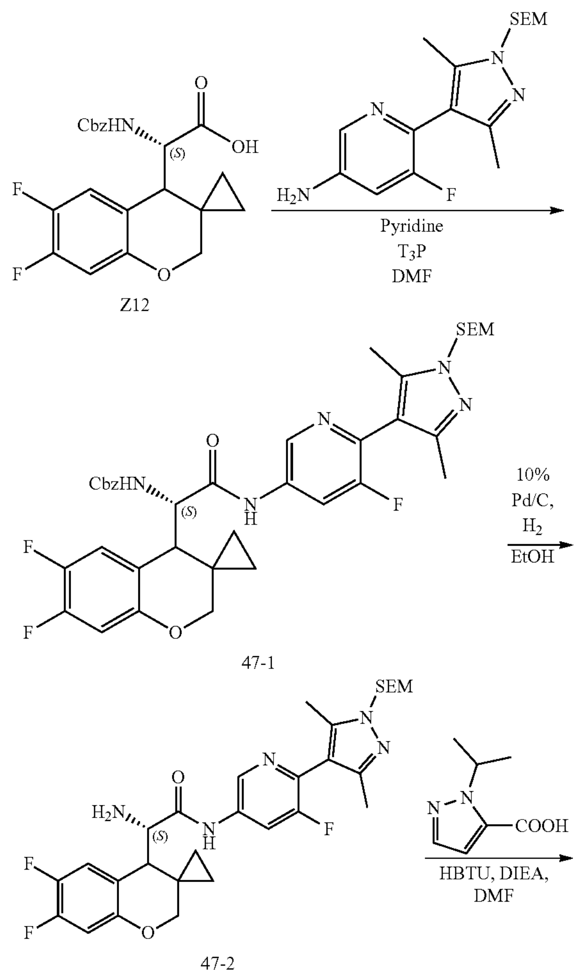

Z12

47-1

47-2

-continued

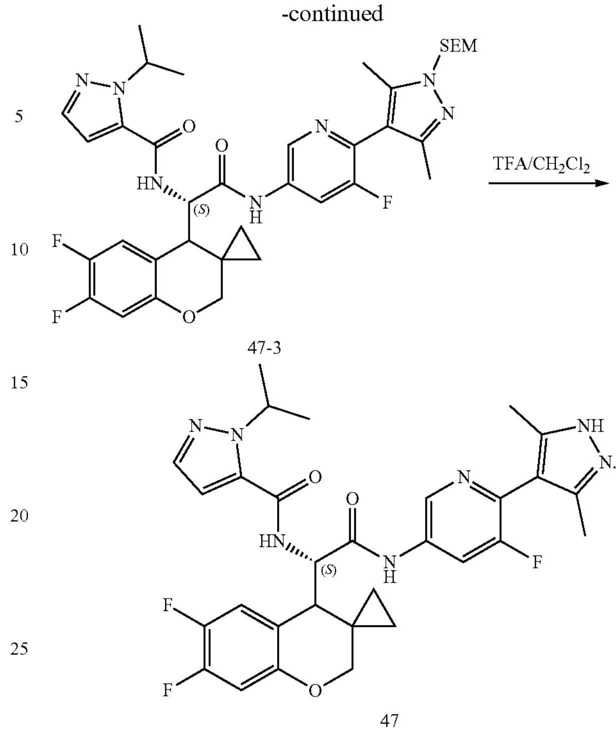

47-3

47

(S1) Preparation of Intermediate 47-1

The intermediate Z12 (10.0 g, 24.81 mmol) and DMF (100 mL) were successively added into a 250 mL single-necked flask. $T_3P$ (47.33 g, 148.86 mmol) and pyridine (19.60 g, 248.1 mmol, 20.0 ml) under stirring and ice bath. The reaction mixture was reacted under stirring and ice bath for 10 min, then added with the intermediate Z11 (10.0 g, 29.77 mmol), and heated to 60° C. for reaction under stirring for 3 h. After the reaction was confirmed by LC-MS to be complete, the reaction mixture was added with 200 mL of ethyl acetate, and washed with a saturated salt solution (200 mL×2) to collect an organic phase. The organic phase was dried with anhydrous sodium sulfate, filtered, and subjected to vacuum concentration to dry and column chromatography for purification, so as to obtain 15.6 (21.64 mmol) of intermediate 47-1 (yield: 87.15%). MS m/z: 722 $(M+1)^+$.

(S2) Preparation of Intermediate 47-2

The intermediate 47-1 (15.6 g, 21.63 mmol) and EtOH (150 mL) were successively added into a 500 mL single-necked flask. 4.68 g of 10% Pd/C (w/w 30%) were added into the 500 mL single-necked flask under a nitrogen atmosphere. The reaction mixture was subjected to hydrogen replacement three times under stirring. Then, the reaction mixture was reacted at room temperature under stirring and hydrogen atmosphere for 3 h, filtered with diatomite by Brønsted funnel, and washed with ethanol. The filtrate was combined, and subjected to vacuum concentration to dry to obtain 9.28 g (15.81 mmol) of intermediate 47-2 (yield: 73.09%), MS m/z: 588 $(M+1)^+$.

(S3) Preparation of Intermediate 47-3

The intermediate 47-2 (5.0 g, 8.52 mmol), 2-isopropylpyrazole-3-carboxylic acid (1.57 g, 10.22 mmol) and DMF (70 mL) were successively added into a 250 mL single-necked flask. HBTU (4.2 g, 11.08 mmol) and DIPEA (4.4 g, 34.08 mmol, 5.6 mL) were successively added into the 250 mL single-necked flask under stirring and ice bath. The reaction mixture was stirred to react under ice bath for 10 min, and heated to room temperature to react under stirring for 1 h. After the reaction was confirmed by LC-MS to be complete, the reaction mixture was added with 180 mL of ethyl acetate, and washed with a saturated salt solution (180 mL×2) to collect an organic phase. The organic phase was dried with anhydrous sodium sulfate, filtered, and subjected to vacuum concentration to dry and column chromatography for purification, so as to obtain 5.08 g (7.03 mmol) of intermediate 47-3 (yield: 82.51%). MS m/z: 724 $(M+1)^+$.

(S4) Preparation of Compound 47

The intermediate 47-3 (5.08 g, 7.03 mmol) and $CH_2Cl_2$ (25 mL) were successively added into a 250 mL single-necked flask. 25 mL of TFA were added into the 250 mL single-necked flask under stirring and ice bath. The reaction mixture was heated to room temperature to react under stirring for 3 h. After the reaction was confirmed by LC-MS to be complete, the reaction mixture was subjected to vacuum concentration to dry, reversed-phase MPLC for purification ($CH_3CN/H_2O$, 0.05% TFA), concentration and vacuum freeze drying to obtain 2.85 g (4.8 mmol) of compound 47 (yield: 68.28%). MS m/z: 594 $(M+1)^+$.

$^1H$ NMR (400 MHz, Methanol-$d_4$) δ 8.68 (d, J=2.2 Hz, 1H), 8.29 (dd, J=11.6, 2.1 Hz, 1H), 7.51 (d, J=2.1 Hz, 1H), 7.03 (dd, J=11.2, 9.0 Hz, 1H), 6.76-6.64 (m, 2H), 5.13 (d, J=10.0 Hz, 1H), 5.04 (p, J=6.7 Hz, 1H), 4.94 (dd, J=11.4, 1.9 Hz, 1H), 3.41 (dd, J=11.5, 1.7 Hz, 1H), 2.60 (d, 1H), 2.34-2.25 (m, 6H), 1.37 (d, J=6.6 Hz, 3H), 1.33 (d, J=6.7 Hz, 3H), 0.91-0.82 (m, 1H), 0.69-0.59 (m, 2H), 0.49-0.42 (m, 1H).

Example 105 Preparation of Compound 105

A preparation of compound 105 is illustrated as follows:

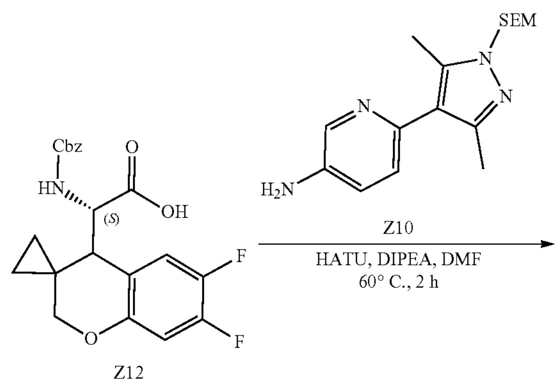

Z12 Z10

-continued

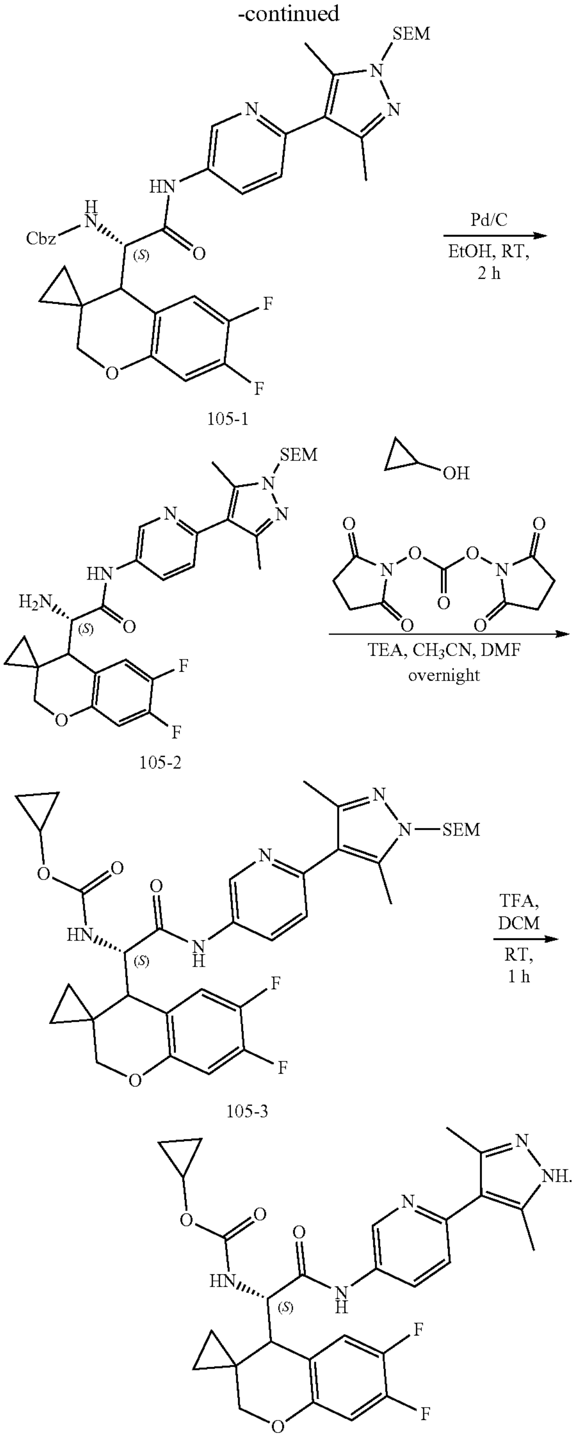

105-1 105-2 105-3 105

(S1)-(S2) Preparation of Intermediate 105-2

The intermediate 105-2 was prepared according to steps (S1)-(S2) of Example 28, in which in step (S1), the intermediate Z8 was replaced with the intermediate Z12, and 4-(3,5-dimethyl-1-{(2-(trimethylsilyl)ethoxy)methyl}-1H-pyrazolyl)aniline was replaced with the intermediate Z10. MS m/z: 570.0 $(M+1)^+$.

(S3) Preparation of Intermediate 105-3

10.66 mg of TEA (105.32 μmol, 14.69 μL) were added into a $CH_3CN$ (3 mL) solution of cyclopropanol (7.34 mg, 126.38 μmol) and N,N'-disuccinimidyl carbonate (32.37 mg, 126.38 μmol) at room temperature. The reaction mixture was reacted under stirring at room temperature for 1 h, and then added with the intermediate 105-2 (1 eq). After the reaction was complete, the reaction mixture was purified through MPLC (ACN/H2O, 0.05% TFA) to obtain 30 mg (45.89 μmol) of intermediate 105-3 (yield: 43.57%). MS m/z: 654 $(M+1)^+$.

(S4) Preparation of Compound 105

3.15 mg of TFA (27.67 μmol, 1.5 mL) were added into a $CH_2CO_2$ (1.5 mL) solution of the intermediate 105-3 (18.09 mg, 27.67 μmol) at 0° C. The reaction mixture was reacted under stirring at room temperature for 1 h. After the reaction was complete, the reaction mixture was concentrated to obtain a crude product. The crude product was purified through MPLC (ACN/H2O, 0.05% TFA) to obtain 7.2 mg (0.014 mmol) of compound 105 (yield: 41%). MS m/z: 524 $(M+1)^+$.

$^1$H NMR (400 MHz, Methanol-$d_4$) δ 9.11 (s, 1H), 8.35 (d, J=8.7 Hz, 1H), 7.72 (d, J=8.7 Hz, 1H), 7.03 (t, 1H), 6.70 (dd, J=12.0, 7.1 Hz, 1H), 4.80 (d, 1H), 4.63 (d, J=9.5 Hz, 1H), 3.85 (s, 1H), 3.35 (d, 1H), 2.43 (d, J=9.5 Hz, 1H), 2.39 (s, 6H), 0.88-0.81 (m, 1H), 0.68-0.57 (m, 5H), 0.55-0.47 (m, 1H), 0.46-0.39 (m, 1H).

Example 106 Preparation of Compound 106

A preparation of compound 106 is illustrated as follows:

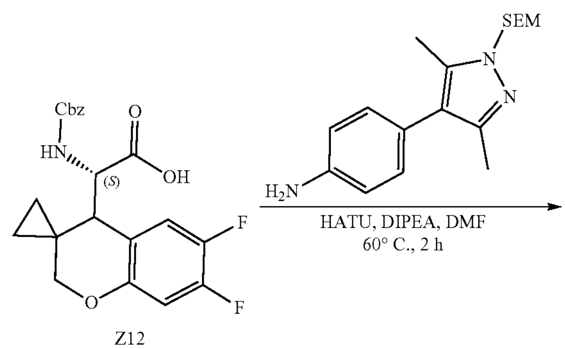

Z12

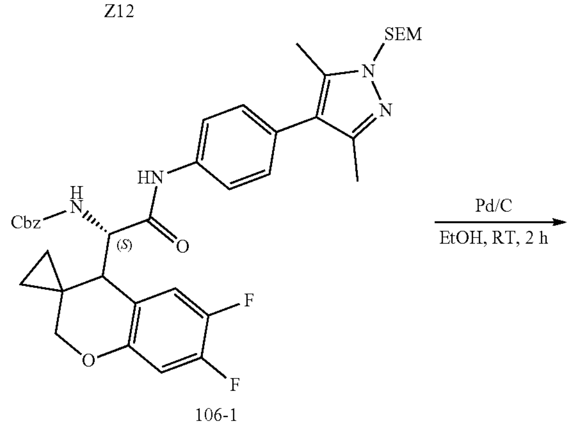

106-1

-continued

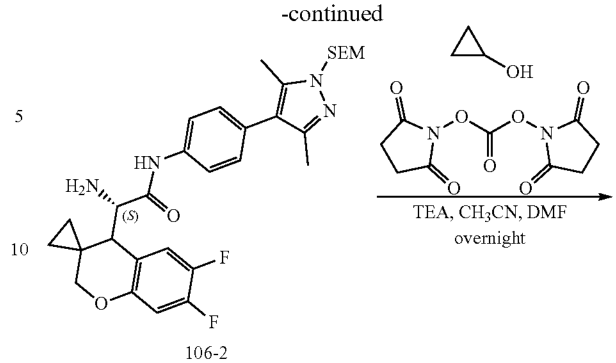

106-2

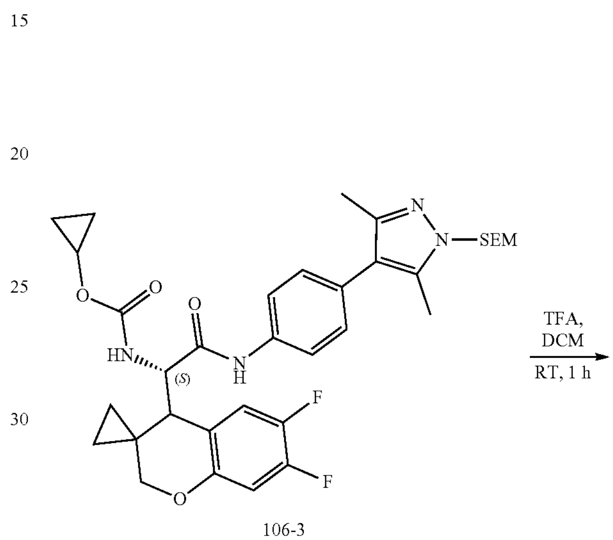

106-3

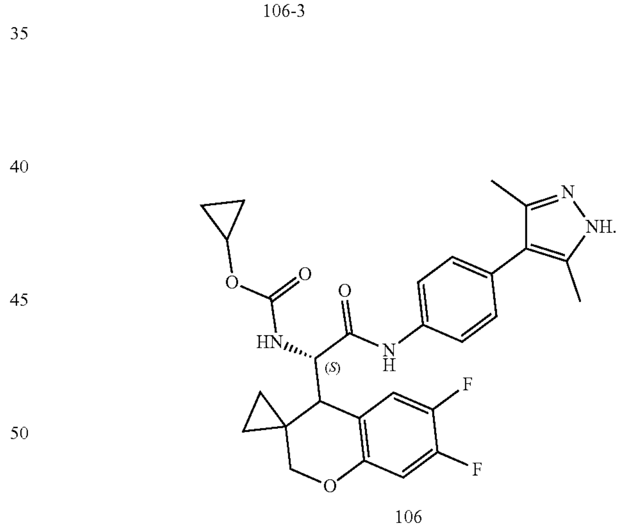

106

The preparation of compound 106 were performed according to steps (S1)-(S4) of the preparation of compound 105, in which in step (S1), the intermediate Z10 was replaced with 4-(3,5-dimethyl-1-{(2-(trimethylsilyl)ethoxy) methyl}-1H-pyrazolyl)aniline. MS m/z: 523 $(M+1)^+$.

$^1$H NMR (400 MHz, Methanol-$d_4$) δ 9.11 (s, 1H), 8.35 (d, J=8.7 Hz, 1H), 7.72 (d, J=8.7 Hz, 1H), 7.03 (t, 1H), 6.70 (dd, J=12.0, 7.1 Hz, 1H), 4.80 (d, 1H), 4.63 (d, J=9.5 Hz, 1H), 3.85 (s, 1H), 3.35 (d, 1H), 2.43 (d, J=9.5 Hz, 1H), 2.39 (s, 6H), 0.88-0.81 (m, 1H), 0.68-0.57 (m, 5H), 0.55-0.47 (m, 1H), 0.46-0.39 (m, 1H).

Example 107 Preparation of Compound 107

A preparation of compound 107 is illustrated as follows:

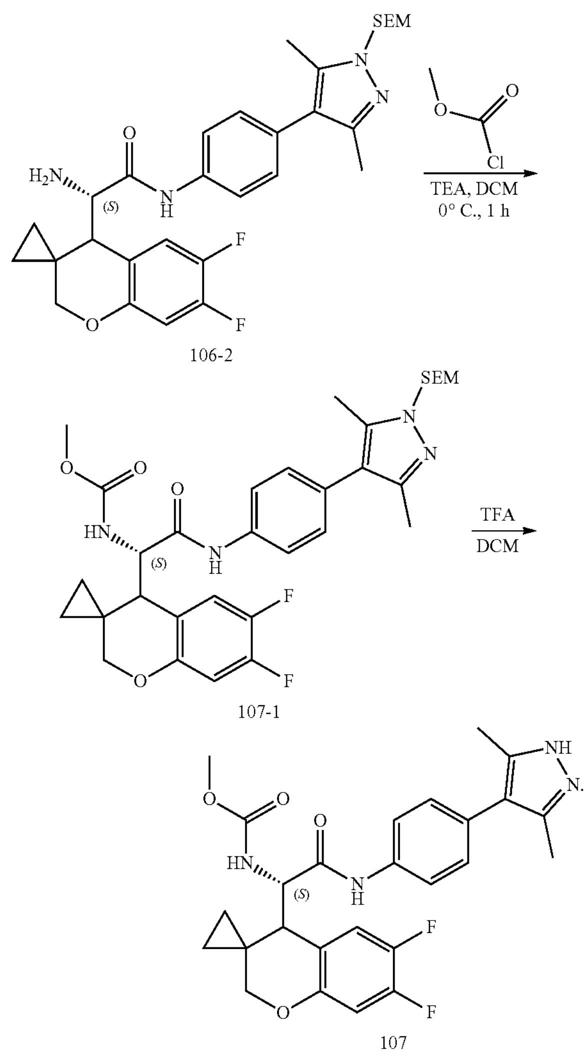

106-2

107-1

107

(S1) Preparation of Intermediate 107-1

17.79 mg of TEA (175.83 μmol, 24.52 μL) were added into a $CH_2Cl_2$ (3 mL) solution of the intermediate 106-2 (100 mg, 175.83 μmol) and methyl chloroformate (16.62 mg, 175.83 μmol) at room temperature. The reaction mixture was reacted under stirring at room temperature for 1 h. After the reaction was complete, the reaction mixture was purified through MPLC (ACN/$H_2O$, 0.05% TF) to obtain 35 mg (55.84 mol) of intermediate 107-1. MS m/z: 627.0 $(M+1)^+$.

(S2) Preparation of Compound 107

6.37 mg of TFA (55.84 μmol, 1.5 mL) were added into a DCM (1.5 mL) solution of the intermediate 107-1 (35 mg, 55.84 μmol) at 0° C. The reaction mixture was reacted under stirring at room temperature for 1 h. After the reaction was complete, the reaction mixture was subjected to vacuum concentration to obtain a crude product. The crude product was purified through MPLC (ACN/$H_2O$, 0.05% TFA) to obtain 14.5 mg (0.03 mmol) of compound 107 (yield: 42.6%). MS m/z: 467 $(M+1)^+$.

$^1H$ NMR (400 MHz, Methanol-$d_4$) δ 7.71 (d, J=8.4 Hz, 2H), 7.32 (d, J=8.3 Hz, 2H), 7.05 (dd, J=11.3, 9.0 Hz, 1H), 6.68 (dd, J=12.0, 7.1 Hz, 1H), 4.82 (d, 1H), 4.58 (d, J=9.4 Hz, 1H), 3.57 (s, 3H), 3.35 (d, 1H), 2.40 (d, J=9.4 Hz, 1H), 2.33 (s, 6H), 0.96-0.85 (m, 1H), 0.66-0.54 (m, 2H), 0.46-0.36 (m, 1H).

Example 108 Preparation of Compound 108

A preparation of compound 108 is illustrated as follows:

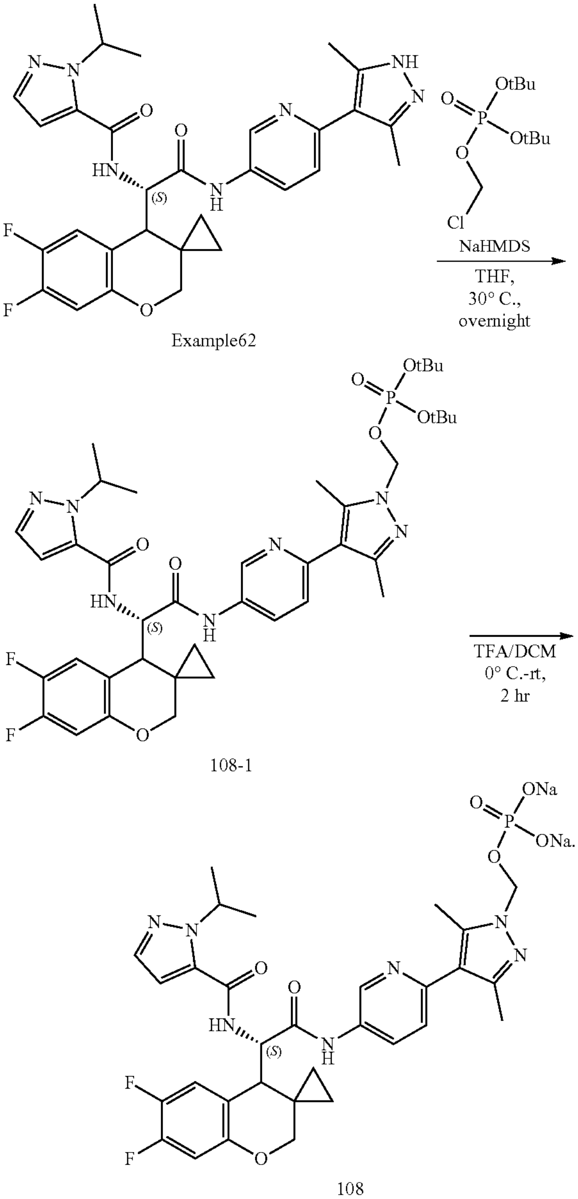

Example62

108-1

108

(S1) Preparation of Intermediate 108-1

A 1 mol/L THE solution (1.30 mmol, 1.3 mL) of sodium hexamethyldisilazide (NaHMDS) (5 equivalents) was added into an anhydrous THE (2 mL) solution of the compound 62

(150 mg, 0.26 mmol) under ice bath and nitrogen atmosphere. The reaction mixture was reacted under stirring at room temperature for 1 h, then added with 202 mg (0.78 mmol) of di-tert butyl (chloromethyl) phosphate, and stirring at room temperature overnight. The reaction mixture was subjected to vacuum concentration to obtain a crude product. The crude product was purified through MPLC (ACN/$H_2O$, 0.05% TFA) to obtain 85 mg (0.09 mmol) of intermediate 108-1 (yield: 36.8%). MS (alkaline process) m/z: 798 $(M+1)^+$.

(S2) Preparation of Compound 108

0.2 mL of TFA were added into an anhydrous DCM (1 mL) solution of the intermediate 108-1 (80 mg, 0.10 mmol) at room temperature under a nitrogen atmosphere. The reaction mixture was reacted under stirring and ice bath for 2 h. After the reaction was complete, the reaction mixture was subjected to vacuum concentration to obtain a crude product. The crude product was adjusted to pH=8 with 1N NaOH, slowly added with 10 mL of acetonitrile under stirring, and subjected to beating and filtration to obtain compound 108, that is, a pre-drug form of disodium phosphate salt of the compound 62 (3 mg, 3.5 μmol, yield: 3.5%). MS (alkaline process) m/z: 686 $(M+1)^+$.

$^1$H NMR (400 MHz, Methanol-$d_4$) δ 8.89 (d, J=2.5 Hz, 1H), 8.22 (dd, J=8.4, 2.6 Hz, 1H), 7.52-7.41 (m, 2H), 7.03 (dd, J=11.0, 9.1 Hz, 1H), 6.74-6.65 (m, 2H), 5.78 (d, J=7.2 Hz, 2H), 5.15 (d, J=10.0 Hz, 1H), 5.03 (dt, J=13.3, 6.7 Hz, 1H), 4.96 (d, J=11.2 Hz, 1H), 3.41 (d, J=11.4 Hz, 1H), 2.59 (d, J=10.0 Hz, 1H), 2.47 (s, 3H), 2.28 (s, 3H), 1.34 (dd, J=17.1, 6.7 Hz, 6H), 0.92-0.85 (m, 1H), 0.71-0.57 (m, 2H), 0.48-0.43 (m, 1H).

Example 109 Preparation of Compound 109

A preparation of compound 109 is shown as follows:

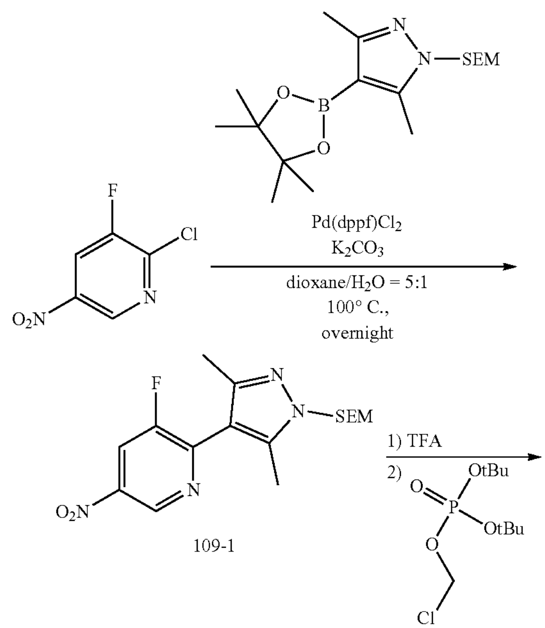

109-1

-continued

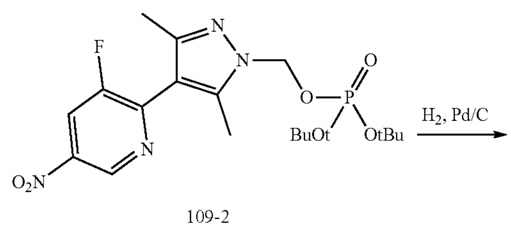

109-2

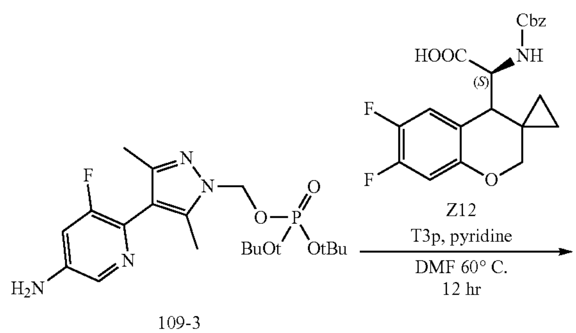

109-3

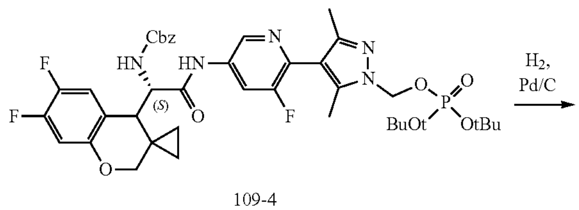

109-4

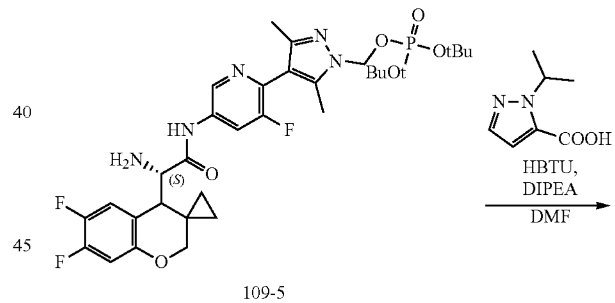

109-5

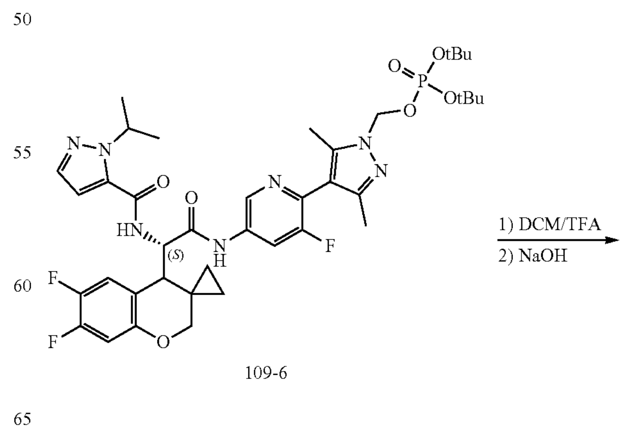

109-6

-continued

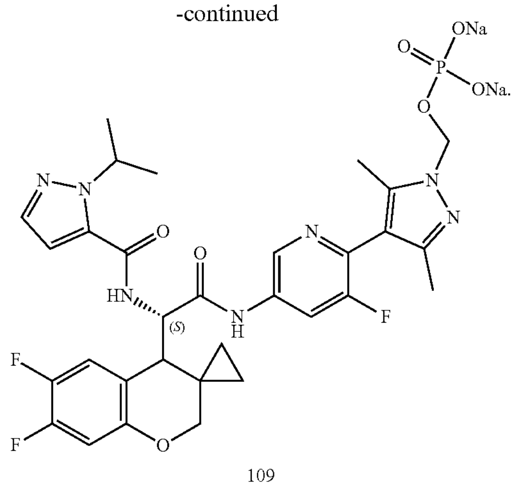

109

(S1) Preparation of Intermediate 109-1

19 g (107 mmol) of 2-chloro-3-fluoro-5-nitropyridine were dissolved in 0.85 L of 1,4-dioxane. The reaction mixture was successively added with N-SEM-dimethylpyrazole borate (49.3 g, 140 mmol) and 170 mL of an aqueous solution of potassium carbonate (29.7 g, 215 mmol), subjected with nitrogen bubbling under ultrasound for 20 min, and added with $Pd(dppf)Cl_2$ (3.93 g, 5.38 mmol) under a nitrogen flow. The reaction mixture was heated to 100° C. for reaction under stirring for 2 h. After the reaction was complete, the reaction mixture was concentrated, and extracted with ethyl acetate (500 mL×3) to collect an organic phase. The organic phase was washed with saturated ammonium chloride and salt water, dried with anhydrous sodium sulfate, and filtered to collect a filtrate. The filtrate was concentrated to obtain a crude product. The crude product was subjected to column chromatography for purification (petroleum ether:ethyl acetate=3:1) to obtain 33 g of intermediate 109-1 (yield: 84%). MS m/z: 367 $(M+1)^+$.

(S2) Preparation of Intermediate 109-2

27 g (74 mmol) of the intermediate 109-1 were dissolved in 70 mL of dichloromethane. The reaction mixture was added with 70 mL of TFA under ice bath and then stirred for 2 h. The first reaction mixture was subjected to vacuum concentration to dry, added with small amount of toluene, and subjected to vacuum concentration to dry again to obtain 22 g of a first crude product. The first crude product was dissolved in 80 mL of water, adjusted to pH=8 with 1N NaOH, and extracted with DCM (100 mL×2) to collect a first organic phase. The first organic phase was washed with washed with saturated ammonium chloride and salt water, dried with anhydrous sodium sulfate, and filtered to collect a filtrate. The filtrate was concentrated to obtain a second crude product. A 2 mol/L THE solution (42 mmol, 21 mL) of NaHMDS (2 equivalents) was added into an anhydrous THE (140 mL) solution of the second crude product (5 g, content at 100%, 21 mmol) under ice bath and nitrogen atmosphere, so as to obtain a second reaction mixture. The second reaction mixture was reacted under stirring at room temperature for 1 h, added with di-tert butyl (chloromethyl) phosphate (42 mmol, 11 g), and then reacted under stirring at room temperature overnight. The second reaction mixture was quenched by pouring into an ice-saturated aqueous ammonium chloride solution, and extracted with dichloromethane to collect a second organic phase. The second organic phase was concentrated and purified by column chromatography on silica gel (petroleum ether:ethyl acetate=(10-1):1) after triethylamine alkalization to obtain 4.8 g (10.5 mmol) of an yellow oil-like substance as intermediate 109-2 (yield: 50%), MS (alkaline process) m/z: 459 $(M+1)^+$.

(S3) Preparation of Intermediate 109-3

4.8 g (10.5 mmol) of intermediate 109-2 were dissolved in 100 mL of methanol. After nitrogen replacement several times, the reaction mixture was added with 0.96 g of 10% Pd/C, followed by hydrogen replacement several times. The reaction mixture was reacted under stirring and hydrogen atmosphere at room temperature for 2 h. After the reaction was complete, the reaction mixture was filtered through diatomite. The filtrate was concentrated to dry, and purified by column chromatography on silica gel after triethylamine alkalization to obtain 4.23 g (10 mmol) of intermediate 109-3 (yield: 94%). MS (alkaline process) m/z: 429 $(M+1)^+$.

(S4) Preparation of Intermediate 109-4

500 mg (1.24 mmol) of the intermediate Z12 were dissolved in 15 mL of DMF. The solution was successively added with T3P (2.37 g, 7.44 mmol) and pyridine (980 mg, 12.4 mmol) and stirred, followed by addition of the intermediate 109-3 (637 mg, 1.49 mmol) and reaction under stirring for 2 h. After the reaction was complete, the reaction mixture was concentrated to dry to obtain a crude product. The crude product was purified by column chromatography on silica gel (petroleum ether:ethyl acetate=(3-2):(1-3)) after triethylamine alkalization to obtain 449 mg (0.55 mmol) of yellow intermediate 109-4 (yield: 44.5%). MS (alkaline process) m/z: 814 $(M+1)^+$.

(S5) Preparation of Intermediate 109-5

449 mg (0.55 mmol) of the intermediate 109-4 were dissolved in 10 mL of methanol. After nitrogen replacement several times, the reaction mixture was added with 70 mg of 10% Pd/C, followed by hydrogen replacement several times. The reaction mixture was reacted under stirring and hydrogen atmosphere at room temperature for 3 h. After the reaction was complete, the reaction mixture was filtered through diatomite. The filtrate was concentrated to dry to obtain 337 mg (0.50 mmol) of intermediate 109-5 (yield: 91%). MS (alkaline process) m/z: 680 $(M+1)^+$. The intermediate 109-5 required no purification for the next step.

(S6) Preparation of Intermediate 109-6

The preparation of intermediate 109-6 was performed according to the preparation of the intermediate 1-3 in Example 1, in which the intermediate 109-5 (168 mg, 0.25 mmol) and 2-isopropylpyrazole-3-carboxylic acid were reacted to obtain a crude product, and the crude product was purified by column chromatography on silica gel (petroleum ether:ethyl acetate=1:(1-10)) after triethylamine alkalization to obtain 97 mg (0.12 mmol) of yellow intermediate 109-6 (yield: 48%). MS (alkaline process) m/z: 816 $(M+1)^+$.

(S7) Preparation of Compound 109

The preparation of compound 109 was performed according to the preparation of compound 108 in Example 108, in which 97 mg (0.12 mmol) of the intermediate 109-6 was de-tert-butylated by TFA, adjusted to pH=8 with 1N NaOH, concentrated, purified with medium pressure chromatography purification system (C-18 column, 1% $NH_4HCO_3$-acetonitrile system: (100-80):(0-20)), and subjected to vacuum freeze drying to obtain 44 mg (0.06 mmol) of the compound 109 (yield: 49%). MS (alkaline process) m/z: 704 $(M+1)^+$.

$^1$H NMR (400 MHz, Methanol-$d_4$) δ 8.66 (dd, J=2.1, 1.0 Hz, 1H), 8.26 (dd, J=11.5, 2.1 Hz, 1H), 7.50 (d, J=2.0 Hz, 1H), 7.04 (dd, J=11.2, 9.0 Hz, 1H), 6.75-6.65 (m, 2H), 5.78 (d, J=6.7 Hz, 2H), 5.15 (d, J=10.0 Hz, 1H), 5.11-4.99 (m, 1H), 4.95 (dd, J=11.5, 2.0 Hz, 1H), 3.41 (dd, J=11.5, 1.7 Hz, 1H), 2.64-2.56 (m, 1H), 2.37 (d, J=1.2 Hz, 3H), 2.18 (d, J=1.0 Hz, 3H), 1.34 (dd, J=18.2, 6.7 Hz, 6H), 0.92-0.82 (m, 1H), 0.72-0.57 (m, 2H), 0.50-0.41 (m, 1H).

Example 110 Preparation of Compound 110

A preparation of compound 110 is illustrated as follows:

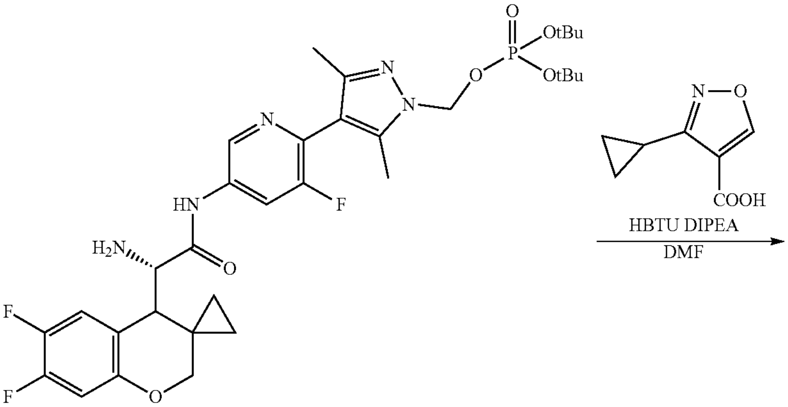

109-5

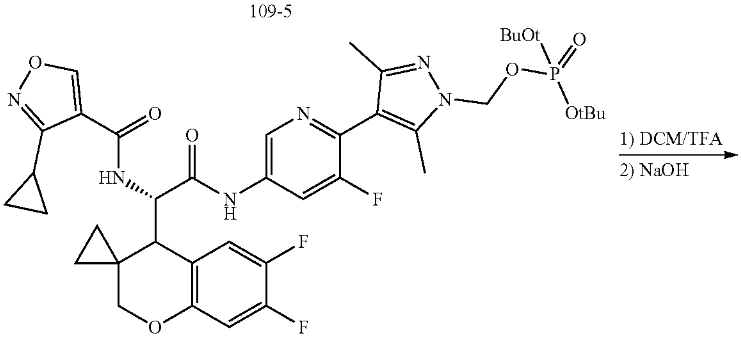

110-1

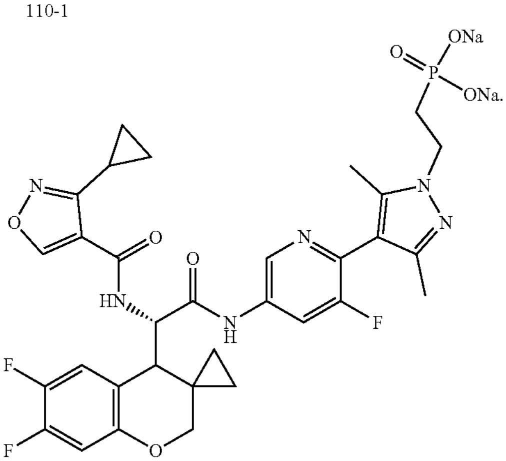

110

The preparation of compound 110 was performed according to the preparation of compound 109 in Example 109, in which the intermediate 109-6 was taken as a raw material, which was subjected to condensation with 3-cyclopropyl-1,2-oxazole-4-carboxylic acid, deprotection with TFA, alkalization with 1N NaOH and purification to obtain the compound 110. MS (alkaline process) m/z: 703 $(M+1)^+$.

$^1$H NMR (400 MHz, Methanol-$d_4$) δ 8.97 (s, 1H), 8.65 (dd, J=2.1, 1.0 Hz, 1H), 8.24 (dd, J=11.5, 2.1 Hz, 1H), 7.00 (dd, J=11.2, 9.0 Hz, 1H), 6.69 (dd, J=12.0, 7.1 Hz, 1H), 5.77

(d, J=6.6 Hz, 2H), 5.17 (d, J=9.6 Hz, 1H), 4.92 (dd, J=11.5, 2.0 Hz, 1H), 3.40 (dd, J=11.6, 1.7 Hz, 1H), 2.57 (d, J=9.6 Hz, 1H), 2.37 (d, J=1.2 Hz, 3H), 2.18 (d, J=1.1 Hz, 3H), 2.15-2.04 (m, 1H), 1.01-0.80 (m, 5H), 0.78-0.56 (m, 2H), 0.45-0.48 (m, 1H).

In order to illustrate an absolute configuration of the compounds of the present disclosure, a crystal of the intermediate Z12 was cultured. According to a result of single-crystal X-ray diffraction, the absolute configurations of two adjacent chiral centers of the intermediate Z12 were S configuration. A method of the single-crystal X-ray diffraction was as follows. Detection instrument was D8 Venture. Instrument model was D8 Venture. Instrument parameters were as follows: light source: Cu target; and X-rays: Cu-K (=1.54178 Å). A detector was a complementary metal-oxide-semiconductor (CMOS) plane detector; resolution was 0.80 Å; a voltage was 50 kV, a current was 1.2 mA; exposure time was 10 s; a distance between the plane detector to sample was 40 mm; and a test temperature was 170 K. A structure analysis and refinement process was as follows: diffraction data was subjected to integration reduction using a SAINT program, followed by empirical absorption correction using a SADABS program; single crystal structure was analyzed by a direct method, and refined by the least square method. A hydrogen atom refinement process adopted isotropic computational treatment. A hydrogen atom on C—H was obtained by computational hydrogenation, and refined by a ride-on model. A Flack constant was −0.02 (4). A chirality of C9 and a chirality of C11 were S configuration. An ellipsoidal diagram of a molecular stereo structure of the intermediate Z12 was shown in FIG. 1.

To illustrate the beneficial effects of the present disclosure, the following Experimental Examples are provided.

Experimental Example 1 IL-17A Enzyme-Linked Immunosorbent Assay (ELISA)

The inhibition of receptor-ligand binding by human IL-17A (hIL-17A) inhibitors was detected by competitive ELISA. A 96-well plate was inoculated 0.2 μg/ml IL-17 (Sino Biological Inc. Cat #12047-H07B) for incubation at 37° C. for 30 min, 100 μL for per well. The 96-well plate was washed four times with phosphate buffered saline (PBS) containing Tween-20 (PBST, 0.05% Tween-20), 200 μL for per well each time. 200 μL of 5% skim milk were added into the 96-well plate for incubation on a shaker at 25° C. for 30 min. The 96-well plate was washed four times with PBST (0.05% Tween-20), and added with 89 μL of PBST and 1 μL of a compound to be measured (100×), in which a concentration the compound to be measured (100×) was 0.003 μM-30 μM. The mixture was mixed evenly and incubated at 25° C. for 10 min. The mixture was added with 10 μL of 16 nM IL-17R, followed by incubation at 25° C. for 30 min. After washing the 96-well plate 4 times, 100 μL of anti-Fc tag horseradish peroxidase (HRP) coupled antibody were added for incubation on a shaker at 25° C. for 30 min. After washing the 96-well plate 4 times, 100 μL of 3,3',5,5'-tetramethylbenzidine (TMB) substrate solution were added to the 96-well plate for incubation away from light at 25° C. After addition of 20% HCl, an absorbance was measure by a microplate reader at 450 nm.

The compounds prepared according to the above method were assayed for human IL-17A inhibitory activity.

Experimental Example 2 Inhibitory of Compounds on hIL-17A-Induced Chemokine GROα/CXCL1 Production in HT-29 Cell Human colorectal adenocarcinoma cell HT-29 was inoculated to a 96-well plate ($5\times10^4$ for per well), and incubated at 37° C. on an incubator overnight. A mixture of 30 ng/mL hIL-17A protein (R&D, #317-ILB) with gradient concentrations of IL-17A small molecule inhibitors or with 0.3 μg/mL positive control IL-17A antibody (R&D, #AF-317-NA) was incubated for 1 h at 37° C., and added into the 96-well plate to incubated with HT-29 at 37° C. for 48 h. A level of GROα in a cell culture supernatant was then detected using an ELISA kit for GROα (Cisbio, #62HCXC1peg).

Inhibitory effect of the compound prepared in Examples on hIL-17A-induced chemokine GROα/CXCL1 production in HT-29 cell was tested according to the methods of Experimental Examples 1 and 2. Table 1 showed ELISA $IC_{50}$ of each compound and inhibition of the $IC_{50}$ inhibitory activity of GROα/CXCL1 in HT-29 cells. "-" indicated not tested. According to the results, the compounds provided herein have good human IL-17A inhibitory activity and can be effectively used in the treatment of diseases associated with abnormal hIL-17A activity.

TABLE 1

Inhibitory activity of compound in Examples on hIL-17A

| Example | ELISA $IC_{50}$ (μmol) | HT-29 $IC_{50}$ (μmol) | Example | ELISA $IC_{50}$ (μmol) | HT-29 $IC_{50}$ (μmol) | Example | ELISA $IC_{50}$ (μmol) | HT-29 $IC_{50}$ (μmol) | Example | ELISA $IC_{50}$ (μmol) | HT-29 $IC_{50}$ (μmol) |
|---|---|---|---|---|---|---|---|---|---|---|---|
| 1 | 0.018 | 0.404 | 2 | 0.041 | 0.196 | 3 | 0.040 | 0.213 | 4 | 0.050 | 0.050 |
| 5 | — | — | 6 | — | — | 9 | — | — | 10 | 0.098 | — |
| 13 | 0.031 | 0.391 | 14 | 0.059 | 0.206 | 15 | 0.048 | 0.071 | 16 | 0.043 | 0.055 |
| 17 | 0.036 | 0.068 | 18 | 0.164 | 0.332 | 19 | 0.190 | 2.052 | 20 | 0.061 | 0.878 |
| 21 | 0.066 | 0.506 | 22 | 0.085 | 1.025 | 23 | 0.098 | 1.051 | 24 | 0.053 | 0.030 |
| 25 | 0.056 | 0.194 | 26 | 0.070 | 0.267 | 27 | 0.119 | 0.672 | 28 | 0.110 | 0.083 |
| 29 | 0.152 | 0.378 | 30 | 0.065 | 0.229 | 31 | 0.072 | 0.872 | 32 | 0.075 | 0.351 |
| 33 | 0.219 | 0.092 | 34 | 0.120 | 0.063 | 35 | 0.311 | 0.085 | 36 | 0.144 | 0.058 |
| 37 | 0.230 | 0.034 | 38 | 0.276 | 0.506 | 39 | 0.111 | 0.856 | 40 | 0.186 | 0.115 |
| 41 | 0.079 | 0.227 | 42 | 0.040 | 0.070 | 43 | 0.055 | 0.057 | 44 | 0.122 | 0.336 |
| 45 | 0.125 | 0.050 | 46 | 0.095 | 0.122 | 47 | 0.088 | 0.172 | 48 | 0.135 | 0.184 |
| 49 | 0.146 | 0.146 | 50 | 0.081 | 0.569 | 51 | 0.155 | 0.313 | 52 | 0.402 | — |
| 53 | 0.554 | — | 54 | 0.136 | — | 55 | 0.065 | 0.228 | 56 | 0.139 | 0.355 |
| 57 | 0.112 | 0.346 | 58 | 0.054 | 0.109 | 59 | 0.222 | 1.485 | 60 | 0.193 | 0.279 |
| 61 | 0.339 | — | 62 | 0.151 | 0.177 | 63 | 0.156 | 0.605 | 64 | 0.154 | 0.335 |
| 65 | 0.222 | 0.212 | 66 | 7.126 | — | 67 | 0.577 | 0.557 | 68 | 0.503 | 1.943 |
| 69 | 0.288 | 0.941 | 70 | 0.201 | 0.112 | 71 | 0.507 | 0.986 | 72 | 0.343 | 1.806 |
| 73 | 0.294 | 0.795 | 74 | 0.413 | 0.609 | 75 | 5.003 | — | 76 | 0.270 | 1.049 |
| 77 | 0.320 | 1.011 | 78 | 0.985 | — | 79 | 32.52 | — | 80 | 0.406 | 0.762 |

TABLE 1-continued

| Inhibitory activity of compound in Examples on hIL-17A | | | | | | | | | | | |
|---|---|---|---|---|---|---|---|---|---|---|---|
| Example | ELISA $IC_{50}$ (μmol) | HT-29 $IC_{50}$ (μmol) | Example | ELISA $IC_{50}$ (μmol) | HT-29 $IC_{50}$ (μmol) | Example | ELISA $IC_{50}$ (μmol) | HT-29 $IC_{50}$ (μmol) | Example | ELISA $IC_{50}$ (μmol) | HT-29 $IC_{50}$ (μmol) |
| 81 | 2.056 | — | 82 | 2.025 | — | 83 | 2.016 | — | 84 | 9.805 | — |
| 85 | 0.133 | 1.219 | 86 | 0.179 | 0.718 | 87 | 0.165 | 0.332 | 88 | 0.100 | — |
| 89 | 0.119 | — | 90 | 0.144 | 0.188 | 91 | 0.067 | 1.082 | 92 | 0.187 | 9.646 |
| 93 | 0.193 | 0.055 | 94 | 0.572 | 0.695 | 95 | 0.094 | 0.457 | 96 | 0.125 | 0.134 |
| 97 | 0.165 | 0.221 | 98 | 0.222 | — | 99 | 0.096 | 0.213 | 100 | 0.189 | 0.563 |
| 101 | — | — | 102 | — | — | 103 | — | — | 104 | 0.116 | |
| 105 | 0.081 | 0.943 | 106 | 0.066 | 0.119 | 107 | 0.051 | 0.383 | | | |

Experimental Example 3 Experiment and Analysis of Reversibility of Compound Binding to hIL-17A Protein Through Surface Plasmon Resonance (SPR)

The binding of the compounds provided herein to the hIL-17A protein was tested using SPR, and analyzed using a Biacore 8K system. A positive compound was the compound of Example 32 in WO2020/127685A1. It was shown that compounds 24, 26, 43, 47 showed strong binding to hIL-17A and were much stronger than the positive compound. The results were shown in Table 2.

TABLE 2

| Binding experiment through SPR | | | |
|---|---|---|---|
| | Parameters | | |
| Example | ka (1/Ms) | kd (1/s) | KD (M) |
| The positive compound | 1.19E+04 | 1.80E−05 | 1.51E−09 |
| 24 | 1.24E+04 | 4.80E−08 | 3.88E−12 |
| 26 | 2.13E+04 | 1.98E−08 | 9.26E−13 |
| 43 | 1.42E+04 | 1.87E−08 | 1.32E−12 |
| 47 | 2.04E+04 | 3.44E−08 | 1.69E−12 |

Experimental Example 4 Verification of Reversibility of Binding of Compounds and Protein Through Enzyme-Linked Immunoassay (ELISA)

The reversibility of the binding of the compounds in Examples to hIL-17A and the binding time of the compound-protein complex were qualitatively and quantitatively analyzed by jump dilution assay. The positive compound was the compound of Example 32 in WO2020/127685 A1. 7 nM hIL-17RA were inoculated to a 96-well plate (100 μL for per well), and incubated at 37° C. for 30 min. A blank group was 100 μL of coating buffer solution. After 5 min incubation at 4° C., the 96-well plate was washed with PBST (0.05% Tween-20) 4 times, 200 μL for per well each time. The 96-well plate was added with 200 μL 3% BSA (PBST diluted) and closed on a shaker at 37° C. for 30 min. During closing, a concentration of hIL 17A was diluted to 0.4 uM with PBST, i.e. 400×1/3 EC50, and a concentration of the compound was diluted to 20× and 10×$IC_{50}$ (depending on the inhibition intensity of different compounds on hIL-17A and hIL-17RA binding, both positive and negative control wells were supplemented with equal amounts of DMSO, and the final concentration of DMSO in each well was ensured to be 2%). The configured hIL7A was mixed with an equal volume of compound in a 200 ul centrifuge tube to obtain a protein-compound mixture. The protein-compound mixture was subjected to pre-incubation at room temperature for 15 min. The protein-compound mixture, positive control group and negative control group were diluted 200×. After closing, the 96-well plate was washed 4 times, and added with dilution 100 μL for per well to incubate at 25° C. for 28, 24, 5, 2 and 0 h. After washing the plate 4 times, 100 μL of Streptavidin-HRP coupled antibody diluted with 1% BSA was added and then incubated for 30 min on a shaker at 25° C. After washing the plate 4 times, 100 μL of TMB substrate solution were added, and incubated away from light for 5-15 min at 25° C. (depending on the color of the reaction). After addition of 20% HCl, an absorbance was measure by a microplate reader at 450 nm. It was shown that compound 26, 43 and 47 were able to maintain binding to and inhibit the activity of hIL-17A protein for a long time and were significantly stronger than the positive compound. Results were shown in Table 3 and FIG. 2.

TABLE 3

| ELISA experiment | | |
|---|---|---|
| | 50% enzyme activity retention time (h) | |
| Example | Value on hIL-17A/RA (10X cpds) | Value on hIL-17A/RA (5X cpds) |
| The positive compound | –2 | <2 |
| 26 | 5 < T < 28 | 5 < T < 28 |
| 43 | >28 | >28 |
| 47 | >28 | –28 |

Experimental Example 5 Drug Metabolism Properties of Compounds in Rats, Mice and Dogs In order to investigate the drug metabolism property of the compounds provided herein in rats, a compound solution was given to 3 rats by intravenous injection/oral gavage at corresponding doses. After 5 min, 15 min, 30 min, 1 h, 2 h, 4 h, 8 h and 24 h administration, anticoagulated whole blood was collected from rats, and plasma was separated.

In order to investigate the drug metabolism property of the compounds provided herein in mice, a compound solution was given to 6 mice by intravenous injection/oral gavage at corresponding doses. Mice were divided into groups A and B for each administration, where anticoagulated whole blood was collected from group A at 5 min, 30 min, 2 h and 8 h after drug administration; and anticoagulated whole blood was collected from group B at 15 min, 1 h, 4 h and 24 h after drug administration. plasma was separated.

In order to investigate the drug metabolism property of the compounds provided herein in dogs, a compound solution was given to 2 groups of dogs (4 dogs (2 males+2 females) for each group) by intravenous injection/oral gavage at corresponding doses. After 55 min, 15 min, 30 min, 1 h, 2 h, 4 h, 8 h, 12 h, 24 h and 36 h administration, anticoagulated whole blood was collected from dogs, and plasma was separated.

Plasma concentrations of compounds were determined by standard curve calibration method using LC-MS. Using Winnolin 5.2 software, plasma concentration-time data were fitted to pharmacokinetic parameters, including elimination half-life (T½), area under the plasma pharmacokinetic curve at the sampling endpoint (AUClast), peak concentration (Cmax), apparent volume of distribution (Vz), total clearance ration (Cl), and absolute bioavailability (F %). Oral bioavailabilities F % of compounds in some Examples were shown in Table 4.

TABLE 4

Oral bioavailabilities F % of compounds in Examples

| Example | F % (mice) | F % (rat) | F % (dog) |
|---|---|---|---|
| 24 | 51 | 56 | 27 |
| 26 | 54 | 16 | — |
| 43 | 49 | 36 | 18 |
| 49 | 37 | 17 | 20 |
| 58 | 26 | 28 | 16 |
| 18 | 55 | 18 | 41 |

Figure 3A:
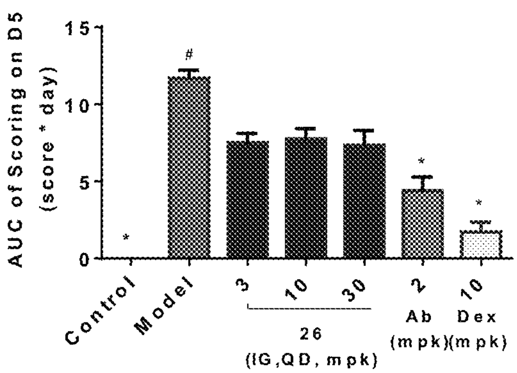
FIGS. 3A-3D show results of pharmacodynamic evaluation of the compound 26 in an imiquimod-induced psoriasis mouse model.
Figure 3B:
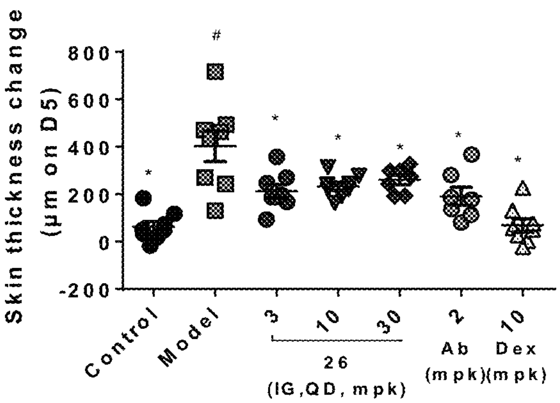

Experimental Example 6 Pharmacodynamic Test of Imiquimod Cream-Induced Psoriasis Model in Mice The backs of 0-week-old female C57BL/6N mice were shaved approximately 2.5×4 cm, and imiquimod (IMQ, Imiquimod) cream was applied continuously from day 1 to day 5 to establish a psoriasis model. The compound 26 provided herein (3, 10, 30 mg/kg) was given once daily by gavage to the mice, an IL-17A antibody solution (Ab, 2 mg/kg) was given by intraperitoneal injection every other day to the mice, or a dexamethasone solution (10 mg/kg) was given once daily by intraperitoneal injection to the mice. Based on an area under curve (AUC) of psoriasis area and severity index (PASI) scoring (FIG. 3A), different doses of compounds attenuated the level of IMQ-induced skin inflammation with effects similar to those of the IL-17A antibody. A skin thickness of mice was measured on the first day and fifth day to examine IMQ-induced skin thickening (FIG. 3B). It showed that each group and IL-17A antibody administration reversed the skin thickening caused by IMQ to varying degrees.

Figure 3C:
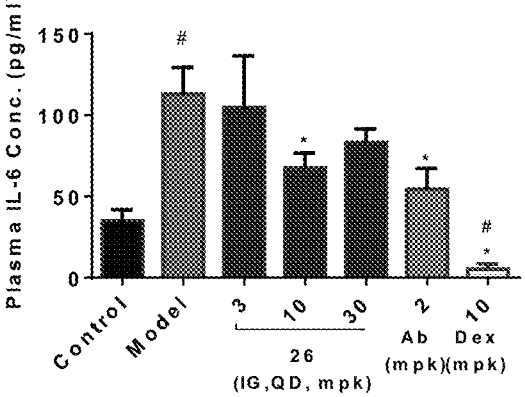
Figure 3D:
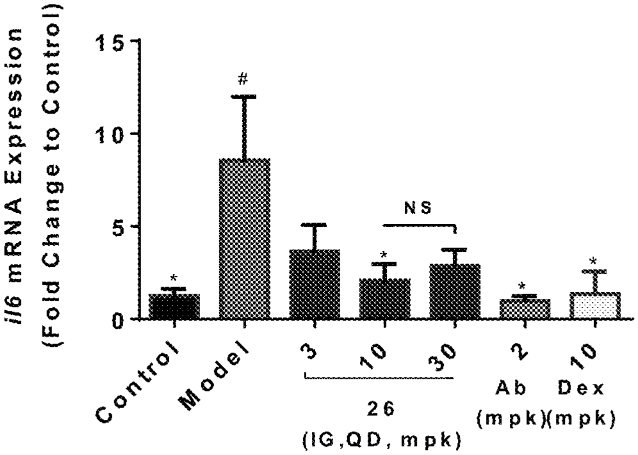
Figure 4A:
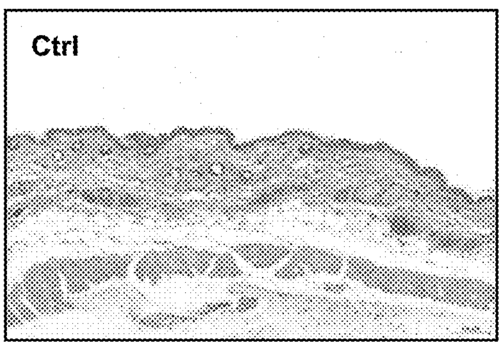
FIGS. 4A-4D show skin tissue sections of the imiquimod cream-induced psoriasis mice model, where 4A: control; 4B: compound 26; 4C: model; and 4D: antibody.
Figure 4B:
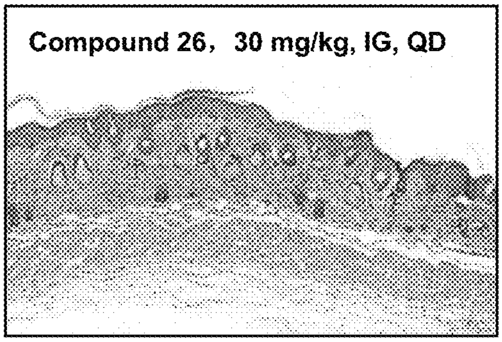
Figure 4C:
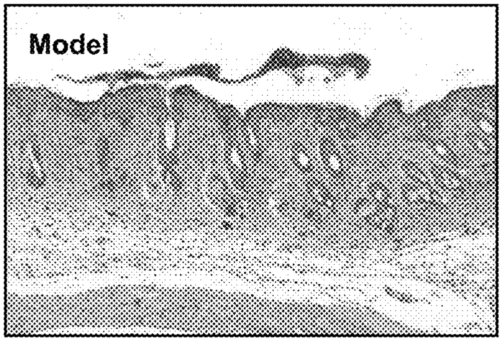
Figure 4D:
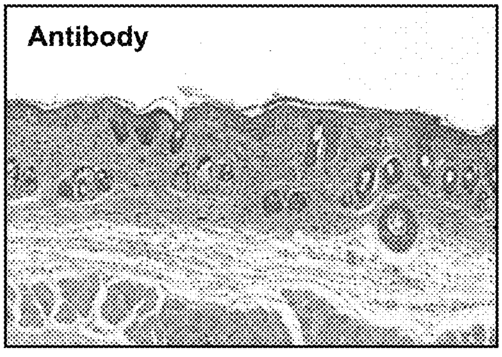

The skin of each group of mice was collected on the fifth day to detect IL6 mRNA levels by RT-qPCR (FIG. 3C). It was shown that the upregulation of IL6 expression levels showed dose-dependent reversion in each group. The plasma of mice in each group was collected on the fifth day to determine the level of IL-6 protein (FIG. 3D). It was shown that the increase of IL6 protein level in plasma was inhibited in a dose-dependent manner.

On the fifth day, back skin samples of mice were collected and fixed in 4% paraformaldehyde for HE staining to investigate a protective effect of compound 26 on skin pathological injury (FIGS. 4A-4D). According to HE staining results, the compound 26 with 30 mg/kg of administration was effective in inhibiting IMQ-induced skin inflammatory cell infiltration and damage.

Experimental Example 7 Pharmacodynamic Test of Encephalomyelitis Model in Mice An encephalomyelitis model was elicit using MOG protein in 10-week female C57BL/6 mice. Before modeling the encephalomyelitis model, the mice were administered with a compound solution by gavage (30 mg/kg) or intraperitoneal injection (3, 10, 30 mg/kg), or with an IL-17A antibody solution by intraperitoneal injection every three days (10 mg/kg at first time and second time, then 5 mg/kg). The control group and the model group were given blank solvent. The mice were scored according to a scoring system of the encephalomyelitis model every day, so as to draw a scoring curve.

On the $21^{st}$ day, brain samples and spinal cord samples of mice were collected and fixed in 4% paraformaldehyde, and HE staining was carried out to investigate the protective effect of the compound on the histopathological injury of brain and spinal cord.

In conclusion, the compound of formula I provided shows good IL-17A in vitro and in vivo inhibitory activity, and provides a new medicinal application for clinical treatment of diseases related to abnormal IL-17A activity.

What is claimed is:

1. A compound of formula (I), or a deuterated compound, a stereoisomer or a pharmacologically acceptable salt thereof:

(I)

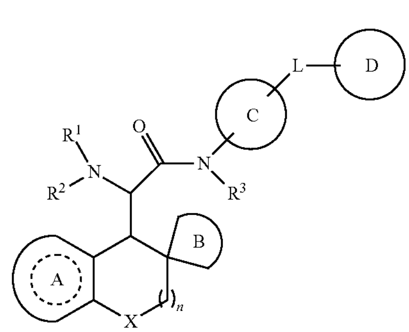

, wherein:

$R^1$ is selected from the group consisting of:

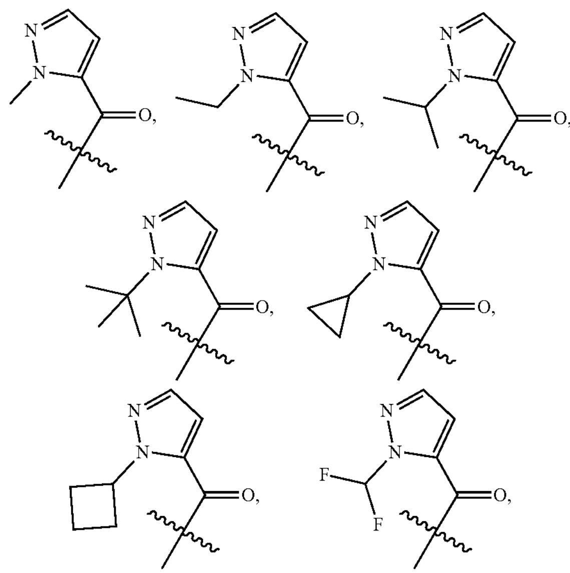

-continued
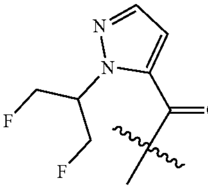, 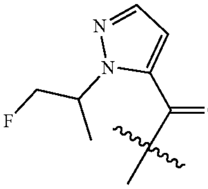, 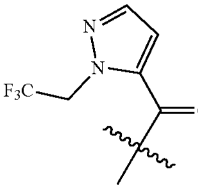, 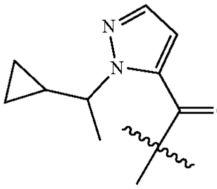, 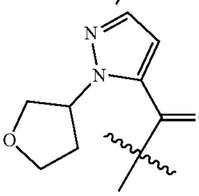, 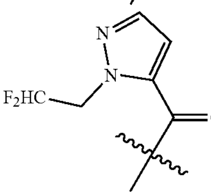, 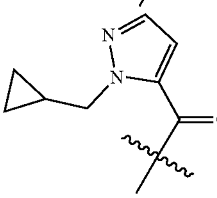, 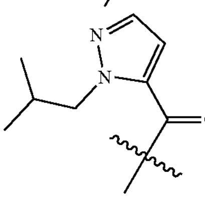, 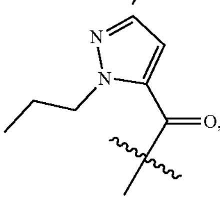, 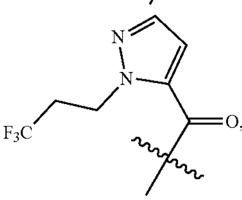, 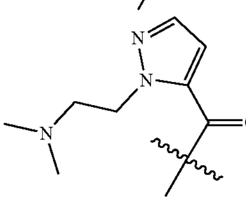, 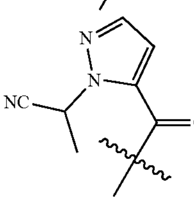, 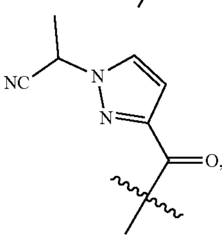, 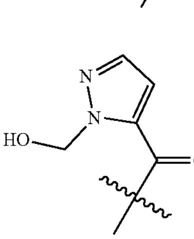, 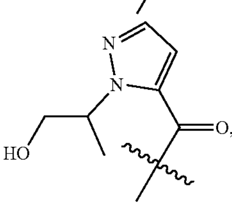, 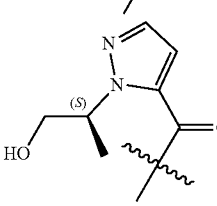, 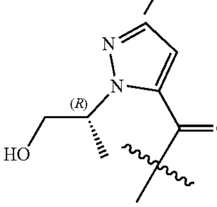, 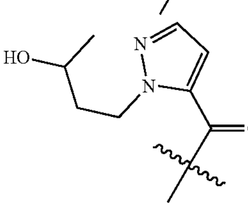,
-continued
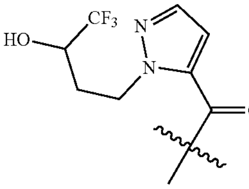, 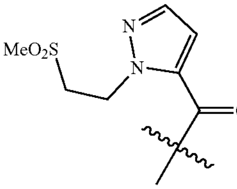, 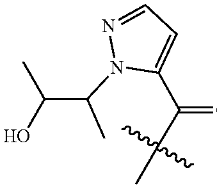, 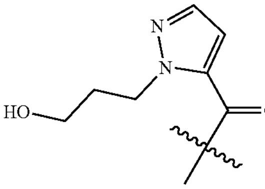, 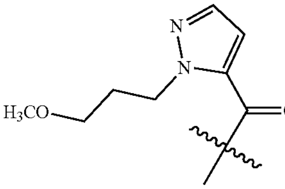, 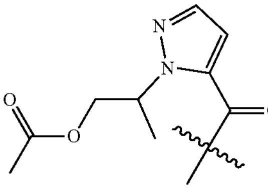, 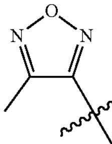, 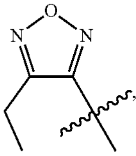, 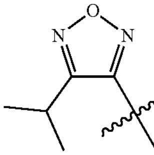, 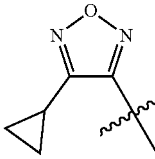, 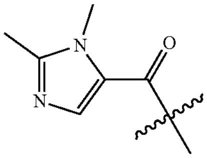, 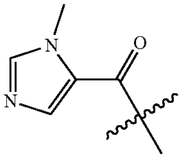, 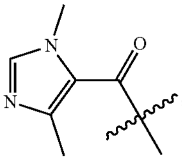, 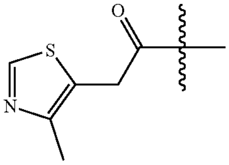, 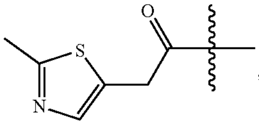, 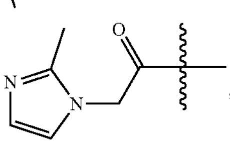, 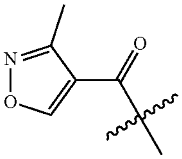, 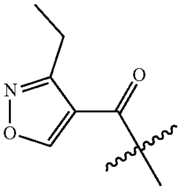, -continued
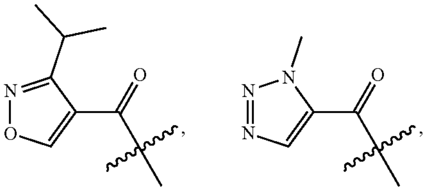
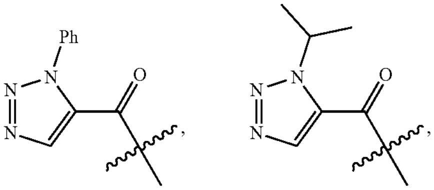
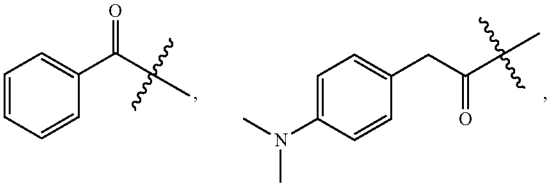
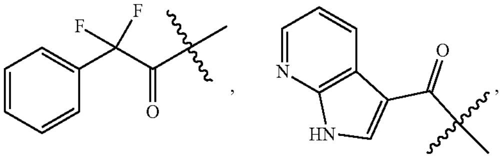
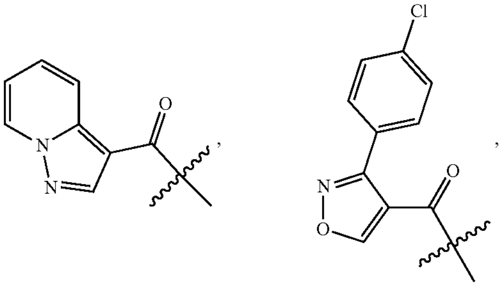
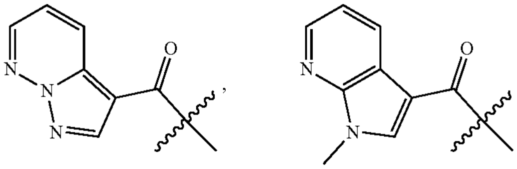
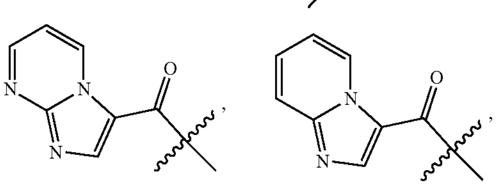
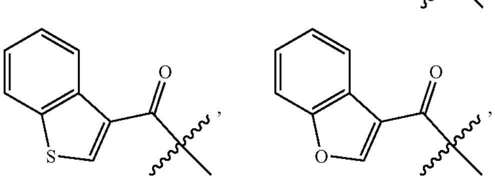
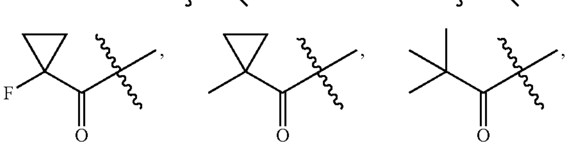
-continued
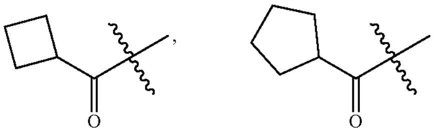
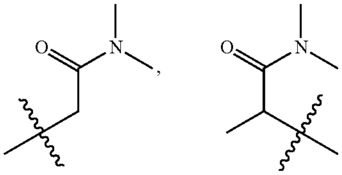
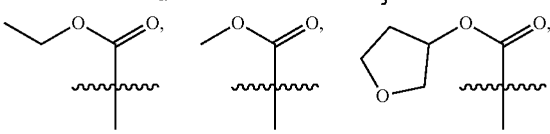
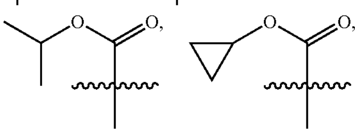
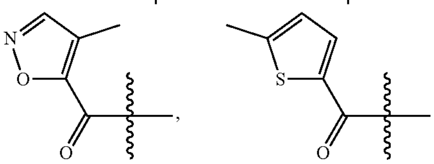
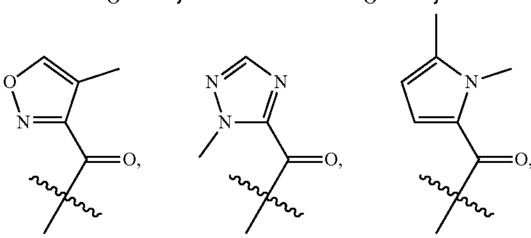
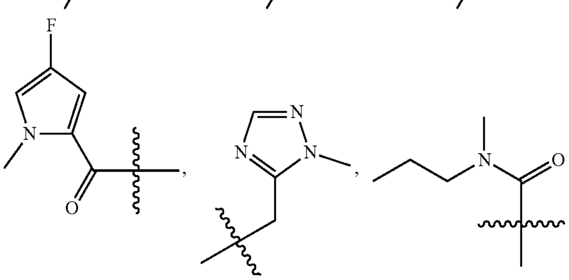
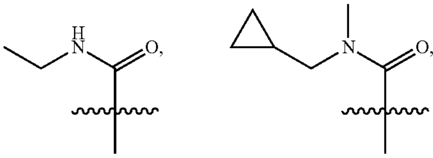
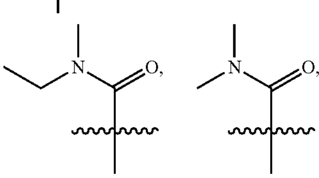
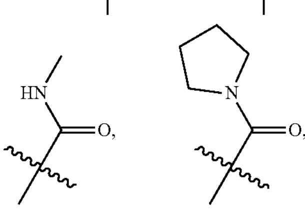

-continued

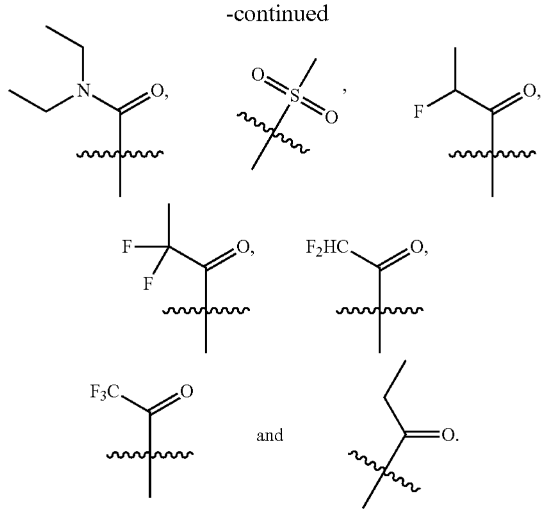

and $R^2$ and $R^3$ are independently selected from the group consisting of hydrogen, —$C_{1-6}$ alkyl and —$C_{0-2}$ alkylidene-(3 to 10-membered cycloalkyl);

A ring is selected from the group consisting of 5 to 10-membered aromatic ring and 5 to 10-membered heteroaromatic ring, wherein aromatic ring and heteroaromatic ring are independently unsubstituted or substituted with one, two or three $R^{A1}$; and each $R^{A1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

X is O, S, $NR^{x1}$ or $CR^{x2}R^{x3}$;

$R^{x1}$ is selected from the group consisting of hydrogen, —$C_{1-6}$ alkyl and —$C_{0-2}$ alkylidene-(3 to 10-membered cycloalkyl); and $R^{x2}$ and $R^{x3}$ are independently selected from the group consisting of hydrogen, —$C_{1-6}$ alkyl, halogen-substituted —$C_{1-6}$ alkyl, halogen, cyano group, nitro, —OH, —O($C_{1-6}$ alkyl), —$NH_2$, —NH($C_{1-6}$ alkyl) and —N($C_{1-6}$ alkyl)($C_{1-6}$ alkyl);

n is 0, 1, 2 or 3;

B ring is selected from the group consisting of 3 to 6-membered cycloalkane and 3 to 6-membered heterocyclic alkylidene, wherein cycloalkane and heterocyclic alkylidene are independently unsubstituted or substituted with one, two or three $R^{B1}$; and each $R^{B1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

C ring is selected from the group consisting of 3 to 10-membered cycloalkyl, 3 to 10-membered heterocycloalkyl, 5 to 10-membered aromatic ring, 5 to 10-membered heteroaromatic ring, 5 to 12-membered spiro ring, 5 to 12-membered spiro heterocycle, 5 to 12-membered bridged ring and 5 to 12-membered bridged heterocycle, wherein cycloalkyl, heterocycloalkyl, aromatic ring, heteroaromatic ring, spiro ring, spiro heterocycle, bridged ring and bridged heterocycle are independently unsubstituted or substituted with one, two or three $R^{C1}$;

each $R^{C1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{C2}$, —$C_{0-2}$ alkylidene-C(O)$R^{C2}$, —$C_{0-2}$ alkylidene-C(O)$NR^{C2}R^{C3}$, —$C_{0-2}$ alkylidene-$NR^{C2}R^{C3}$, —$C_{0-2}$ alkylidene-$NR^{C2}C(O)R^{C3}{}_2$, 3 to 10-membered cycloalkyl and 3 to 10-membered heterocycloalkyl, wherein alkyl and alkylidene are independently unsubstituted or substituted with one, two or three $R^{C4}$;

$R^{C2}$ and $R^{C3}$ are independently selected from the group consisting of hydrogen, —$C_{1-6}$ alkyl, —$C_{0-2}$ alkylidene-(3 to 10-membered cycloalkyl) and —$C_{0-2}$ alkylidene-(3 to 10-membered heterocycloalkyl), wherein alkyl and alkylidene are independently unsubstituted or substituted with one, two or three $R^{C4}$; and each $R^{C4}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl); or if two $R^{C1}$ are linked to the same atom, the two $R^{C1}$ are linked to form 3 to 10-membered cycloalkyl or 3 to 10-membered heterocycloalkyl;

L is O, S, $CR^{D1}R^{D1}$, $NR^L$, $NR^L$C(O), $NR^L$S(O), $NR^L$S(O)$_2$, C(O)$NR^L$, C(O), S(O)$NR^L$ or S(O)$_2NR^L$, or absent;

$R^L$ is hydrogen, —$C_{1-6}$ alkyl or —$C_{0-2}$ alkylidene-(3 to 10-membered cycloalkyl);

D ring is 3 to 10-membered cycloalkyl, 3 to 10-membered heterocycloalkyl, 5 to 10-membered aromatic ring, 5 to 10-membered heteroaromatic ring, 5 to 12-membered spiro ring, 5 to 12-membered spiro heterocycle, 5 to 12-membered bridged ring, or 5 to 12-membered bridged heterocycle, or absent, wherein cycloalkyl, heterocycloalkyl, aromatic ring, heteroaromatic ring, spiro ring, spiro heterocycle, bridged ring and bridged heterocycle are independently unsubstituted or substituted by one, two or three $R^{D1}$;

when L is absent and the D ring is not absent, the C ring is directly linked to the D ring;

each $R^{D1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-C(O)$R^{D2}$, —$C_{0-2}$ alkylidene-OC(O)$R^{D2}$, —$C_{0-2}$ alkylidene-C(O)$NR^{D2}R^{D3}$, —$C_{0-2}$ alkylidene-$NR^{D2}R^{D3}$, —$C_{0-2}$ alkylidene-$NR^{D2}$C(O)$R^{D3}$, —$C_{0-4}$ alkylidene-OP(O)(OH)$_2$, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{D4}$;

$R^{D2}$ and $R^{D3}$ are independently selected from the group consisting of hydrogen, —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{D4}$; and each $R^{D4}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl), —N($C_{1-6}$ alkyl)($C_{1-6}$ alkyl), —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring).

2. The compound of claim 1, wherein the A ring is benzene ring, wherein the benzene ring is unsubstituted or substituted with one, two or three halogen atoms.

3. The compound of claim 1, wherein X is O or $CH_2$.

4. The compound of claim 1, wherein the B ring is 3 to 4-membered cycloalkane.

5. The compound of claim 1, wherein the C ring is selected from the group consisting of benzene ring and 5 to 6-membered heteroaromatic ring, wherein the benzene ring and 5 to 6-membered heteroaromatic ring are independently unsubstituted or substituted with one, two or three $R^{C1}$; and each $R^{C1}$ is independently selected from the group consisting of hydrogen, halogen, cyano group, =O, =S, nitro, —$C_{1-6}$ alkyl, halogen-substituted —$C_{1-6}$ alkyl, —$OR^{C2}$, —C(O)$R^{C2}$, —C(O)$NR^{C2}R^{C3}$, —$R^{C2}R^{C3}$, —$NR^{C2}$C(O)$R^{C3}{}_2$, 3 to 6-membered cycloalkyl and 3 to 6-membered heterocycloalkyl.

6. The compound of claim 1, wherein the C ring is selected from the group consisting of

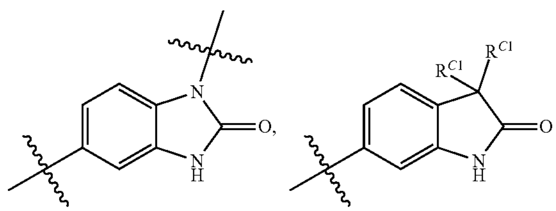

and

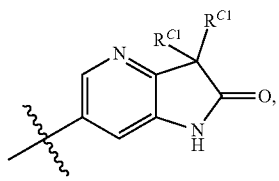

wherein two $R^{C1}$ are independent or linked to form 3 to 10-membered cycloalkyl or 3 to 10-membered heterocycloalkyl.

7. The compound of claim 1, wherein the D ring is 5 to 6-membered cycloalkyl, 5 to 6-membered heterocycloalkyl, benzene ring or 5 to 6-membered heteroaromatic ring, or absent, wherein cycloalkyl, heterocycloalkyl, benzene and heteroaromatic ring are independently unsubstituted or substituted with one, two or three $R^{D1}$.

8. A compound represented by formula (II), or a deuterated compound, a stereoisomer or a pharmacologically acceptable salt thereof:

(II)

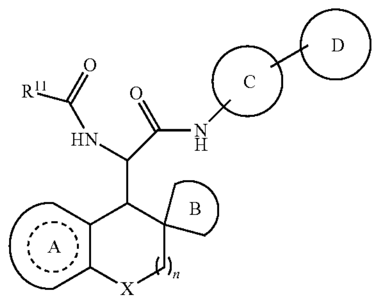

;

wherein $R^{11}$ is selected from the group consisting of hydrogen, —$C_{1-6}$ alkyl, halogen-substituted —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1a}$;

each $R^{1a}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{1b}$, —$C_{0-2}$ alkylidene-C(O)$R^{1b}$, —$C_{0-2}$ alkylidene-C(O)$NR^{1b}R^{1c}$, —$C_{0-2}$ alkylidene-$NR^{1b}R^{c1}$, —$C_{0-2}$ alkylidene-$NR^{1b}$C(O)$R^{1c}$, —$C_{0-4}$ alkylidene-S(O)$_2R^{1b}R^{1c}$, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1b}$;

$R^{1b}$ and $R^{1c}$ are independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

the A ring is selected from the group consisting of 5 to 10-membered aromatic ring and 5 to 10-membered heteroaromatic ring, wherein aromatic ring and heteroaromatic ring are independently unsubstituted or substituted with one, two or three $R^{A1}$; and each $R^{A1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

X is O, S or —$CH_2$—;

n is 0 or 1;

the B ring is selected from the group consisting of 3-membered cycloalkane, 4-membered cycloalkane, 5-membered cycloalkane and 6-membered cycloalkane, wherein cycloalkane is unsubstituted or substituted with one, two or three $R^{B1}$;

each $R^{B1}$ is independently selected from the group consisting of hydrogen, —$C_{1-6}$ alkyl, halogen-substituted —$C_{1-6}$ alkyl, halogen, cyano group, =O, =S, nitro, —OH, —O($C_{1-6}$ alkyl), —$NH_2$, —NH($C_{1-6}$ alkyl) and —N($C_{1-6}$ alkyl)($C_{1-6}$ alkyl);

the C ring is selected from the group consisting of 5 to 10-membered heterocycloalkyl, 5 to 10-membered aromatic ring and 5 to 10-membered heteroaromatic ring, wherein heterocycloalkyl, aromatic ring and heteroaromatic ring are independently unsubstituted or substituted with one, two or three $R^{C1}$; and each $R^{C1}$ is independently selected from the group consisting of hydrogen, halogen, cyano group, =O, =S, nitro, —$C_{1-6}$ alkyl and halogen-substituted —$C_{1-6}$ alkyl;

the D ring is selected from the group consisting of 3 to 10-membered cycloalkyl, 3 to 10-membered heterocycloalkyl, 5 to 10-membered aromatic ring and 5 to 10-membered heteroaromatic ring, wherein cycloalkyl, heterocycloalkyl, aromatic ring and heteroaromatic ring are independently unsubstituted or substituted with one, two or three $R^{D1}$;

each $R^{D1}$ is independently selected from the group consisting of hydrogen, halogen, cyano group, =O, =S, nitro, —$C_{1-6}$ alkyl, halogen-substituted —$C_{1-6}$ alkyl, —$C_{0-2}$ alkylidene-$OR^{D2}$, —$C_{0-2}$ alkylidene-C(O)$R^{D2}$, —$C_{0-2}$ alkylidene-C(O)$NR^{D2}R^{D3}$, —$C_{0-2}$ alkylidene-$NR^{D2}R^{D3}$, —$C_{0-2}$ alkylidene-$NR^{D2}C(O)R^{D3}$ and —$C_{0-4}$ alkylidene-OP(O)$(OH)_2$; and $R^{D2}$ and $R^{D3}$ are independently selected from the group consisting of hydrogen, —$C_{1-6}$ alkyl, —$C_{0-2}$ alkylidene-(3 to 10-membered cycloalkyl), —$C_{0-2}$ alkylidene-(3 to 10-membered heterocycloalkyl), —$C_{0-2}$ alkylidene-(5 to 10-membered aromatic ring) and —$C_{0-2}$ alkylidene-(5 to 10-membered heteroaromatic ring).

9. The compound of claim 8, wherein $R^{11}$ is selected from the group consisting of 3 to 6-membered cycloalkyl, 3 to 6-membered heterocycloalkyl, 5 to 6-membered aromatic ring and 5 to 6-membered heteroaromatic ring, wherein cycloalkyl, heterocycloalkyl, aromatic ring and heteroaromatic ring are independently unsubstituted or substituted with one, two or three $R^{1a}$.

10. The compound of claim 9, wherein $R^{11}$ is selected from the group consisting of

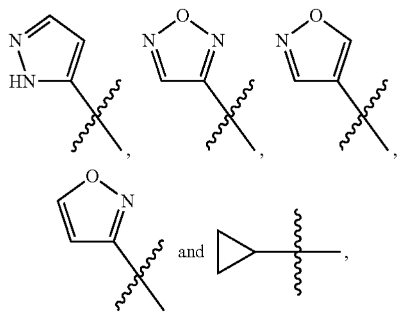

wherein

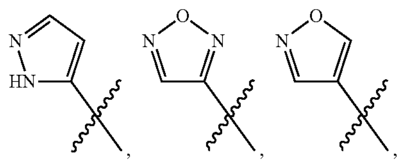

-continued

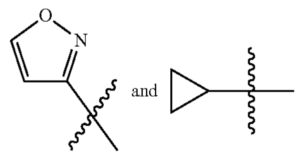

are independently unsubstituted or substituted with one, two or three $R^{1a}$;

each $R^{1a}$ is independently selected from the group consisting of hydrogen, halogen, cyano group, —$C_{1-6}$ alkyl, halogen-substituted —$C_{1-6}$ alkyl, 3 to 6-membered cycloalkyl and —$C_{0-2}$ alkylidene-$OR^{1b}$; and $R^{1b}$ is selected from the group consisting of hydrogen, —$C_{1-6}$ alkyl and halogen-substituted —$C_{1-6}$ alkyl.

11. The compound of claim 10, wherein $R^{11}$ is selected from the group consisting of

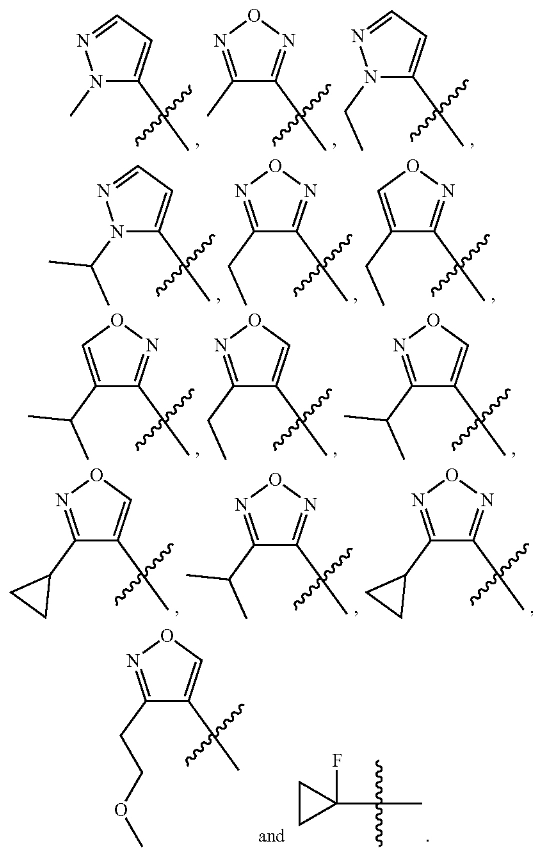

12. The compound of claim 8, wherein the A ring is selected from the group consisting of benzene ring and 6-membered heteroaromatic ring, wherein the benzene and the 6-membered heteroaromatic ring are independently unsubstituted or substituted with one, two or three $R^{A1}$; and each $R^{A1}$ is independently selected from the group consisting of hydrogen, —$C_{1-6}$ alkyl, halogen-substituted —$C_{1-6}$ alkyl, halogen and cyano group.

13. The compound of claim 12, wherein the A ring is selected from the group consisting of

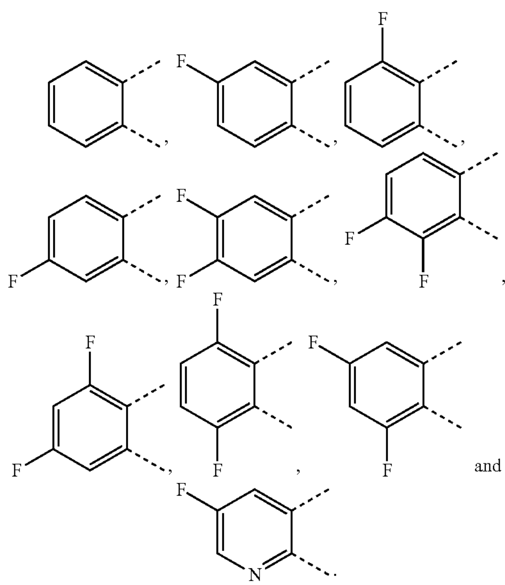

14. The compound of claim 8, wherein the B ring is cyclopropane.

15. The compound of claim 8, wherein the C ring is selected from the group consisting of 6-membered heterocycloalkyl, benzene ring, 5-membered heteroaromatic ring and 6-membered heteroaromatic ring, wherein heterocycloalkyl, benzene ring and heteroaromatic ring are independently unsubstituted or substituted with one, two or three $R^{C1}$; and each $R^{C1}$ is independently selected from the group consisting of hydrogen, halogen, =O, =S, cyano group, $-C_{1-6}$ alkyl and halogen-substituted $-C_{1-6}$ alkyl.

16. The compound of claim 15, wherein the C ring is selected from the group consisting of

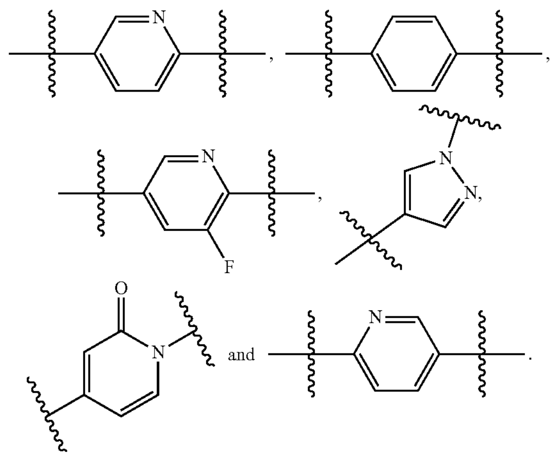

17. The compound of claim 8, wherein the D ring is selected from the group consisting of 5 to 6-membered cycloalkyl, 5 to 6-membered heterocycloalkyl, 5 to 6-membered aromatic ring and 5 to 6-membered heteroaromatic ring, wherein cycloalkyl, heterocycloalkyl, aromatic ring and heteroaromatic ring are independently unsubstituted or substituted with one, two or three $R^{D1}$;

each $R^{D1}$ is independently selected from the group consisting of hydrogen, halogen, cyano group, $-C_{1-6}$ alkyl, halogen-substituted $-C_{1-6}$ alkyl, $-C_{0-2}$ alkylidene-$OR^{D2}$, $C_{0-2}$ alkylidene-$NR^{D2}R^{D33}$ and $-C_{0-4}$ alkylidene-$OP(O)(OH)_2$; and $R^{D2}$ and $R^{D3}$ are independently selected from the group consisting of hydrogen and $-C_{1-6}$ alkyl.

18. The compound of claim 17, wherein the D ring is selected from the group consisting of

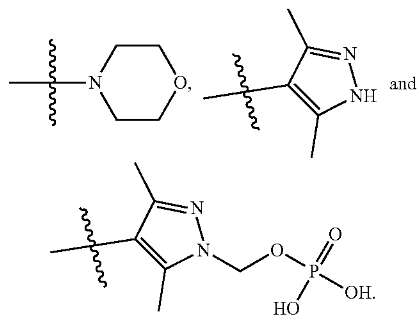

19. A compound represented by formula (III), or a deuterated compound, a stereoisomer or a pharmacologically acceptable salt thereof:

(III)

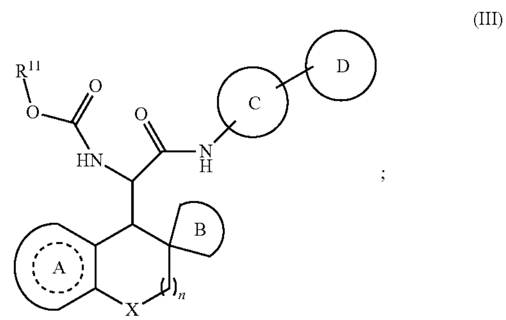

;

wherein $R^{11}$ is selected from the group consisting of $-C_{1-6}$ alkyl, halogen-substituted $-C_{1-6}$ alkyl, $-C_{0-2}$ alkylidene-(3 to 10-membered cycloalkyl), $-C_{0-2}$ alkylidene-(3 to 10-membered heterocycloalkyl), $-C_{0-2}$ alkylidene-(5 to 10-membered aromatic ring) and $-C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1a}$;

each $R^{1a}$ is independently selected from the group consisting of hydrogen, halogen, cyano group, =O, =S, nitro, $-C_{1-6}$ alkyl, halogen-substituted $-C_{1-6}$ alkyl, $-C_{0-2}$ alkylidene-$OR^{1b}$, $-C_{0-2}$ alkylidene-$C(O)R^{1b}$, $-C_{0-2}$ alkylidene-$C(O)NR^{1b}R^{1c}$, $-C_{0-2}$ alkylidene-$NR^{1b}R^{1c}$, $-C_{0-2}$ alkylidene-$NR^{1b}C(O)R^{1c}$, $-C_{0-4}$ alkylidene-$S(O)_2R^{1b}R^{1c}$, $-C_{0-2}$ alkylidene-(3 to 10-membered cycloalkyl), $-C_{0-2}$ alkylidene-(3 to 10-membered heterocycloalkyl), $-C_{0-2}$ alkylidene-(5 to 10-membered aromatic ring) and $-C_{0-2}$ alkylidene-(5 to 10-membered heteroaromatic ring), wherein alkyl, alkylidene, cycloalkyl, heterocycloalkyl, aromatic ring and heteroaromatic ring are independently unsubstituted or substituted with one, two or three $R^{1b}$;

$R^{1b}$ and $R^{1c}$ are independently selected from the group consisting of hydrogen, $—C_{1-6}$ alkyl, halogen-substituted $—C_{1-6}$ alkyl, halogen, cyano group, =O, =S, nitro, —OH, $—O(C_{1-6}$ alkyl), $—NH_2$, $—NH(C_{1-6}$ alkyl) and $—N(C_{1-6}$ alkyl)($C_{1-6}$ alkyl);

the A ring is selected from the group consisting of 5 to 10-membered aromatic ring and 5 to 10-membered heteroaromatic ring, wherein aromatic ring and heteroaromatic ring are independently unsubstituted or substituted with one, two or three $R^{A1}$;

each $R^{A1}$ is independently selected from the group consisting of hydrogen, $—C_{1-6}$ alkyl, halogen-substituted $—C_{1-6}$ alkyl, halogen, cyano group, =O, =S, nitro, —OH, $—O(C_{1-6}$ alkyl), $—NH_2$, $—NH(C_{1-6}$ alkyl) and $—N(C_{1-6}$ alkyl)($C_{1-6}$ alkyl);

X is O, S or $—CH_2—$;

n is 0 or 1;

the B ring is selected from the group consisting of 3-membered cycloalkane, 4-membered cycloalkane, 5-membered cycloalkane and 6-membered cycloalkane, wherein cycloalkane is unsubstituted or substituted with one, two or three $R^{B1}$; and each $R^{B1}$ is independently selected from the group consisting of hydrogen, $—C_{1-6}$ alkyl, halogen-substituted $—C_{1-6}$ alkyl, halogen, cyano group, =O, =S, nitro, —OH, $—O(C_{1-6}$ alkyl), $—NH_2$, $—NH(C_{1-6}$ alkyl) and $—N(C_{1-6}$ alkyl)($C_{1-6}$ alkyl);

the C ring is selected from the group consisting of 5 to 10-membered heterocycloalkyl, 5 to 10-membered aromatic ring and 5 to 10-membered heteroaromatic ring, wherein aromatic ring and heteroaromatic ring are independently unsubstituted or substituted with one, two or three $R^{C1}$;

each $R^{C1}$ is independently selected from the group consisting of hydrogen, halogen, cyano group, =O, =S, nitro, $—C_{1-6}$ alkyl and halogen-substituted $—C_{1-6}$ alkyl;

the D ring is selected from the group consisting of 3 to 10-membered cycloalkyl, 3 to 10-membered heterocycloalkyl, 5 to 10-membered aromatic ring and 5 to 10-membered heteroaromatic ring, wherein cycloalkyl, heterocycloalkyl, aromatic ring and heteroaromatic ring are independently unsubstituted or substituted with one, two or three $R^{D1}$;

each $R^{D1}$ is independently selected from the group consisting of hydrogen, halogen, cyano group, =O, =S, nitro, $—C_{1-6}$ alkyl, halogen-substituted $—C_{1-6}$ alkyl, $—C_{0-2}$ alkylidene-$OR^{D2}$, $—C_{0-2}$ alkylidene-$C(O)R^{D2}$, $—C_{0-2}$ alkylidene-$C(O)NR^{D2}R^{D3}$, $—C_{0-2}$ alkylidene-$NR^{D2}R^{D3}$, $—C_{0-2}$ alkylidene-$NR^{D2}C(O)R^{D3}$ and $—C_{0-4}$ alkylidene-$OP(O)(OH)_2$; and $R^{D2}$ and $R^{D3}$ are independently selected from the group consisting of hydrogen, $—C_{1-6}$ alkyl, $—C_{0-2}$ alkylidene-(3 to 10-membered cycloalkyl), $—C_{0-2}$ alkylidene-(3 to 10-membered heterocycloalkyl), $—C_{0-2}$ alkylidene-(5 to 10-membered aromatic ring) and $—C_{0-2}$ alkylidene-(5 to 10-membered heteroaromatic ring).

20. The compound of claim 19, wherein $R^{11}$ is selected from the group consisting of $—C_{1-6}$ alkyl and 3 to 6-membered cycloalkyl;

the A ring is selected from the group consisting of

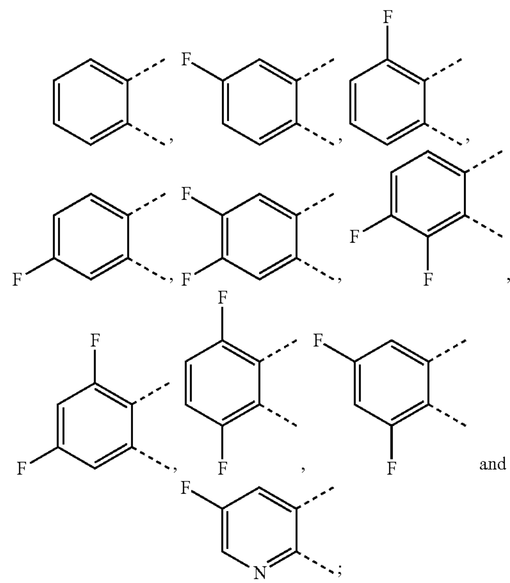

the B ring is cyclopropane;

the C ring is selected from the group consisting of

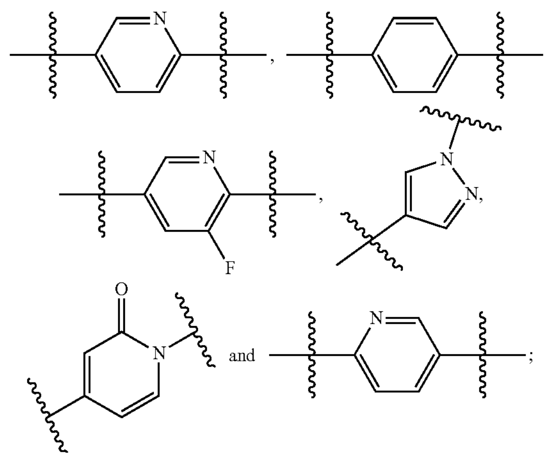

the D ring is selected from the group consisting of

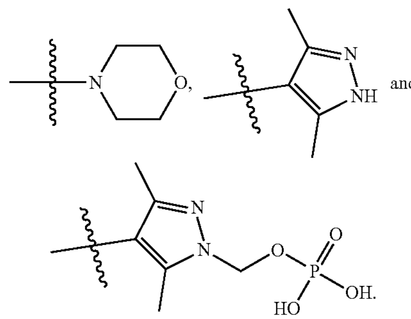

21. The compound of claim 1, wherein the compound is selected from the group consisting of -continued
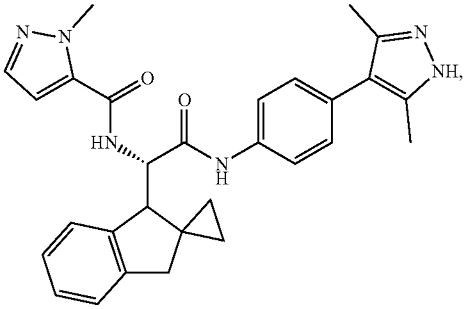
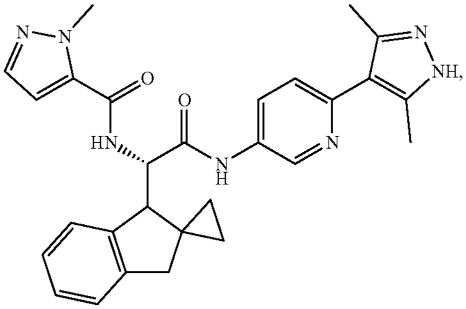
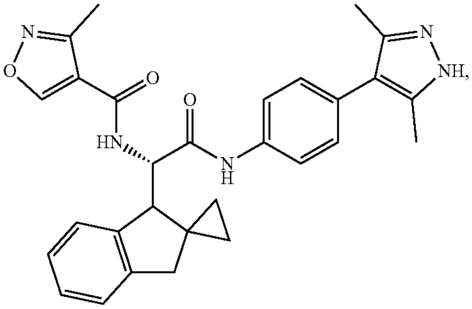
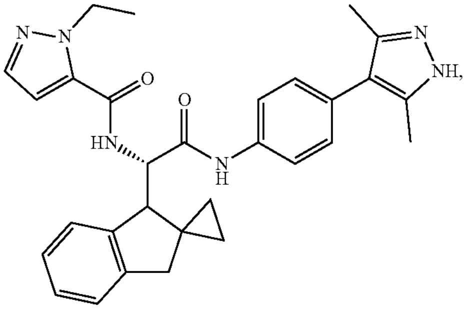
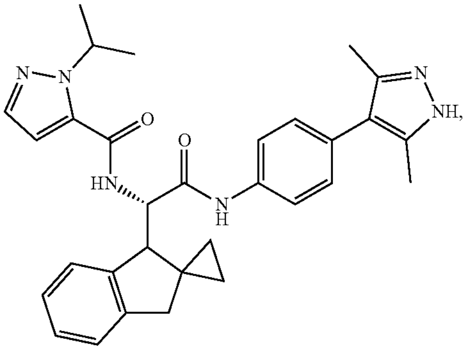
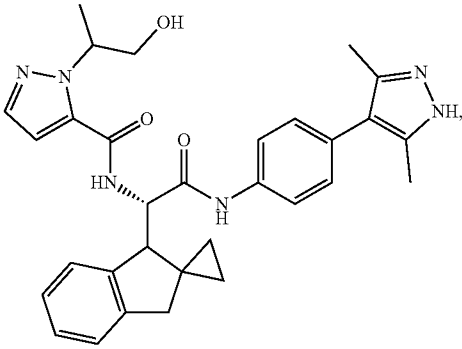
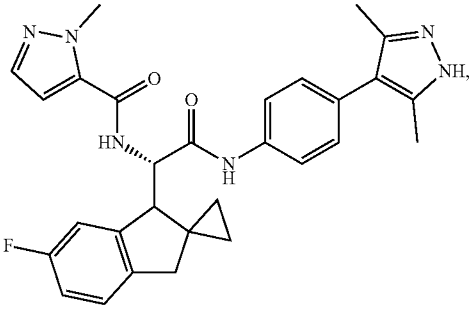
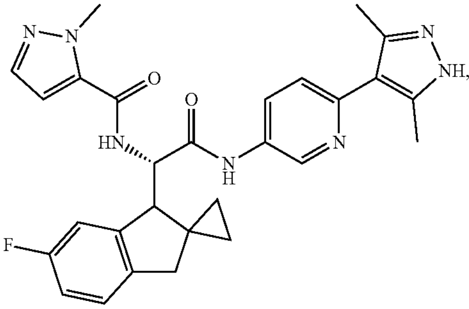
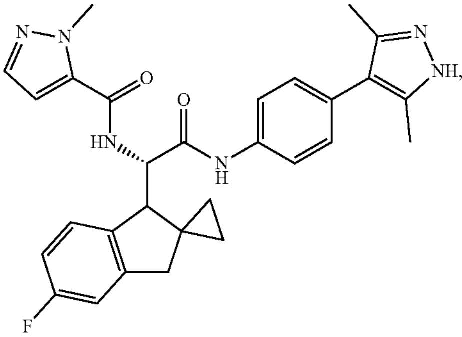
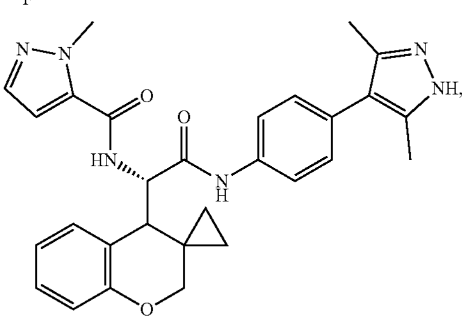

-continued
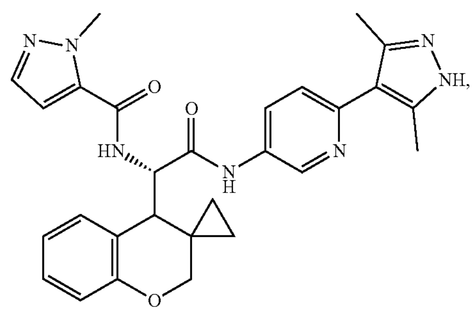
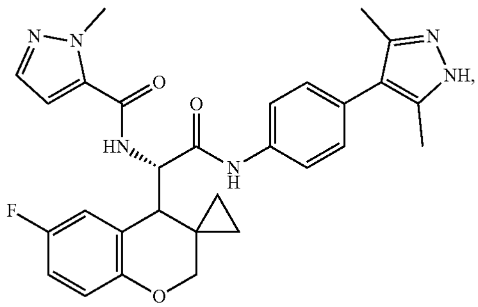
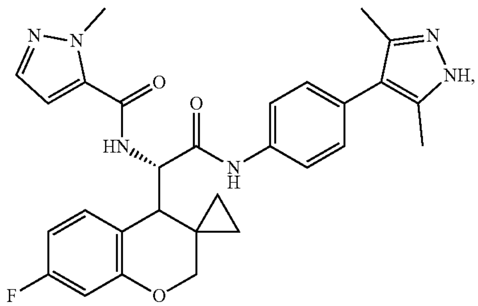
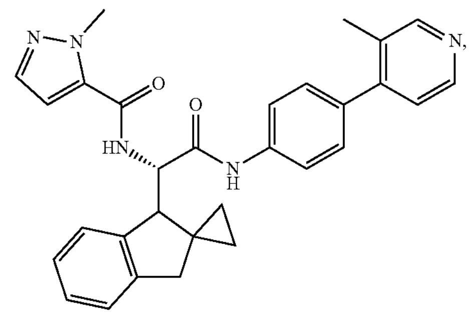
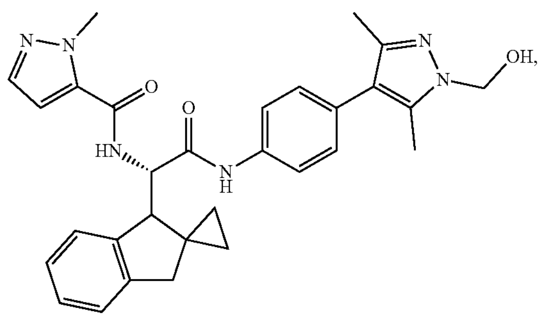
-continued
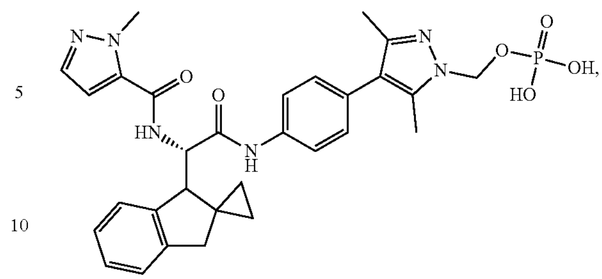
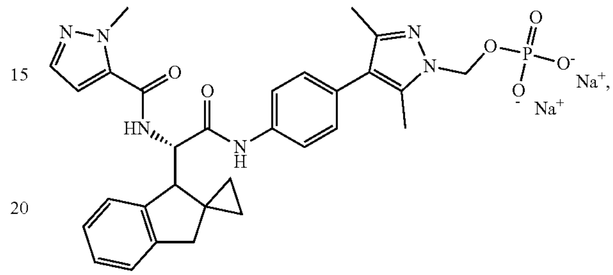
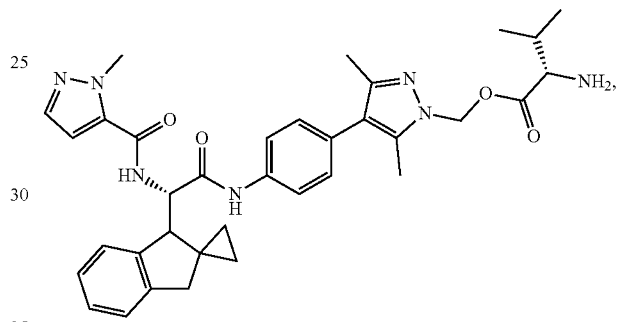
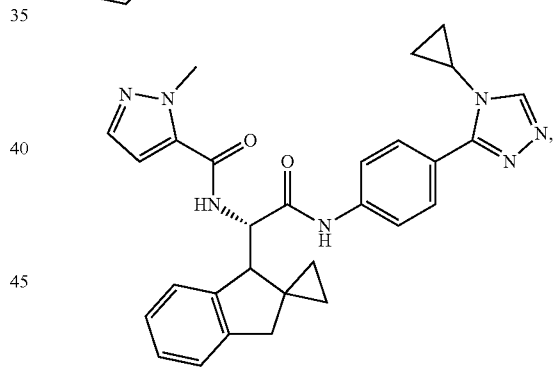
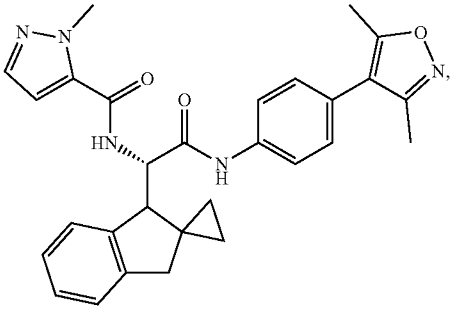

-continued
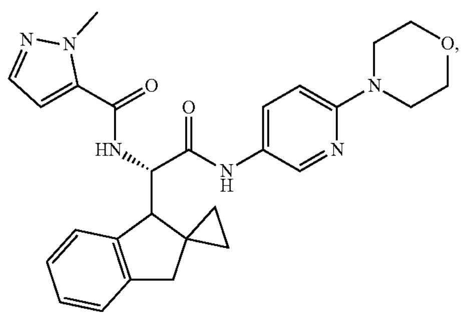
,
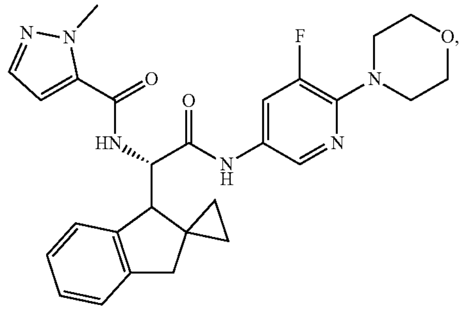
,
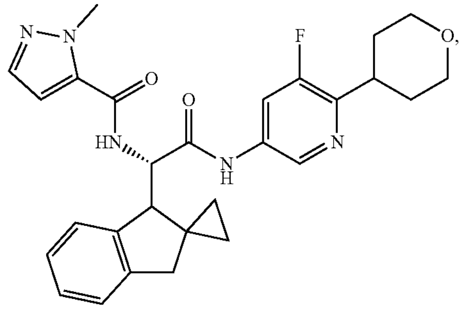
,
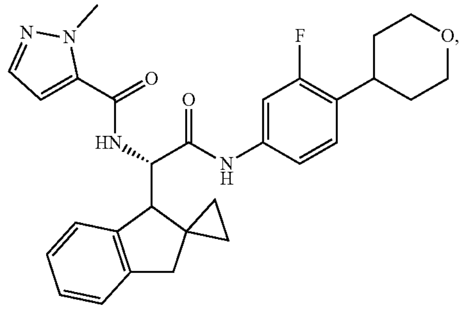
,
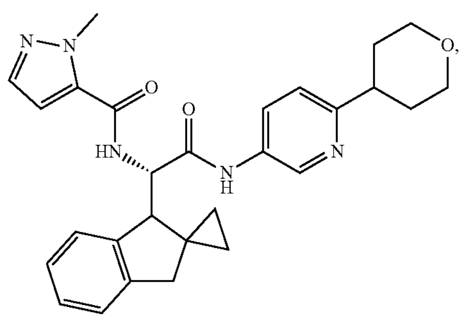
,
-continued
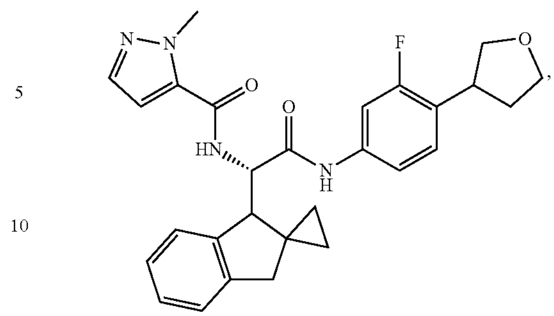
,
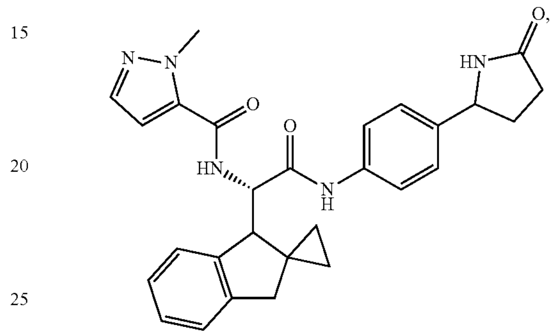
,
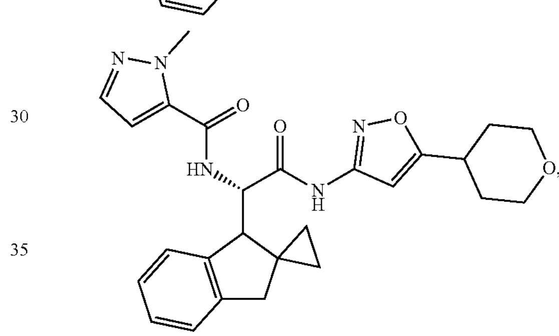
,
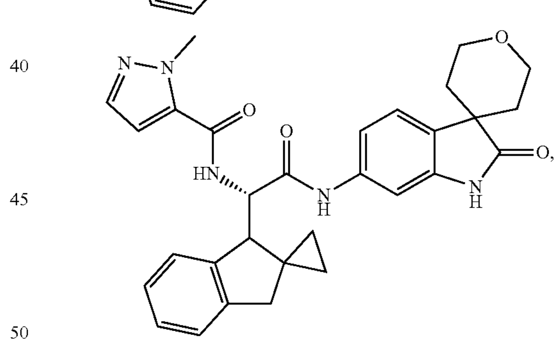
,
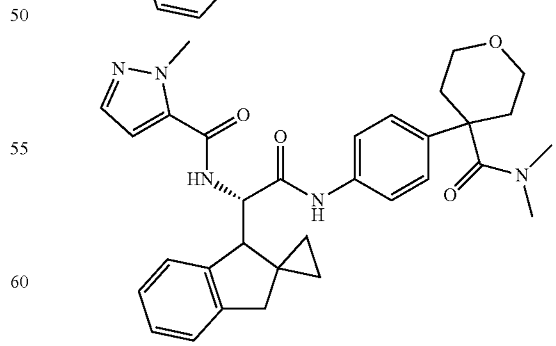
,
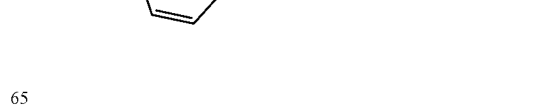

-continued
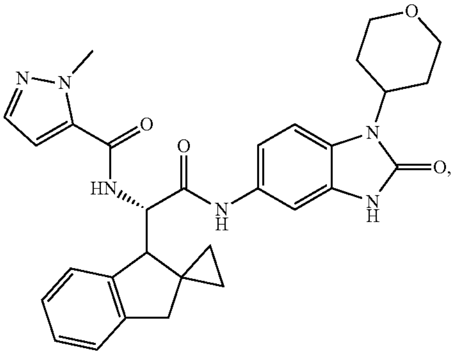
,
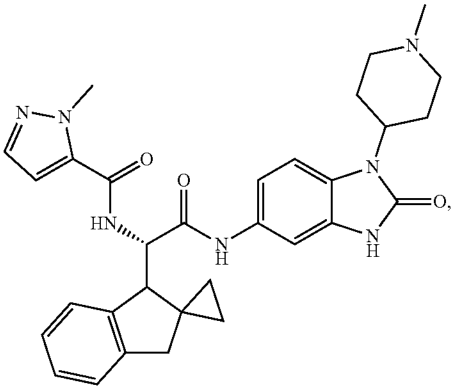
,
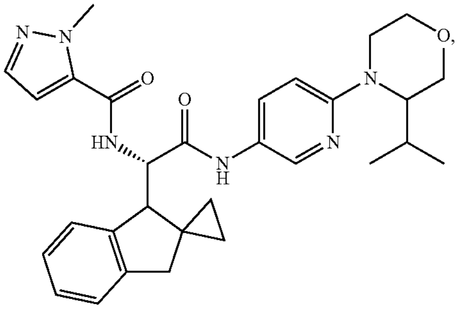
,
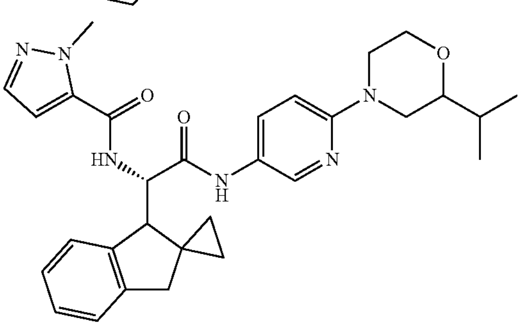
,
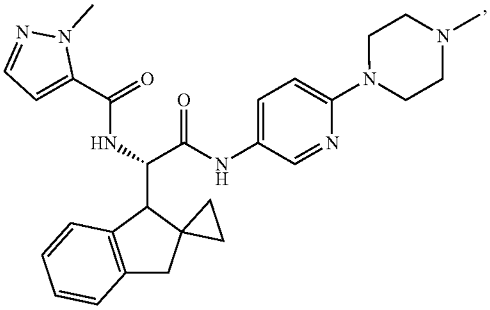
,
-continued
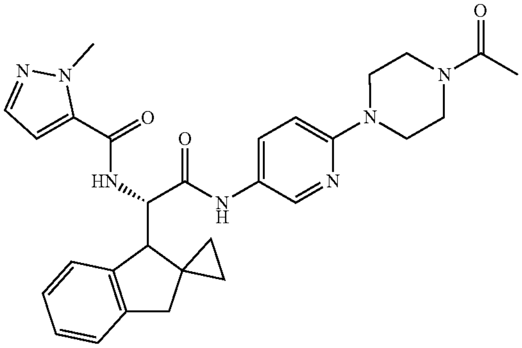
,
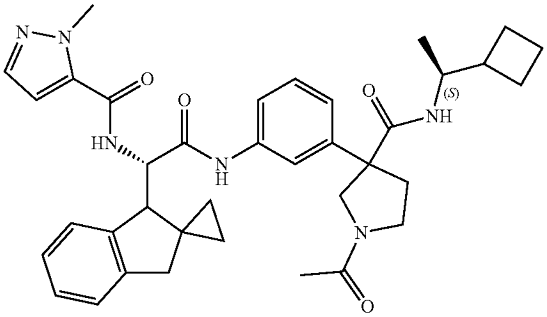
,
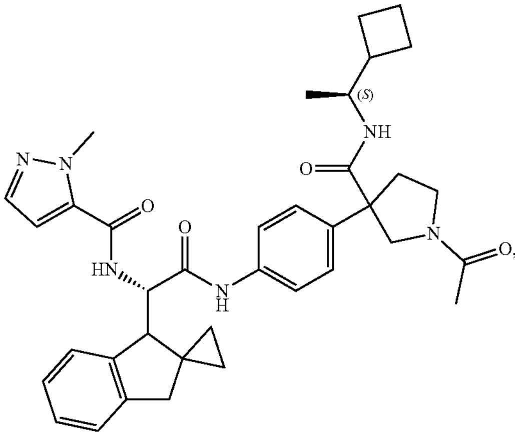
,
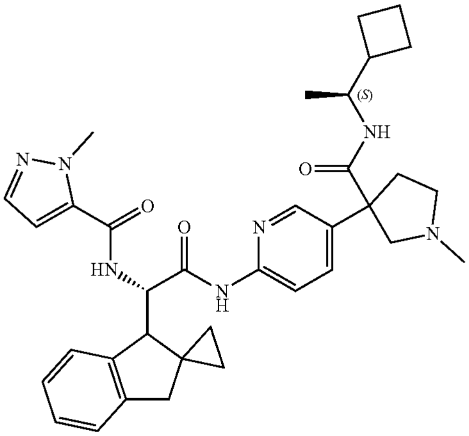
, -continued
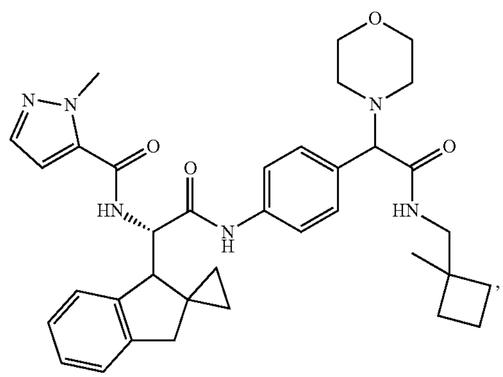
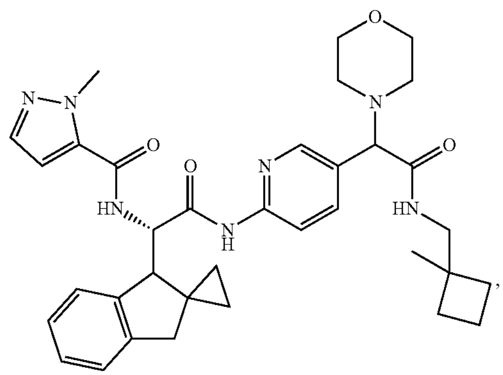
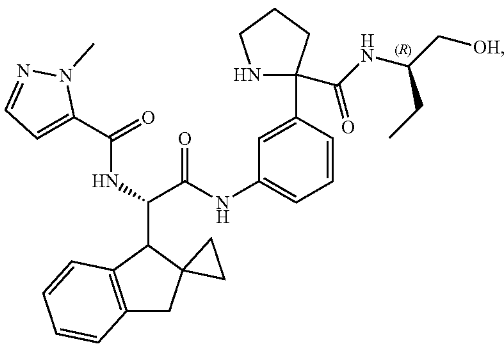
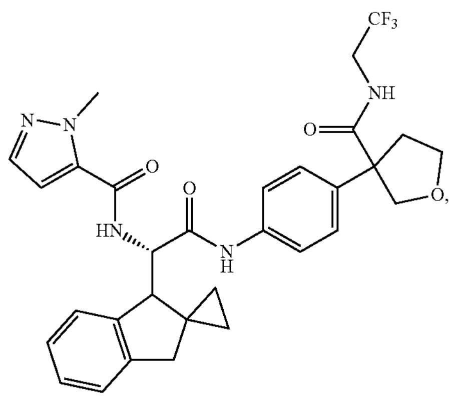
-continued
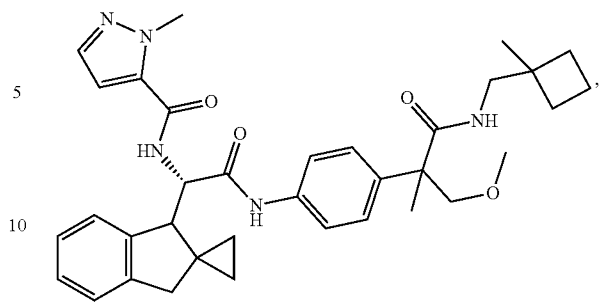
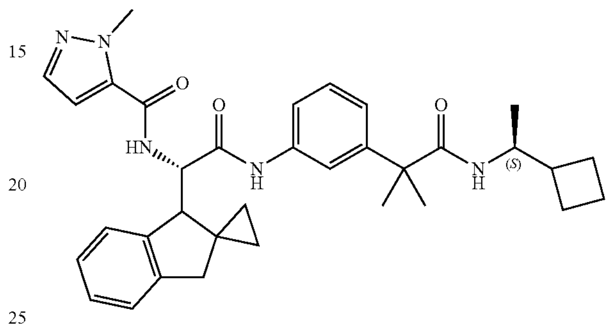
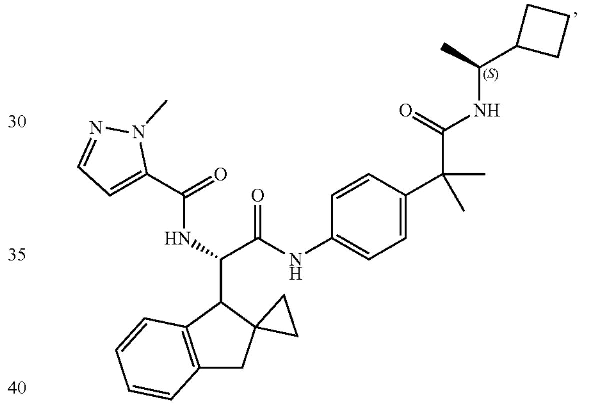
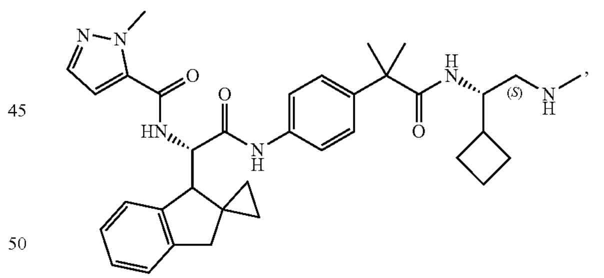
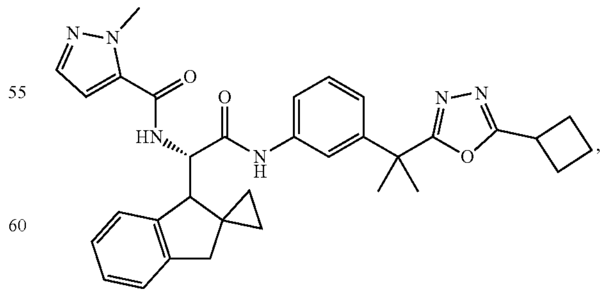

-continued
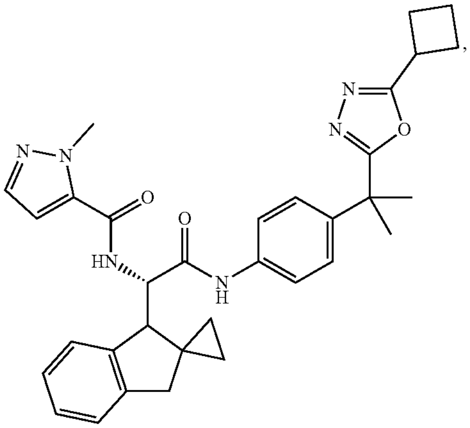
,
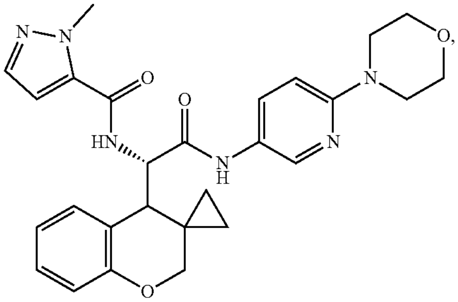
,
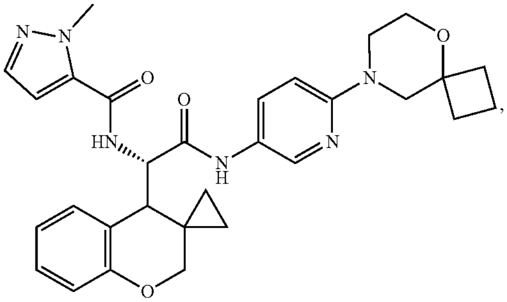
,
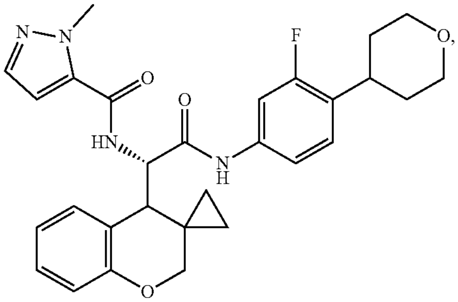
,
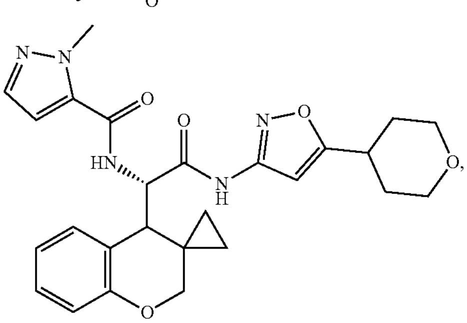
,
-continued
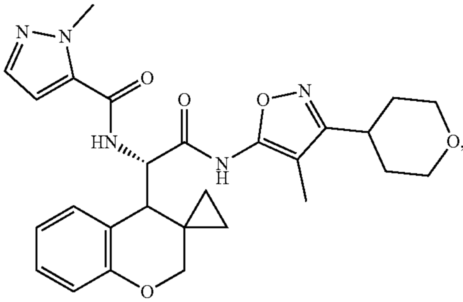
,
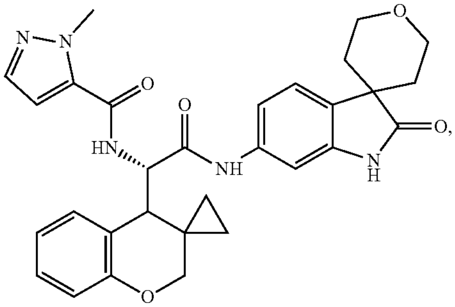
,
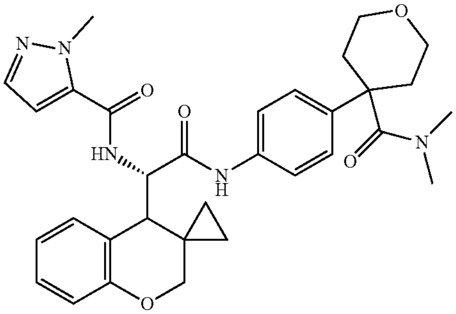
,
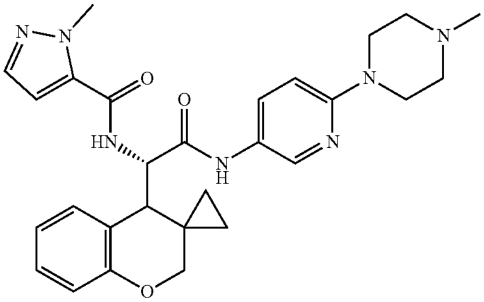
,
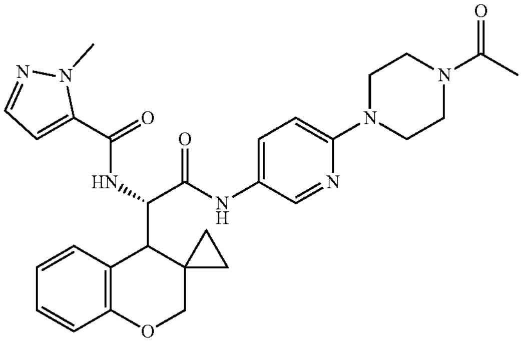
, -continued
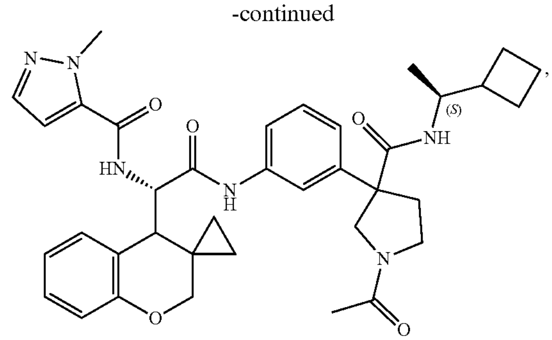
,
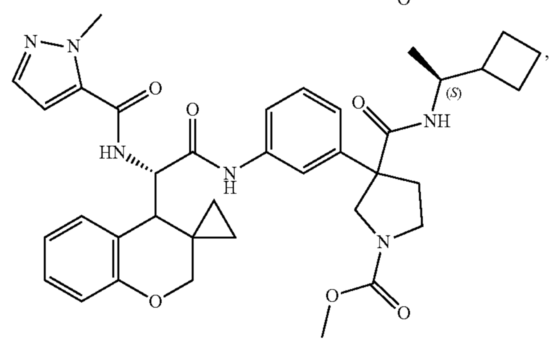
,
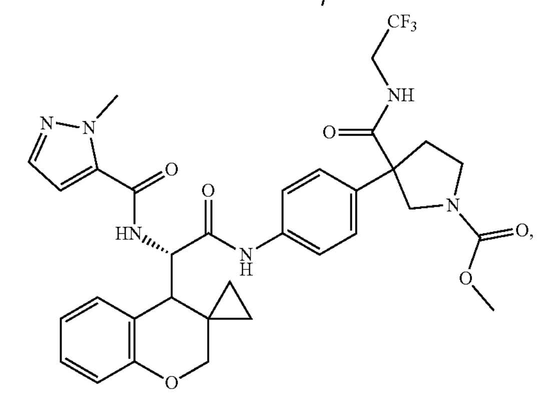
,
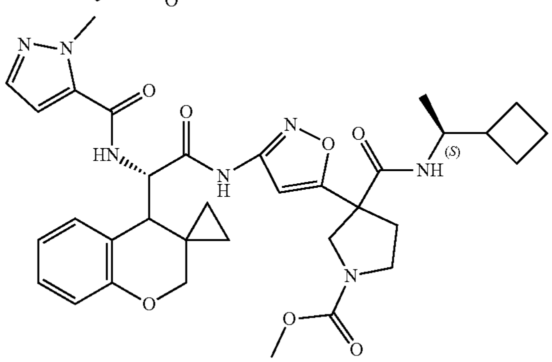
,
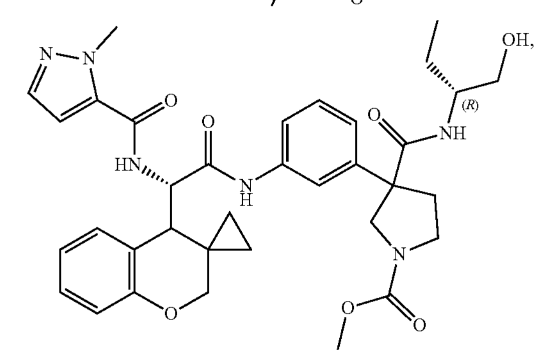
,
-continued
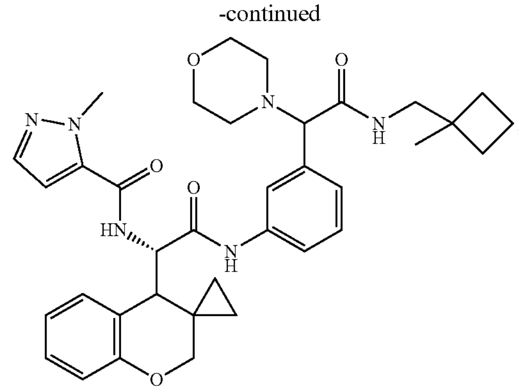
,
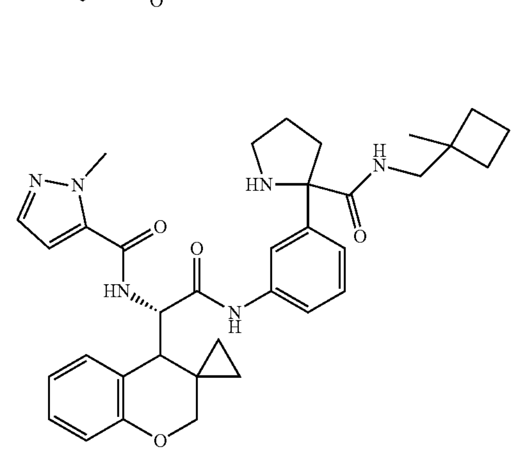
,
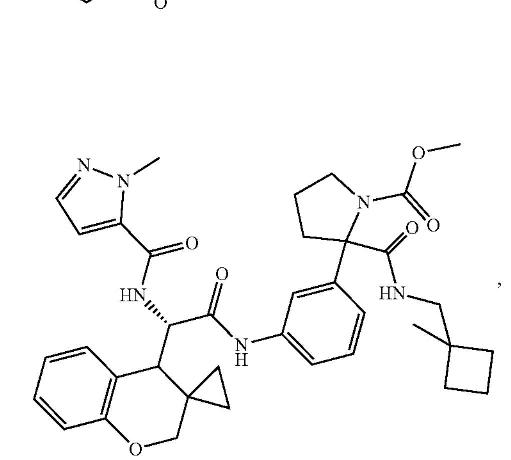
,
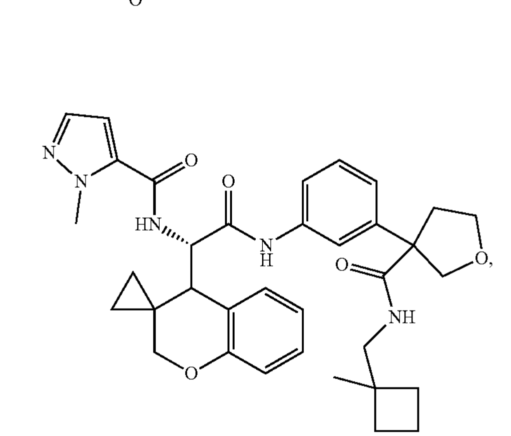
, -continued
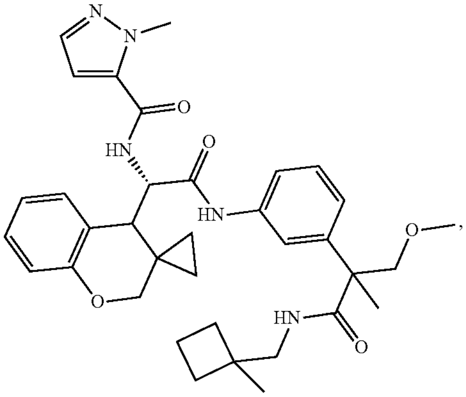
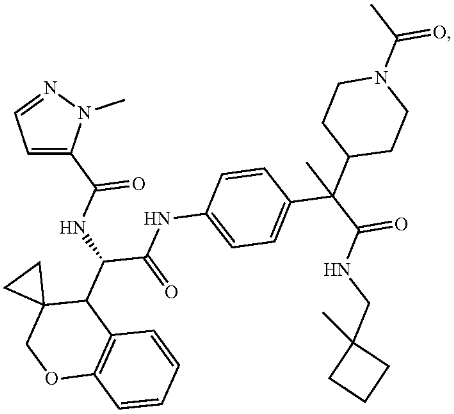
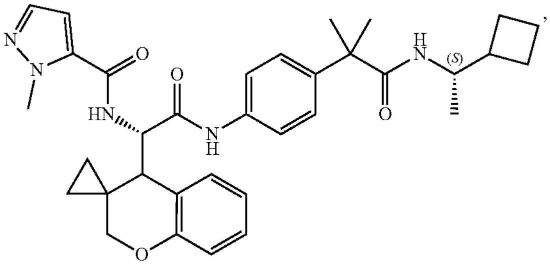
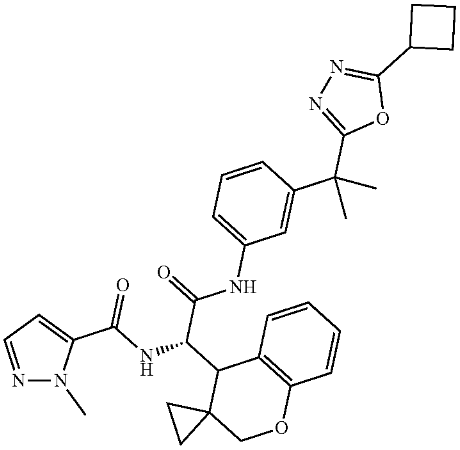
-continued
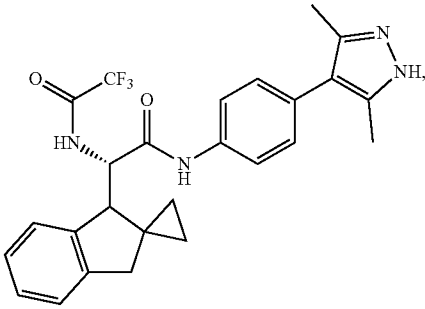
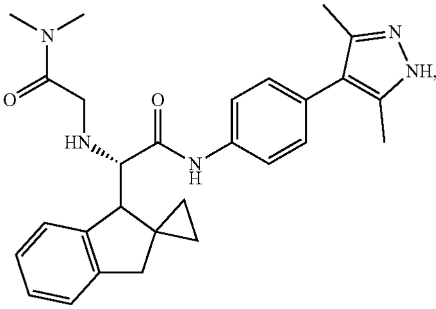
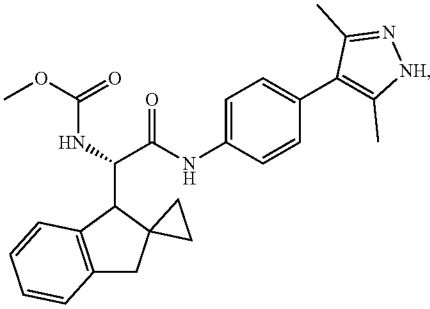
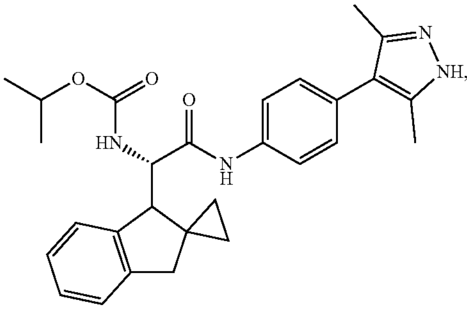
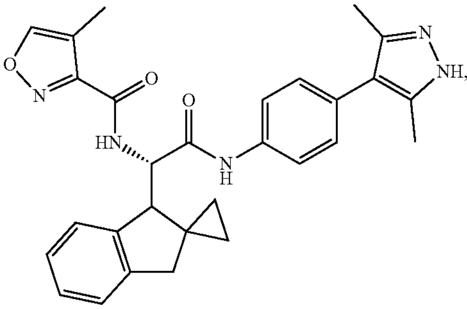

-continued
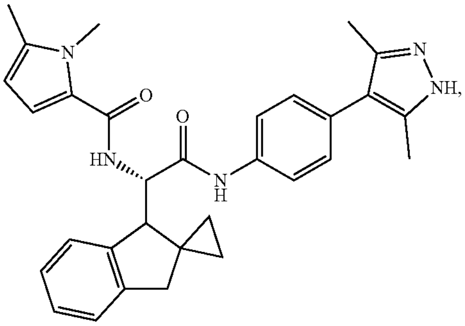
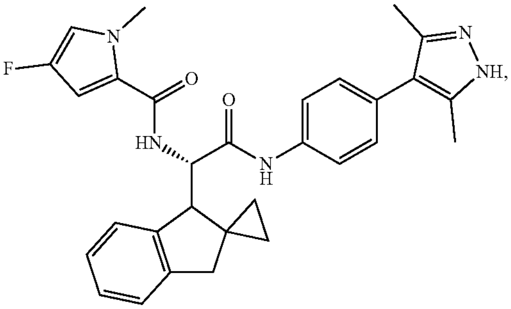
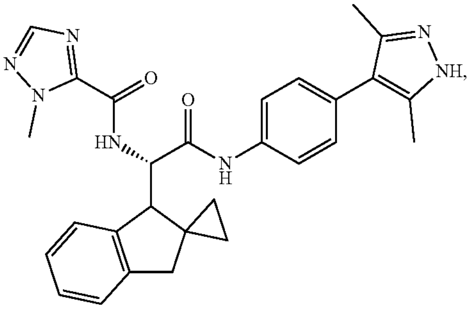
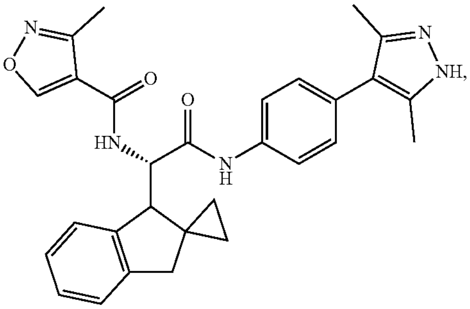
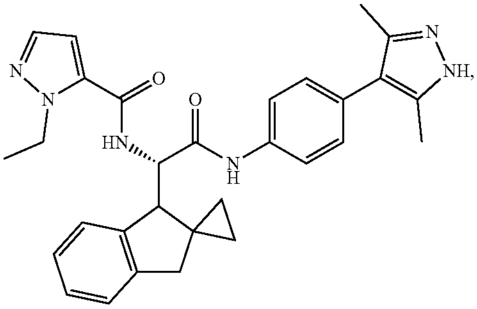
-continued
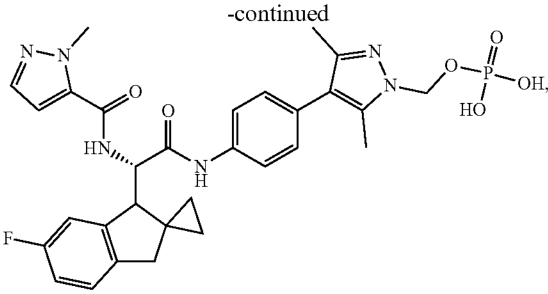
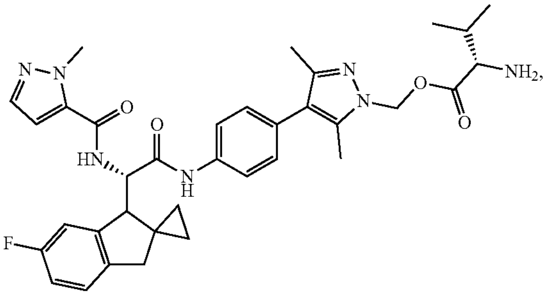
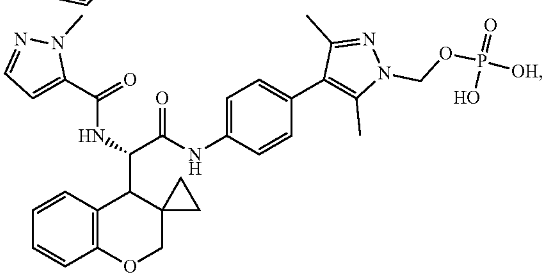
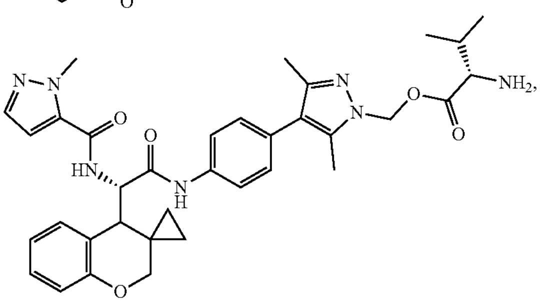
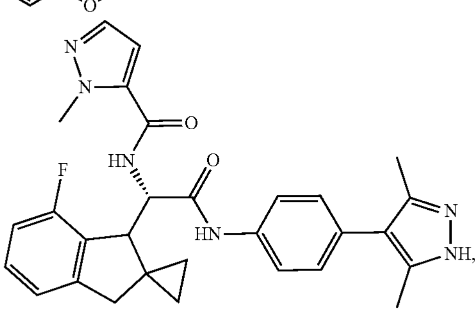
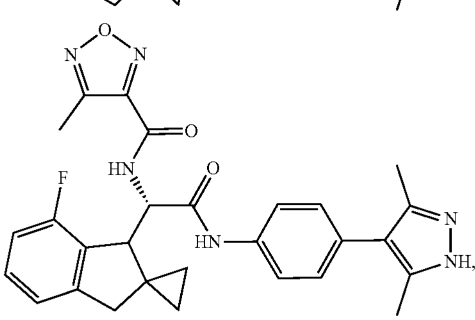

-continued
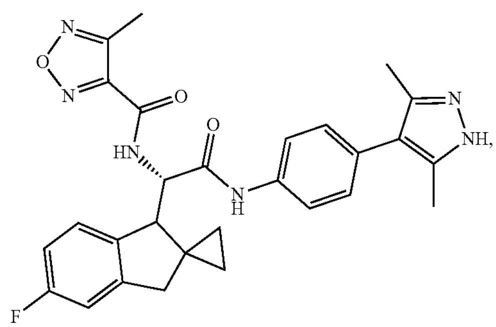
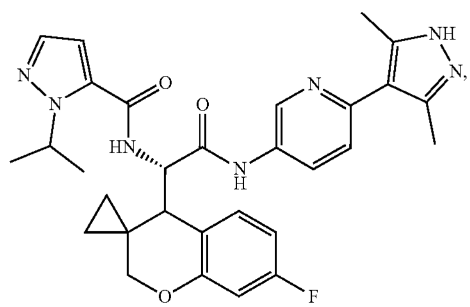
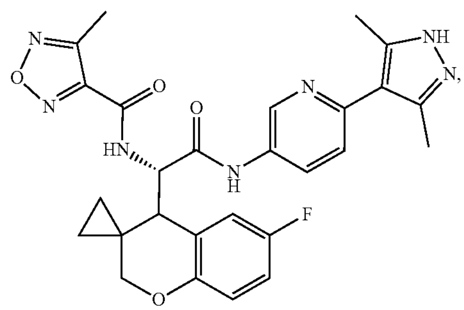
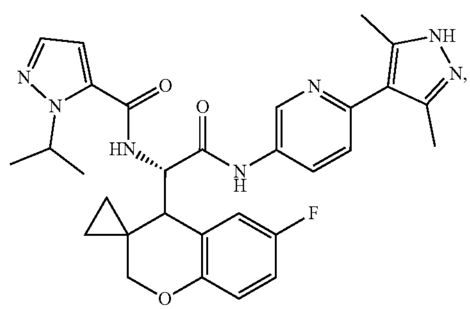
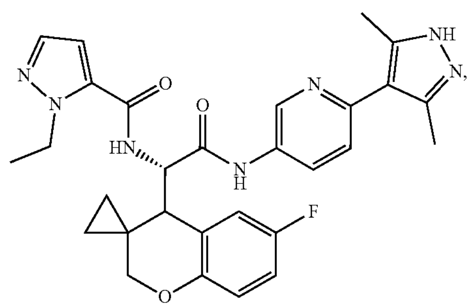
-continued
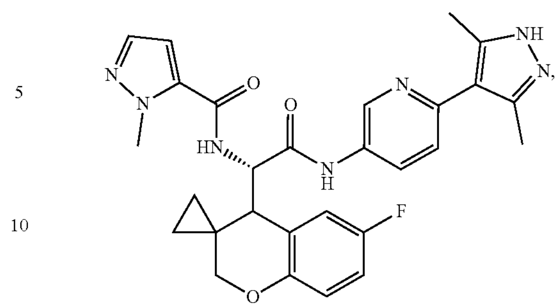
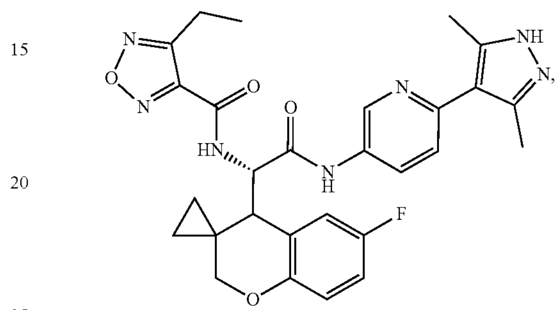
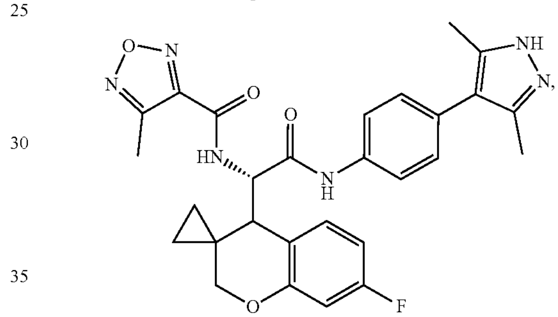
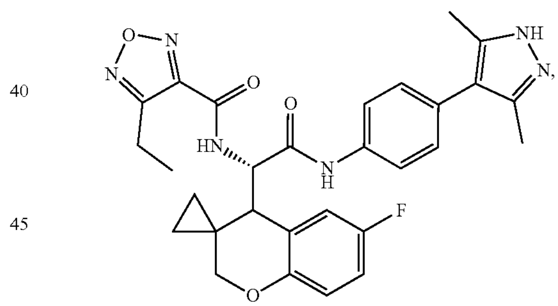
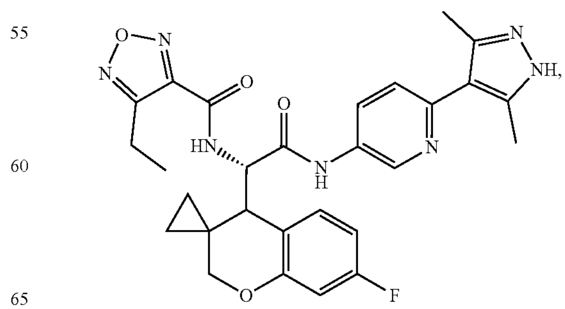

-continued
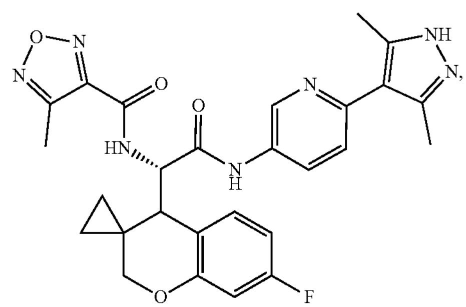
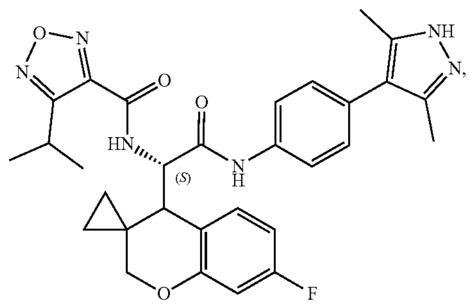
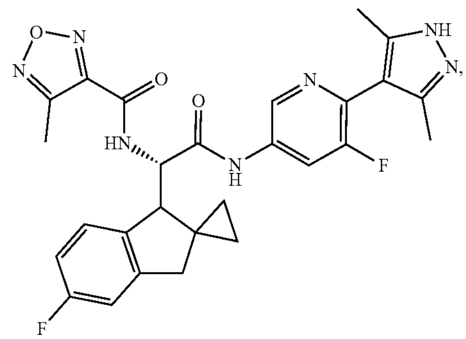
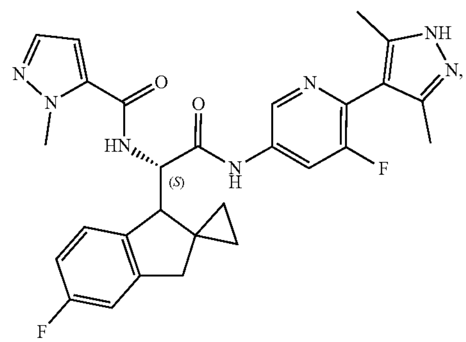
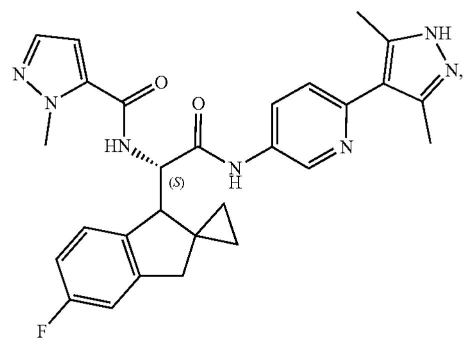
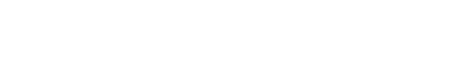
-continued
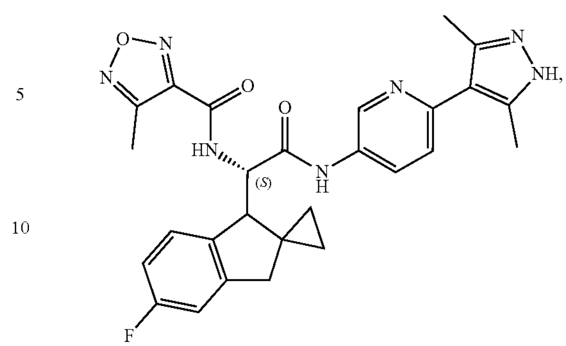
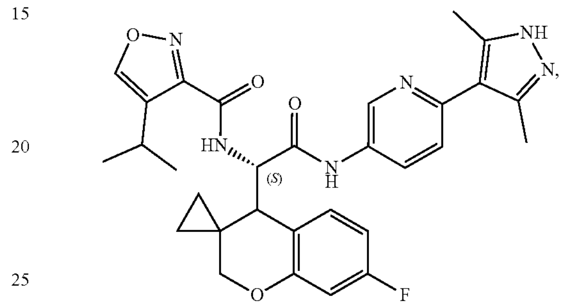
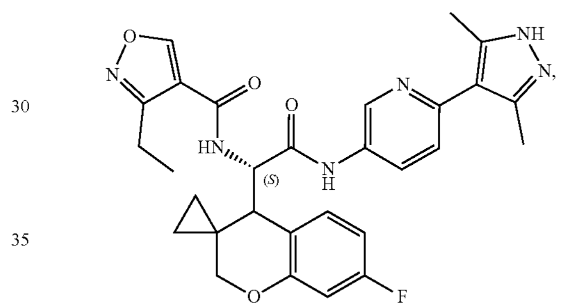
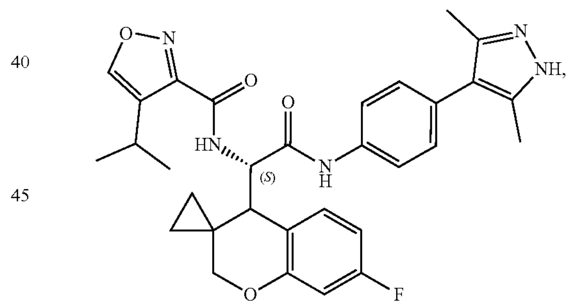
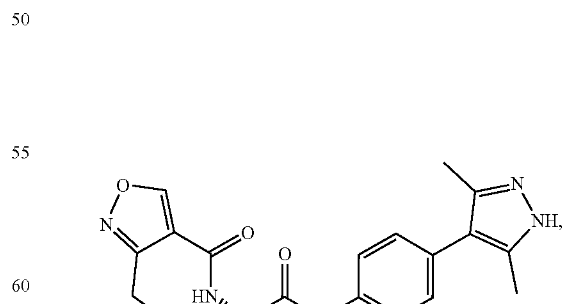
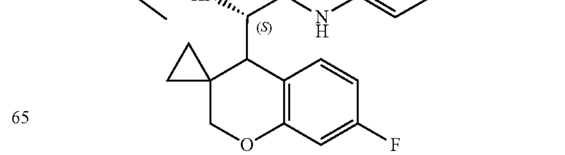
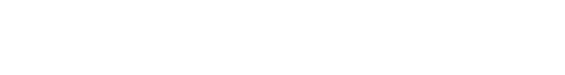

-continued
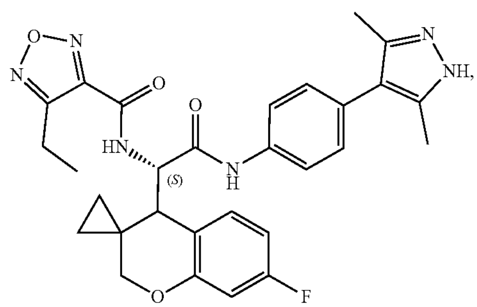
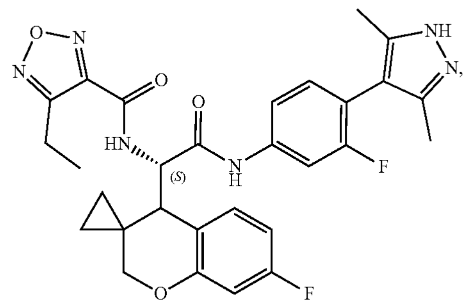
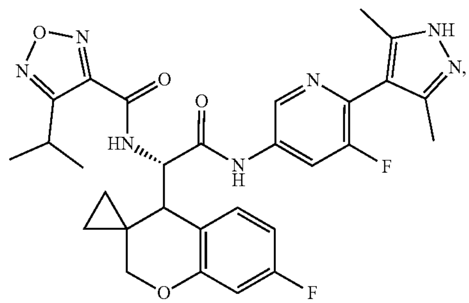
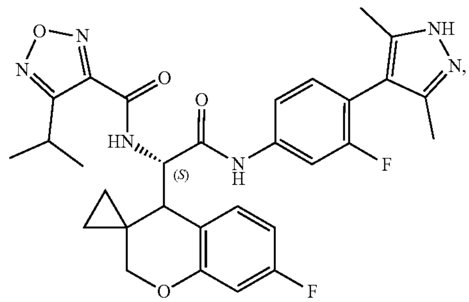
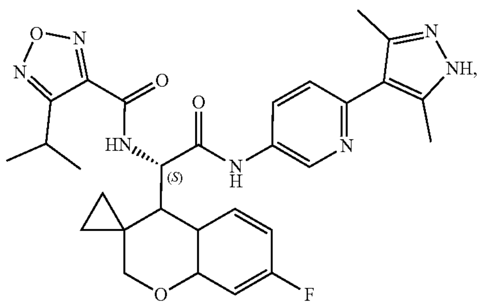
-continued
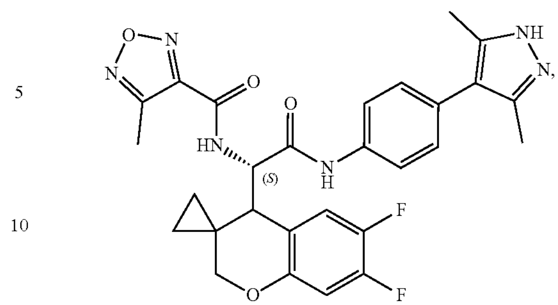
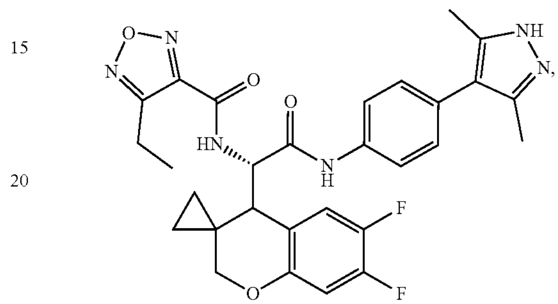
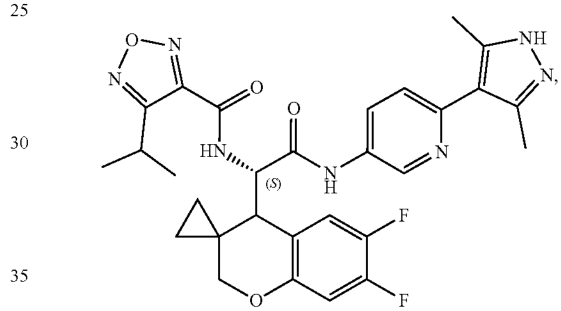
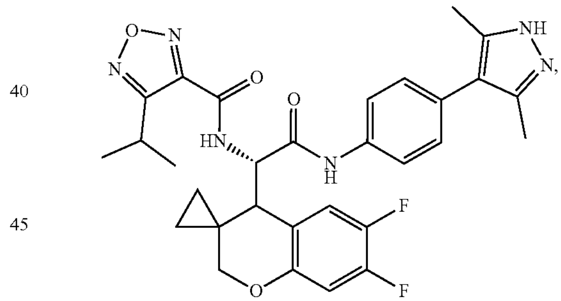
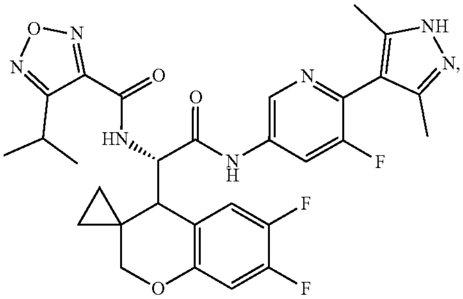

-continued
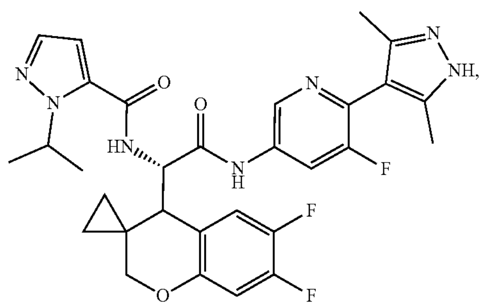
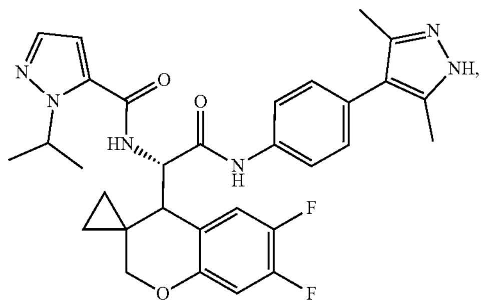
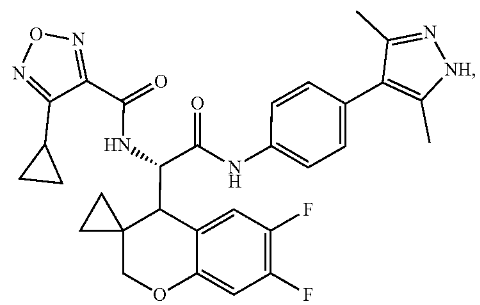
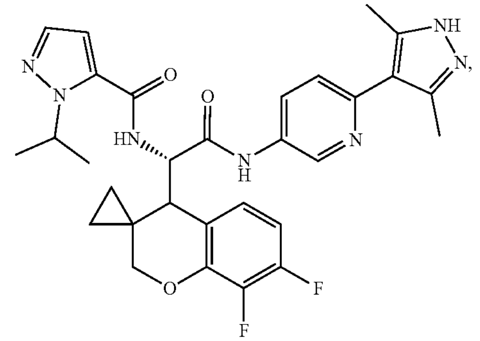
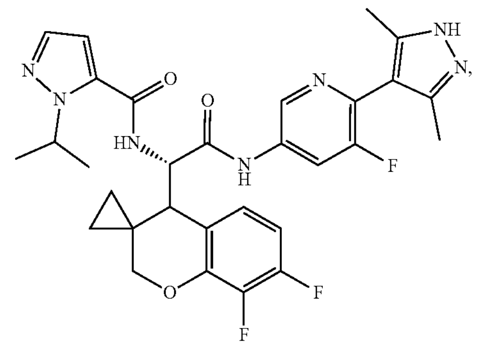
-continued
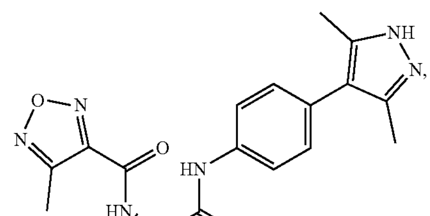
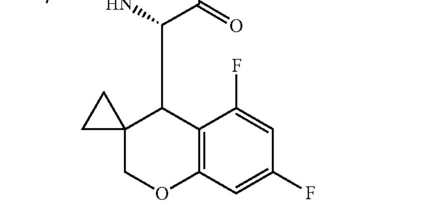
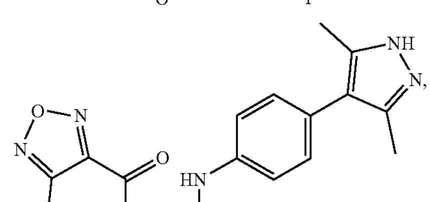
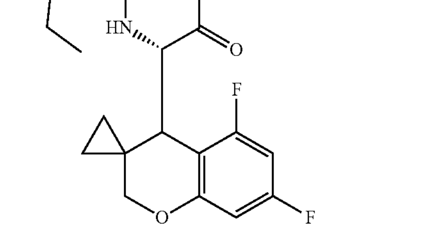
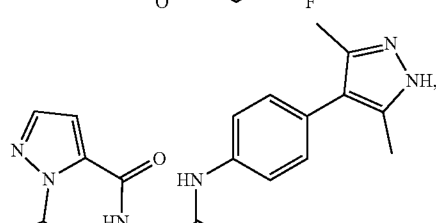
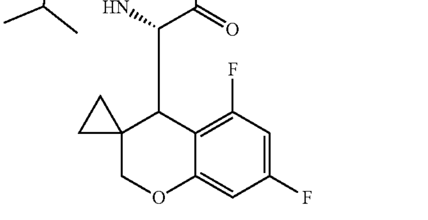
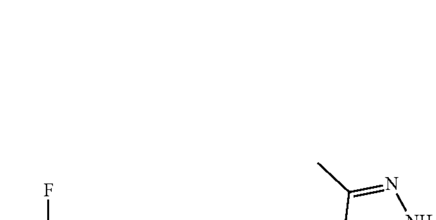
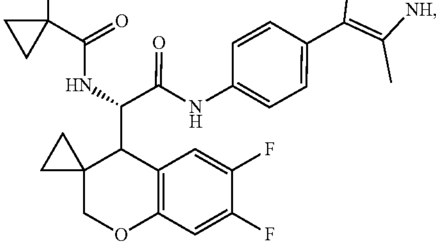

-continued
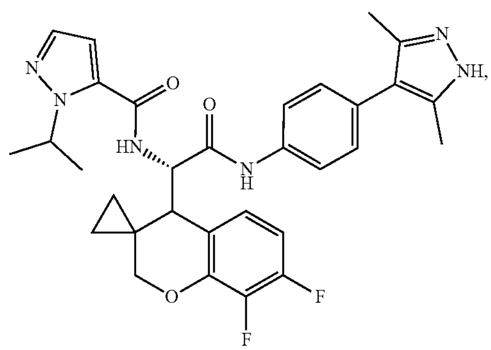
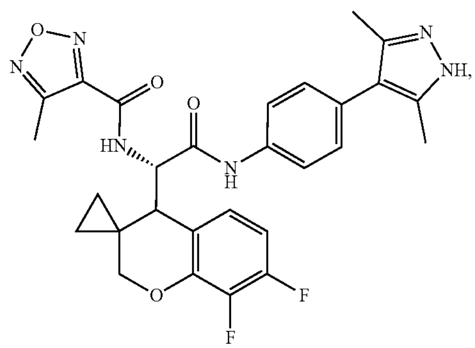
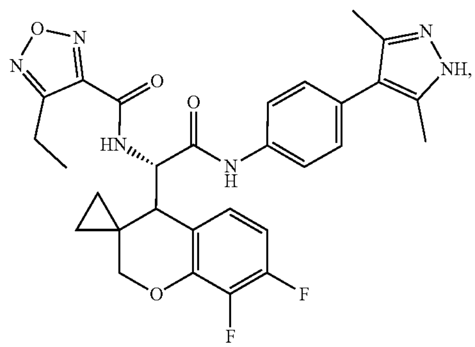
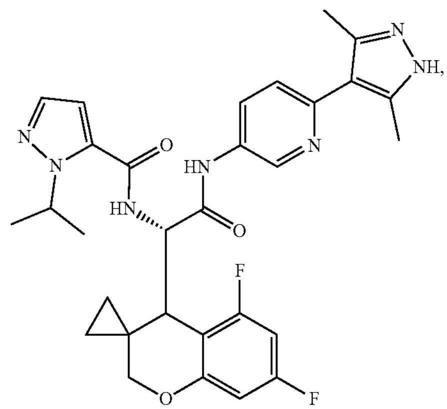
-continued
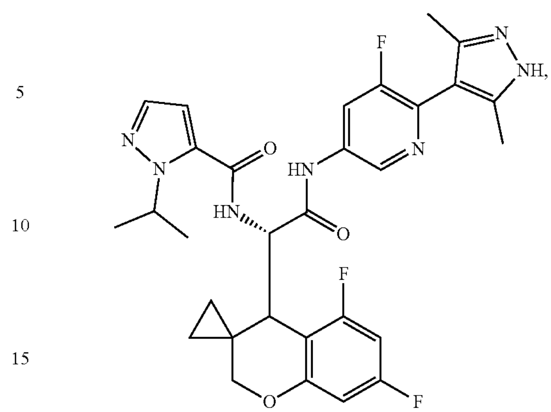
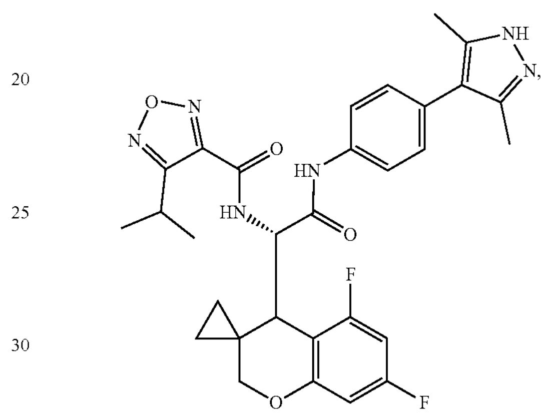
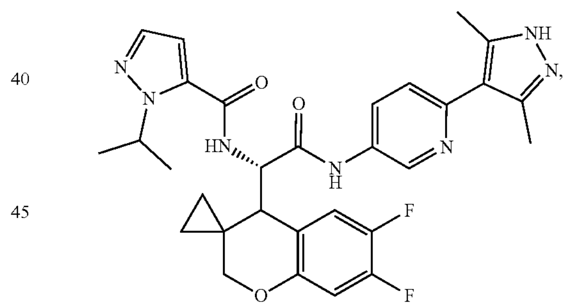
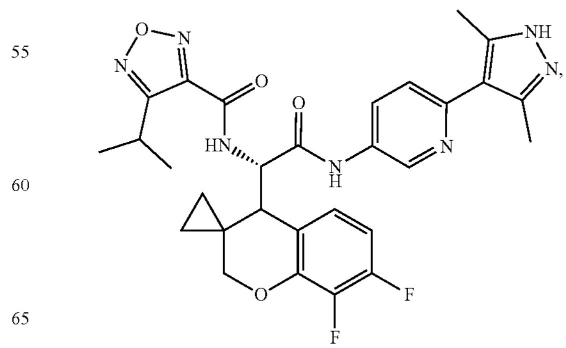

-continued
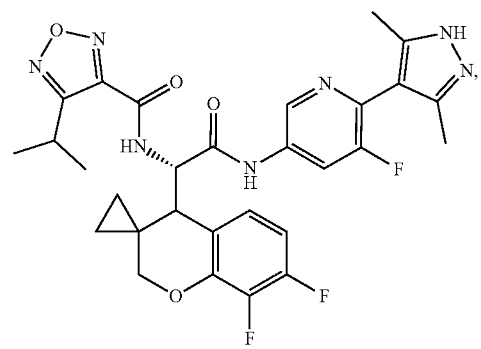
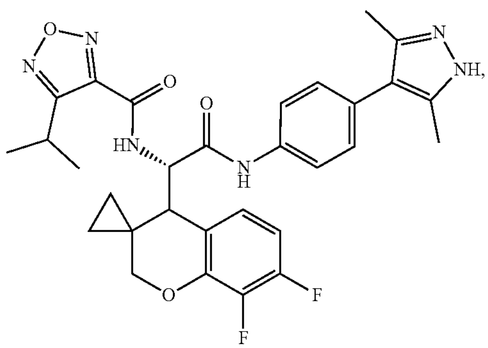
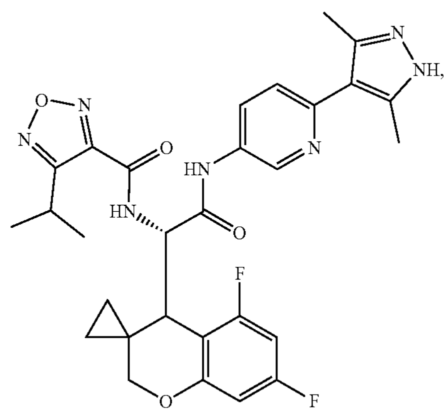
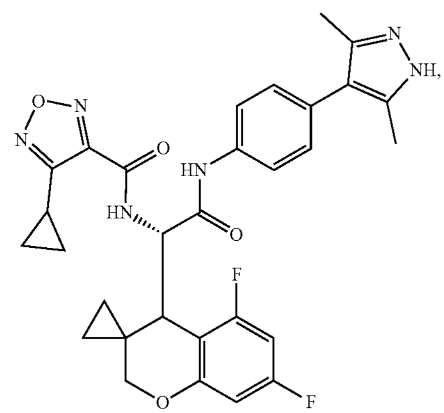
-continued
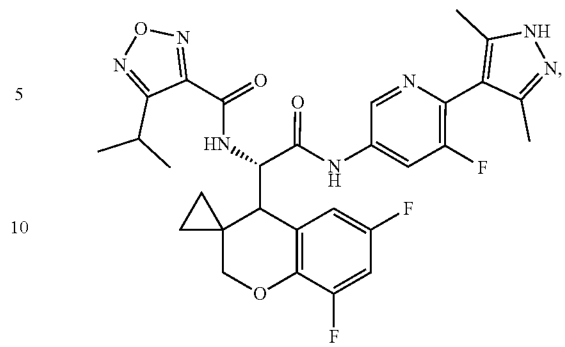
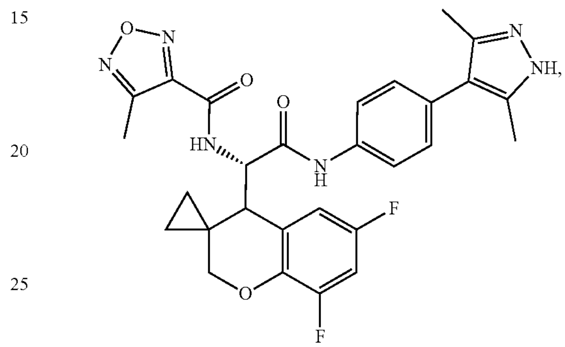
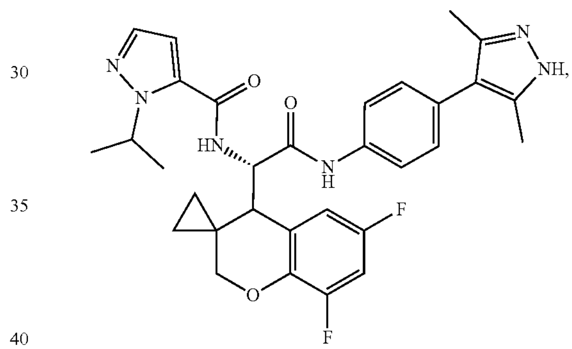
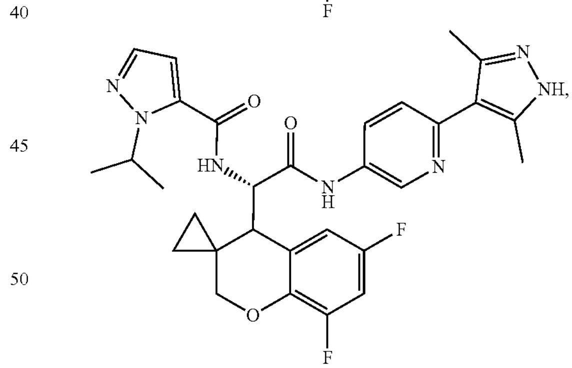
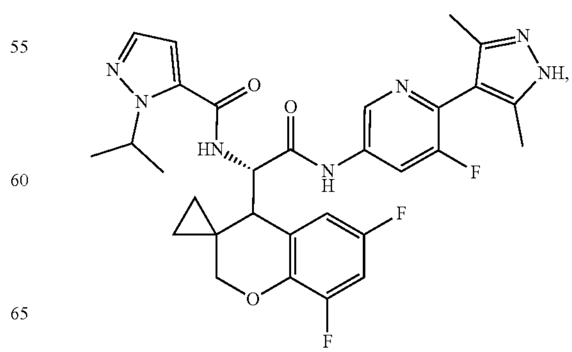

-continued
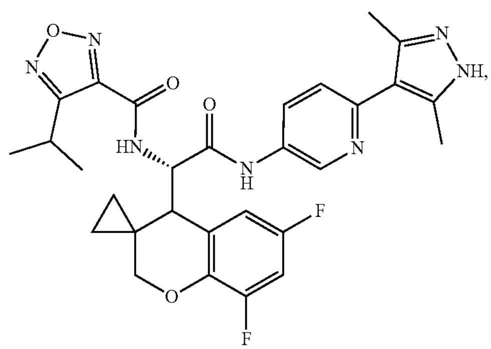
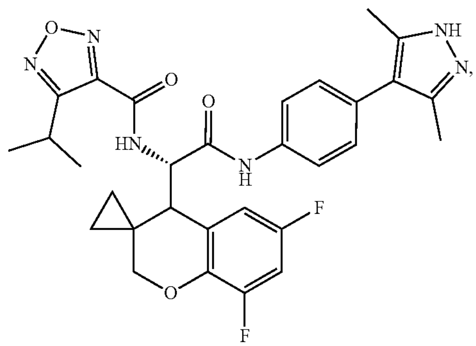
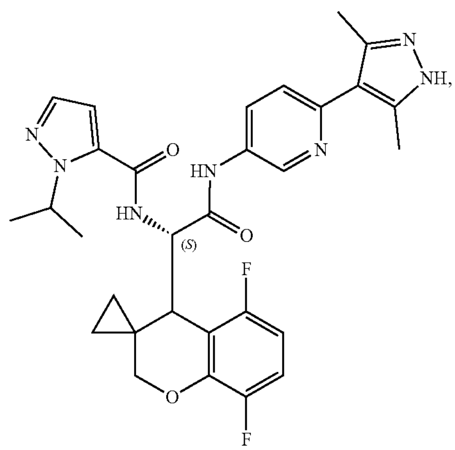
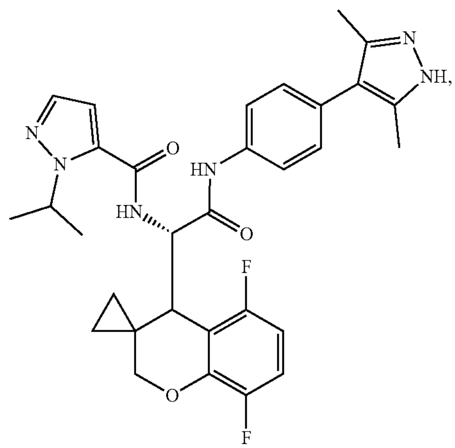
-continued
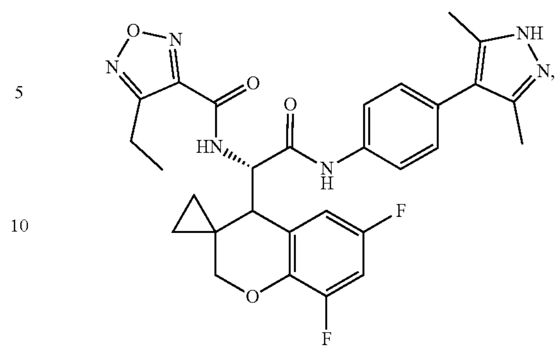
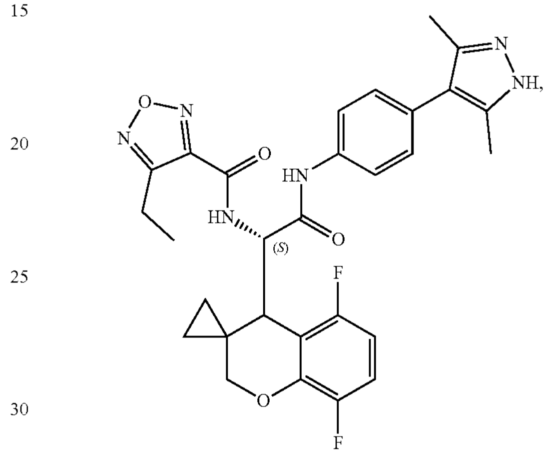
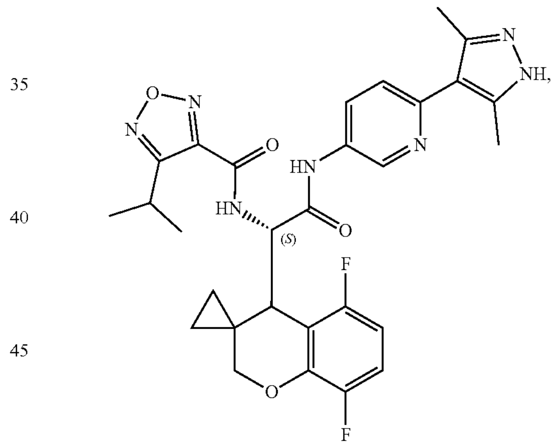
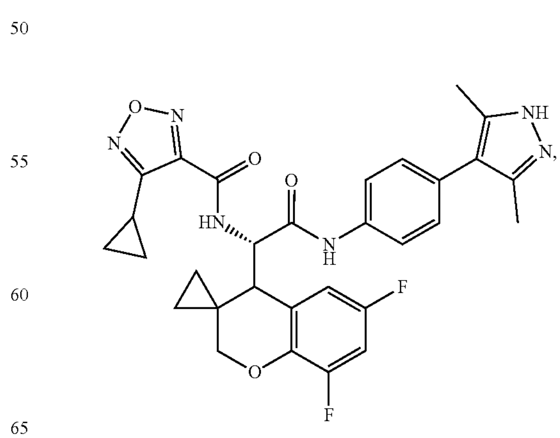

-continued
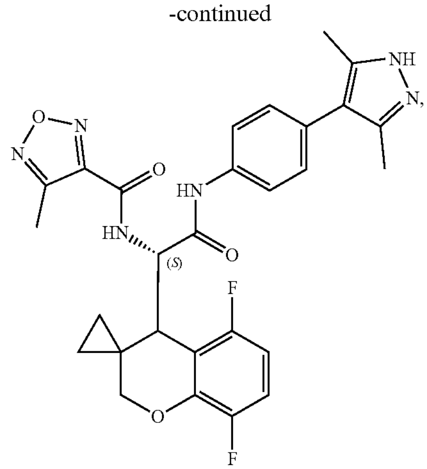
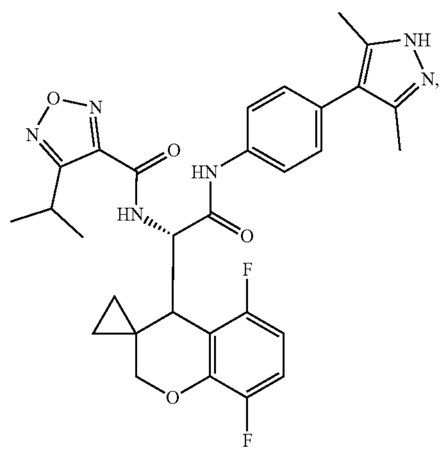
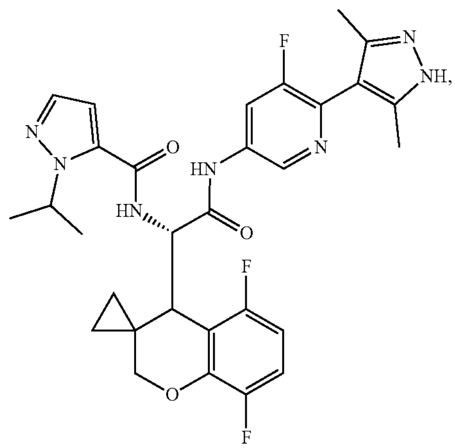
-continued
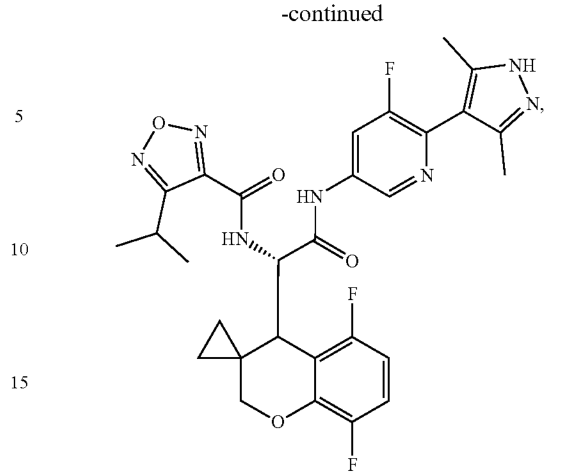
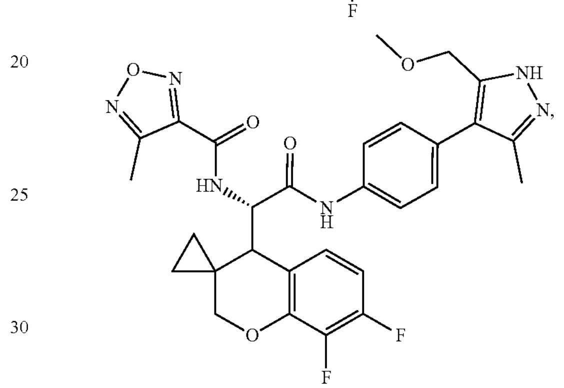
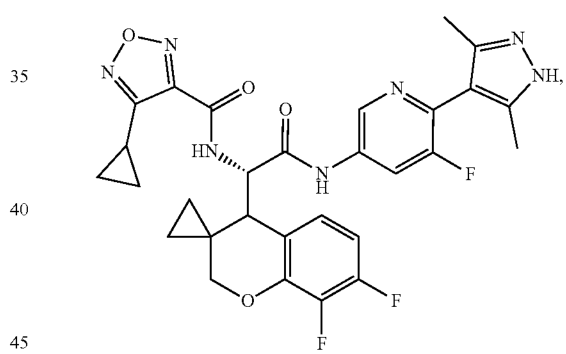
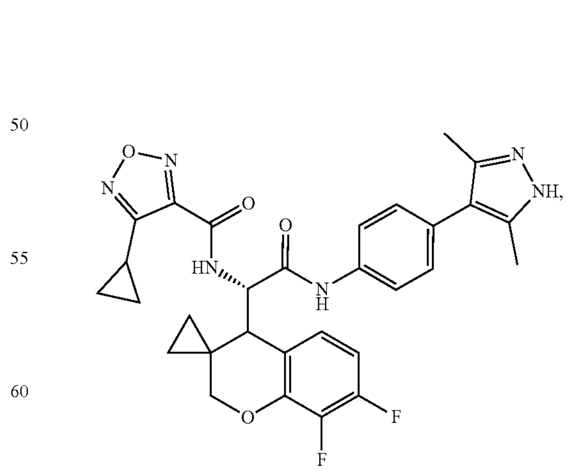

-continued
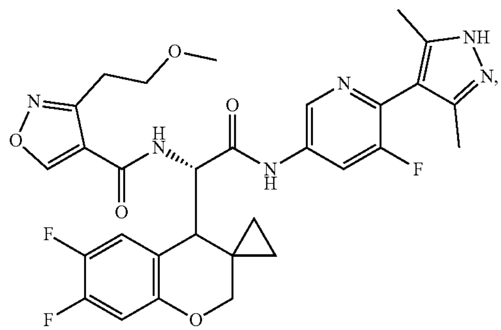
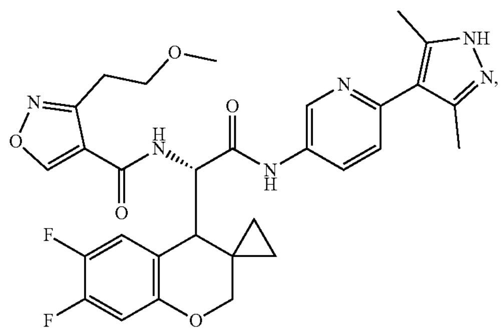
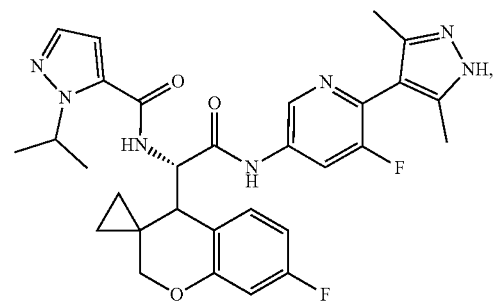
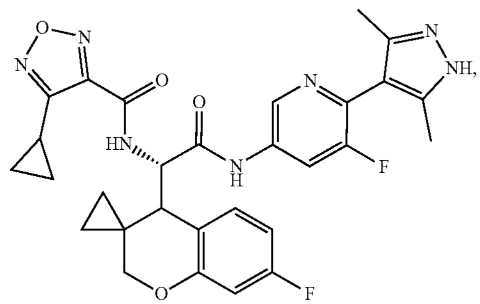
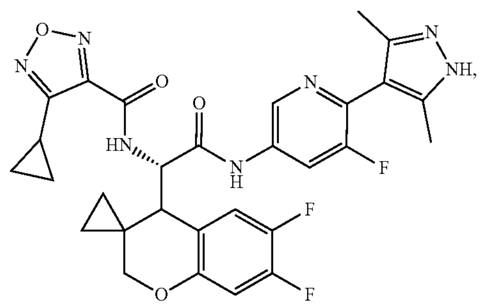
-continued
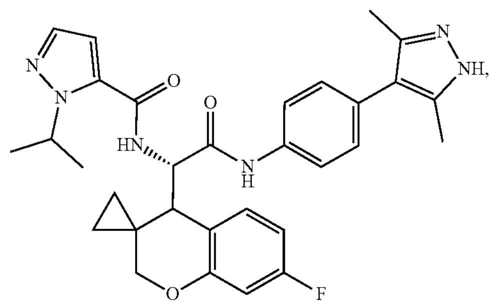
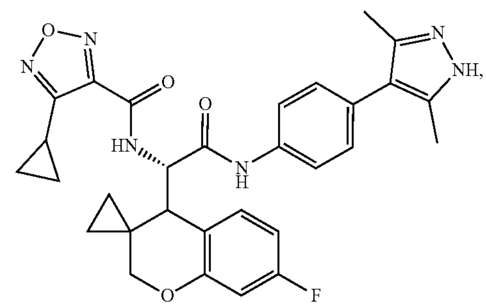
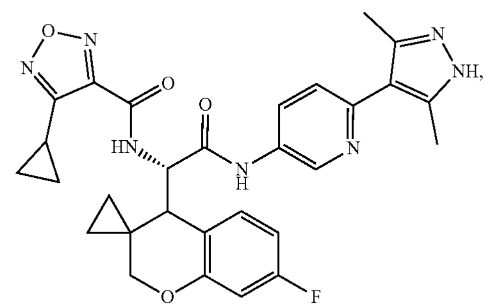
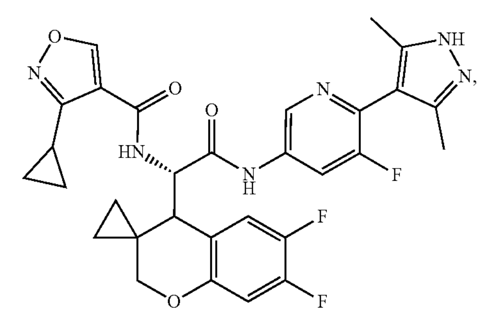
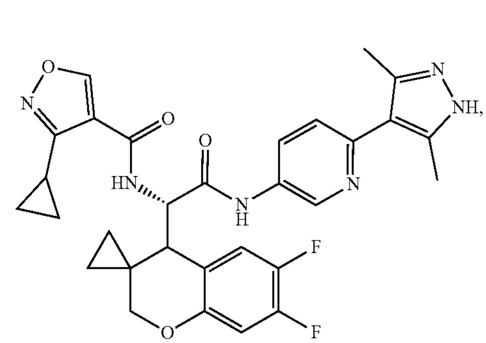

-continued
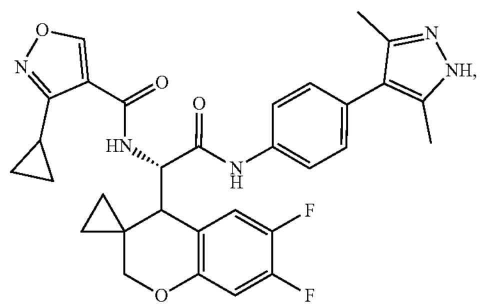
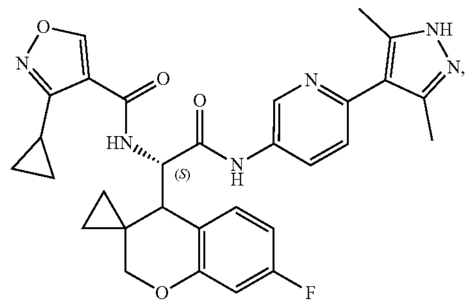
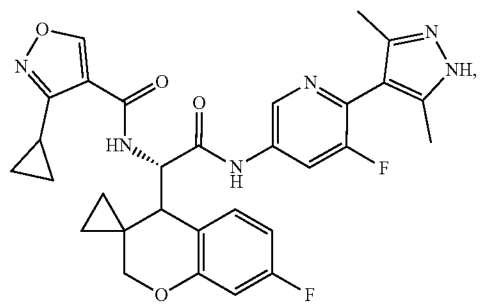
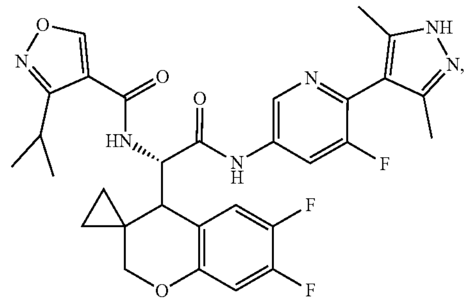
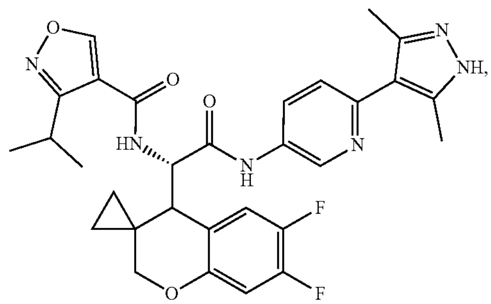
-continued
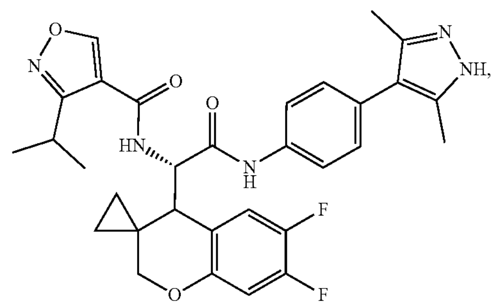
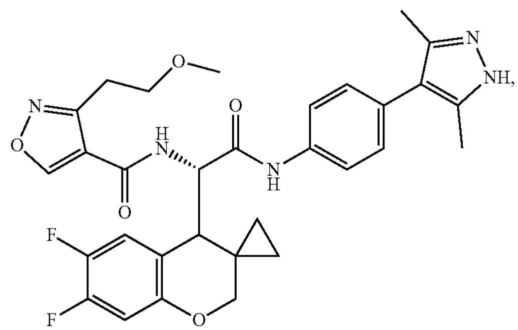
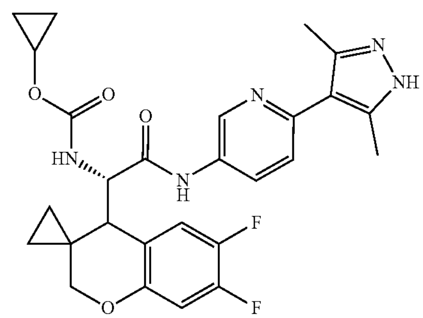
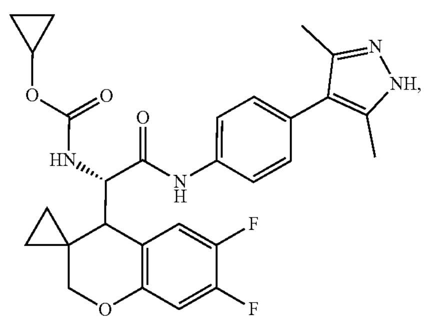
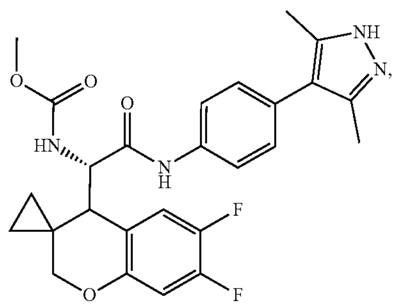

-continued
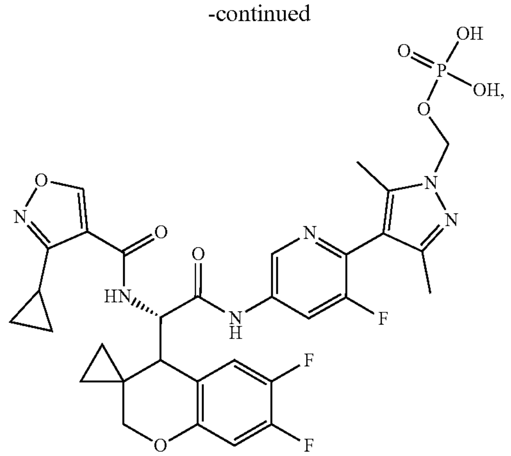
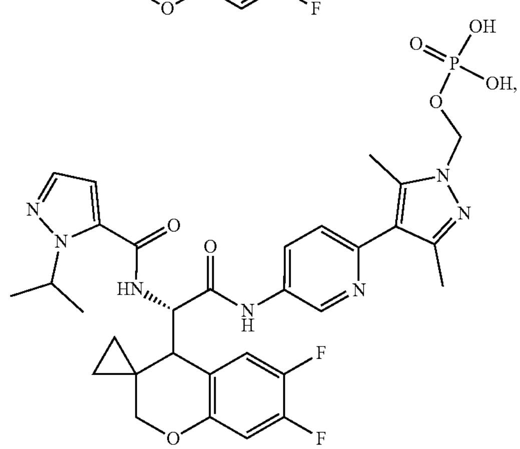
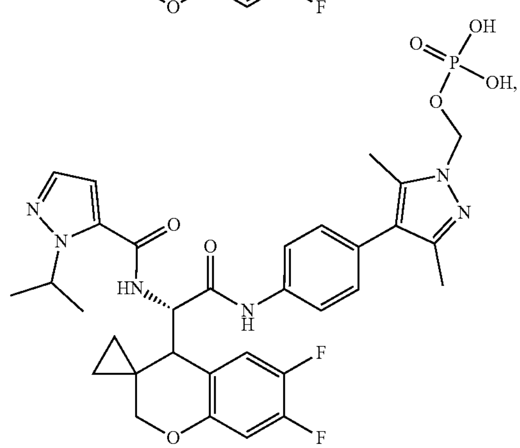
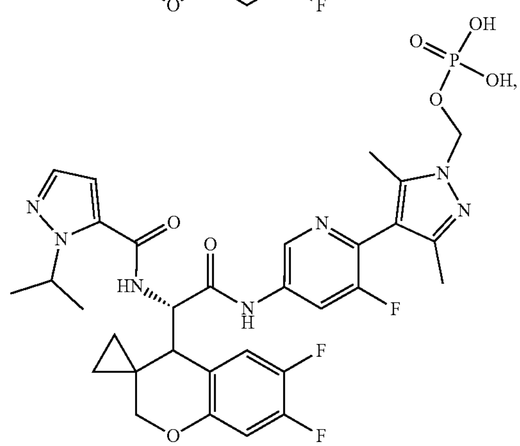
-continued
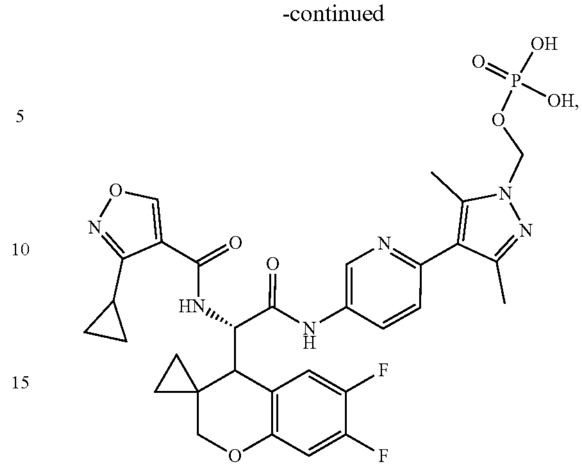
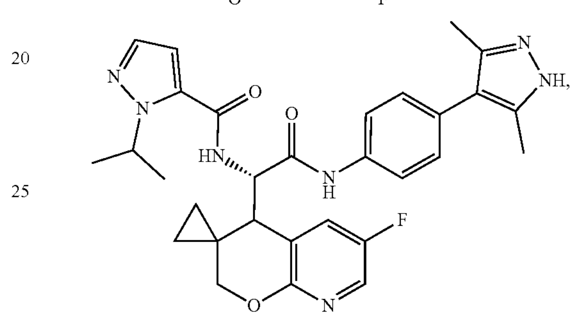
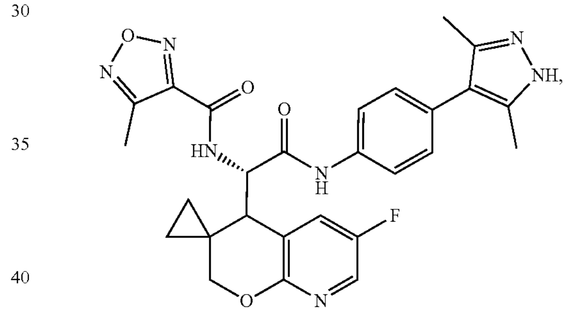
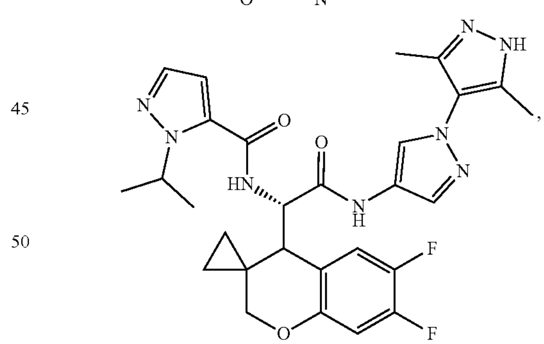
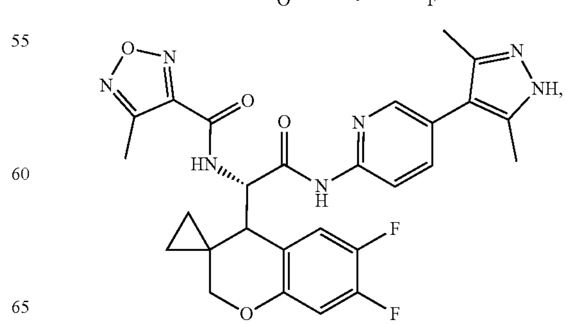

-continued

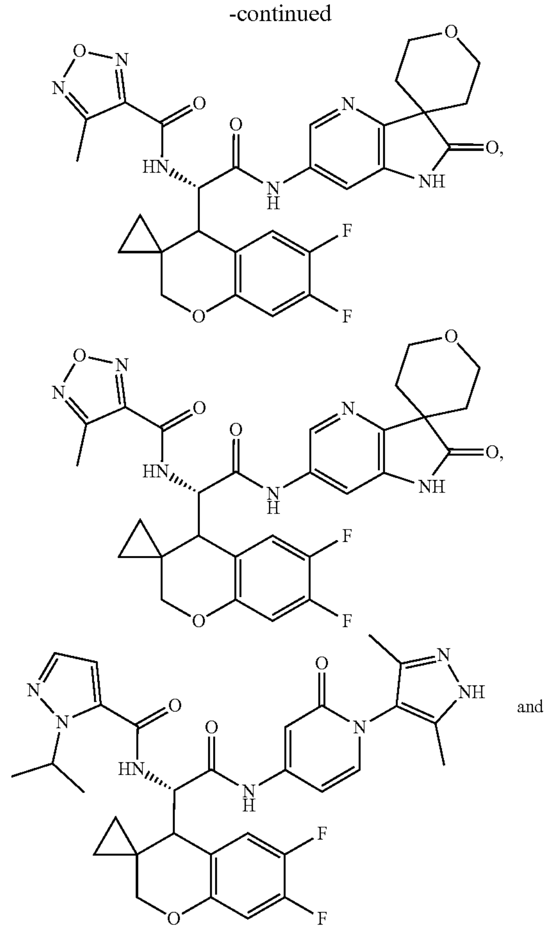

and

-continued

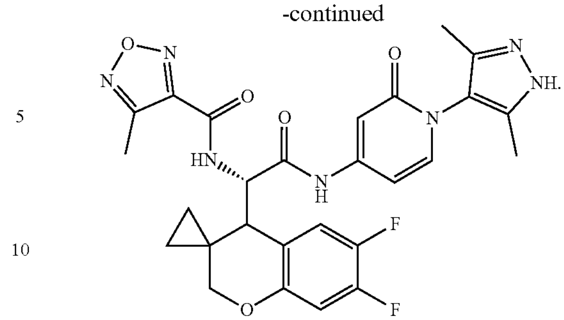

22. A method for treating an interleukin-17A (IL-17A)-mediated disease in a subject in need thereof, comprising:

administering to the subject a therapeutically effective amount of the compound of claim 1, or a deuterated compound, a stereoisomer or a pharmacologically acceptable salt thereof.

23. The method of claim 22, wherein the IL-17A-mediated disease is selected from the group consisting of inflammation, autoimmune disease, infectious disease, cancer, precancerous syndrome and a combination thereof.

24. A pharmaceutical composition, comprising:

the compound of claim 1, or a deuterated compound, a stereoisomer or a pharmacologically acceptable salt thereof; and a pharmaceutically acceptable excipient.

* * * * *